US007494647B2

(12) United States Patent
Sato et al.

(10) Patent No.: US 7,494,647 B2
(45) Date of Patent: Feb. 24, 2009

(54) HUMANIZED ANTIBODY AGAINST HUMAN TISSUE FACTOR (TF) AND PROCESS OF PRODUCTION OF THE HUMANIZED ANTIBODY

(75) Inventors: Koh Sato, Gotenba (JP); Hideki Adachi, Gotenba (JP); Naohiro Yabuta, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 54 days.

(21) Appl. No.: 10/462,062

(22) Filed: Jun. 16, 2003

(65) Prior Publication Data

US 2004/0044187 A1    Mar. 4, 2004

Related U.S. Application Data

(62) Division of application No. 09/647,468, filed as application No. PCT/JP99/01768 on Apr. 2, 1999, now Pat. No. 6,677,436.

(30) Foreign Application Priority Data

Apr. 3, 1998    (JP)    .................................. 10-91850

(51) Int. Cl.
*A61K 39/395*    (2006.01)
(52) U.S. Cl. .............. 424/133.1; 424/139.1; 424/141.1; 424/145.1; 435/7.1; 435/7.92
(58) Field of Classification Search ....................... None
See application file for complete search history.

(56) References Cited

U.S. PATENT DOCUMENTS 5,223,427 A    6/1993    Morrissey et al.
6,180,370 B1    1/2001    Queen et al.

FOREIGN PATENT DOCUMENTS

| EP | 0 239 400 | 8/1994 |
|---|---|---|
| JP | 1-503438 | 11/1989 |
| JP | 4-505398 | 9/1992 |
| WO | WO 88/07543 | 10/1988 |
| WO | WO 90/07861 | 7/1990 |
| WO | WO 91/09968 | 7/1991 |
| WO | WO 91/16928 | 11/1991 |
| WO | WO 94/05328 | 3/1994 |
| WO | WO 94/05328 A1 | 3/1994 |
| WO | WO 94/11029 | 5/1994 |
| WO | WO 94/11523 | 5/1994 |
| WO | WO 96/40921 | 12/1996 |
| WO | WO 96/40921 A | 12/1996 |

OTHER PUBLICATIONS

Singer et al., "Optimal humanization of 1B4, an anti-CD18 murine monoclonal antibody, is achieved by correct choice of human V-region framework sequences" 1993, J Immunol, 150:2844-2857.*

Janeway et al., Immunobiology, third edition, Garland Publishing Inc., 1997, pp. 3:2-3:9.*
Gavilondo et al. "Antibody engineering at the millennium" BioTechniques, 2000, 29:128-145.*
Hiroshi Noguchi "Theory and Clinical Application of Chimera Antibody and Humanized Antibody," *Journal of Clinical and Experimental Medicine*, 167: 457-462 (1993).
Ruf et al, "Purification, sequence and crystallization of an anti-tissue factor Fab and its use for the Crystallization of tissue factor", J. of Crystal Growth 122 (1992), pp. 253-264, Elsevier Science. Pub. B.V.
Maeda et al, "Construction of reshaped human antibodies with HIV-neutralizing activity", Hum. Antibod. Hybridomas, vol. 2 (1991), pp. 124-134, Butterworth-Heinemann.
Hougs et al, "Rapid analysis of rearranged Kappa light chain genes of circulating polysaccharide-specific B Lymphocytes by means of immunomagnetic beads and the polymerase chain reaction", Exp. Clin. Immunogenet, 10 (1993), pp. 141-151, S. Karger AG, Basel.
Epp et al, "The molecular structure of a dimer composed of the variable portions of the Bence-Jones Protein REI refined at 2.0-å Resolution", Biochemistry, vol. 14, No. 22, (1975), pp. 4943-4952, Max-Planck Institute.
Bejeck et al, "Development and characterization of three recombinant single chain antibody fragments (scFvs) Directed against the CD19 antigen[1]" Cancer Research 55, (1995), pp. 2346-2351.
Sato et al, Reshaping a human antibody to inhibit the interleukin 6-dependent tumor cell growth[1] Cancer Research 53, (1993), pp. 851-856.
Welschof et al, "Amino acid sequence based PCR primers for amplification of rearranged human heavy and light chain immunoglobulin variable region genes", J. of Immunological Methods 179, (1995) pp. 203-214 Elsevier Science B.V.
Tempest et al, "Reshaping a human monoclonal antibody to inhibit human respiratory syncytial virus Infection in vivo", Bio/Technology vol. 9 (1991) pp. 266-271, Scotgen Limited.

(Continued)

*Primary Examiner*—Michael Szperka
(74) *Attorney, Agent, or Firm*—Foley & Lardner LLP

(57) ABSTRACT

A humanized antibody against tissue factor (TF), comprising:

A: a humanized H chain comprising (1) a H chain V region comprising the H chain CDRs of a mouse monoclonal antibody against TF and the H chain FRs of a human antibody, and (2) the H chain C region of a human antibody; and B: a humanized L chain comprising (1) an L chain V region comprising the L chain CDRs of a mouse monoclonal antibody against TF and the L chain FRs of a human antibody, and (2) the L chain C region of a human antibody.

After generating a humanized V region by grafting the CDRs of a mouse monoclonal antibody onto a human antibody, a humanized antibody having a higher activity is searched by replacing the FR of the above region with the corresponding FR of the human antibody having a high homology.

5 Claims, 35 Drawing Sheets

OTHER PUBLICATIONS

Kettleborough et al, "Humanization of a mouse monoclonal antibody by CDR-grafting: the importance of Framework residues on loop conformation", Protein Engineering vol. 4, No. 7 (1991) pp. 773-783 Oxford University Press.

Ngo et al., The Protein Folding Problem and Tertiary Structure Prediction, 1994, pp. 492-495.

Kuby et al., Immunology, Second Edition, 1994, pp. 86-96.

Colman et al., A structural View of Immune Recognition by Antibodies, 1994, pp. 33-36.

Cunningham et al, "The covalent structure of a human γG-Immunoglobulin. VII. Amino Acid Sequence of Heavy-Chain Cyanogen Bromide Fragments $H_1$-$H_4$*", Biochemistry, vol. 9, No. 16, (1970), Rockerfeller Univ.

Poljak et al, Amino Acid sequence of the VH Region of a human myeloma immunoglobulin (IgG New) BioChemistry vol. 16, No. 15, (1977) pp. 3412-3420.

Tonge et al, "Cloning and characterization of 1116NS19.9 heavy and light chain cDNAs and expression of Antibody fragments in *Escherichia coli*", Terhorst C, Malavasi F, Albertini A (eds): Generation of Antibodies by Cell and Gene Immortalizaiton, Year Immunol. Basel, Karger, vol. 7, pp. 56-62 (1993).

Man Sung Co et al, "Humanized antibodies for antiviral therapy", Proc. Natl. Acad. Sci., vol. 88, pp. 2869-2873 (1991), Protein Design Labs, Inc.

Gorman et al, "Reshaping a therapeutic CD4 antibody", Proc. Natl. Acad. Sci. vol. 88, pp. 4181-4185 (1991) Dept of Pathology, Univ of Cambridge.

Collet et al, "A binary plasmid system for shuffling combinatorial antibody libraries", Proc. Natl. Acad. Sci. vol. 89, pp. 10026-10030 (1992), Dept. of Chemistry & Molecular Biology.

Borretzen et al, "Control of autoantibody affinity by selection against amino acid replacements in the Complementarity-determining regions", Proc. Natl. Acad. Sci., vol. 91, pp. 12917-12921 (1994).

Verhoeyen et al, "Reshaping human antibodies: grafting an antilysozyme activity", Science vol. 239 (1988) Medical research council lab. Of molecular biology.

Ito et al, "Characterization of functionally important regions of tissue factor by using monoclonal antibodies", J. Biochem. vol. 114, No. 5, pp. 691-696, (1993), Dept. of Molecular Biology.

Pascual et al, "The complete nucleotide sequences of the heavy chain variable regions of six monospecific Rheumatoid factors derived from epstein-barr virus-transformed B cells isolated from the synovial tissue Of patients with rheumatoid arthritis", J. Clin. Invest. (1990), vol. 86, pp. 1320-1328, Amer.Soc. of Clin. Invt.

N. van der Stoep et al, "Molecular evolution of the human immunoglobulin E response: high incidence of Shared mutations and clonal relatedness among ε $V_H 5$ transscripts from three unrelated patients with atopic Dermatitis", J. Exp. Med., vol. 177, (1993) pp. 99-107, The Rockerfeller University Press.

Hillson et al, "The structural basis of germline-encoded $V_H 3$ Immunoglobulin binding to staphylococcal Protein A", J. Exp. Med., vol. 178, (1993) pp. 331-336, The Rockerfeller University Press.

Man Sung CO et al, "Chimeric and humanized antibodies with specificity for the CD33 antigen", J. of Immun. vol. 148, No. 4, pp. 1149-1154, (1992), Amer. Assoc. of Immunologists.

Riechmann et al, "Reshaping human antibodies for therapy", Nature, vol. 332, pp. 323-327 (1988) Dept. of Molecular Biology, The research institute of Scripps Clinic.

Cox et al, "A directory of human germ-line $V_x$ segments reveals a strong bias in their usage", Eur. J. Immunol. 24:827-823, (1994), VCH Verlagsgesellschaft mbH.

Carter et al, "Humanization of an anti-p185$^{RER2}$ antibody for human cancer therapy", Proc. Natl. Acad. Sci. vol. 89, pp. 4285-4289, (1992).

* cited by examiner

Fig. 35

|  | Chimera | | | bb | | | ib | | | ib2 | | | Control | | |
|---|---|---|---|---|---|---|---|---|---|---|---|---|---|---|---|
|  | A | B | C | A | B | C | A | B | C | A | B | C | A | B | C |
| 6ng | | | | | | | | | | | | | | | |
| 3ng | | | | | | | | | | | | | | | |
| 1.5ng | | | | | | | | | | | | | | | |

A, NON-DENATURED TF
B, TF DENATURED UNDER NON-REDUCED CONDITION
C, TF DENATURED UNDER REDUCED CONDITION

HUMANIZED ANTIBODY AGAINST HUMAN TISSUE FACTOR (TF) AND PROCESS OF PRODUCTION OF THE HUMANIZED ANTIBODY

This application is divisional of application Ser. No. 09/647,468, filed Sep. 29, 2000, now U.S. Pat. No. 6,677,436, which application is a 35 U.S.C §371 of PCT/JP99/01768, filed Apr. 2, 1999, in a non-English language.

TECHNICAL FIELD

The present invention relates to a human/mouse chimeric antibody comprising variable region (V region) of a mouse monoclonal antibody against human tissue factor (TF) and constant region (C region) of a human antibody; a humanized antibody in which complementarity determining regions (CDRs) of light chain (L chain) V region and heavy chain (H chain) V region of a mouse monoclonal antibody against human TF have been grafted onto a human antibody; the L chain and H chain of said antibody; and a V region fragment constituting the L chain or H chain of said antibody. The present invention also relates to a process of production of a humanized antibody against human TF.

The present invention also relates to DNA encoding the above antibody, specifically a V region fragment thereof, and DNA encoding an L chain or H chain that contains a V region. The present invention also relates to a recombinant vector comprising said DNA, and a host transformed with said vector.

The present invention also relates to a process of preparing a chimeric antibody and a humanized antibody against human TF. The present invention also relates to a pharmaceutical composition and a therapeutic agent for disseminated intravascular coagulation (DIC) syndrome comprising as an active ingredient a humanized antibody against human TF.

BACKGROUND ART

Tissue factor (TF), a receptor of the coagulation factor VII expressed on the cell surface, plays an indispensable role in the activation of coagulation factors IX and X through the formation of a complex with the coagulation factor VII, and has been defined as a practical initiating factor of blood coagulation reactions.

TF is known to be expressed in fibroblasts, smooth muscle cells, etc. that constitute the blood vessel, and to play a hemostatic function by activating the coagulation system at the time of blood vessel injury.

DIC is a disease in which the activation of the coagulation system in a blood vessel leads to systemic multiple occurrence of blood clots, mainly in the microvasculature. It is not uncommon that the reduction of platelets and coagulation factors due to consumption leads to bleeding which is the opposite phenomenon to blood clotting. The multiple microthrombi can cause deficient microcirculation in the major organs, which, once developed, leads to irreversible functional deficiency and to bad prognosis of DIC, and in this sense DIC is considered an important disease.

The incidence of underlying diseases estimated from the 1990 and 1992 research reports by the Ministry of Health and Welfare Specified Diseases Blood Coagulation Disorders Survey and Study Group is: hematological malignancies, about 30%; solid tumors about, 20%; infections, about 15%; obstetric diseases, about 10%; hepatic diseases about, 6%; shocks, about 5%; and cardiovascular diseases, about 3%. The incidence of DIC is as high as about 15% in leukemia and about 6 to 7% in malignant lymphoma, and about 3% in solid tumors.

DIC develops accompanied by various diseases mentioned above, but the causative agent thereof is the same, which is TF. Thus, the onset mechanism of DIC is believed to be: abnormally high formation and/or expression of TF in cancer cells in acute leukemia, malignant lymphoma, and solid tumors; the enhanced formation and/or expression of TF in monocytes and/or endothelial cells in infections (in particular, sepsis caused by Gram-negative *bacilli*); TF influx into the blood from the necrotized liver tissue in fulminant hepatitis; TF expression on the lumina of the blood vessel in aortic aneurysm, cardiac aneurysm, and giant hemangioma; and also TF influx into the blood in obstetric diseases (amniotic fluid embolism and abruptio placentae) and surgeries, injuries, and burns.

The treatment of the original (underlying) diseases is of utmost concern, which, however, is not easy in practical terms.

As a current method of treating DIC, anticoagulant therapy and substitution therapy are in use. Heparin preparations (fractionated heparin, low molecular weight heparin) are mainly used for anti-coagulant therapy. Synthetic protease inhibitors (gabexate mesilate, nafamostat mesilate) and concentrated plasma (antithrombin III, activated protein C preparations) are also used. As a substitution therapy, there are platelet concentrates, fresh frozen plasmas (supply of fibrinogen), washed red blood cells, and the like.

However, the current therapeutic agents are not satisfactory in terms of efficacy and side effects, and in most cases complete withdrawal from DIC is impossible. Therefore, there is a need for the use of drugs having high therapeutic effects and low side effects.

On the other hand, as new attempts in DIC treatments there can be mentioned thrombomodulin preparations, hirudin, and anti-PAF agents, Tissue factor pathway inhibitor (TFPI). FXa-selective inhibitors are attracting attention as orally administrable anticoagulant and/or antithrombotic agents. Also as an agent that neutralizes the activity of TF, WO 88/07543 discloses mouse anti-human TF monoclonal antibody, and WO 96/40921 discloses humanized anti-human TF antibody.

Mouse anti-human TF monoclonal antibodies are expected to make a safe and effective therapeutic agent in that it does not exhibit a symptom of bleeding associated with main efficacy in DIC. However, mouse monoclonal antibodies are highly immunogenic (sometimes referred to as "antigenic"), and thus the medical therapeutic value of mouse antibodies in humans is limited. For example, the half life of mouse antibodies in humans is relatively short and therefore they cannot fully exhibit their anticipated effects. Furthermore, human anti-mouse antibody (HAMA) that develops in response to the mouse antibody administrated causes immunological reactions that are unfavorable and dangerous to patients. Thus, mouse monoclonal antibodies cannot be repeatedly administered to humans.

In order to solve these problems, methods have been developed that intend to reduce the immunogenicity of antibodies derived from non-humans, such as (monoclonal antibodies derived from) mice. One of them is a method of making chimeric antibody in which a variable region (v region) of the antibody is derived from mouse monoclonal antibody, and a constant region (C region) thereof is derived from a suitable human antibody.

Since the chimeric antibody obtained contains variable region of an original mouse antibody in the complete form, it is expected to bind to an antigen with the identical affinity as that of the original mouse antibody. Furthermore, in chimeric antibody the ratio of the amino acid sequences derived from non-humans is substantially reduced, and thereby it is expected to have a reduced immunogenicity compared to the original mouse antibody. However, it is still possible for an immunological response to the mouse variable region to arise (LoBuglio, A. F. et al., Proc. Natl. Acad. Sci. USA, 86: 4220-4224, 1989).

A second method of reducing the immunogenicity of mouse antibody is, though much more complicated, expected to drastically reduce the potential immunogenicity of mouse antibody. In this method, the complementarity determining region (CDR) alone of a mouse antibody is grafted onto a human variable region to make a "reshaped" human variable region. As desired, however, some amino acid sequences of framework regions (FRs) supporting the CDRs may be grafted from the variable region of a mouse antibody onto the human variable region in order to obtain the closest possible approximation of the original mouse antibody structure. Then, the humanized reshaped human variable region is ligated to the human constant region. In the finally reshaped humanized antibody, portions derived from non-human amino acid sequences are only the CDRs and a small portion of the FRs. The CDRs comprise hypervariable amino acid sequences and they do not show species-specific sequences.

For humanized antibody, see also Riechmann, L. et al., Nature 332: 323-327, 1988; Verhoeye, M. et al., Scienece 239: 1534-1536, 1998; Kettleborough, C. A. et al., Protein Engng., 4: 773-783, 1991; Maeda, H., Human Antibodies and hybridoma, 2: 124-134, 1991; Gorman, S. D. et al, Proc. Natl. Acad. Sci. USA, 88: 4181-4185, 1991; Tempest, P R., Bio/Technology, 9: 226-271, 1991; Co, M. S. et al., Proc. Natl. Acad. Sci. USA 88: 2869-2873, 1991; Cater, P. et al., Proc. Natl. Acad. Sci. USA, 89: 4285-4289, 1992; Co, M. S. et al., J. Immunol., 148: 1149-1154, 1992; and Sato, K. et al., Cancer Res., 53: 851-856, 1993.

In the conventional humanization technology, part of the framework region (FR) includes an amino acid sequence that was grafted from the variable region of a mouse antibody to the human variable region. Thus, when it is administered as a therapeutic agent in humans, there is a risk that antibodies are formed against a site having an amino acid sequence not present in humans, though it is merely one to a few amino acids. In order to circumvent the risk, a third humanization technology was devised. Thus, the method involves, for four FRs (FR1-4) required to support the three dimensional structure of three CDRs, the substitution of the FR of a human antibody having a high homology with the FR of the mouse antibody present in the database using one FR as a unit. In this case, several FRs are selected from human antibodies present in the database, and are sequentially shuffled to prepare a humanized antibody having a high activity.

By so doing, it is possible to construct humanized antibodies in which all the FRs except the CDRs in the variable region have amino acid sequences derived from human antibody. Thus, the humanized antibody carrying the mouse CDR should no longer have immunogenicity more potent than a human antibody containing the human CDR.

Although humanized antibody is expected to be useful for the purpose of treatment, as mentioned above, there is no fixed process present which is universally applicable to any antibody in the method of producing humanized antibody, and thereby various contrivances are required to construct a humanized antibody that exhibits a sufficient binding activity and neutralizing activity to a specific antigen (see, for example, Sato, K. et al., Cancer Res., 53: 851-856, 1993).

DISCLOSURE OF THE INVENTION

It is an object of the present invention to provide a human/mouse chimeric antibody comprising the variable region (V region) of a mouse monoclonal antibody against human tissue factor (TF) and the constant region (C region) of a human antibody, a humanized antibody in which the complementarity determining regions (CDRs) of the light chain (L chain) V region and the heavy chain (H chain) V region of a mouse monoclonal antibody against human TF have been grafted onto a human antibody, the L chain and H chain of said antibody, and a V region fragment constituting the L chain or H chain of said antibody. It is a further object of the present invention to provide a process of making a humanized antibody against human TF.

It is a further object of the present invention to provide DNA encoding the above antibody, specifically a V region fragment thereof, and DNA encoding an L chain or H chain that contains a V region. It is a further object of the present invention to provide a recombinant DNA vector comprising said DNA, and a host transformed with said vector. It is a further object of the present invention to provide a pharmaceutical composition and a therapeutic agent for disseminated intravascular coagulation syndrome (DIC) comprising as an active ingredient a humanized antibody against human TF.

After intensive study to solve the above problems, the inventors of the present invention have successfully obtained an antibody in which immunogenicity in humans of the mouse monoclonal antibody against human TF is reduced, and also developed a process of making a novel humanized antibody, and thereby have completed the present invention.

Thus, the present invention relates to a chimeric H chain comprising the H chain C region of a human antibody and a fragment of the H chain V region of a mouse monoclonal antibody against human TF. As the H chain V region, there can be mentioned one that comprises an amino acid sequence as set forth in SEQ ID NO: 9, and as the C region, there can be mentioned one that is derived from the Cγ4 region.

Furthermore, the present invention relates to a chimeric L chain comprising the L chain C region of a human antibody and a fragment of the L chain V region of a mouse monoclonal antibody against human TF. As the L chain V region, there can be mentioned one that comprises an amino acid sequence as set forth in SEQ ID NO: 15, and as the L chain C region, there can be mentioned one that is derived from the Cκ region.

Furthermore, the present invention relates to a human/mouse chimeric monoclonal antibody against human TF, said antibody comprising the above chimeric H chain and chimeric L chain.

The present invention also relates to a H chain V region fragment of a humanized antibody, said fragment comprising the framework regions (FRs) 1-4 of the H chain V region of a human antibody and the complementarity determining regions (CDRs) 1-3 of the H chain V region of a mouse monoclonal antibody against human TF. As the CDR 1-3, there can be mentioned one that includes the amino acid sequence as set forth in SEQ ID NO: 133-135, respectively. As the FR1 of the H chain V region of a human antibody, there can be mentioned the human antibody FR1 that has a homology of 40% or greater with the FR1 of the H chain V region of a mouse antibody; as the FR2, there can be mentioned the human antibody FR2 that has a homology of 40% or greater with the FR2 of the H chain V region of a mouse antibody; as the FR3, there can be mentioned the human antibody FR3 that has a homology of 40% or greater with the FR3 of the H chain V region of a mouse antibody; and as the FR4, there can be mentioned the human antibody FR4 that has a homology of 40% or greater with the FR4 of the H chain V region of a mouse antibody Preferably, as the FR1 of the H chain V region of a human antibody, there can be mentioned the human antibody FR1 that has a homology of 50% or greater with the FR1 of the H chain V region of a mouse antibody; as the FR2, there can be mentioned the human antibody FR2 that has a homology of 70% or greater with the FR2 of the H chain V region of a mouse antibody; as the FR3, there can be mentioned the human antibody FR3 that has a homology of 65% or greater with the FR3 of the H chain V region of a mouse antibody; and as the FR4, there can be mentioned the human antibody FR4 that has a homology of 80% or greater with the FR4 of the H chain V region of a mouse antibody. As specific examples, as the FR1 of the H chain V region of a human antibody, there can be mentioned the human antibody L39130; as the FR2, there can be mentioned the human antibody L39130, the human antibody P01742, and the human antibody Z80844; as the FR3, there can be mentioned the human antibody L39130, the human antibody Z34963, the human antibody P01825, the human antibody M62723, the human antibody Z80844, the human antibody L04345, the human antibody S78322, the human antibody Z26827, the human antibody U95239, and the human antibody L03147; and as the FR4, there can be mentioned the human antibody L39130.

As preferred examples, as the FR1 of the H chain V region of a human antibody, there can be mentioned the human antibody L39130; as the FR2, there can be mentioned the human antibody L39130 and the human antibody Z80844; as the FR3, there can be mentioned the human antibody Z34963, the human antibody M62723, and the human antibody U95239; and as the FR4, there can be mentioned the human antibody L39130. As more preferred examples, as the FR1 of the H chain V region of a human antibody, there can be mentioned the human antibody L39130; as the FR2, there can be mentioned the human antibody L39130; as the FR3, there can be mentioned the human antibody Z34963 and the human antibody U95239; and as the FR4, there can be mentioned the human antibody L39130.

Furthermore, as used herein, numbers in the framework regions are based on definition by Kabat (Kabat, E. A. et al., US Dept. Health and Services, US Government Printing Offices, 1991).

The present invention also relates to a H chain V region fragment of a humanized antibody, said fragment comprising either of the amino acid sequences as set forth in SEQ ID NO: 30, 40, 42, 50, 52, 58, 60, 64, 70, 72, 76, 78, 82, and 84.

The present invention also relates to an L chain V region fragment of a humanized antibody, said fragment comprising the FRs 1-4 of the L chain V region of a human antibody and the CDRs 1-3 of the L chain V region of a mouse monoclonal antibody against human TF. As the CDRs 1-3, there can be mentioned one that includes the amino acid sequence as set forth in SEQ ID NO: 136-138, respectively. As the FR1 of the L chain V region of a human antibody, there can be mentioned one that has a homology of 40% or greater with the FR1 of the L chain V region of a mouse antibody; as the FR2, there can be mentioned the human antibody FR2 that has a homology of 40% or greater with the FR2 of the L chain V region of a mouse antibody; as the FR3, there can be mentioned the human antibody FR3 that has a homology of 40% or greater with the FR3 of the L chain V region of a mouse antibody; and as the FR4, there can be mentioned the human antibody FR4 that has a homology of 40% or greater with the FR4 of the L chain V region of a mouse antibody Preferably, as the FR1 of the L chain V region of a human antibody, there can be mentioned the human antibody FR1 that has a homology of 75% or greater with the FR1 of the L chain V region of a mouse antibody; as the FR2, there can be mentioned the human antibody FR2 that has a homology of 80% or greater with the FR2 of the L chain V region of a mouse antibody; as the FR3, there can be mentioned the human antibody FR3 that has a homology of 70% or greater with the FR3 of the L chain V region of a mouse antibody; and as the FR4, there can be mentioned the human antibody FR4 that has a homology of 80% or greater with the FR4 of the L chain V region of a mouse antibody. AS specific examples, as the FR1 of the L chain V region of a human antibody, there can be mentioned the human antibody Z37332; as the FR2, there can be mentioned the human antibody Z37332 and the human antibody X93625; as the FR3, there can be mentioned the human antibody Z37332, the human antibody S68699, and the human antibody P01607; and as the FR4, there can be mentioned the human antibody Z37332. As more preferred examples, as the FR1 of the L chain V region of a human antibody, there can be mentioned the human antibody Z37332; as the FR2, there can be mentioned the human antibody X93625; as the FR3, there can be mentioned the human antibody S68699; and as the FR4, there can be mentioned the human antibody Z37332.

Furthermore, as used herein, numbers in the framework regions are based on definition by Kabat (Kabat, E. A. et al., US Dept. Health and Services, US Government Printing Offices, 1991).

The present invention also relates to an L chain V region fragment of a humanized antibody, said fragment comprising the amino acid sequences as set forth in SEQ ID NO: 93, 99, 101, 107, and 109.

The present invention also relates to the H chain of a humanized antibody against human TF, said chain comprising a H chain V region fragment of the above humanized antibody and a H chain C region fragment of a human antibody. There can be mentioned the Cγ4 region as the C region; as the FRs 1-4 derived from a human antibody, there can be mentioned those each derived from the human antibody L39130 (FR1), the human antibody L39130 (FR2), the human antibody Z34963 (FR3) or the human antibody U95239 (FR3), the human antibody L39130 (FR4); and as the CDRs 1-3, there can be mentioned those each derived from the amino acid sequence as set forth in SEQ ID NO: 133-135, respectively.

The present invention also relates to the L chain of a humanized antibody against human TF, said chain comprising an L chain V region fragment of the above humanized antibody and an L chain C region fragment of a human antibody. There can be mentioned the Cκ region as the C region; as the FRs 1-4 derived from a human antibody, there can be mentioned those each derived from the human antibody Z37332 (FR1), the human antibody X93625 (FR2), the human antibody S68699 (FR3), and the human antibody Z37332 (FR4); and as the CDRs 1-3, there can be mentioned those each derived from the amino acid sequence as set forth in SEQ ID NO: 136-138, respectively.

The present invention also relates to a humanized antibody against human TF, said antibody comprising the L chain and H chain of the above humanized antibody.

The present invention also relates to a process of making a humanized antibody against human TF. The process of humanization relates to the method of selecting the FRs 1-4 supporting the structure of the CDRs 1-3 that are the antigen recognition site for the H chain or L chain. Thus, the present invention relates to the method of selecting some of FRs of a human antibody having a high homology with the FR of a mouse antibody with each FR as a unit, and generating a humanized antibody having the desired activity by a sequential reshuffling of the FR.

More specifically, one example of a process of preparing a natural humanized antibody that has a complementarity determining region (CDR) derived from non-humans and a framework region (FR) derived from a natural human antibody and that has a reduced immunogenicity, said method comprising the steps of:

(1) preparing a non-human monoclonal antibody responsive to the antigen of interest;

(2) preparing some of human antibodies having a high homology with the amino acid sequence of the FR in the monoclonal antibody of the above (1);

(3) replacing the four FRs of one human antibody in the above (2) with the corresponding FRs of the non-human monoclonal antibody of the above (1) to generate the first humanized antibody;

(4) determining the ability of the humanized antibody generated in the above (3) to bind to the antigen or to neutralize the biological activity of the antigen;

(5) replacing one to three FRs of the humanized antibody generated in the above (3) with the corresponding FRs of a human antibody that is different from the one used in (3) among the human antibodies prepared in (2) to generate the second humanized antibody;

(6) comparing the ability of the second humanized antibody generated in the above (5) and the first humanized antibody generated in the above (3) for the ability to bind to the antigen or to neutralize the biological activity of the antigen thereby to select a humanized antibody that has a favorable activity;

(7) performing the above steps of (3) to (6) for the humanized antibody selected in the above (6); and (8) repeating the above steps of (3) to (6) until a humanized antibody having an equivalent activity to the non-human monoclonal antibody in the above (1) is obtained.

Once a humanized antibody having a certain degree of activity of neutralizing human TF is obtained, further homology search is carried out for a specific FR in the H chain and L chain V region so that a human antibody having a high homology can be selected. By adding the thus obtained human antibody to a group of some human antibodies in the above step (2) and further repeating the steps of (3) to (6), a humanized antibody having the desired activity can be obtained.

The present invention also relates to DNA encoding a H chain V region fragment or an L chain V region fragment of a mouse monoclonal antibody against human TF. As the amino acid sequence and coding DNA of the H chain V region fragment or L chain V region fragment, there can be mentioned one that includes the nucleotide sequence as set forth in SEQ ID NO: 9 or 15, respectively.

The present invention also relates to DNA encoding the above chimeric H chain or chimeric L chain. As DNA encoding said H chain, there can be mentioned one that includes the nucleotide sequence as set forth in SEQ ID NO: 9, and as DNA encoding said L chain, there can be mentioned one that includes the nucleotide sequence as set forth in SEQ ID NO: 15.

The present invention also relates to DNA encoding a H chain V region fragment or L chain V region fragment of the above humanized antibody. As the DNA encoding the H chain V region fragment, there can be mentioned one that includes either of the nucleotide sequences as set forth in SEQ ID NO: 29, 39, 41, 49, 51, 57, 59, 63, 69, 71, 75, 77, 81, or 83, and as the DNA encoding the L chain V region fragment, there can be mentioned one that includes either of the nucleotide sequences as set forth in SEQ ID NO: 92, 98, 100, 106, or 108.

The present invention also relates to DNA encoding the H chain of a humanized antibody.

The present invention also relates to the H chain DNA of a humanized antibody, said DNA comprising DNA encoding either of the amino acid sequences as set forth in SEQ ID NO: 30, 40, 42, 50, 52, 58, 60, 64, 70, 72, 76, 78, 82, or 84. As said DNA, there can be mentioned one that includes either of the nucleotide sequences as set forth in SEQ ID NO: 29, 39, 41, 49, 51, 57, 59, 63, 69, 71, 75, 77, 81, or 83.

The present invention also relates to DNA encoding the L chain of the above humanized antibody.

The present invention also is the L chain DNA of a humanized antibody, said DNA comprising DNA encoding the amino acid sequences as set forth in SEQ ID NO: 93, 99, 101, 107, or 109. As said DNA, there can be mentioned one that includes either of the nucleotide sequences as set forth in SEQ ID NO: 92, 98, 100, 106, or 108.

The present invention also relates to a recombinant DNA vector containing either of the DNA described above.

The present invention also relates to a transforming transformed with a recombinant DNA vector described above.

The present invention also relates to a process of generating a chimeric antibody or a humanized antibody against human TF, said method comprising culturing the above transformant and obtaining a chimeric antibody or a humanized antibody against human TF from the culture harvested.

The present invention also relates to a pharmaceutical composition and a therapeutic agent for DIC comprising the above humanized antibody as an active ingredient.

BRIEF DESCRIPTION OF DRAWINGS

FIG. 35 is a figure that compares the reactivity to human TF treated under various conditions of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.

BEST MODE FOR CARRYING OUT THE INVENTION

Figure 1:
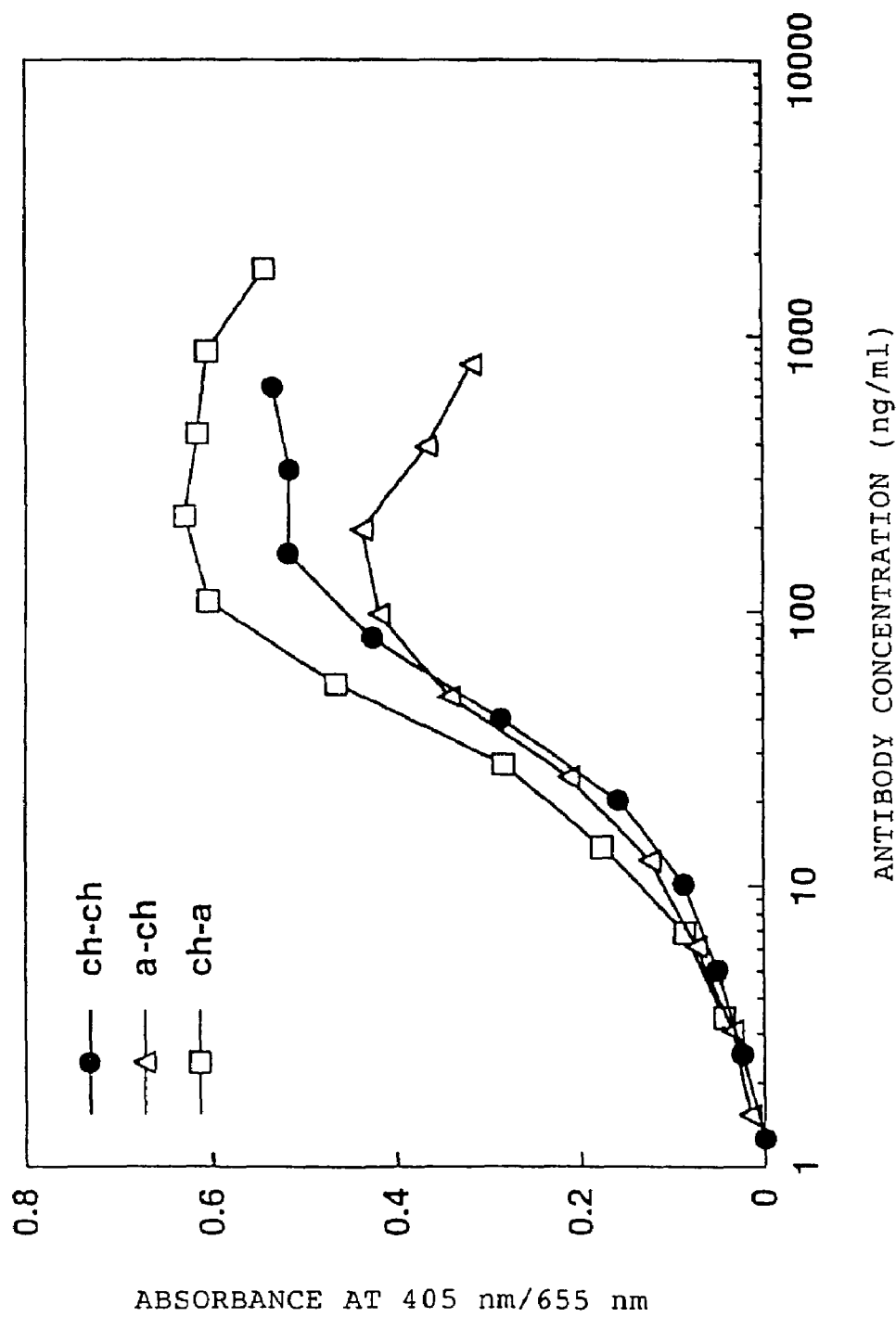
FIG. 1 is a graph that compares the activity of binding to antigen of a H chain chimeric/L chain chimeric antibody, a H chain humanized version a/L chain chimeric antibody, and a H chain chimeric/L chain humanized version a antibody.

The present invention will now be explained in further details.

1. Preparation of a Mouse Monoclonal Antibody Against Human TF

A mouse monoclonal antibody against TF may be generated by generating a hybridoma by a fusion of antibody-producing cells obtained from animals immunized with the antigen to myeloma cells, and then by selecting from the hybridoma obtained a clone that produces antibody that specifically inhibits TF activity.

Thus, spleen cells of a mouse immunized with TF that was purified from human placenta as the antigen were fused to myeloma cells to prepare a hybridoma. For the purpose of screening the hybridoma, the binding ability of the antibody to TF was determined by a Cell-ELISA that employs the TF-high expression cell line J82, and its activity of neutralizing TF was determined in an assay system that employed as an index the activity of inhibiting the activation of coagulation factor X (Factor X: FX). As a result, hybridomas were successfully established that produce 6 antibodies which strongly inhibit the FX-activation of the TF/VIIa complex.

(1) Preparation of Antigen

As TF for immunization of animals, there can be mentioned a peptide that is part of the amino acid sequence of TF generated by the recombinant DNA technology or chemical synthesis, or TF derived from human placenta. For example, TF purified from human placenta according to the method of Ito et al. (Ito T. et al., J. Biochem. 114: 691-696, 1993) can be used as the antigen.

The obtained TF is mixed with an adjuvant and then the mixture is used as the antigen. As the adjuvant, there can be mentioned Freund's complete adjuvant or Freund's incomplete adjuvant, any of which may be mixed.

(2) Immunization and Harvesting of Antibody-producing Cells

The antigen obtained as above may be administered to non-human mammals, for example mammals such as mice, rats, horses, monkeys, rabbits, goats, sheep, and the like. Immunization can be carried out using any of the existing methods, and is mainly carried out by intravenous, subcutaneous, and intraperitoneally injection and the like. The period of immunization is, but not limited to, at an interval of a few days to a few weeks, preferably an interval of 4-21 days.

Antibody-producing cells may be collected 2-3 days after the last day of immunization. As the antibody-producing cells, there can be mentioned spleen cells, lymphatic cells, and peripheral blood cells, and generally spleen cells are used. The amount of the antigen to be used for each immunization is 0.1-100 μg per mouse.

(3) Determination of Antibody Titer

In order to confirm the level of immune response of the immunized animal and to select the desired hybridoma from the cells after cell fusion treatment, antibody titer in the blood of the immunized animal and that in the culture supernatant of antibody-producing cells are determined.

As methods of detecting antibody, there can be mentioned known methods such as enzymeimmunoassay (EIA), radioimmunoassay (RIA), enzyme-linked immunosorbent assay (ELISA), and the like.

(4) Cell Fusion

As the myeloma cells fused to the antibody-producing cells, lined cells that are derived from mice, rats, humans, etc. and that are generally available to a person skilled in the art are used. As cell lines to be used, there can be mentioned those that have the properties of being drug resistant, being unable to survive in the selection medium (for example the HAT medium) at the non-fused state, and being able to survive only at the fused state. Generally 8-azaguanine-resistant strains are used, and these cell lines lack hypoxanthine-guanine-phosphoribosyl transferase and therefore cannot survive in the containing hypoxanthine, aminopterin, and thymidine (HAT) medium.

As myeloma cells, various known cell lines such as P3 (P3X63Ag8.653) (J. Immunol. 123: 1548-1550, 1979), P3X63Ag8.1 (Current Topics in Microbiology and Immunology 81: 1-7, 19778), NS-1 (Kohler, G. and Milstein, C., Eur. J. Immunol. 6: 511-519, 1976), MPC-11 (Margulies, D. H., Cell 8: 405-415, 1976), SP2/0 (Shulman, M. et al., Nature 276: 269-270, 1978), F0 (de St. Groth, S. F. et al., J. Immunol. Methods (1980) 35: 1-21, 1980), S194 (Trowbridge, I. S., J. Exp. Med. 148: 313-323, 1978), R210 (Galfre, G. et al., Nature 277: 131-133, 1979) and the like are preferably used.

Antibody-producing cells may be obtained from spleen cells, lymphatic cells, and the like. Thus, from the above animals, spleens, lymph nodes etc. are removed or collected, and these tissues are dispersed. The dispersed cells are suspended into a medium or a buffer such as PBS, DMEM, and RPMI1640, filtered with stainless mesh etc., and centrifuged to prepare the desired antibody-producing cells.

The above myeloma cells and the antibody-producing cells are subjected to cell fusion.

Cell fusion may be carried out by contacting the myeloma cells and the antibody-producing cells at 30-37° C. for 1-15 minutes in the presence of a fusion accelerant at a mixed ratio of 1:1 to 1:10 in a culture medium for animal cell culture such as MEM, DMEM, RPMI1640, and the like. In order to accelerate cell fusion, a cell fusion accelerator or a fusion virus such as polyethylene glycol (PEG) of a molecular weight 1,000-6,000, polyvinyl alcohol, or Sendai virus (HVJ) may be used. Furthermore, commercially available cell fusion instruments (for example, electroporation) utilizing electric stimulation may be used to fuse the antibody-producing cells to the myeloma cells.

(5) Selection and Cloning of a Hybridoma

The desired hybridoma may be selected from the fused cells. By way of example, there can be mentioned methods that utilize the selective growth of cells in a selection medium. Thus, after dilution of a cell suspension with a suitable medium, it is plated on a microtiter plate and a selection medium (such as the HAT medium) is added thereto, which is cultured with appropriate replacement of the selection medium. As a result, the growing cells can be obtained as the hybridoma.

The screening of a hybridoma is carried out by the limiting dilution method, the fluorescence-activated cell sorter method, and the like, and finally a monoclonal antibody-producing hybridoma can be obtained.

The selection of a hybridoma that produces monoclonal antibody can be carried out by combining various assay systems. For example, an antigen-recognition system such as the Cell-ELISA, a TF-neutralizing activity assay system that utilizes the Factor Xa activity as an index, and a neutralizing activity assay system such as the assay system measuring plasma coagulation-inhibition activity are combined to obtain a monoclonal antibody-producing hybridoma that has the desired activity. By so doing, a monoclonal antibody-producing hybridoma can be obtained such as ATR-2, ATR-3, ATR-4, ATR-5, ATR-7, and ATR-8.

(6) Collection of Monoclonal Antibody

As a method of collecting monoclonal antibody from the hybridoma obtained, there can be mentioned a conventional cell culture method, an ascites-forming method, and the like.

In the cell culture method, a hybridoma is cultured in a culture medium for animal cell culture such as an RPMI1640 medium supplemented with 10-20% fetal calf serum, the DMEM medium, a serum-free medium or the like, under a culture condition (for example, 37° C., 5% $CO_2$ concentration) for 2-14 days, and then antibody is obtained from the culture supernatant.

In the ascites-forming method, a hybridoma is intraperitoneally given to an animal species similar to the mammal from which the myeloma cells are derived, and the hybridoma is proliferated at large amounts. Then the ascites or serum is collected 1-4 weeks later.

When purification of antibody is required in the above method of obtaining antibody, purification is carried out by selecting, as appropriate, a known method such as the ammonium sulfate fractionation, ion-exchange chromatography, and affinity chromatography, or by combining them.

2. Cloning of DNA Encoding the V Region of a Monoclonal Antibody Against Human TF (i) Preparation of mRNA In order to clone DNA encoding the H chain and L chain V region of a mouse monoclonal antibody against human TF, total RNA is isolated from the harvested hybridoma by a known method such as the guanidine-ultracentrifugation method (Chirgwin, J. M. et al., Biochemistry, 18: 5294-5299, 1979), and the AGPC method (Chomczynski, P. et al., 162: 156-159, 1987), and then mRNA is purified by the oligo (dT)-cellulose spun column attached to the mRNA Purification Kit (Pharmacia Biotech), and the like. mRNA can also be purified, without extracting total RNA, by using the Quick-Prep mRNA Purification Kit (Pharmacia Biotech).

(ii) Preparation and Amplification of cDNA

From the mRNA obtained in the above (i), cDNA in the V region of L chain and H chain, respectively, is synthesized using a reverse transcriptase. The synthesis of cDNA can be carried out using an Oligo-dT primer or a suitable primer (for example, the cDNA synthetic primer attached to the kit) that hybridizes with the L chain C region or the H chain C region.

Amplification of cDNA may be carried out by PCR based on 5'-RACE method (Frohman, M. A. et al., Proc. Natl. Acad. Sci. USA 85: 8998-9002, 1988; Belyavsky, A. et al., Nucleic Acids Res. 17: 2919-2932, 1989) that uses the 5'-Ample FINDER RACE kit (CLONETECH) together with the L chain and H chain. Thus, a cDNA adapter is linked to the ends of a double-stranded cDNA synthesized above, and then a polymerase chain reaction (PCR) is carried out for DNAs encoding the H chain V region and the L chain V region (DNA encoding a fragment of the L chain V region is hereinafter abbreviated as "L chain V region DNA" or "DNA encoding the L chain V region"; the same holds true for the H chain V region etc.).

As a primer for amplifying DNA of a H chain V region, the Adapter primer 1 may be used for the 5'-end primer, and the mouse antibody H chain constant region MHC-G1 primer (SEQ ID NO: 1) (ATR-2, ATR-3, ATR-4, and ATR-5) (cγ1 region) or MHC-G2a primer (SEQ ID NO: 2) (ATR-7 and ATR-8) (cγ2a region) (S. T. Jones et al., Biotechnology, 9: 88, 1991). For example, for the 5'-end primer, the Adapter primer 1 attached to the kit, and for the 3'-end primer the L chain κ chain constant region (Cκ region) primer of a mouse antibody (such as the MKC primer having the nucleotide sequence as set forth in SEQ ID NO: 3) can be used.

(iii) DNA Purification and Determination of the Nucleotide Sequence

PCR products are subjected to agarose gel electrophoresis according to a known method. After excising the desired DNA fragment, DNA is recovered and purified, and then ligated to a vector DNA.

DNA may be purified either by extraction with phenol and chloroform (J. Sambrook et al., "Molecular Cloning", Cold Spring Harbor Laboratory Press, 1989) or using a commercially available kit (for example, GENECLEAN II; BIO101). A vector DNA used for retaining DNA fragments may be any of known ones (for example, pUC19 and Bluescript, etc.).

The above DNA and a vector DNA are ligated using a known ligation kit (manufactured by Takara Shuzo) to obtain a recombinant vector. After the resulting recombinant DNA vector is introduced into an *Escherichia coli* JM109 competent cell (Nippongene) etc., ampicillin-resistant colonies are selected, and then a vector DNA is prepared based on a known method (J. Sambrook et al., "Molecular Cloning", Cold Spring Harbor Laboratory Press, 1989). After the above vector is digested with a restriction enzyme, the nucleotide sequence of DNA of interest can be determined by a known method (for example the dideoxy method) (J. Sambrook et al., "Molecular Cloning", Cold Spring Harbor Laboratory Press, 1989). According to the present invention, an automatic instrument for determining nucleotide sequence (DNA Sequencer 373A, Perkin-Elmer) may be used.

(iv) Complementarity Determining Region (CDR)

The H chain V region and L chain V region form an antigen-binding site, and the overall structure is similar to each other. Thus, each four framework regions (FRs) are ligated by three hypervariable regions, i.e. complementarity determining regions (CDRs). The amino acid sequences of FRs are well conserved, whereas the amino acid sequences of the CDRs are very highly variable (Kabat, E. A. et al., "Sequence of Proteins of Immunological Interest", US Dept. Health and Human Services, 1983).

Many regions of the above four FRs take the form of a β-sheet structure, with a result that the CDR forms a loop. The CDR may sometimes form parts of the β-sheet structure. Thus, the three CDRs are retained in close proximity to one another three-dimensionally, and the FRs constitute a antigen-binding site together with the three CDRs.

Based on such facts, by fitting the amino acid sequence of a mouse monoclonal antibody against human TF into the database on the amino acid sequences of antibodies generated by Kabat ("Sequence of Proteins of Immunological Interest", US Dept. Health and Human Services, 1983), its homology can be examined and thereby the CDRs can be found.

The sequence of a CDRs altered by insertion, substitution, or deletion may be included in the present invention, as long as it retains the activity of binding to or neutralizing human TF when a humanized antibody is generated using it. For example, there can be mentioned those that have a homology of 90-100% with each CDRs for SEQ ID NO: 133-138 or with each CDR in the V region of SEQ ID NO: 139-141, 143-144, 145-147, and 149-150. Preferably there can be mentioned those sequences that have a homology of 95-100%. More preferably, there can be mentioned those sequences that have a homology of 98-100%.

3. Preparation of an Expression Vector of Chimeric Antibody

Once a DNA fragments encoding the mouse L chain (L chain or H chain of antibody may hereinafter referred to as "mouse L chain" for mouse antibody and "human H chain" for the H chain of human antibody) and the mouse H chain V region have been cloned, DNA encoding the mouse V region is ligated to DNAs encoding the constant region of a human antibody and expressed to obtain a chimeric anti-human TF antibody.

Basic methods for generating chimeric antibody comprise linking a mouse leader sequence and V region sequence in the cloned cDNA to a sequence encoding the human antibody constant region already in an expression vector for mammalian cells. Alternatively, they comprise linking a mouse leader sequence and a V region sequence in the cloned cDNA to a sequence encoding the human antibody C region, and then linking it to an expression vector for mammalian cells.

Fragments of the human antibody C regions may be those of the H chain C region and L chain C region of any human antibody. For example, there can be mentioned cγ1, cγ2, cγ3, or cγ4 for those of the human H chain, and Cλ or Cκ for the L chain, respectively.

For the production of chimeric antibody, an expression vector containing DNA encoding a mouse H chain V region and a human H chain C region under the control of an expression regulatory region like an enhancer/promoter system, and a single expression vector (see, for example, WO 94/11523) containing DNA encoding a mouse L chain V region and a human L chain C region under the control of an expression regulatory region like an enhancer/promoter system is prepared. Then, the expression vector is used to co-transform a host cell such as a mammalian cell and the transformed cells are cultured in vitro or in vivo to produce chimeric antibody (see, for example, WO 91/16928). As the single vector, an IgG1κ-type antibody expression vector N5KG1(V) and an IqG4κ-type antibody expression vector N5KG4P may be used.

(i) Construction of Chimeric Antibody H Chain

An expression vector for a chimeric antibody H chain may be obtained by introducing cDNA encoding a mouse H chain V region into a suitable expression vector containing DNA encoding the H chain C region of a human antibody. As the H chain C region, there can be mentioned, for example, the Cγ1, Cγ2, Cγ3, or Cγ4 region.

As used herein, in order to introduce cDNA encoding a mouse H chain V region into an expression vector, a suitable nucleotide sequence may be introduced into said cDNA by the PCR method. For example, such a suitable nucleotide sequence may be introduced into an expression vector by performing PCR using PCR primers designed to have a recognized sequence of a suitable restriction enzyme at the 5'-end of said cDNA, and, for improved transcription efficiency, the Kozak consensus sequence (Kozak, M. et al., J. Mol. Biol., 196: 947-950, 1987) immediately prior to the initiation codon of said cDNA, and PCR primers designed to have a recognized sequence of a suitable restriction enzyme at the 3'-end of said cDNA.

After treating a cDNA encoding the mouse H chain V region thus constructed with a suitable restriction enzyme, it is inserted into the above expression vector and then a chimeric H chain expression vector containing DNA encoding the H chain C region (Cγ1 or Cγ4) is constructed.

(ii) Construction of an Expression Vector Containing cDNA Encoding the L Chain κ Chain of a Chimeric Antibody An expression vector for a chimeric antibody L chain may be obtained by introducing cDNA encoding a mouse L chain V region into a suitable expression vector containing DNA encoding the L chain C region of a human antibody. As the L chain C region, there can be mentioned, for example, the Cκ and Cλ region.

As used herein, in order to construct an expression vector containing cDNA encoding a mouse L chain V region, a suitable nucleotide sequence may be introduced into said cDNA by the PCR method. For example, such a suitable nucleotide sequence may be introduced into said cDNA by performing PCR using PCR primers designed to have a recognized sequence of a suitable restriction enzyme at the 5'-end of said cDNA, and, for improved transcription efficiency, the Kozak consensus sequence, and PCR primers designed to have a recognized sequence of a suitable restriction enzyme at the 3'-end of said cDNA.

After treating a cDNA encoding the mouse L chain V region thus constructed with a suitable restriction enzyme, it is inserted into the above expression vector and then a chimeric L chain expression vector containing DNA encoding the L chain C region (Cκ region) is constructed.

4. Preparation of Humanized Antibody (1) Homology Search of Human Antibody

In order to generate a humanized antibody in which the CDRs of a mouse monoclonal antibody is grafted onto a human antibody, there is preferably a high homology between the FRs of a mouse monoclonal antibody and the FRs of a human antibody. Thus, the H chain and L chain V regions of a mouse anti-human TF monoclonal antibody are compared to the V region of all known antibodies whose structure has been published using a Data Bank. At the same time, they are compared to the subgroups of human antibody (HSG: human subgroup) (Kabat, E. A. et al., US Dep. Health and Human Services, US Government Printing Offices, 1991) classified by Kabat et al. based on the length of the FR and amino acid homology.

Based on the HSG classification by Kabat et al., human H chain V regions can be grouped into HSGI to III; for example, the H chain V region of the mouse anti-human TF monoclonal antibody ATR-5 has a homology of 67.8% with the consensus sequence of HSGI. On the other hand, human L chain κ chain V regions can be grouped into HSGI to IV; for example, the L chain κ chain V region of the mouse anti-human TF monoclonal antibody ATR-5 has a homology of 72.3% with the consensus sequence of HSGI.

When a mouse antibody is humanized by a conventional technology, the amino acid sequence of some of the V region FRs of a mouse antibody supporting the CDR may be grafted onto the FR of a human V region, as desired, so that the CDR structure of a humanized V region may resemble more closely to that of the original mouse antibody. However, there are no fixed rules as to which amino acids of the V region FR of a mouse antibody to be grafted onto the V region FR of a human antibody. Accordingly, a lot of efforts are required to specify amino acids that are essential for retaining the CDR structure.

There is also a risk that a human antibody against the amino acid sequence grafted onto the human V region from the V region of a mouse antibody may be formed on part of the FR.

According to the present invention, in order to change all amino acid sequences except the CDR in the humanized antibody into amino acid sequences derived from human antibody, FRs of a human antibody having a high homology with the FR of mouse antibodies present on the database were searched, with one FR as a unit, for the four FRs (FR1-4) that are required to retain the three dimensional structure of CDR. The following is a result of the homology search with the database for each FR of the H chain V region and L chain V region of a monoclonal antibody ATR-5.

TABLE 1

| No. of FR | Accession No. | Homology with each FR of mouse antibody H chain V region (%) | SEQ ID NO: |
|---|---|---|---|
| H chain FR1 | L39130 | 53.0 | 110 |
| H chain FR2 | L39130 | 92.9 | 111 |
|  | P01742 | 71.4 | 112 |
|  | Z80844 | 78.6 | 113 |
| H chain FR3 | L39130 | 62.5 | 114 |
|  | Z34963 | 71.9 | 115 |
|  | P01825 | 53.1 | 116 |
|  | M62723 | 68.8 | 117 |
|  | Z80844 | 68.8 | 118 |
|  | L04345 | 65.6 | 119 |
|  | S78322 | 75.0 | 120 |
|  | Z26827 | 56.3 | 121 |
|  | U95239 | 65.6 | 122 |
|  | L03147 | 65.6 | 123 |
| H chain FR4 | L39130 | 90.9 | 124 |

TABLE 2

| No. of FR | Accession No. | Homology with each FR of mouse antibody L chain V region (%) | SEQ ID NO: |
|---|---|---|---|
| L chain FR1 | Z37332 | 78.3 | 125 |
| L chain FR2 | Z37332 | 80.0 | 126 |
|  | S65921 | 80.0 | 127 |
|  | X93625 | 80.0 | 128 |
| L chain FR3 | Z37332 | 71.9 | 129 |
|  | S68699 | 75.0 | 130 |
|  | P01607 | 71.9 | 131 |
| L chain FR4 | Z37332 | 90.0 | 132 |

(2) Design of DNA Encoding a Humanized Antibody V Region

The first step in the design of DNA encoding a humanized antibody V region is to select each FR of a human antibody V region that bases the design. In FR shuffling, a highly varied FR of human antibody V region needs to be selected for each FR.

For monoclonal antibody ATR-5, according to the present invention, three V region FRs of human antibody for FR2 and 10 for FR3 were selected based on the result of homology search between the H chain V region of all mouse antibodies and each FR for the H chain. For the L chain, three V region FRs of human antibody for FR2 and three for FR3 can be selected based on the result of the homology search between the L chain V region of mouse antibodies and each FR.

For both of the humanized H chain and L chain V regions, it is possible to select the L chain V regions, L39130 and Z37332, having a high homology with the H chain and L chain V region of the mouse antibody ATR-5, respectively. In order to enable easy FR shuffling in the generation of these humanized antibodies, it is possible to design suitable restriction enzyme recognition sites at suitable sites in each CDR and FR. By so doing, only one of the FRs can be easily replaced.

Examples of such sites include a recognition site of the restriction enzyme EcoT22I in the humanized H chain CDR1, a recognition site of the restriction enzyme BalI in CDR2, a recognition site of the restriction enzyme NcoI in CDR3 and a recognition site of the restriction enzyme XhoI in FR3, for example a recognition site of the restriction enzyme AflII in the humanized L chain CDR1, a recognition site of the restriction enzyme SpeI in CDR2, a recognition site of the restriction enzyme PstI in CDR3, and a recognition site of the restriction enzyme AccIII in FR3.

Based on version a thus designed, FR shuffling may be carried out for each FR to obtain a humanized antibody having the desired activity.

(3) Preparation of a Humanized Antibody V Region Fragment

The humanized antibody of the present invention is such that the FRs of the C region and the V region of said antibody are derived from a human antibody and the CDR of the V region is derived from a mouse antibody. V region fragments of the humanized antibody of the present invention may be generated by a method called CDR-grafting by the PCR method, if DNA fragments of the human antibody as a template are available. As used herein "CDR-grafting" is a method in which a DNA fragment encoding the CDR of a mouse antibody is generated, which is exchanged for the CDR of a human antibody as the template.

When DNA fragments of a human antibody as a template are not available, the nucleotide sequence registered in the database may be synthesized using a DNA synthesizer, and the humanized antibody V region can be generated using the PCR method. Furthermore, when the amino acid sequence is only registered in the database, the entire nucleotide sequence can be deduced based on the amino acid sequence based on the frequency of codon use of antibodies reported by Katat, E. A. et al. (US Dep. Health and Human Services, US Government Printing Offices, 1991). The nucleotide sequence may be synthesized using a DNA synthesizer, and the humanized antibody V region fragments can be generated using the PCR method.

(i) Construction of DNA and an Expression Vector Encoding the Humanized H Chain V Region According to the present invention, DNA encoding the humanized H chain V region can be constructed by obtaining the gene encoding the H chain V region of a human antibody to be used as a template for humanized antibody and then synthesizing the entire nucleotide sequence of DNA encoding the humanized H chain V region using a DNA synthesizer, followed by the PCR method. For example, L39130 having a high homology with the H chain V region of mouse anti-human TF monoclonal antibody ATR-5 can be generated as the humanized H chain V region version "a". In order to generate the humanized H chain V region version "a", for example 5 primers as set forth in SEQ ID NOs: 22-26 and 2 exogenous primers as set forth in SEQ ID NOs: 27 and 28 are used separately.

The CDR-grafting primers hR5Hv1S (SEQ ID NO: 22), hR5Hv2S (SEQ ID NO: 23), and hR5Hv4S (SEQ ID NO: 24) have a sense DNA sequence and the CDR-grafting primers hR5Hv3A (SEQ ID NO: 25) and hR5Hv5A (SEQ ID NO: 26) have an antisense DNA sequence, each having a 18-35 bp complementary sequence at the both ends of the primers hR5Hv1S is designed so as to have the Kozak consensus sequence (Kozak, M. et al., J. Mol. Biol. 196: 947-950, 1987)

and a SalI recognition site, and hR5Hv5A is designed so as to have a NheI recognition site. The exogenous primers hR5HvPrS (SEQ ID NO: 27) and hR5HvPrA (SEQ ID NO: 28) also have a homology with the CDR-grafting primers hR5Hv1S and hR5Hv5A.

Using the PCR method, five primers are assembled to synthesize a full-length cDNA, and after adding an exogenous primer thereto DNA is amplified. Assembling by the PCR method as used herein means that hR5Hv1S, hR5Hv2S, hR5Hv4S, hR5Hv3A, and hR5Hv5A are annealed by their complementary sequences and the DNA of the full-length humanized H chain V region is synthesized.

The human antibody H chain C region can be any human H chain C region, and for example the human H chain Cγ1, Cγ2, Cγ3, or Cγ4 can be mentioned.

The DNA of the humanized antibody H chain V region constructed as above can be linked to the DNA of any human antibody H chain C region, for example the human H chain C region Cγ1 or Cγ4. As described in the construction of a chimeric antibody H chain, after treating with a suitable restriction enzyme, it is linked to the DNA encoding a human H chain C region under the control of an expression regulatory region such as an enhancer/promoter system to generate an expression vector containing the DNA of the humanized H chain V region and human H chain C region.

(ii) Construction of DNA and an Expression Vector Encoding the Humanized L Chain V Region As in the case of DNA encoding the H chain V region, according to the present invention, DNA encoding the humanized L chain V region can be constructed by obtaining a gene of the L chain V region of a human antibody to be used as a template and then synthesizing the entire nucleotide sequence of the DNA encoding the humanized L chain V region using a DNA synthesizer, followed by the PCR method. For example, Z37332 having a high homology with the L chain V region of the mouse anti-human TF monoclonal antibody ATR-5 can be generated as the humanized L chain V region version "a".

In order to generate the humanized L chain V region version "a", the CDR-grafting primers h5Lv1S (SEQ ID NO: 85) and h5Lv4S (SEQ ID NO: 86) have a sense DNA sequence and the CDR-grafting primers h5Lv2A (SEQ ID NO: 87), h5Lv3A (SEQ ID NO: 88), and h5Lv5A (SEQ ID NO: 89) have an antisense DNA sequence, each having a 20 bp complementary sequence at the both ends of the primer. The primer h5Lv1S is designed so as to have the Kozak consensus sequence (Kozak, M. et al., J. Mol. Biol. 196: 947-950, 1987) and a recognition site of the restriction enzyme BglII, and h5Lv5A is also designed so as to have a recognition site of the restriction enzyme SplI. The exogenous primers. h5LvS (SEQ ID NO: 90) and h5LvA (SEQ ID NO: 91) also have a homology with the CDR-grafting primers h5Lv1S and h5Lv5A.

As for the humanized H chain V region, using the PCR method, five primers are assembled to synthesize a full-length cDNA, and after adding an exogenous primer thereto the DNA can be amplified.

The human antibody L chain C region can be any human L chain C region, and for example the human L chain Cλ an Cκ can be mentioned.

The DNA of the humanized antibody L chain V region constructed as above can be linked to the DNA of any human L chain C region, for example one derived from the human L chain Cκ or Cλ region. After treating with a suitable restriction enzyme, it is linked to the DNA encoding a human L chain C region under the control of an expression regulatory region such as an enhancer/promoter system to generate an expression vector containing DNA encoding the humanized L chain V region and human L chain κ chain C region.

Even if a V region fragment of a humanized antibody is generated as mentioned above, it is not always clear whether said V region fragment has an activity as antibody (i.e. activity of binding to the antigen, of neutralizing the antigen, etc.). Thus, it is necessary to investigate the presence of the activity by combining it with a humanized H chain and express it in an animal cell such as COS-7.

(iii) FR Shuffling of the H Chain and L Chain V Region of Humanized Antibody

The present inventors have performed transient expression of a humanized antibody containing a humanized H chain and L chain V region in an animal cell such as COS-7 to investigate the antigen binding activity and neutralizing activity, and have found that the antibody has the antigen binding and neutralizing activity but that the activity is not adequate compared to chimeric antibody.

The present inventors can resolve this problem by sequentially shuffling each FR of the humanized H chain and L chain V region. The antibody used in the shuffling of FR can be selected from the existing databases. The FR of the selected human antibody can be synthesized based on the nucleotide sequence demonstrated in the databases using a DNA synthesizer. At this time, as mentioned above, by adding the designed restriction enzyme recognition sequence to CDR or FR, it can be easily shuffled with the FR of H chain and L chain V region of the humanized antibody generated above. By investigating the activity of the humanized antibody thus generated, a humanized antibody can be obtained having the antigen binding and neutralizing activity.

For example, the humanized antibody V region H chain FR3 can be shuffled to the FR3 derived from human antibody Z34963 (GenbBank, Borrentzen M. et al., Proc. Natl. Acad. Sci. USA, 91: 12917-12921, 1994).

The FR-shuffling primer F3RFFS (SEQ ID NO: 35) and F3RFBS (SEQ ID NO: 36) have a sense DNA sequence, and F3RFFA (SEQ ID NO: 37) and F3RFBA (SEQ ID NO: 38) have an antisense DNA sequence. The FR-shuffling primers F3RFFS, F3RFBS, F3RFFA, and F3RFBA can be synthesized using a DNA synthesizer.

F3RFFS and F3RFFA, and F3RFBS and F3RFBA were annealed, which were digested with BalI and XhoI, and NcoI and XhoI, respectively. By introducing them into the plasmid hATR5Hva/CVIDEC (BalI/NcoI) prepared by digesting with BalI and NcoI, and confirming the nucleotide sequence thereof, a plasmid having the correct sequence can be obtained. The plasmid thus obtained containing the humanized antibody H chain was designated as hATR5Hvb/CVIDEC, and the humanized H chain contained in the plasmid hATR5Hvb/CVIDEC was designated as version "b". The nucleotide sequence and the corresponding amino acid sequence are shown in SEQ ID NO: 39, and the amino acid sequence of version "b" is shown in SEQ ID NO: 40.

In a similar manner, the FR derived from the V region H chain and L chain of another human antibody selected from the database can also be shuffled with the FR of the V region H chain and L chain of a humanized antibody.

In order to select a more preferable human antibody for shuffling the FR of the H chain V region and L chain V region of a humanized antibody, the following may be carried out.

Thus, a combination of the humanized antibody H chain version "b" and a chimeric antibody L chain has a neutralizing activity equal to that of a chimeric antibody or a mouse antibody. However, the combination of the humanized antibody H chain version "b" and the humanized antibody L chain version "a" has a neutralizing activity lower than that of a chimeric antibody or a mouse antibody.

In such cases, in order to select a human antibody so as to be a candidate for shuffling FR, homology search, for example, for the FR3 (accession No. Z34963: SEQ ID NO: 115) of the humanized antibody H chain version "b" can be carried out and a human antibody having a high homology with this sequence can be obtained. For example, as the H chain V region FR3 of the human antibody thus selected, U95239 (SEQ ID NO: 122) and L03147 (SEQ ID NO: 123) can be mentioned.

The amino acid sequences of the humanized antibody V region H chain thus generated is shown in Table 3 and 4, and the amino acid sequence of the V region L chain of the humanized antibody is shown in Table 5. The Table 3-4 amino acid sequences correspond to residues 1 to 117 of SEQ ID NO: 30, residues 1 to 117 of SEQ ID NO: 40, residues 1 to 117 of SEQ ID NO: 42, residues 1 to 117 of SEQ ID NO: 50, residues 1 to 117 of SEQ ID NO: 52, residues 1 to 117 of SEQ ID NO: 58, residues 1 to 117 of SEQ ID NO: 60, residues 1 to 117 of SEQ ID NO: 64, residues 1 to 117 of SEQ ID NO: 70, residues 1 to 117 of SEQ ID NO: 72, residues 1 to 117 of SEQ ID NO: 76, residues 1 to 117 of SEQ ID NO: 78, residues 1 to 117 of SEQ ID NO: 82, and residues 1 to 117 of SEQ ID NO: 84, respectively, in order of appearance. The Table 5 amino acid sequences are shown in SEQ ID NOS 93, 99, 101, 107 and 109, respectively, in order of appearance.

TABLE 3

Amino acid sequences of H chain V region

| | FR1 | | | CDR1 | FR2 | CDR2 |
|---|---|---|---|---|---|---|
| | 1 | 2 | 3 | 4 | 5 | 6 |
| | 123456789012345678901234567890 | | | 12345 | 67890123456789 | 012A3456789012345 |
| L39130(a) | QVQLLESGAVLARPGTSVKISCKASGFNIK | | | DYYMH | WVKQRPGQGLEWIG | GNDPANGHSMYDPKFQC |
| Z34963(b) | ------------------------------ | | | ----- | -------------- | ----------------- |
| M30885(c) | ------------------------------ | | | ----- | -------------- | ----------------- |
| M62723(d) | ------------------------------ | | | ----- | -------------- | ----------------- |
| Z80844(e) | ------------------------------ | | | ----- | -------------- | ----------------- |
| L04345(f) | ------------------------------ | | | ----- | -------------- | ----------------- |
| S78322(g) | ------------------------------ | | | ----- | -------------- | ----------------- |
| Z26827(h) | ------------------------------ | | | ----- | -------------- | ----------------- |
| U95239(i) | ------------------------------ | | | ----- | -------------- | ----------------- |
| L03147(j) | ------------------------------ | | | ----- | -------------- | ----------------- |
| P01742(b1) | ------------------------------ | | | ----- | --R-A-------M- | ----------------- |
| P01742(d1) | ------------------------------ | | | ----- | --R-A-------M- | ----------------- |
| Z80844(b3) | ------------------------------ | | | ----- | --R-A--------- | ----------------- |
| Z80844(d3) | ------------------------------ | | | ----- | --R-A--------- | ----------------- |

TABLE 4

Amino acid sequences of H chain V region (continued)

| | FR3 | | | CDR3 | FR4 |
|---|---|---|---|---|---|
| | 7 | 8 | 9 | 10 | 11 |
| | 67890123456789012ABC345678901234 | | | 56789012 | 34567890123 |
| L39130(a) | RAKLTAATSASIAYLEFSSLTNEDSAVYYCAR | | | DSGYAMDY | WGQGTLVTVSS |
| Z34963(b) | -VTI--D--TNT--M-L---RS--T-I----- | | | -------- | ----------- |
| M30885(c) | -VTMLVD--KNQFS-RL--V-AA-T------- | | | -------- | ----------- |
| M62723(d) | -VTI--DE-T-T--M-L---RS------F--- | | | -------- | ----------- |
| Z80844(e) | -VSI--DE-TK---M-LN--RS--T---F--- | | | -------- | ----------- |

TABLE 4-continued

Amino acid sequences of H chain V region (continued)

| | |
|---|---|
| L04345(f) | -VTI--DT-T-T--M-LR--RSD-T------- -------- ---------- |
| S78322(g) | K-T---DE-S-T--MQL---RS------S--- -------- ---------- |
| Z26827(h) | -VTMS-DK-S-A---QWT--KAS-T-I-F--- -------- ---------- |
| U95239(i) | -VTI--D--T-TVFM-L---RS--T------- -------- ---------- |
| L03147(j) | -VTF--D---NT--M-LR--RSA-T------- -------- ---------- |
| P01742(b1) | -VTI--D--TNT--M-L---RS--T-I----- -------- ---------- |
| P01742(d1) | -VTI--DE-T-T--M-L---RS------F---- -------- ---------- |
| Z80844(b3) | -VTI--D--TNT--M-L---RS--T-I----- -------- ---------- |
| Z80844(d3) | -VTI--DE-T-T--M-L---RS------F--- -------- ---------- |

TABLE 5

Amino acid sequences of L chain V region

| | FR1 | | CDR1 | FR2 | CDR2 |
|---|---|---|---|---|---|
| | 1 | 2 | 3 | 4 | 5 |
| | 12345678901234567890123 | | 45678901234 | 567890123456789 | 0123456 |
| Z37332(a) | DIQMTQSPSSLSASVGDRVTITC | | KASQDIKSFLS | WYQQKPGKAPKLLIY | YATSLAD |
| S68699(b) | ----------------------- | | ----------- | --------------- | ------- |
| P01607(c) | ----------------------- | | ----------- | --------------- | ------- |
| S65921(b1) | ----------------------- | | ----------- | -F------S--T--- | ------- |
| X93625(b2) | ----------------------- | | ----------- | ------E----S--- | ------- |

| | FR3 | | | CDR3 | FR4 |
|---|---|---|---|---|---|
| | 6 | 7 | 8 | 9 | 10 |
| | 78901234567890123456789012345678 | | | 901234567 | 8901234567 |
| Z37332(a) | GVPSRFSGSGSGTDFTLTISSLQPEDFATYYC | | | LQHGESPYT | FGGGTKVEIK |
| S68699(b) | --------------Y----------------- | | | --------- | ---------- |
| P01607(c) | --------------Y-----------I----- | | | --------- | ---------- |
| S65921(b1) | --------------Y----------------- | | | --------- | ---------- |
| X93625(b2) | --------------Y----------------- | | | --------- | ---------- |

Each version of the H chain and L chain V region of the humanized antibody thus constructed can be linked to the DNA of any human H chain C region or L chain C region, for example human H chain Cγ4 and human L chain Cκ regions, respectively. After treating with a suitable restriction enzyme, it is linked to a DNA encoding the human H chain Cγ4 and human L chain Cκ region under the control of an expression regulatory region such as an enhancer/promoter system, and an expression vector containing a DNA encoding each version of the humanized H chain and L chain V region and a DNA encoding the human H chain Cγ4 and human L chain Cκ region is generated.

A DNA encoding the humanized antibody H chain V region and the human H chain C region constructed as above and a DNA encoding the humanized L chain V region and the human L chain C region are introduced into a single vector (see, for example, WO 94/11523), and then said vector is used to transform a host cell. Then, the transformed host can be cultured in vivo or in vitro to produce the desired humanized antibody.

5. Production of Chimeric Antibody and Humanized Antibody

In order to produce chimeric antibody or humanized antibody, a DNA encoding a H chain V region and a H chain C region and a DNA encoding an L chain V region and an L chain C region can be linked to a single vector, which is transformed into a suitable host cell to produce antibody. Thus, for the expression of chimeric antibody, a DNA encoding a mouse leader sequence in the cloned cDNA and a mouse H chain V region and human H chain C region and a DNA encoding a mouse leader sequence and mouse L chain V region and human H chain C region are introduced into a single expression vector (see, for example, WO 94/11523) under the control of an expression regulatory region such as an enhancer/promoter system.

For the expression of humanized antibody, a DNAs encoding a humanized H chain V region and a human H chain C region and a DNAs encoding a humanized L chain V region and a human H chain C region are introduced into a single expression vector (see, for example, WO 94/11523) under the control of an expression regulatory region such as an enhancer/promoter system. These vectors are used to transform a host cells. Then, the transformed host cell can be cultured in vivo or in vitro, and thereby the chimeric antibody or the humanized antibody can be produced.

Two expression vectors can also be generated, each containing a H chain V region and an L chain V region. Thus, for chimeric antibody an expression vector containing a DNA encoding a mouse H chain V region and a human H chain C region under the control of an enhancer/promoter system and an expression vector containing a DNA encoding a mouse L chain V region and a human L chain C region under the control of an enhancer/promoter system are generated, and for humanized antibody an expression vector containing a DNA encoding a humanized H chain V region and a human H chain C region under the control of an enhancer/promoter system and an expression vector containing a DNA encoding a humanized L chain V region and a human L chain C region under the control of an enhancer/promoter system are generated.

Alternatively, for the chimeric antibody an expression vector is generated that contains a DNA encoding a mouse H chain V region and a human H chain C region and a DNA encoding a mouse L chain V region and a human L chain C region under the control of an expression regulatory region such as an enhancer/promoter system, and for the humanized antibody an expression vector is generated that contains a DNA encoding a humanized H chain V region and a human H chain C region and a DNA encoding a humanized L chain V region and a human L chain C region under the control of an expression regulatory region such as an enhancer/promoter system.

Then, these expression vectors are used to co-transform host cells such as mammalian cells, and the transformed cells are culture in vitro or in vivo to produce a chimeric antibody or a humanized antibody (see, for example, WO 91/16928).

As hereinabove stated, a transformant transformed with a gene encoding the desired chimeric antibody or humanized antibody is cultured, and the produced chimeric antibody or humanized antibody can be separated from the inside or outside of the cell and purified to homogeneity.

The isolation and/or purification of the chimeric antibody or humanized antibody, or the desired protein of the present invention, may be carried out using a Protein A sepharose column. Other methods include, but not limited to, those separation and/or purification methods used for common proteins. By way of example, chimeric antibody or humanized antibody can be isolated and/or purified by combining, as appropriate, various chromatographic methods, ultracentrifugation, salting out, dialysis, and the like.

In order to produce the chimeric antibody or humanized antibody of the present invention against human TF, any expression system may be used. For example, when eukaryotic cells are used, there can be used animal cells (for example, established mammalian cell lines), fungal cells or yeast cells, and when prokaryotic cells are used bacterial cells (such as *Escherichia coli* cells) may be used. Preferably, the chimeric antibody or humanized antibody of the present invention is expressed in mammalian cells such as COS cells or CHO cells.

In these cases, useful common promoters may be used for expression in mammalian cells. For example, human cytomegalovirus immediate early (HCMV) promoter is preferably used. Examples of expression vectors that contain the HCMV promoter include HCMV-VH-HCγ1, HCMV-VL-HCκ, and the like, and those that are derived from pSV2neo (WO 92-19759).

Other promoters for gene expression in mammalian cells that can be used in the present invention include viral promoters such as promoters of retrovirus, polyoma virus, adenovirus, and simian virus 40 (SV40), and promoters derived from mammalian cells such as human polypeptide chain elongation factor 1α (HEF1α). For example, expression may be readily accomplished by the method of Mulligan et al. (Nature (1979) 277: 108) when the SV40 promoter is used, or by the method of Mizushima et al. (Nucleic Acids Res. (1990) 18: 5322) when the HEF1α promoter is used.

As the origin of replication, there can be used those derived from SV40, polyoma virus, adenovirus, bovine papilloma virus (BPV) and the like. Furthermore, for the amplification of gene copy number in the host cell system, expression vectors can include as selectable markers the phosphotransferase APH (3') II or I (neo) gene, the thymidine kinase (TK) gene, the *E. coli* xanthine guaninephosphoribosyl transferase (Ecogpt) gene, the dihydrofolate reductase (dhfr) gene and the like.

6. Evaluation of the Activity of Binding to the Antigen and Neutralizing Activity of Chimeric antibody and Humanized Antibody (1) Measurement of Antibody Concentration by ELISA Concentration of the purified antibody obtained may be measured by ELISA.

ELISA plates for measurement of antibody concentration may be prepared as follows: Each well of a 96-well ELISA plate (for example, Maxisorp, NUNC) is immobilized with 100 µl of goat anti-human IgGγ antibody (BioSource) prepared to a concentration of 1 µg/ml.

After blocking with 200 µl of the dilution buffer (hereinafter referred to as DB; 50 mM Tris-HCl, 1 mM $MgCl_2$, 0.15 M NaCl, 0.05% Tween 20, 0.02% $NaN_3$, 1% bovine serum albumin (BSA), pH 7.2), the culture supernatants of the COS-7 cells or CHO cells in which the chimeric antibody or humanized antibody were expressed, or the purified chimeric antibody or humanized antibodies are serially diluted, and then are added to each well. Then 100 µl of alkaline phosphatase-conjugated goat anti-human IgG antibody is added, 100 µl of 1 mg/ml substrate solution (Sigma104, p-nitrophenyl phosphate, SIGMA) is added, and then the absorbance at 405/655 nm is measured using the Microplate Reader (Bio Rad). As the standard for the measurement of concentration, human IgG4κ (The Binding Site) may be used.

(2) Measurement of the Activity of Binding to the Antigen

Cell ELISA plates for measurement of the activity of binding to the antigen are prepared as follows: Human bladder carcinoma cells J82 (ATCC HTB-1) are inoculated into 60 wells of a 96-well cell culture plate at a cell count of $1 \times 10^5$ cells. This is cultured (RPMI1640 medium containing 10% fetal bovine serum (GIBCO)) for one day in a $CO_2$ incubator to allow the cells to be attached thereto. After discarding the culture liquid, each well is washed twice with 300 µl PBS. 100 µl of PBS containing 4% paraformaldehyde (hereinafter referred to as PFA/PBS) is added to each well, and placed on ice for 10 minutes to immobilize the cells.

PFA/PBS is discarded, and each well is washed twice with 300 µl of PBS, and then blocked with 250 µl of DB. 100 µl of the culture supernatants containing a chimeric antibody or a humanized antibody, or a purified chimeric antibody or humanized antibodies are serially diluted, and then are added to each well, and incubated at room temperature for 2 hours. After washing with rinse buffer (hereinafter referred to as RB PBS containing 0.05% Tween 20), 100 µl of alkaline phosphatase-conjugated goat anti-human IgGγ antibody (BioSource) diluted 1000-fold with DB is added. After incubating at room temperature for 1 hour and washing with RB, the substrate solution is added, and then absorbance at 405/655 nm is measured using the Microplate Reader (Bio-Rad).

(3) Measurement of Neutralizing Activity

The neutralizing activity of mouse antibody, chimeric antibody, and humanized antibodies can be measured with the inhibiting activity against Factor Xa production by human placenta-derived thromboplastin, Thromborel S (Boehringer A G), as an index. Thus, 60 µl of the buffer (TBS containing 5 mM $CaCl_2$ and 0.1% BSA) is added to 10 µl of 1.25 mg/ml Thromborel S and 10 µl of an appropriately diluted antibody, which is then incubated in a 96-well plate at room temperature for 1 hour.

Ten µl each of 3.245 µg/ml human Factor X (Celsus Laboratories) and 82.5 ng/ml human Factor VIIa (Enzyme Research) are added thereto, and then are incubated at room temperature for another 1 hour. After 10 µl of 0.5 M EDTA was added to stop the reaction, 50 µl of the chromogenic substrate solution is added and the absorbance at 405/655 nm is determined. After reacting at room temperature for 1 hour, the absorbance at 405/655 nm is determined again. The neutralizing activity may be determined by calculating the residual activity (%) from each change in absorbance with the absorbance change at no antibody addition as a 100% activity.

The chromogenic substrate solution is prepared by dissolving the Testzyme chromogenic substrate S-2222 (Chromogenix) according to the attached instructions, diluting 2-fold with purified water and then mixing with a polybrene solution (0.6 mg/ml hexadimethylene bromide, SIGMA) at 1:1.

7. Kinetic Analysis in Interaction of Humanized Antibody and Soluble TF

The kinetic parameters, i.e. dissociation constants (KD), dissociation rate constants (kdiss), and binding rate constants (kass), of the anti-TF antibody of the present invention can be determined by BIACORE.

Recombinant Protein G is immobilized on a sensor chip, to which the antibody is coupled, and purified recombinant TF (a soluble TF 1-219 in which the FLAG peptide was tagged) (hereinafter referred to as a soluble TF) is used as the antigen while soluble TF prepared at various concentrations are used as analytes. From the sensorgram obtained, kinetics parameters (dissociation rate constant kdiss, and binding rate constant kass) are calculated, from which the dissociation constant can be determined. For kinetic analysis, see, for example, "Kinetic analysis of monoclonal antibody-antigen interactions with a new biosensor based analytical system" (Karlsson, R. et al., (1991) J. Immunol. Methods 145: 229-240).

The anti-TF antibody of the present invention is preferred to have a smaller value of dissociation constants (KD) since it will have a higher neutralizing activity. In the anti-TF antibody of the present invention, KD values are preferably not greater than $2.30\times10^{-8}$ [1/M], more preferably not greater than $2.30\times10^{-9}$ [1/M], and most preferably not greater than $1.17\times10^{-9}$ [1/M].

Furthermore, KD values are determined from two parameters, the dissociation rate constant (kdiss) and the binding rate constant (kass) (KD=kdiss/kass). Thus, it is evident that when a kdiss is small and a kass is great, then a KD value becomes small.

Specifically, in the case of the anti-TF antibody of the present invention, kdiss values may be not greater than $9.52\times10^{-3}$ [1/sec]. Preferably kdiss values are not greater than $9.52\times10^{-4}$ [1/sec], most preferably not greater than $6.35\times10^{-4}$ [1/sec].

On the other hand, kass values may be not smaller than $4.15\times10^{4}$ [1/M·sec]. Preferably, kass values are not smaller than $4.15\times10^{5}$ [1/M·sec], and most preferably not smaller than $4.65\times10^{5}$ [1/M·sec].

Furthermore, preferably anti-TF antibodies has a kdiss value of not greater than $9.52\times10^{-3}$ [1/sec] and a kass value of not smaller than $4.15\times10^{4}$ [1/M·sec].

More specifically, for the anti-TF antibody of the present invention, KD values are in the range of $1.09\times10^{-10}$-$2.30\times10^{-8}$ [1/M], preferably $1.09\times10^{-9}$-$2.30\times10^{-9}$ [1/M], and most preferably $1.09\times10^{-9}$-$1.39\times10^{-9}$ [1/M].

Furthermore, kdiss values are in the range of $5.06\times10^{-4}$-$9.52\times10^{-3}$ [1/sec], preferably $5.06\times10^{-4}$-$9.52\times10^{-4}$ [1/sec], and most preferably $5.06\times10^{-4}$-$6.49\times10^{-4}$ [1/sec].

And, kass values are in the range of $4.15\times10^{4}$-$5.44\times10^{5}$ [1/M·sec], preferably $4.15\times10^{5}$-$5.44\times10^{5}$ [1/M·sec], and most preferably $4.65\times10^{5}$-$5.44\times10^{5}$ [1/M·sec].

Although these KD values, kdiss values, and kass values can be obtained by, in addition to BIACORE, Scatchard analysis, and the like, it is preferred to use BIACORE.

8. Measurement of the Reactivity of Humanized Antibody to Human TF

The dot-blot hybridization method can be used to investigate the reactivity of the non-denatured TF, denatured TF under non-reduced condition, and denatured TF under reduced condition.

TF may be one that was purified from human tissue, or was expressed in mammalian cells such as CHO cells and purified, and may used for investigation. As the denaturing agent, guanidine hydrochloride or SDS etc. may be used in stead of urea. As the reducing agent, a SH reducing agent such as 2-mercaptoethanol can be used in stead of DTT. For detection of humanized antibody, anti-human IgG antibody labeled with various substances may be used. As used herein, labeling agents may be radioisotopes, biotin, fluorogenic substances such as FITC, enzymes such as peroxidase and alkaline phosphatase, and the like. The anti-TF antibody of the present invention react to any of non-denatured TF, denatured TF under non-reduced condition, and denatured TF under reduced condition.

9. Pharmaceutical Compositions and Therapeutic Agents for DIC Comprising a Humanized Antibody as an Active Ingredient In order to confirm the therapeutic effect of humanized antibody on human TF, humanized anti-human TF antibody is administered to an animal having a high DIC symptom, and then indices of DIC are measured to confirm the therapeutic effects.

Antibody as used herein is a humanized antibody to human TF. The antibody neutralizes the activity of human TF by binding to human TF, and there can be mentioned preferably a humanized ATR5 antibody. The method of generating humanized ATR5 antibody is described in Examples.

Antibody as used herein can be purified to a high purity by combining common purification methods such as salting out, gel filtration method such as HPLC, affinity chromatography using Protein A column, and the like. The antibody thus purified can be confirmed to recognize human TF with a high precision using common immunological means such as radioimmunoassay (RIA), enzymeimmunoassay (EIA, ELISA), or a immunofluorescent antibody method (Immunofluorescence Analysis) and the like.

Pharmaceutical compositions or therapeutic agents for DIC of the present invention comprising as an active ingredient the humanized antibody against TF may be administered non-perorally either systemically or locally. For example, the method of administration can be selected from intravenous injection such as drip infusion, intramuscular injection, intraperitoneal injection, and subcutaneous injection, and can be selected, as appropriate, based on the age and the conditions of the patient. The effective dosage is chosen from the range of 0.01 mg to 1000 mg per kg of body weight per administration. Alternatively, the dosage of 10 mg/body, preferably 1 to 1000 mg/body per patient may be chosen.

Pharmaceutical compositions and therapeutic agents for DIC of the present invention containing a humanized antibody against human TF as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

Effects of the Invention

According to the present invention, there is provided a chimeric antibody and a humanized antibody against human TF, and a process of generating a humanized antibody. These antibodies are useful as therapeutic agents because of their low antigenicity.

EXAMPLES

The present invention will now be explained in further details with reference to the following Examples.

Example 1

Cloning of DNA Encoding the V Region of a Mouse Monoclonal Antibody Against Human TF (1) Preparation of mRNA mRNA was prepared from hybridomas ATR-2, ATR-3, ATR4, ATR-5 (IgG1κ), ATR-7, and ATR-8 (IgG2aκ) using the QuickPrep mRNA Purification Kit (Pharmacia Biotech). Each hybridoma cell was completely homogenized in the extraction buffer according to instructions attached to the kit, and then mRNA was purified by the oligo (dT)-cellulose spun column, followed by ethanol precipitation. The mRNA precipitate was dissolved in the elution buffer.

(2) Preparation and Amplification of cDNA of the Gene Encoding a Mouse Antibody V Region (i) Cloning of H Chain V Region cDNA The cloning of the gene encoding the H chain V region of a mouse monoclonal antibody against human TF was carried out using the 5'-RACE method (Frohman, M. A. et al., Proc. Natl. Acad. Sci. USA 85: 8998-9002, 1988; Belyavsky, A. et al., Nucleic Acids Res. 17: 2919-2932, 1989). For the 5'-RACE method, the Marathon cDNA Amplification Kit (CLONTECH) was used and the procedure carried out according to the instructions attached to the kit.

Using about 1 μg of mRNA prepared as above as a template, the cDNA synthesis primer attached to the kit was added, which was reacted with a reverse transcriptase at 42° C. for 60 minutes to effect reverse transcription to cDNA. This was reacted with DNA polymerase I, DNA ligase, and RNaseH at 16° C. for 1.5 hour, and with T4 DNA polymerase at 16° C. for 45 minutes thereby to synthesize a double stranded cDNA. The double stranded cDNA was extracted with phenol and chloroform, and recovered by ethanol precipitation.

By overnight reaction with T4 DNA ligase at 16° C., a cDNA adapter was ligated to both ends of the double stranded cDNA. The reaction mixture was diluted 50-fold with a 10 mM Tricine-KOH (pH 8.5) containing 0.1 mM EDTA. Using this as a template, the gene encoding the H chain V region was amplified by PCR. The adapter primer 1 attached to the kit was used for the 5'-end primer, and for the 3'-end primer the MHC-G1 primer (SEQ ID NO: 1) (ATR-2, ATR-3, ATR-4, and ATR-5) or the MHC-G2a primer (SEQ ID NO: 2) (ATR-7 and ATR-8) (S. T. Jones, et al., Biotechnology, 9: 88-89, 1991) were used.

PCR solutions for the ATR-2, 3, 4, and 5 antibody H chain V region contained, in 100 μl, 120 mM Tris-HCl (pH 8.0), 10 mM KCl, 6 mM $(NH_4)_2SO_4$, 0.1% Triton X-100, 0.001% BSA, 0.2 mM dNTPs (dATP, dGTP, dCTP, dTTP), 1 mM $MgCl_2$, 2.5 units of KOD DNA polymerase (Toyo Boseki), 30-50 pmole of adapter primer 1, as well as MHC-G1 primer, and 1-5 μl of a reaction mixture of cDNA to which the cDNA adapter was ligated.

All PCRs were carried out using the DNA Thermal Cycler 480 (Perkin-Elmer), and the PCR was performed for thirty cycles at a temperature cycle of 94° C. for 30 seconds, 55° C. for 30 seconds, and 74° C. for 1 minute.

(ii) Cloning of L Chain V Region cDNA

The cloning of the gene encoding the L chain V region of a mouse monoclonal antibody against human TF was carried out using the 5'-RACE method (Frohman, M. A. et al., Proc. Natl. Acad. Sci. USA 85: 8998-9002, 1988; Belyavsky, A. et al., Nucleic Acids Res. 17: 2919-2932, 1989). For the 5'-RACE method, the Marathon cDNA Amplification Kit (CLONTECH) was used and carried out according to the instructions attached to the kit. Using about 1 μg of mRNA prepared as above as a template, the cDNA synthesis primer was added, which was reacted with a reverse transcriptase at 42° C. for 60 minutes to effect reverse transcription to cDNA. This was reacted with DNA polymerase I, DNA ligase, and RNaseH at 16° C. for 1.5 hour, and with T4 DNA polymerase at 16° C. for 45 minutes thereby to synthesize a double stranded cDNA. The double stranded cDNA was extracted with phenol and chloroform, and recovered by ethanol precipitation. By overnight reaction with T4 DNA ligase at 16° C., a cDNA adapter was ligated to both ends of the double stranded cDNA. The reaction mixture was diluted 50-fold with a 10 mM Tricine-KOH (pH 8.5) containing 0.1 mM EDTA. Using this as a template, the gene encoding the L chain V region was amplified by PCR. The adapter primer 1 was used for the 5'-end primer, and for the 3'-end primer the MKC primer (SEQ ID NO: 3) (S. T. Jones, et al., Biotechnology, 9: 88-89, 1991) was used.

PCR solutions contained, in 100 µl, 120 mM Tris-HCl (pH 8.0), 10 mM KCl, 6 mM $(NH_4)_2SO_4$, 0.1% Triton X-100, 0.001% BSA, 0.2 mM dNTPs (dATP, dGTP, dCTP, dTTP), 1 mM $MgCl_2$, 2.5 units of KOD DNA polymerase (Toyo Boseki), 30-50 pmole of adapter primer 1, as well as MKC primer, and 1 µl of a reaction mixture of cDNA to which the cDNA adapter was ligated.

All PCRs were carried out using the DNA Thermal Cycler 480 (Perkin-Elmer), and the PCR was performed for thirty cycles at a temperature cycle of 94° C. for 30 seconds, 55° C. for 30 seconds, and 74° C. for 1 minute.

(3) Purification and Fragmentation of PCR Products

The above PCR reaction mixture was extracted with phenol and chloroform, and the amplified DNA fragments were recovered by ethanol precipitation. DNA fragments were digested with the restriction enzyme XmaI (New England Biolabs) at 37° C. for 1 hour. The XmaI-digestion mixture was separated by agarose gel electrophoresis using 2%-3% NuSieve GTG agarose (FMC BioProducts), and the agarose strips containing about 500 bp long DNA fragments as the H chain V region and about 500 bp Long DNA fragments as the L chain V region were excised. The agarose strips were extracted with phenol and chloroform, DNA fragments were precipitated with ethanol, which were then dissolved in 10 µl of 10 mM Tris-HCl (pH 8.0) containing 1 mM EDTA (hereinafter referred to as TE).

The xmaI-digested DNA fragments prepared as above containing a genes encoding a mouse H chain V region and L chain V region and the pUC19 plasmid vector prepared by digesting with XmaI were ligated using the DNA ligation kit ver. 2 (Takara Shuzo) by reacting at 16° C. for 1 hour according to the instructions attached to the kit.

The ligation mixture was added to 100 µl of *E. coli* JM109 competent cells (Nippongene) and was incubated for 30 minutes on ice and for 1 minute at 42° C.

Then, 300 µl of the Hi-Competence Broth (Nippongene) was added thereto, incubated at 37° C. for 1 hour. Then, *Escherichia coli* was plated on a LB agar medium (Molecular Cloning: A Laboratory Manual, Sambrook, et al., Cold Spring Harbor Laboratory Press, 1989) containing 100 µg/ml ampicillin (hereinafter referred to as LBA agar medium), and incubated overnight at 37° C. to obtain an *E. coli* transformant.

The transformant was cultured overnight in 3 ml or 4 ml of a LB medium containing 50 µg/ml ampicillin (hereinafter referred to as LBA medium) at 37° C., and from the cell fractions, plasmid DNA was prepared using the QIAprep Spin Plasmid Kit (QIAGEN), and then the nucleotide sequence was determined.

(4) Determination of the Nucleotide Sequence of the Gene Encoding a Mouse Antibody V Region The nucleotide sequence of the cDNA coding region in the above plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) (SEQ ID NO: 4) and M13 Primer RV (Takara Shuzo) (SEQ ID NO: 5) were used, and the sequence was determined by confirming the nucleotide sequence in both directions.

Thus obtained plasmids containing the gene encoding the mouse H chain V region derived from the hybridomas ATR-2, ATR-3, ATR-4, ATR-5, ATR-7, and ATR-8 were designated as ATR-xHv/pUC19 (x=2, 3, 4, 5, 7, or 8), and the thus obtained plasmids containing the gene encoding a mouse L chain V region derived from the hybridomas ATR-2, ATR-3, ATR-4, ATR-5, ATR-7, and ATR-8 were designated as ATR-xLv/pUC19 (x=2, 3, 4, 5, 7, or 8). The nucleotide sequences of the genes encoding the H chain V region of each mouse antibody contained in the plasmid ATR-xHv/pUC19 (x=2, 3, 4, 5, 7, or 8) (including the corresponding amino acid sequences) is shown in SEQ ID NO: 6 to 11, respectively, and the nucleotide sequences of the genes encoding the L chain V region of each mouse antibody contained in the plasmid ATR-xLv/pUC19 (x=2, 3, 4, 5, 7, or 8) (including the corresponding amino acid sequences) is shown in SEQ ID NO: 12 to 17, respectively.

Example 2

Construction of Chimeric Antibody

A chimeric ATR-5 antibody was generated in which the mouse ATR-5 antibody V region was ligated to the human antibody C region. A chimeric antibody expression vector was constructed by ligating the gene encoding the ATR-5 antibody V region to an expression vector encoding the human antibody C region.

(1) Construction of a Chimeric Antibody H Chain V Region

The ATR-5 antibody H chain V region was modified by the PCR method in order to ligate it to an expression vector encoding the human antibody H chain C region. The 5'-end primer ch5HS (SEQ ID NO: 18) was designed so as to hybridize the 5'-end of DNA encoding the V region and to have the Kozak consensus sequence (Kozak, M. et al., J. Mol. Biol. 196: 947-950, 1987) and a recognition sequence of the restriction enzyme SalI. The 3'-end primer ch5HA (SEQ ID NO: 19) was designed so as to hybridize 3'-end of DNA encoding the J region and to have a recognition sequence of the restriction enzyme NheI.

The PCR solutions contained, in 100 µl, 120 mM Tris-HCl (pH 8.0), 10 mM KCl, 6 mM $(NH_4)_2SO_4$, 0.1% Triton X100, 0.001% BSA, 0.2 mM dNTPs (dATP, dGTP, dCTP, dTTP), 1 mM $MgCl_2$, 2.5 units of KOD DNA polymerase (Toyo Boseki), 50 pmole of the ch5HS primer and the ch5HA primer, as well as 1 µl of the plasmid ATR5Hv/pUC19 as a template DNA. For PCR, the DNA Thermal Cycler 480 (Perkin-Elmer) was used, and the PCR was performed for thirty cycles at a temperature cycle of 94° C. for 30 seconds, 55° C. for 30 seconds, and 74° C. for 1 minute.

The PCR reaction mixture was extracted with phenol and chloroform, and the amplified DNA fragments were recovered by ethanol precipitation. The DNA fragments were digested with the restriction enzyme NheI (Takara Shuzo) at 37° C. for 1 hour, and then with the restriction enzyme SalI (Takara Shuzo) at 37° C. for 1 hour. The digestion mixture was separated by agarose gel electrophoresis using a 3% NuSieve GTG agarose (FMC BioProducts), and the agarose strips containing about 450 bp long DNA fragments were excised. The agarose strips were extracted with phenol and chloroform, and the DNA fragments were precipitated with ethanol, which were then dissolved in 20 µl of TE.

As the cloning vector, an altered promoter vector (hereinafter referred to as CVIDEC) was used in which the recognition sequences of the-restriction enzymes NheI, SalI, and SplI, BglII were introduced. The gene fragment prepared as above encoding the mouse H chain V region and the CVIDEC vector prepared by digesting with NheI and SalI were ligated using the DNA ligation kit ver. 2 (Takara Shuzo) by reacting at 16° C. for 1 hour according to the instructions attached to the kit.

The ligation mixture was added to 100 µl of *E. coli* JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the *E. coli* was plated on the LBA agar medium and incubated overnight at 37° C. to obtain an *E. coli* transformant. The transformant was cultured overnight at 37° C. in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions. The plasmid that contains the gene encoding the ATR-5 antibody H chain V region, a SalI recognition sequence and the Kozak consensus sequence at the 5'-end, and a NheI recognition sequence at the 3'-end was designated as chATR5Hv/CVIDEC.

(2) Construction of a Chimeric Antibody L Chain V Region

The ATR-5 antibody L chain V region was modified by the PCR method in order to ligate it to an expression vector encoding the human antibody L chain C region. The 5'-end primer ch5LS (SEQ ID NO: 20) was designed so as to hybridize to the 5'-end of the DNA encoding the V region and to have the Kozak consensus sequence (Kozak, M. et al., J. Mol. Biol. 196: 947-950, 1987) and a recognition sequence of the restriction enzyme BglII. The 3'-end primer ch5LA (SEQ ID NO: 21) was designed so as to hybridize to the 3'-emd of the DNA encoding the J region and to have a recognition sequence of the restriction enzyme SplI.

The PCR solutions contained, in 100 µl, 120 mM Tris-HCl (pH 8.0), 10 mM KCl, 6 mM $(NH_4)_2SO_4$, 0.1% Triton X-100, 0.001% BSA, 0.2 mM dNTPs (dATP, dGTP, dCTP, dTTP), 1 mM $MgCl_2$, 2.5 units of KOD DNA polymerase (Toyo Boseki), 50 pmole of the ch5LS primer and the ch5LA primer, as well as 1 µl of the plasmid ATR5Lv/pUC19 as a template DNA. For PCR the DNA Thermal Cycler 480 (Perkin-Elmer) was used, and the PCR was performed for thirty cycles at a temperature cycle of 94° C. for 30 seconds, 55° C. for 30 seconds, and 74° C. for 1 minute.

The PCR reaction mixture was extracted with phenol and chloroform, and the amplified DNA fragments were recovered by ethanol precipitation. The DNA fragments were digested with the restriction enzyme SplI (Takara Shuzo) at 37° C. for 1 hour, and then with the restriction enzyme BglII (Takara Shuzo) at 37° C. for 1 hour. The digestion mixture was separated by agarose gel electrophoresis using a 3% NuSieve GTG agarose (FMC BioProducts), and the agarose strips containing about 400 bp long DNA fragments were excised. The agarose strips were extracted with phenol and chloroform, the DNA fragments were precipitated with ethanol, which were then dissolved in 20 µl of TE.

The gene fragment prepared as above encoding the mouse L chain V region and the CVIDEC vector prepared by digesting with SplI and BglII were ligated using the DNA ligation kit ver. 2 (Takara Shuzo) by reacting at 16° C. for 1 hour according to the instructions attached to the kit.

The ligation mixture was added to 100 µl of *E. coli* JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the *E. coli* was plated on a 100 µg/ml LBA agar medium and incubated overnight at 37° C. to obtain an *E. coli* transformant. The transformant was cultured overnight at 37° C. in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions. The plasmid that contains the gene encoding the ATR-5 antibody L chain V region and that has a BglII recognition sequence and the Kozak consensus sequence at the 5'-end and a SplI recognition sequence at the 3'-end was designated as chATR5Lv/CVIDEC.

(3) Construction of a Chimeric Antibody Expression Vector

A chimeric antibody expression vector was constructed using an antibody expression vector introduced from IDEC Pharmaceuticals. As the vector, the IgG1-type antibody expression vector H5KG1(V) and the IgG4-type antibody expression vector N5KG4P were used. The chimeric ATR-5 antibody expression vector was generated by ligating a gene encoding the H chain V region of ATR-5 to the SalI-NheI site located immediately before the human antibody H chain C region of the expression vector N5KG1(V) or N5KG4P and ligating a gene encoding the L chain V region of ATR-5 to the BglII-SplI site located immediately before the human antibody L chain C region of the expression vector N5KG1(V) or N5KG4P.

(i) Introduction of H Chain V Region

The plasmid chATR5Hv/CVIDEC was digested with the restriction enzyme NheI (Takara Shuzo) at 37° C. for 3 hours, and with the restriction enzyme SalI (Takara Shuzo) at 37° C. for 3 hours. The digestion mixture was separated by agarose gel electrophoresis using 1.5% NuSieve GTG agarose (FMC BioProducts), and the agarose strips containing about 450 bp long DNA fragments were excised. The agarose strips were extracted with phenol and chloroform, and the DNA fragments were precipitated with ethanol, which were then dissolved in 20 µl of TE.

The expression vector N5KG1(V) and N5KG4P were digested with the restriction enzyme NheI (Takara Shuzo) at 37° C. for 3 hours, and with the restriction enzyme SalI (Takara Shuzo) at 37° C. for 3 hours. The digestion mixture was separated by agarose gel electrophoresis using 1.5% NuSieve GTG agarose (FMC BioProducts), and the agarose strips containing about 9000 bp long DNA fragments were excised. The agarose strips were extracted with phenol and chloroform, and the DNA fragments were precipitated with ethanol, which were then dissolved in 20 µl of TE.

The SalI-NheI DNA fragment prepared as above containing the gene encoding the H chain V region and N5KG1(V) or N5KG4P digested with SalI and NheI were ligated using the DNA ligation kit ver. 2 (Takara Shuzo) by reacting at 16° C. for 1 hour according to the attached instructions.

The ligation mixture was added to 100 µl of *E. coli* JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the *E. coli* was plated on a 100 µg/ml LBA agar medium and incubated overnight at 37° C. to obtain an *E. coli* transformant. The transformant was cultured overnight at 37° C. in 3 ml of the LBA medium, and from the cell fractions, plasmid DNA was prepared using the QIAprep Spin Plasmid Kit (QIAGEN). These plasmids containing the genes encoding the chimeric ATR-5 antibody H chain were designated as chATR5Hv/N5KG1(V) and chATR5Hv/N5KG4P, respectively.

(ii) Introduction of the L Chain V Region

The plasmid chATR5Lv/CVIDEC was digested with the restriction enzymes BglII (Takara Shuzo) and SplI (Takara Shuzo) at 37° C. for 1.5 hour. The digestion mixture was separated by agarose gel electrophoresis using 1.5% NuSieve GTG agarose (FMC BioProducts), and the agarose strips containing about 400 bp long DNA fragments were excised. The agarose strips were extracted with phenol and chloroform, and the DNA fragments were precipitated with ethanol, which were then dissolved in 20 µl of TE.

The plasmids chATR5Hv/N5KG1(V) and chATR5Hv/N5KG4P were digested with the restriction enzymes BglII (Takara Shuzo) and SplI (Takara Shuzo) at 37° C. for 1.5 hour. The digestion mixture was separated by agarose gel electrophoresis using 1.5% NuSieve GTG agarose (FMC BioProducts), and the agarose strips containing about 9400 bp long DNA fragments were excised. The agarose strips were extracted with phenol and chloroform, DNA fragments were precipitated with ethanol, which were then dissolved in 20 µl of TE.

The SplI-BglII DNA fragment prepared as above containing the gene encoding the L chain V region and chATR5Hv/N5KG1(V) or chATR5Hv/N5KG4P digested with SplI and BglII were ligated using the DNA ligation kit ver. 2 (Takara Shuzo) by reacting at 16° C. for 1 hour according to the attached instructions.

The ligation mixture was added to 100 µl of *E. coli* JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the *E. coli* was plated on a 100 µg/ml LBA agar medium and incubated overnight at 37° C. to obtain an *E. coli* transformant. The transformant was cultured overnight at 37° C. in 1l of the 2xYT medium containing 50 µl/ml ampicillin, and from the cell fractions, plasmid DNA was prepared using the Plasmid Maxi Kit (QIAGEN). These plasmids containing the gene encoding the chimeric ATR-5 antibody were designated as chATR5/N5KG1(V) and chATR5/N5KG4P, respectively.

(4) Transfection into COS-7 Cells

In order to evaluate the activity of binding to the antigen and the neutralizing activity of chimeric antibody, the above expression plasmid was transfected to COS-7 cells and the antibody was transient expressed.

The plasmid chATR5/N5KG1(V) or chATR5/N5KG4P was transduced into COS-7 cells by electroporation using the Gene Pulser instrument (Bio Rad). Fifty µg of the plasmid was added to 0.78 ml of the COS-7 cells suspended in the Dulbecco PBS (−) (hereinafter referred to as PBS) at a cell concentration of $1 \times 10^7$ cells/ml, which was subjected to pulses of 1,500 V and 25 µF capacity.

After 10 minutes of the recovery period at room temperature, the electroporated cells were suspended in a DMEM medium containing 5% Ultra low IgG fetal bovine serum (GIBCO), and cultured using a 10 cm culture dish in a 5% $CO_2$ incubator. After culturing for 24 hours, the culture supernatant was aspirated off, and then a serum-free medium HBCHO (Irvine Scientific) was added. After further culturing for 72 hours, the culture supernatant was collected and centrifuged to remove cell debris.

(5) Purification of Antibody

From the culture supernatant of the COS-7 cells, chimeric antibody was purified using the rProtein A Sepharose Fast Flow (Pharmacia Biotech) as follows.

One ml of rProtein A Sepharose Fast Flow was filled into a column and the column was equilibrated by 10 volumes of TBS. The culture supernatant of COS-7 cells was applied to the equilibrated column, which was then washed with 10 volumes of TBS.

The adsorbed antibody fraction was then eluted by 13.5 ml of 2.5 mM HCl (pH 3.0), and the eluate was immediately neutralized by adding 1.5 ml of 1 M Tris-HCl (pH 8.0).

By performing ultrafiltration twice for the purified antibody fraction using the Centriprep 100 (Amicon), the solvent was replaced to 50 mM Tris-HCl (pH 7.6) containing 150 mM NaCl (hereinafter referred to as TBS), and was finally concentrated to about 1.5 ml.

(6) Establishment of a Stably-producing CHO Cell Line

In order to establish a cell line that stably produces chimeric antibody, the above expression plasmid was introduced into CHO cells (DG44) acclimated to the CHO-S-SFMII serum-free medium (GIBCO).

The plasmid chATR5/N5KG1(V) or chATR5/N5KG4P was cleaved with the restriction enzyme SspI (Takara Shuzo) to linearize DNA, and after extraction with phenol and chloroform, DNA was recovered by ethanol precipitation. The linearized plasmid was transduced into the DG44 cells by electroporation using the Gene Pulser instrument (Bio Rad). Ten µg of the plasmid was added to 0.78 ml of DG44 cells suspended in PBS at a cell concentration of $1 \times 10^7$ cells/ml, which was subjected to pulses of 1,500 V and 25 µF capacity.

After 10 minutes of the recovery period at room temperature, the electroporated cells were suspended in a CHO-S-SFMII medium (GIBCO) containing hypoxanthine/thymidine (GIBCO), and cultured using two 96-well plates (Falcon) in a 5% $CO_2$ incubator. On the day after the start of culturing, the medium was changed to a selection medium containing the CHO-S-SFMII medium (GIBCO) containing hypoxanthine/thymidine (GIBCO) and 500 µg/ml GENETICIN (G418Sulfate, GIBCO) to select cells into which the antibody gene had been introduced. After changing the selection medium, the cells were examined under a microscope about two weeks later. After a favorable cell growth was observed, the amount of antibody produced was measured by the ELISA described below for determining antibody concentration, and cells having a high production yield of antibody were selected.

Example 3

Construction of Humanized Antibody (1) Construction of Humanized Antibody H Chain (i) Construction of the Humanized H Chain Version "a"

Humanized ATR-5 antibody H chain was generated using CDR-grafting by the PCR method. In order to generate the humanized antibody H chain version "a" having the FRs derived from human antibody L39130 (DDBJ, Gao L. et al., unpublished, 1995), seven PCR primers were used. The CDR-grafting primers hR5Hv1S (SEQ ID NO: 22), hR5Hv2S (SEQ ID NO: 23), and hR5Hv4S (SEQ ID NO: 24) have a sense DNA sequence, and the CDR grafting primers hR5Hv3A (SEQ ID NO: 25) and hR5Hv5A (SEQ ID NO: 26) have an antisense DNA sequence, each primer having a 18-35 bp complementary sequence on both ends thereof.

hR5Hv1S was designed to have the Kozak consensus sequence (Kozak, M. et al., J. Mol. Biol. 196: 947-950, 1987)

and a SalI recognition site, and hR5Hv5A was designed to have a NheI recognition site. The exogenous primer hR5HvPrS (SEQ ID NO: 27) has a homology with the CDR-grafting primer hR5Hv1S, and hR5HvPrA (SEQ ID NO: 28) has a homology with the CDR-grafting primer hR5Hv5A.

The CDR-grafting primers hR5Hv1S, hR5Hv2S, hR5Hv3A, hR5Hv4S, and hR5Hv5A, and exogenous primers hR5HvPrS and hR5HvPrA were synthesized and purified by Pharmacia Biotech.

PCR was performed using the KOD DNA polymerase (Toyo Boseki) and using the attached buffer under the condition of containing 120 mM Tris-HCl (pH 8.0), 10 mM KCl, 6 mM $(NH_4)_2SO_4$, 0.1% Triton X100, 0.001% BSA, 0.2 mM dNTPs (dATP, dGTP, dCTP, dTTP), 1 mM $MgCl_2$, 2.5 units of KOD DNA polymerase (Toyo Boseki), and 5 pmole each of the CDR-grafting primers hR5Hv1S, hR5Hv2S, hR5Hv3A, hR5Hv4S, and hR5Hv5A in 98 µl, for 5 cycles at a temperature cycle of 94° C. for 30 seconds, 50° C. for 1 minute, and 72° C. for 1 minute. After further addition of 100 pmole of exogenous primers hR5HvPrS and hR5HvPrA, PCR was performed for 25 cycles in a system of 100 µl with the same temperature cycle. DNA fragments amplified by the PCR method were separated by agarose gel electrophoresis using a 2% NuSieve GTG agarose (FMC BioProducts).

The agarose strips containing about 430 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 17 µl of water. The PCR reaction mixture obtained was digested with NheI and SalI, and was ligated to the plasmid vector CVIDEC prepared by digesting with NheI and SalI, using the DNA ligation kit ver. 2 (Takara Shuzo) according to the instructions attached to the kit.

The ligation mixture was added to 100 µl of E. coli JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the E. coli was plated on the LBA agar medium and incubated overnight at 37° C. to obtain an E. coli transformant. The transformant was cultured overnight at 37° C. in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions.

Since mutation and/or deletion were observed before or after the EcoT221 recognition site, each of fragments having the correct sequence was ligated and then subcloned again to CVIDEC to determine the nucleotide sequence. The plasmid having the correct sequence was designated as hATR5Hva/CVIDEC. The nucleotide sequence and the corresponding amino acid sequence of the humanized H chain version "a" contained in the plasmid hATR5Hva/CVIDEC are shown in SEQ ID NO: 29. The amino acid sequence of version "a" is also shown in SEQ ID NO: 30.

(ii) Construction of Humanized H Chain Versions "b" and "b"

Versions "b" and "c" were generated by replacing the FR3 of version "a"0 with the FR3 derived from another human antibody using the FR-shuffling method. In order to replace the FR3 in version "b" with one derived from human antibody Z34963 (DDBJ, Borretzen M. et al., Proc. Natl. Acad. Sci. USA, 91: 12917-12921, 1994), the four DNA primers encoding the FR3 were generated. The FR-shuffling primers F3RFFS (SEQ ID NO: 31) and F3RFBS (SEQ ID NO: 32) have a sense DNA sequence and F3RFFA (SEQ ID NO: 33) and F3RFBA (SEQ ID NO: 34) have an antisense DNA sequence. F3RFFS and F3RFFA have a sequence complementary to each other, and have BalI and XhoI recognition sequences on both ends. F3RFBS and F3RFBA have a sequence complementary to each other, and have XhoI and NcoI recognition sequences on both ends.

In order to replace the FR3 in version "c" with one derived from human antibody P01825 (SWISS-PROT, Poljak RJ. et al., Biochemistry, 16: 3412-3420, 1977), four DNA primers encoding the FR3 were generated. The FR-shuffling primers F3NMFS (SEQ ID NO: 35) and F3NMBS (SEQ ID NO: 36) have a sense DNA sequence and F3NMFA (SEQ ID NO: 37) and F3NMBA (SEQ ID NO: 38) have an antisense DNA sequence.

F3NMFS and F3NMFA have a sequence complementary to each other, and have BalI and XhoI recognition sequences on both ends.

F3NMBS and F3NMBA have, and have XhoI and NcoI recognition sequences on both ends.

F3RFFS, F3RFBS, F3RFFA, F3RFBA, F3NMFS, F3NMBS, F3NMFA, and F3NMBA were synthesized by Pharmacia Biotech. F3RFFS and F3RFFA, and F3RFBS and F3RFBA were annealed, and were digested with BalI and XhoI, and NcoI and XhoI, respectively. They were introduced to the plasmid hATR5Hva/CVIDEC (BalI/NcoI) prepared by digesting with BalI and NcoI, and the nucleotide sequence was determined. The plasmid having the correct sequence was designated as hATR5Hvb/CVIDEC. The nucleotide sequence and the corresponding amino acid sequence of the humanized H chain version "b" contained in the plasmid hATR5Hvb/CVIDEC are shown in SEQ ID NO: 39. The amino acid sequence of version "b" is also shown in SEQ ID NO: 40.

F3NMFS and F3NMFA, and F3NMBS and F3NMBA were annealed, and were digested with BalI and XhoI, and NcoI and XhoI, respectively. They were introduced to the plasmid hATR5Hva/CVIDEC (BalI/NcoI) prepared by digesting with BalI and NcoI, and the nucleotide sequence was determined. The plasmid having the correct sequence was designated as hATR5Hvc/CVIDEC. The nucleotide sequence and the corresponding amino acid sequence of the humanized H chain version "c" contained in the plasmid hATR5Hvc/CVIDEC are shown in SEQ ID NO: 41. The amino acid sequence of version "c" is also shown in SEQ ID NO: 42.

(iii) Construction of Humanized H Chain Versions "d" and "e"

Versions "d" and "e" were generated by replacing the FR3 of version "a" with the FR3 derived from another human antibody using the FR-shuffling method. In order to replace the FR3 in version "d" with one derived from human antibody M62723 (DDBJ, Pascual V. et al., J. Clin. Invest., 86: 1320-1328, 1990), four DNA primers encoding the FR3 were generated. The FR-shuffling primer F3EPS (SEQ ID NO: 43) has a sense DNA sequence and F3EPA (SEQ ID NO: 44) has an antisense DNA sequence, and the 3'-end of the primers has a complementary sequence of 18 bp.

Exogenous primers F3PrS (SEQ ID NO: 45) and F3PrA (SEQ ID NO: 46) have a homology with the FR-shuffling primers F3EPS and F3EPA, and can also be used for other FR3's FR-shuffling. In order to replace the FR3 in version "e"

with one derived from the human antibody Z80844 (DDBJ, Thomsett AR. et al., unpublished), two DNA primers encoding the FR3 were generated. The FR-shuffling primers F3VHS (SEQ ID NO: 47) has a sense DNA sequence and F3VHA (SEQ ID NO: 48) has an antisense DNA sequence, and the 3-end of the primers has a complementary sequence of 18 bp. F3EPS, F3EPA, F3PrS, F3PrA, F3VHS and F3VHA were synthesized by Pharmacia Biotech.

PCR was performed using the KOD DNA polymerase (Toyo Boseki) using the attached buffer under the condition of containing 5 µl each of 1 µM FR-shuffling primers F3EPS and F3EPA, or F3VHS and F3VHA, 0.2 mM dNTPs, 1.0 mM MgCl$_2$, and 2.5 units of KOD DNA polymerase in 100 µl of the reaction mixture, for 5 cycles at a temperature cycle of 94° C. for 30 seconds, 50° C. for 1 minute, and 74° C. for 1 minute. After further addition of 100 pmole of exogenous primers F3PrS and F3PrA, PCR was performed for 25 cycles with the same temperature cycle.

DNA fragments amplified by the PCR method were separated by agarose gel electrophoresis using a 2% Nu Sieve GTG agarose (FMC BioProducts). The agarose strips containing about 424 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 14 µl of water. The PCR reaction mixture obtained was digested with BalI and NcoI, and was introduced to the plasmid hATR5Hva/CVIDEC (BalI/NcoI) prepared by digesting with BalI and NcoI, and the nucleotide sequence was determined.

The plasmids having the correct sequence were designated as hATR5Hvd/CVIDEC and hATR5Hve/CVIDEC. The nucleotide sequence and the corresponding amino acid sequence of the humanized H chain version "d" contained in the plasmid hATR5Hvd/CVIDEC are shown in SEQ ID NO: 49, and the amino acid sequence of version "d" is also shown in SEQ ID NO: 50. The nucleotide sequence and the corresponding amino acid sequence of the humanized H chain version "e" contained in the plasmid hATR5Hve/CVIDEC are shown in SEQ ID NO: 51, and the amino acid sequence of version "e" is also shown in SEQ ID NO: 52.

(iv) Construction of Humanized H Chain Versions "f" and "g"

Versions "f" and "g" were generated by replacing the FR3 of version "a" with the FR3 derived from another human antibody using the FR-shuffling method. In order to replace the FR3 in version "f" with one derived from human antibody L04345 (DDBJ, Hillson J L. et al., J. Exp. Med., 178: 331-336, 1993) and to replace the FR3 in version "g" with one derived from human antibody S78322 (DDBJ, Bejcek BE. et al., Cancer Res., 55: 2346-2351, 1995), two primers each encoding the FR3 were synthesized. The FR-shuffling primer F3SSS (SEQ ID NO: 53) of version "f" has a sense DNA sequence and F3SSA (SEQ ID NO: 54) has an antisense DNA sequence, and the 3'-end of the primers has a complementary sequence of 18 bp.

F3CDS (SEQ ID NO: 55) of version "g" has a sense DNA sequence and F3CDA (SEQ ID NO: 56) has an antisense DNA sequence, and the 3'-end of the primers has a complementary sequence of 18 bp. F3SSS, F3SSA, F3CDS, and F3CDA were synthesized and purified by Pharmacia Biotech. PCR was performed using the KOD DNA polymerase (Toyo Boseki) using the attached buffer under the condition of containing 5 µl each of 1 µM FR-shuffling primers F3SSS and F3SSA, or F3CDS and F3CDA, 0.2 mM dNTPs, 1.0 mM MgCl$_2$, and 2.5 units of KOD DNA polymerase in 100 µl of the reaction mixture, for 5 cycles at a temperature cycle of 94° C. for 30 seconds, 50° C. for 1 minute, and 74° C. for 1 minute. After further addition of 100 pmole of exogenous primers F3PrS and F3PrA, PCR was performed for 25 cycles with the same temperature cycle.

DNA fragments amplified by the PCR method were separated by agarose gel electrophoresis using a 2% NuSieve GTG agarose (FMC BioProducts). The agarose strips containing about 424 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 14 µl of water. The PCR reaction mixture obtained was digested with BalI and NcoI, and was introduced to the plasmid hATR5Hva/CVIDEC (BalI/NcoI) prepared by digesting with BalI and NcoI, and the nucleotide sequence was determined.

The plasmids having the correct sequence were designated as hATR5Hvf/CVIDEC and hATR5Hvg/CVIDEC. The nucleotide sequence and the corresponding amino acid sequence of the humanized H chain version "f" contained in the plasmid hATR5Hvf/CVIDEC, and the amino acid sequence of version "f" are shown in SEQ ID NO: 57 and 58. The nucleotide sequence and the corresponding amino acid sequence of the humanized H chain version "g" contained in the plasmid hATR5Hvg/CVIDEC, and the amino acid sequence of version "g" are shown in SEQ ID NO: 59 and 60.

(v) Construction of the Humanized H Chain Version "h"

Version "h" was generated by replacing the FR3 of version "a" with the FR3 derived from another human antibody using the FR-shuffling method. In order to replace the FR3 in version "h" with one derived from the human antibody Z26827 (DDBJ, van Der Stoep et al., J. Exp. Med., 177: 99-107, 1993), two primers each encoding the FR3 were synthesized. The FR-shuffling primer F3ADS (SEQ ID NO: 61) of version "h" has a sense DNA sequence and F3ADA (SEQ ID NO: 62) has an antisense DNA sequence, and the 3'-end of the primers has a complementary sequence of 18 bp.

F3ADS and F3ADA were synthesized and purified by Pharmacia Biotech. PCR was performed using the KOD DNA polymerase (Toyo Boseki) using the attached buffer under the condition of containing 5 µl each of 1 µM FR-shuffling primers F3ADS and F3ADA, 0.2 mM dNTPs, 1.0 mM MgCl$_2$, and 2.5 units of KOD DNA polymerase in 100 µl of the reaction mixture, for 5 cycles at a temperature cycle of 94° C. for 30 seconds, 50° C. for 1 minute, and 74C for 1 minute. After further addition of 100 pmole of exogenous primers F3PrS and F3PrA, PCR was performed for 25 cycles with the same temperature cycle. DNA fragments amplified by the PCR method were separated by agarose gel electrophoresis using a 2% NuSieve GTG agarose (FMC BioProducts).

The agarose strips containing about 424 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 14 µl of water. The PCR reaction mixture obtained was digested with BalI and NcoI, and was introduced to the plasmid hATR5Hva/CVIDEC (BalI/NcoI) prepared by digesting with BalI and NcoI, and the nucleotide sequence was determined. The plasmids having the correct sequence were designated as hATR5Hvh/CVIDEC. The nucleotide sequence and the corresponding amino acid sequence of the humanized H chain version "h" contained in the plasmid hATR5Hvh/CVIDEC, and the amino acid sequence of version "h" are shown in SEQ ID NO: 63. The amino acid sequence of version "h" is shown in SEQ ID NO: 64.

(vi) Construction of Humanized H Chain Versions "i" and "j"

Versions "i" and "j" were generated by replacing the FR3 of version "a" with the FR3 derived from another human antibody using the FR-shuffling method. In order to replace the FR3 in version "i" with one derived from the human antibody U95239 (DDBJ, Manheimer-Lory AAJ., unpublished) and to replace the FR3 in version "j" with one derived from the human antibody L03147 (DDBJ, Collect TA. et al., Proc. Natl. Acad. Sci. USA, 89: 10026-10030, 1992), two primers each encoding the FR3 were synthesized. The FR-shuffling primer F3MMS (SEQ ID NO: 65) of version "i" has a sense DNA sequence and F3MMA (SEQ ID NO: 66) has an antisense DNA sequence, and the 3'-end of the primers has a complementary sequence of 18 bp.

F3BMS (SEQ ID NO: 67) of version "j" has a sense DNA sequence and F3BMA (SEQ ID NO: 68) has an antisense DNA sequence, and the 3'-end of the primers has a complementary sequence of 18 bp. F3MMS, F3MMA, F3BMS, and F3BMA were synthesized and purified by Pharmacia Biotech. PCR was performed using the Ampli Taq Gold (Perkin-Elmer) using the attached buffer under the condition of containing 5 µl each of 1 µM FR-shuffling primers F3MMS and F3MMA, or F3BMS and F3BMA, 0.2 mM dNTPs, 1.0 mM MgCl$_2$, and 2.5 units of Ampli Taq Gold in 100 µl of the reaction mixture, for 5 cycles at a temperature cycle of 94° C. for 30 seconds, 50° C. for 1 minute, and 74° C. for 1 minute. After further addition of 100 pmole of exogenous primers F3PrS and F3PrA, PCR was performed for 25 cycles with the same temperature cycle.

DNA fragments amplified by the PCR method were separated by agarose gel electrophoresis using a 2% Nu Sieve GTG agarose (FMC BioProducts). The agarose strips containing about 424 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 14 µl of water. The PCR reaction mixture obtained was digested with BalI and NcoI, and was introduced to the plasmid hATR5Hva/CVIDEC (BalI/NcoI) prepared by digesting with BalI and NcoI, and the nucleotide sequence was determined.

The plasmids having the correct sequence were designated as hATR5Hvi/CVIDEC and hATR5Hvj/CVIDEC. The nucleotide sequence and the corresponding amino acid sequence of the humanized H chain version "i" contained in the plasmid hATR5Hvi/CVIDEC, and the amino acid sequence of version "i" are shown in SEQ ID NO: 69 and 70. The nucleotide sequence and the corresponding amino acid sequence of the humanized H chain version "j" contained in the plasmid hATR5Hvj/CVIDEC, and the amino acid sequence of version "j" are shown in SEQ ID NO: 71 and 72.

(vii) Construction of Humanized H Chain Versions "b1" and "d1"

Versions "b1" and "d1" were generated by replacing the FR2 of versions "b" and "d" with the FR2 derived from another human antibody using the FR-shuffling method. In order to replace the FR2 with one derived from the human antibody P01742 (SWISS-PROT, Cunningham BA. et al., Biochemistry, 9: 3161-3170, 1970), two DNA primers encoding the FR2 were synthesized. The FR-shuffling vector F2 MPS (SEQ ID NO: 73) has a sense DNA sequence and F2 MPA (SEQ ID NO: 74) has an antisense DNA sequence. They also have a sequence complementary to each other, and have recognition sequences of EcoT22I and BalI on both ends thereof.

F2 MPS and F2 MPA were synthesized and purified by Pharmacia Biotech. F2 MPS and F2 MPA were annealed and were digested with EcoT22I and BalI. They were introduced to plasmids hATR5Hvb/CVIDEC (EcoT22I/BalI) and hATR5Hvd/CVIDEC (EcoT22I/BalI) prepared by digesting with EcoT22I and BalI, and the nucleotide sequence was determined. The plasmids having the correct sequence were designated as hATR5Hvb1/CVIDEC and hATR5Hvd1/CVIDEC. The nucleotide sequence and the corresponding amino acid sequence of the humanized H chain version "b1" contained in the plasmid hATR5Hvb1/CVIDEC, and the amino acid sequence of version "b1" are shown in SEQ ID NO: 75 and 76. The nucleotide sequence and the corresponding amino acid sequence of the humanized H chain version "d1" contained in the plasmid hATR5Hvd1/CVIDEC, and the amino acid sequence of version "d1" are shown in SEQ ID NO: 77 and 78.

(viii) Construction of Humanized H Chain Versions "b3" and "d3"

Versions "b3" and "d3" were generated by replacing the FR2 of versions "b" and "d" with the FR2 derived from another human antibody using the FR-shuffling method. In order to replace the FR2 with one derived from the human antibody Z80844 (DDDJ, Thomsett AR. et al., unpublished), two DNA primers encoding the FR2 were synthesized. The FR-shuffling vector F2VHS (SEQ ID NO: 79) has a sense DNA sequence and F2VHA (SEQ ID NO: 80) has an antisense DNA sequence. They also have a sequence complementary to each other, and have recognition sequences of EcoT22I and BalI on both ends thereof. The synthesis and purification of F2VHS and F2VHA was referred to Pharmacia Biotech.

F2VHS and F2VHA were annealed and were digested with EcoT22I and BalI. They were introduced to plasmids hATR5Hvb/CVIDEC (EcoT22I/BalI) and hATR5Hvd/CVIDEC (EcoT22I/BalI) prepared by digesting with EcoT22I and BalI, and the nucleotide sequence was determined. The plasmids having the correct sequence were designated as hATR5Hvb3/CVIDEC and hATR5Hvd3/CVIDEC. The nucleotide sequence and the corresponding amino acid sequence of the humanized H chain version "b3" contained in the plasmid hATR5Hvb3/CVIDEC, and the amino acid sequence of version "b3" are shown in SEQ ID NO: 81 and 82. The nucleotide sequence and the corresponding amino acid sequence of the humanized H chain version "d3" contained in the plasmid hATR5Hvd3/CVIDEC, and the amino acid sequence of version "d3" are shown in SEQ ID NO: 83 and 84.

(2) Construction of a Humanized Antibody L Chain V Region (i) Version "a"

The humanized ATR-5 antibody L chain V region was generated by the CDR-grafting using the PCR method. For the generation of a humanized antibody L chain (version "a") having framework regions derived from human antibody z37332 (DDBJ, Welschof M. et al., J. Immunol. Methods, 179: 203-214, 1995), seven PCR primers were used.

CDR-grafting primers h5Lv1S (SEQ ID NO: 85) and h5Lv4S (SEQ ID NO: 86) have a sense DNA sequence, CDR-grafting primers h5Lv2A (SEQ ID NO: 87), h5Lv3A (SEQ ID NO: 88), and h5Lv5A (SEQ ID NO: 89) have an antisense DNA sequence, and each primer has 20 bp complementary sequences on both ends thereof. Exogenous primers h5LvS (SEQ ID NO: 90) and h5LvA (SEQ ID NO: 91) have a homology with CDR-grafting primers h5Lv1S and h5Lv5A. The synthesis and purification of CDR-grafting primers h5Lv1S, h5Lv4S, h5Lv2A, h5Lv3A, h5Lv5A, h5LvS, and h5LvA were referred to Pharmacia Biotech.

The PCR solutions contain, in 100 pl, 120 mM Tris-HCl (pH 8.0), 10 mM KCl, 6 mM $(NH_4)_2SO_4$, 0.1% Triton X100, 0.001% BSA, 0.2 mM dNTPs (dATP, dGTP, dCTP, dTTP), 1 mM $MgCl_2$, 2.5 units of KOD DNA polymerase (Toyo Boseki), 50 pmole of the CDR-grafting primers h5Lv1S, h5Lv2A, h5Lv3A, h5Lv4S, and h5Lv5A.

PCR was performed using the DNA Thermal Cycler 480 (Perkin-Elmer) for 5 cycles with the temperature cycle of 94° C. for 30 seconds, 50° C. for 1 minute, and 72° C. for 1 minute to assemble 5 CDR-grafting primers. After further addition of 100 pmole of exogenous primers h5LvS and h5LvA to the reaction mixture, PCR was performed for 30 cycles with the temperature cycle of 94° C. for 30 seconds, 52° C. for 1 minute, and 72° C. for 1 minute to amplify the assembled DNA fragments.

The PCR reaction mixture was separated by agarose gel electrophoresis using a 3% NuSieve GTG agarose (FMC BioProducts), and the agarose strips containing about 400 bp long DNA fragments were excised. The agarose strips were extracted with phenol and chloroform, DNA fragments were recovered by ethanol precipitation. The recovered DNA fragments were digested with the restriction enzymes SplI (Takara Shuzo) and BglII (Takara Shuzo) at 37° C. for 4 hours. The digestion mixture was extracted with phenol and chloroform, and after the ethanol precipitation of the DNA fragments, they were dissolved in 10 µl of TE. The SplI-BglII DNA fragment prepared as above encoding the humanized L chain V region and the CVIDEC vector prepared by digesting with SplI and BglII were ligated using the DNA ligation kit ver. 2 (Takara Shuzo) by reacting at 16° C. for 1 hour according to the instructions attached to the kit.

The ligation mixture was added to 100 µl of E. coli JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the E. coli was plated on the LBA agar medium and incubated overnight at 37° C. to obtain an E. coli transformant. The transformant was cultured overnight in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions. The plasmid that contains the gene encoding the humanized antibody L chain V region and that has a BglII recognition sequence and the Kozak sequence at the 5'-end, and a SplI recognition sequence at the 3'-end was designated as hATR5Lva/CVIDEC. The nucleotide sequence (including the corresponding amino acid sequence) of the humanized L chain version "a" is shown in SEQ ID NO: 92. The amino acid sequence of version "a" is also shown in SEQ ID NO: 93.

(ii) Versions "b" and "c"

Versions "b" and "c" were generated by replacing (FR-shuffling) the FR3 of version "a". For version "b" the FR3 derived from human antibody S68699 (DDBJ, Hougs L. et al., Exp. Clin. Immunogen et., 10: 141-151, 1993) was used, and for version "c" the FR3 derived from human antibody P01607 (SWISS-PROT, Epp O et al., Biochemistry, 14: 4943-4952, 1975) was used, respectively.

Primers F3SS (SEQ ID NO: 94) and F3SA (SEQ ID NO: 95) encoding the FR3 of version "b", or primers F3RS (SEQ ID NO: 96) and F3RA (SEQ ID NO: 97) encoding the FR3 of version "c" have a sequence complementary to each other, and have the recognition sequences of the restriction enzymes KpnI and PstI on both ends thereof. The synthesis and purification of F3SS, F3SA, F3RS, and F3RA were referred to Pharmacia Biotech. 100 pmole each of F3SS and F3SA, or F3RS and F3RA were annealed by treating at 96° C. for 2 minutes and at 50° C. for 2 minutes and the double stranded DNA fragments were generated.

These double stranded DNA fragments were digested with the restriction enzyme KpnI (Takara Shuzo) at 37° C. for 1 hour, and then with the restriction enzyme PstI (Takara Shuzo) at 37° C. for 1 hour. The digestion mixture was extracted with phenol and chloroform, and after it was precipitated with ethanol, it was dissolved in TE.

The plasmid hATR5Lva/CVIDEC was digested with the restriction enzyme KpnI (Takara Shuzo) at 37° C. for 1 hour, and then with the restriction enzyme PstI (Takara Shuzo) at 37° C. for 1 hour. The digestion mixture was separated by agarose gel electrophoresis using a 1.5% NuSieve GTG agarose (FMC BioProducts), and the agarose strips having about 3000 bp long DNA fragments were excised. The agarose strip was extracted with phenol and chloroform, and after the DNA fragments were precipitated with ethanol, they were dissolved in TE.

The KpnI-PstI DNA fragment prepared as above encoding the FR3 of versions "b" or "c" and the hATR5Lva/CVIDEC vector in which the FR3 was removed by digesting with KpnI and PstI were ligated using the DNA ligation kit ver. 2 (Takara Shuzo) by reacting at 16° C. for 1 hour according to the instructions attached to the kit.

The ligation mixture was added to 100 µl of E. coli JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the E. coli was plated on the LBA agar medium and incubated overnight at 37° C. to obtain an E. coli transformant. The transformant was cultured overnight in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions.

The plasmids that contain the gene encoding version "b" or version "c" in which the FR3 of humanized antibody L chain version "a" was replaced was designated as hATR5Lvb/CVIDEC or hATR5Lvc/CVIDEC, respectively. The nucleotide sequence and the corresponding amino acid sequence of the humanized L chain version "b" contained in plasmid hATR5Lvb/CVIDEC and the amino acid sequence of version "b" are shown in SEQ ID NO: 98 and 99. The nucleotide sequence and the corresponding amino acid sequence of the humanized L chain version "c" contained in plasmid hATR5Lvc/CVIDEC and the amino acid sequence of version "c" are shown in SEQ ID NO: 100 and 101.

(iii) Versions "b1" and "b2"

Versions "b1" and "b2" were generated by replacing the FR2 of version "b". For version "b1" the FR2 derived from human antibody S65921 (DDBJ, Tonge D W et al., Year Immunol., 7: 56-62, 1993) was used, and for version "b2" the FR2 derived from human antibody X93625 (DDBJ, Cox J P et al., Eur. J. Immunol., 24: 827-836, 1994) was used, respectively.

Primers F2SS (SEQ ID NO: 102) and F2SA (SEQ ID NO: 103) encoding the FR2 of version "b1", or primers F2XS (SEQ ID NO: 104) and F2XA (SEQ ID NO: 105) encoding the FR2 of version "b2" have a sequence complementary to each other, and have the recognition sequences of the restriction enzymes AflII and SpeI on both ends thereof. F2SS, F2SA, F2XS, and F2XA were synthesized by Pharmacia Biotech. 100 pmole each of F2SS and F2SA, or F2XS and F2XA were annealed by treating at 96° C. for 2 minutes and at 50° C. for 2 minutes, and the double stranded DNA fragments were generated.

These double stranded DNA fragments were digested with the restriction enzymes AflII (Takara Shuzo) and SpeI (Takara Shuzo) at 37° C. for 1 hour. The digestion mixture was extracted with phenol and chloroform, and after the DNA fragments were precipitated with ethanol, they were dissolved in TF.

The plasmid hATR5Lvb/CVIDEC was digested with the restriction enzymes AflII (Takara Shuzo) and SpeI (Takara Shuzo) at 37° C. for 1 hour. The digestion mixture was separated by agarose gel electrophoresis using a 1.5% NuSieve GTG agarose (FMC BioProducts), and the agarose strips having about 3000 bp long DNA fragments were excised. The agarose strip was extracted with phenol and chloroform, and after the DNA fragments were precipitated with ethanol, they were dissolved in TF.

The AflII-SpeI DNA fragment prepared as above encoding the FR2 of version "b1" or "b2" and the hATR5Lvb/CVIDEC vector in which the FR2 was removed by digesting with AflII and SpeI were ligated using the DNA ligation kit ver. 2 (Takara Shuzo) by reacting at 16° C. for 1 hour according to the instructions attached to the kit.

The ligation mixture was added to 100 µl of E. coli JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the E. coli was plated on the LBA agar medium and incubated overnight at 37° C. to obtain an E. coli transformant. The transformant was cultured overnight at 37° C. in 4 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions.

The plasmids that contain the gene encoding version "b1" or "b2" in which the FR2 of humanized antibody L chain version "b" was replaced was designated as hATR5Lvb1/CVIDEC and hATR5Lv2/CVIDEC, respectively. The nucleotide sequence and the corresponding amino acid sequence of the humanized L chain version "b1" contained in plasmid hATR5Lvb1/CVIDEC and the amino acid sequence of version "b1" are shown in SEQ ID NO: 106 and 107. The nucleotide sequence and the corresponding amino acid sequence of the humanized L chain version "b2" contained in plasmid hATR5Lvb2/CVIDEC and the amino acid sequence of version "b2" are shown in SEQ ID NO: 108 and 109.

(3) Construction of the Expression Vector of Humanized Antibody (i) Combination of Humanized H Chain ad Chimeric L Chain The plasmid hATR5Hva/CVIDEC containing a H chain V region was digested with NheI and SalI, and a cDNA fragment of the humanized H chain V region was recovered and introduced to chATR5/N5KG4P (SalI/NheI) prepared by digesting chATR5/N5KG4P, a chATR-5 antibody expression plasmid vector, with NheI and SalI. The plasmid thus generated was designated as hHva-chLv/N5KG4P.

The plasmid hATR5Hvb/CVIDEC containing a H chain V region was digested with NheI and SalI, and a cDNA fragment of the humanized H chain V region was recovered and introduced to chATR5/N5KG4P (SalI/NheI) prepared by digesting chATR5/N5KG4P, a chATR-5 antibody expression plasmid vector, with NheI and SalI. The plasmid thus generated was designated as hHvb-chLv/N5KG4P.

The plasmids hATR5Hvc/CVIDEC, hATR5Hvd/CVIDEC, and hATR5Hve/CVIDEC containing a H chain V region were digested with NheI and SalI, and cDNA fragments of the humanized H chain V region were recovered and introduced to chATR5/N5KG4P (SalI/NheI) prepared by digesting chATR5/N5KG4P, a chATR-5 antibody expression plasmid vector, with NheI and SalI. The plasmids thus generated were designated as hHvc-chLv/N5KG4P, hHvd-chLv/N5KG4P, and hHve-chLv/N5KG4P.

The plasmids hATR5Hvf/CVIDEC and hATR5Hvh/CVIDEC containing a H chain V region were digested with NheI and SalI, and cDNA fragments of the humanized H chain V region were recovered and introduced to chATR5/N5KG4P (SalI/NheI) prepared by digesting chATR5/N5KG4P, a chATR-5 antibody expression plasmid vector, with NheI and SalI. The plasmids thus generated were designated as hHvf-chLv/N5KG4P and hHvh-chLv/N5KG4P.

The plasmids hATR5Hvi/CVIDEC and hATR5Hvj/CVIDEC containing a H chain V region were digested with NheI and SalI, and cDNA fragments of the humanized H chain V region were recovered and introduced to chATR5/N5KG4P (SalI/NheI) prepared by digesting chATR5/N5KG4P, a chATR5 antibody expression plasmid vector, with NheI and SalI. The plasmids thus generated were designated as hHvi-chLv/N5KG4P and hHvj-chLv/N5KG4P.

The plasmids hATR5Hb1/CVIDEC and hATR5Hvd1/CVIDEC containing a H chain V region were digested with NheI and SalI, and cDNA fragments of the humanized H chain V region were recovered and introduced to chATR5/N5KG4P (SalI/NheI) prepared by digesting chATR5/N5KG4P, a chATR-5 antibody expression plasmid vector, with NheI and SalI. The plasmids thus generated were designated as hHvb1-chLv/N5KG4P and hHvd1-chLv/N5KG4P.

(ii) Combination of Humanized L Chain ad Chimeric H Chain

Using an antibody expression vector N5KG4P, it was combined with a chimeric H chain and was expressed, and the humanized L chain was evaluated.

The plasmids hATR5Lva/CVIDEC, hATR5Lvb/CVIDEC, hATR5Lvc/CVIDEC, hATR5Lvb1/CVIDEC, and hATR5Lvb2/CVIDEC were digested with the restriction enzymes BglII (Takara Shuzo) and SplI (Takara Shuzo) at 37° C. for 2-3 hours. The digestion mixture was separated by agarose gel electrophoresis using a 1.5% or 2% NuSieve GTG agarose (FMC BioProducts), and the agarose strips having about 400 bp long DNA fragments were excised. The agarose strips were extracted with phenol and chloroform, and after the DNA fragments were precipitated with ethanol, they were dissolved in TF.

The SplI-BglII DNA fragment containing the gene encoding the a humanized L chain V region of each of these versions and the hATR5Hv/N5KG4P digested with SplI and BglII were ligated using the DNA ligation kit ver. 2 (Takara Shuzo) by reacting at 16° C. for 1 hour according to the instructions attached to the kit.

The ligation mixture was added to 100 µl of E. coli JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the E. coli was plated on the LBA agar medium and incubated overnight at 37° C. to obtain an E. coli transformant.

The transformant was cultured overnight at 37° C. in 250 ml or 500 ml of the LBA medium, and from the cell fractions, plasmid DNA was prepared using the Plasmid Maxi Kit (QIAGEN). The plasmids in which a gene encoding the chimeric H chain and humanized L chain was introduced were designated as chHv-hLva/N5KG4P, chHv-hLvb/N5KG4P, chHv-hLvc/N5KG4P, chHv-hLvb1/N5KG4P, and chHv-hLvb2/N5KG4P.

(iii) Combination of Humanized H Chain and Humanized L Chain

The plasmid hATR5Hva/CVIDEC containing a H chain V region was digested with NheI and SalI, and a cDNA fragment of the humanized H chain V region was recovered and introduced to hLva/N5KG4P (SalI/NheI) prepared by digesting plasmid chHv-hLva/N5KG4P containing the cDNA sequence of humanized ATR-5 antibody L chain version "a" with NheI and SalI. The plasmid thus generated was designated as hHva-hLva/N5KG4P.

The plasmids hATR5Hvb/CVIDEC and hATR5Hvc/CVIDEC containing a H chain V region were digested with NheI and SalI, and cDNA fragments of the humanized H chain V region were recovered and introduced to hLva/N5KG4P (SalI/NheI) prepared by digesting plasmid chHv-hLva/N5KG4P containing the cDNA sequence of humanized ATR-5 antibody L chain version "a" with NheI and SalI. The plasmids thus generated were designated as hHvb-hLva/N5KG4P and hHvc-hLva/N5KG4P.

The plasmids hATR5Hvb/CVIDEC, hATR5Hvd/CVIDEC, and hATR5Hve/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvb-hLvb/N5KG4P, hHvd-hLvb/N5KG4P, and hHve-hLvb/N5KG4P.

The plasmids hATR5Hvf/CVIDEC, hATR5Hvg/CVIDEC, and hATR5Hvh/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvf-hLvb/N5KG4P, hHvg-hLvb/N5KG4P, and hHvh-hLvb/N5KG4P.

The plasmids hATR5Hvi/CVIDEC and hATR5Hvj/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvi-hLvb/N5KG4P and hHvj-hLvb/N5KG4P.

The plasmids hATR5Hvb1/CVIDEC and hATR5Hvd1/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvb1-hLvb/N5KG4P and hHvd1-hLvb/N5KG4P.

The plasmids hATR5Hvb3/CVIDEC and hATR5Hvd3/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvb3-hLvb/N5KG4P and hHvd3-hLvb/N5KG4P.

The plasmid hATR5Hvb/CVIDEC containing a H chain V region was digested with NheI and SalI, and a cDNA fragment of the humanized H chain V region was recovered and introduced to hLvb1/N5KG4P (SalI/NheI) and hLvb2/N5KG4P (SalI/NheI) prepared by digesting plasmids chHv-hLvb1/N5KG4P and chHv-hLvb2/N5KG4P containing the cDNA sequence of humanized ATR-5 antibody L chain versions "b1" and "b2" with NheI and SalI. The plasmids thus generated were designated as hHvb-hLvb1/N5KG4P and hHvb-hLvb2/N5KG4P.

The plasmid hATR5Hvi/CVIDEC containing a H chain V region was digested with NheI and SalI, and a cDNA fragment of the humanized H chain V region was recovered and introduced to hLvb1/N5KG4P (SalI/NheI) and hLvb2/N5KG4P (SalI/NheI) prepared by digesting plasmids chHv-hLvb1/N5KG4P and chHv-hLvb2/N5KG4P containing the cDNA sequence of humanized ATR-5 antibody L chain versions "b1" and "b2" with NheI and SalI. The plasmids thus generated were designated as hHvi-hLvb1/N5KG4P and hHvi-hLvb2/N5KG4P.

(4) Transfection into COS-7 Cells

In order to evaluate the activity of binding to the antigen and neutralizing activity of humanized antibody, the above antibody was transiently expressed in COS-7 cells.

The constructed expression plasmid vector was transduced into COS-7 cells by electroporation using the Gene Pulser instrument (Bio Rad). Fifty µg or 20 µg of the plasmid was added to 0.78 ml of COS-7 cells suspended in PBS at a cell concentration of $1 \times 10^7$ cells/ml, which was subjected to pulses of 1,500 V and 25 µF capacity.

After 10 minutes of the recovery period at room temperature, the electroporated cells were suspended in a DMEM medium (GIBCO) containing 5% Ultra low IgG fetal bovine serum (GIBCO), and cultured using a 10 cm culture dish or 15 cm culture dish in a 5% $CO_2$ incubator. After culturing for 24 hours, the culture supernatant was aspirated off, and then a serum-free medium HBCHO (Irvine Scientific) was added. After further culturing for 72 hours or 96 hours, the culture supernatant was collected and centrifuged to remove cell debris.

(5) Purification of Antibody

From the culture supernatant of the COS-7 cells, the antibody was purified using the AffiGel Protein A MAPSII kit (Bio Rad) or the rProtein A Sepharose Fast Flow (Pharmacia Biotech). Purification using the AffiGel Protein A MAPSII kit was carried out according to the instructions attached to the kit. Purification using the rProtein A Sepharose Fast Flow was carried out as follows:

One ml of rProtein A Sepharose Fast Flow was filled into a column and the column was equilibrated by 10 volumes of TBS. The culture supernatant of COS-7 cells was applied to the equilibrated column, which was then washed with 10 volumes of TBS. The adsorbed antibody fraction was eluted by 13.5 ml of 2.5 mM HCl (pH 3.0). The eluate was neutralized by adding 1.5 ml of 1 M Tris-HCl (pH 8.0).

By performing ultrafiltration two or three times for the purified antibody fraction using the Centriprep 30 or 100 (amicon), the solvent was replaced to TBS, and was finally concentrated to about 1.5 ml.

Example 4

Antibody Quantitation and Activity Evaluation (1) Measurement of Antibody Concentration by ELISA ELISA plates for measurement of antibody concentration were prepared as follows: Each well of a 96-well ELISA plate (Maxisorp, NUNC) was immobilized by 100 μl of goat anti-human IgGγ antibody (BIO SOURCE) prepared to a concentration of 1 μg/ml in the immobilization buffer (0.1 M $NaHCO_3$, 0.02% $NaN_{31}$ pH 9.6) (hereinafter referred to as CB). After blocking with 200 μl of the dilution buffer (50 mM Tris-HCl, 1 mM $MgCl_{21}$ 0.1 M NaCl, 0.05% Tween 20, 0.02% $NaN_3$, 1% bovine serum albumin (BSA), pH 8.1) (hereinafter referred to as DB), the culture supernatant of the COS-7 cells in which antibody was expressed or purified antibody were serially diluted with DB, and then added to each well.

After incubating at room temperature for 1 hour followed by washing with the Dulbecco PBS containing 0.05% Tween 20 (hereinafter referred to as RB), 100 μl of alkaline phosphatase-conjugated goat anti-human IgGγ antibody (Biosource) which was diluted 1000-fold with DB was added. After incubating at room temperature for 1 hour followed by washing with the RB, Sigma104 (p-nitrophenyl phosphate, SIGMA) dissolved in the substrate buffer (50 mM $NaHCO_3$, 10 mM $MgCl_2$, pH 9.8) to 1 mg/ml was added, and then the absorbance at 405/655 nm was measured using the Microplate Reader (Bio Rad). As the standard for the measurement of concentration, IgG4κ (Binding Site) was used.

(2) Measurement of the Activity of Binding to the Antigen

Cell ELISA plates for measurement of antigen binding were prepared as follows. Cells used were human bladder carcinoma cells J82 (ATCC HTB-1). To 60 wells of a 96-well cell culture plate, $1 \times 10^5$ J82 cells were inoculated. This was cultured (RPMI1640 medium containing 10% fetal bovine serum (GIBCO)) for one day in a $CO_2$ incubator to allow the cells to be attached thereto. After discarding the culture liquid, each well was washed twice with 300 μl PBS. 100 μl of PBS containing 4% paraformaldehyde (hereinafter referred to as PFA/PBS) was added to each well, and placed on ice for 10 minutes to immobilize the cells.

PFA/PBS was discarded, and each well was washed twice with 300 μl of PBS, and then blocked with 250 μl of DB. The culture supernatant or purified antibody was serially diluted with DB, 100 μl of which was added to each well. After incubating at room temperature for 2 hours followed by washing with RB, 100 μl of alkaline phosphatase-conjugated goat anti-human IgGγ antibody (BioSource) diluted 1000-fold with DB was added. After incubating for 1 hour followed by washing with RB, the substrate solution was added, and then absorbance at 405/655 nm was measured using the Microplate Reader (Bio-Rad).

(3) Measurement of Neutralizing Activity

The neutralizing activity of mouse antibody, chimeric antibody, and humanized antibody was measured with the inhibiting activity against the Factor Xa-production activity by human placenta-derived thromboplastin, Thromborel S (Boehringer A G), as an index. Thus, 60 μl of the buffer (TBS containing 5 mM $CaCl_2$ and 0.1% BSA) was added to 10 μl of 1.25 mg/ml Thromborel S and 10 μl of appropriately diluted antibody, which was then incubated in a 96-well plate at room temperature for 1 hour. Ten μl each of 3.245 μg/ml human Factor X (Celsus Laboratories) and 82.5 ng/ml human Factor VIIa (Enzyme Research) were added thereto, and then were incubated at room temperature for 1 hour.

Ten μl of 0.5 M EDTA was added to stop the reaction, to which 50 μl of the chromogenic substrate solution was added and the absorbance at 405/655 nm was determined using the Microplate Reader (Bio Rad). After reacting at room temperature for 1 hour, the absorbance at 405/655 nm was determined again. The neutralizing activity may be determined by calculating the residual activity (%) from each change in absorbance with the hourly absorbance change at no antibody addition as a 100% activity.

The chromogenic substrate solution was prepared by dissolving the Testzyme chromogenic substrate S-2222 (Chromogenix) according to the attached instructions, diluting 2-fold with purified water and mixing with a polybrene solution (0.6 mg/ml hexadimethylene bromide, SIGMA) at 1:1.

Figure 2:
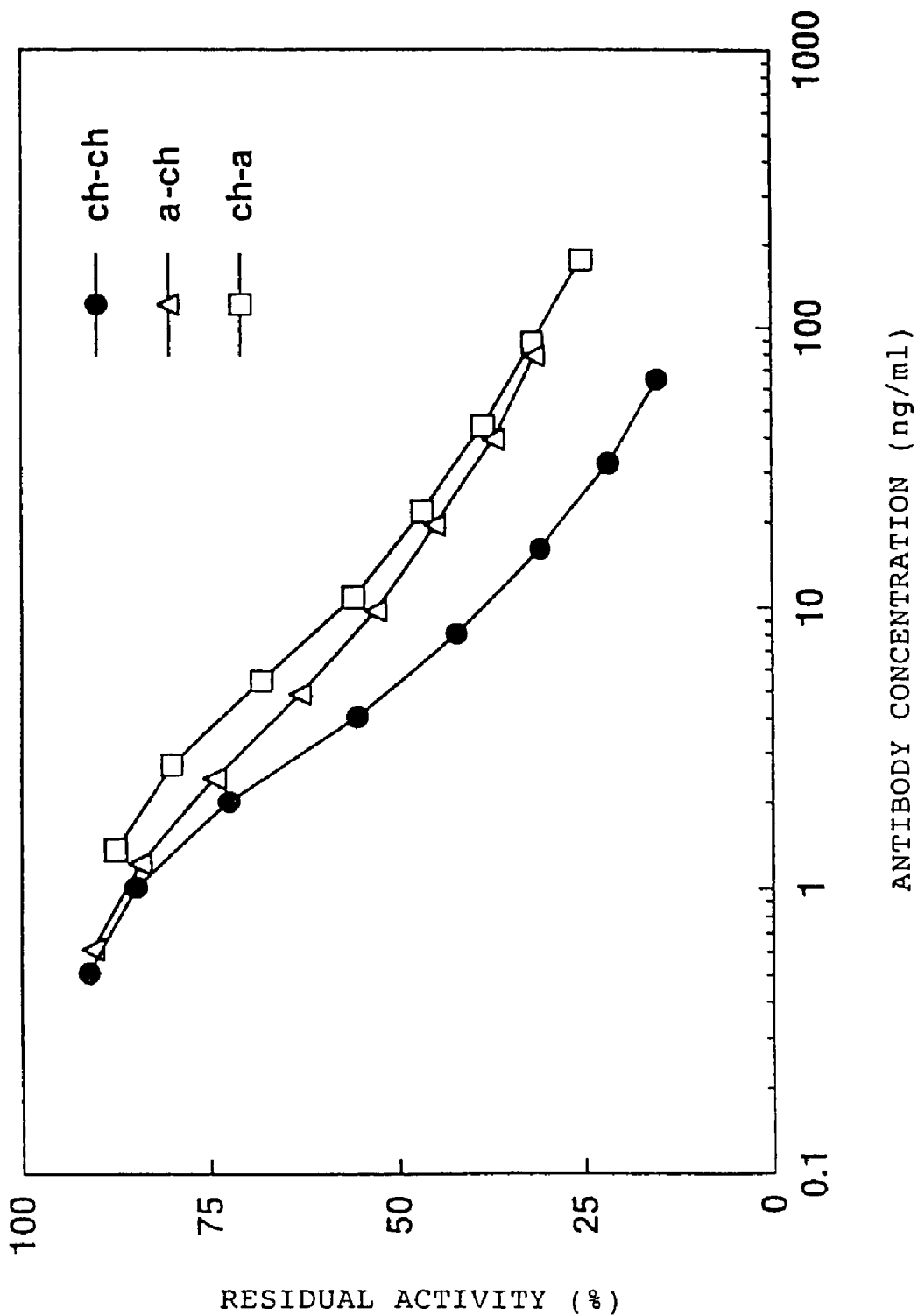
FIG. 2 is a graph that compares the neutralizing activity against human TF of a H chain chimeric/L chain chimeric antibody, a H chain humanized version a/L chain chimeric antibody, and a H chain chimeric/L chain humanized version a antibody.

(4) Evaluation of Activity (i) Combination of the Humanized H Chain Version "a" and a Chimeric L Chain An antibody (a-ch) which is the humanized H chain version "a" combined with a chimeric L chain was generated, and was tested for the binding activity to the antigen by the cell ELISA. The amount bound to the antigen was found to be decreased at the high concentration (FIG. 1). The neutralizing activity against the antigen by FXa production-inhibition was weak as compared that of to the positive control chimeric antibody (cha-cha) (FIG. 2). Therefore, it was decided to perform the version-up of the humanized H chain by FR-shuffling. The chimeric antibody used herein was the one that was expressed in COS-7 cells, purified, and evaluated.

(ii) Combination of the Humanized L Chain Version "a" and a Chimeric H Chain

An antibody (ch-a) which is the humanized L chain version "a" combined with a chimeric H chain was generated, and was tested for the binding activity to the antigen by the cell ELISA. It was found to have the binding activity equal to or higher than that of the chimeric antibody (FIG. 1). On the other hand, the neutralizing activity against the antigen was weak as compared to that of the positive control chimeric antibody (FIG. 2). Therefore, it was decided to perform the version-up of the humanized L chain by FR-shuffling. The chimeric antibody used herein was the one that was expressed in COS-7 cells, purified, and evaluated.

(iii) Combination of the Humanized H Chain Version "a" and the Humanized L Chain Version "a"

Figure 3:
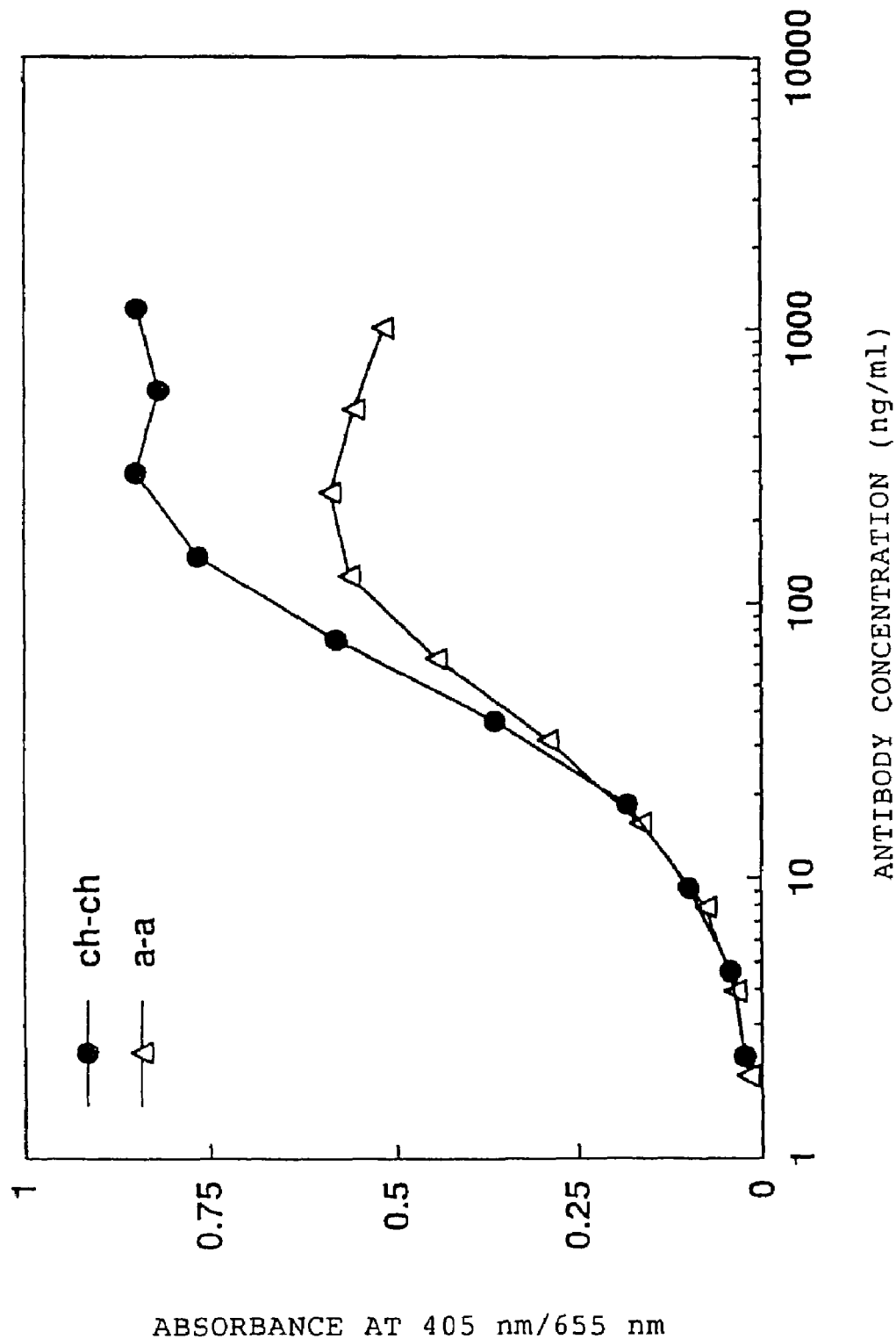
FIG. 3 is a graph that compares the activity of binding to antigen of a H chain chimeric/L chain chimeric antibody and a H chain humanized version a/L chain chimeric version a antibody.
Figure 4:
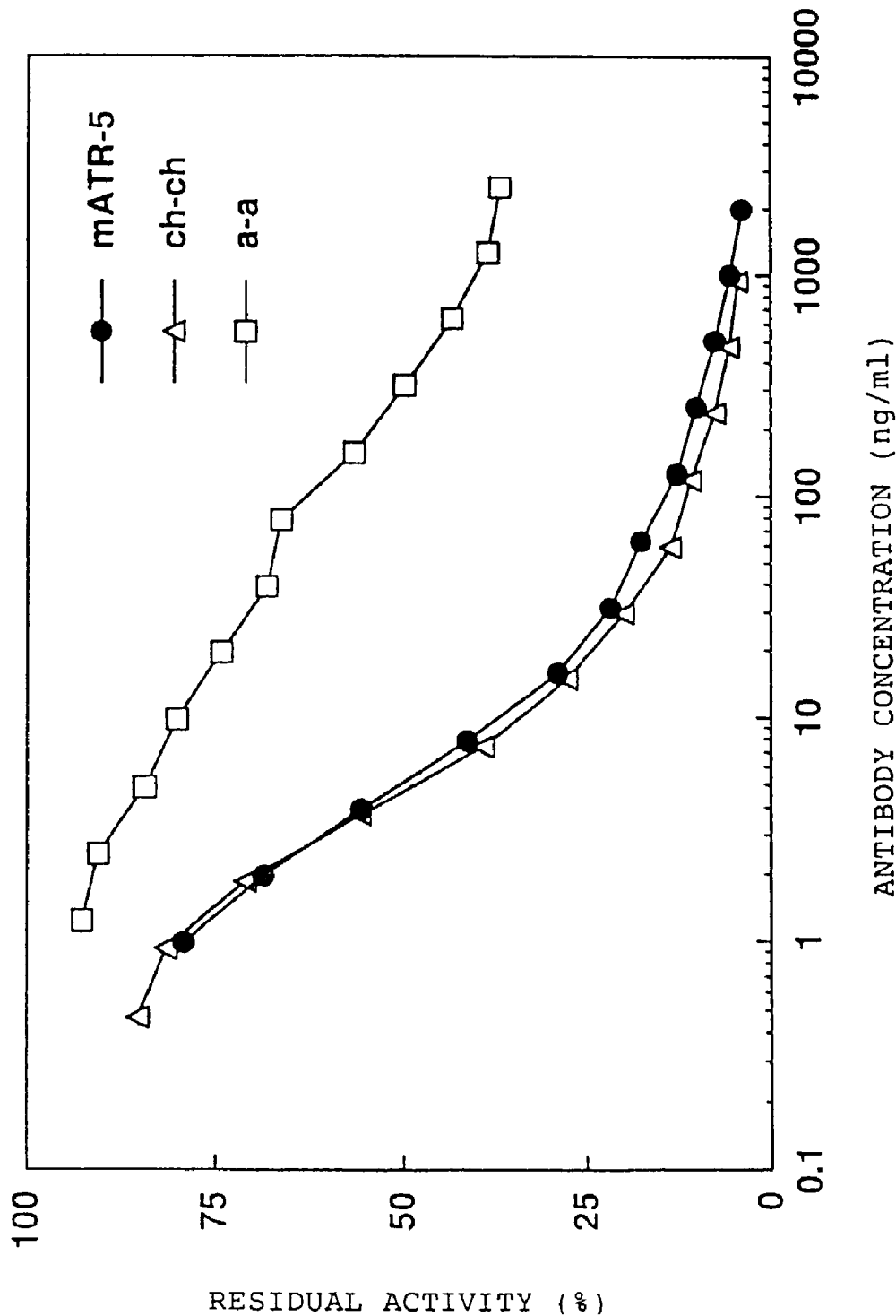
FIG. 4 is a graph that compares the neutralizing activity against human TF of an anti-TF-mouse monoclonal antibody ATR-5, a H chain chimeric/L chain chimeric antibody, and a H chain humanized version a/L chain humanized version a antibody.
Figure 5:
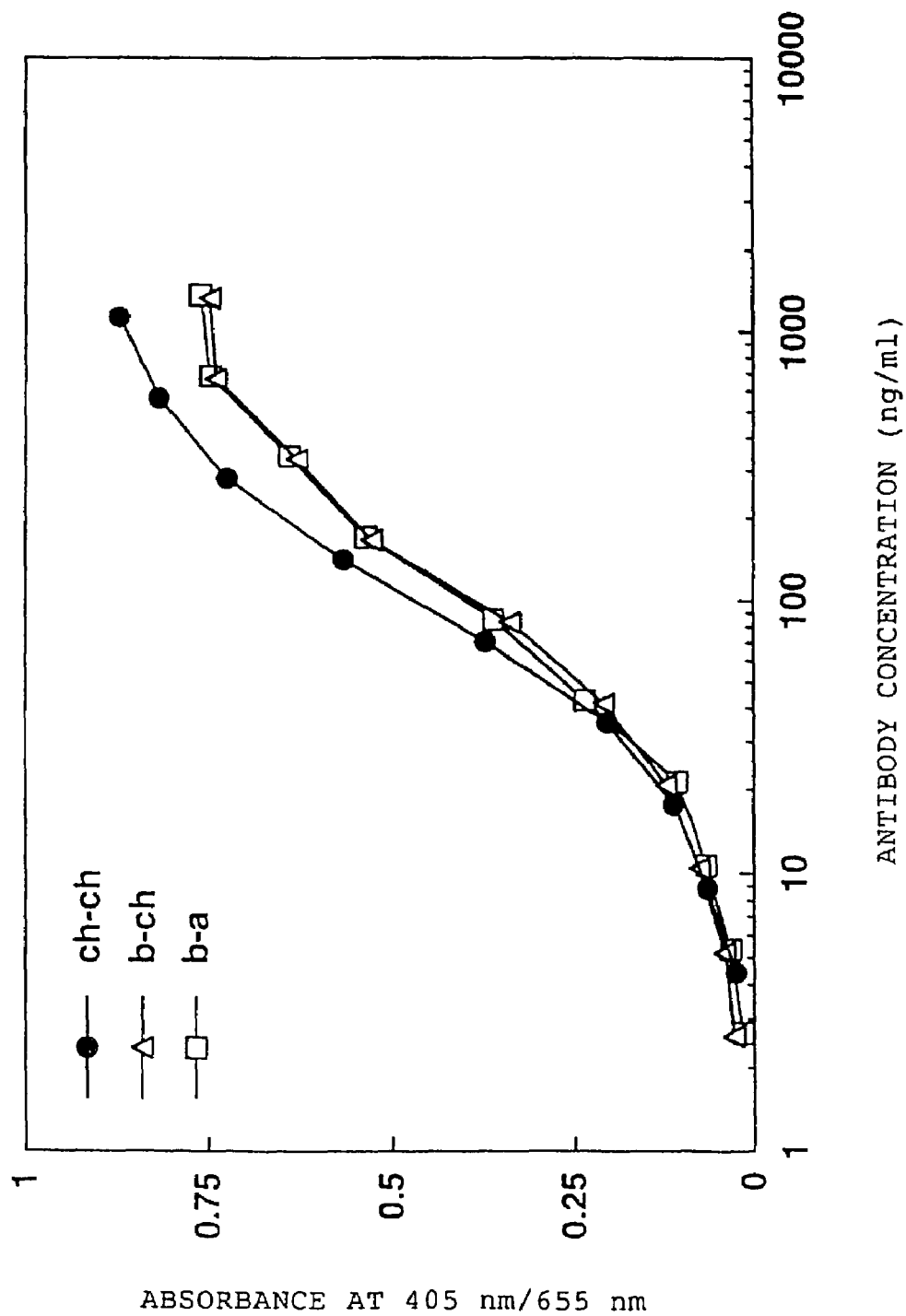
FIG. 5 is a graph that compares the activity of binding to antigen of a H chain chimeric/L chain chimeric antibody, a H chain humanized version b/L chain chimeric antibody, and a H chain humanized version b/L chain humanized version a antibody.
Figure 6:
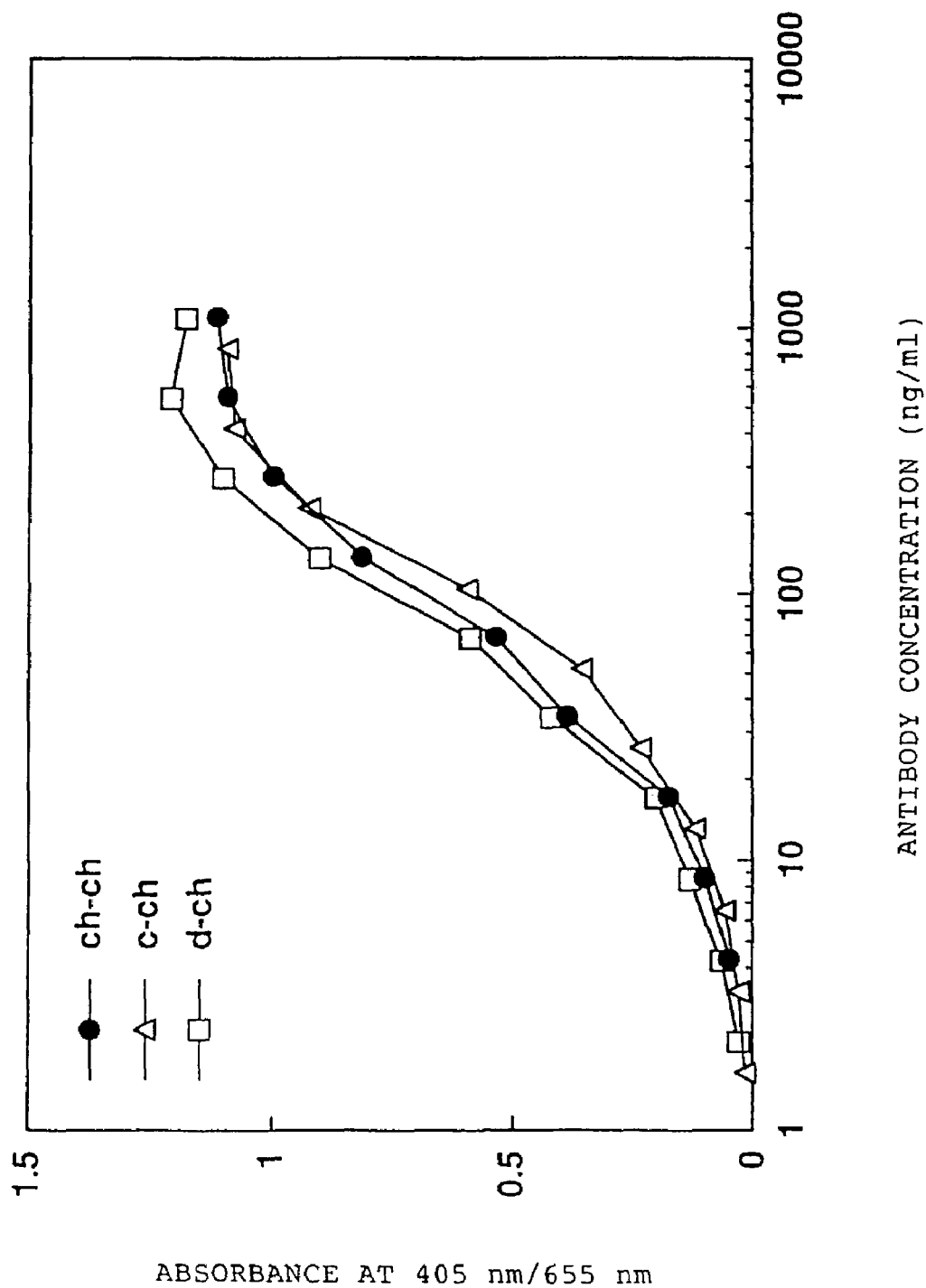
FIG. 6 is a graph that compares the activity of binding to antigen of a H chain chimeric/L chain chimeric antibody, a H chain humanized version c/L chain chimeric antibody, and a H chain humanized version d/L chain chimeric antibody.
Figure 7:
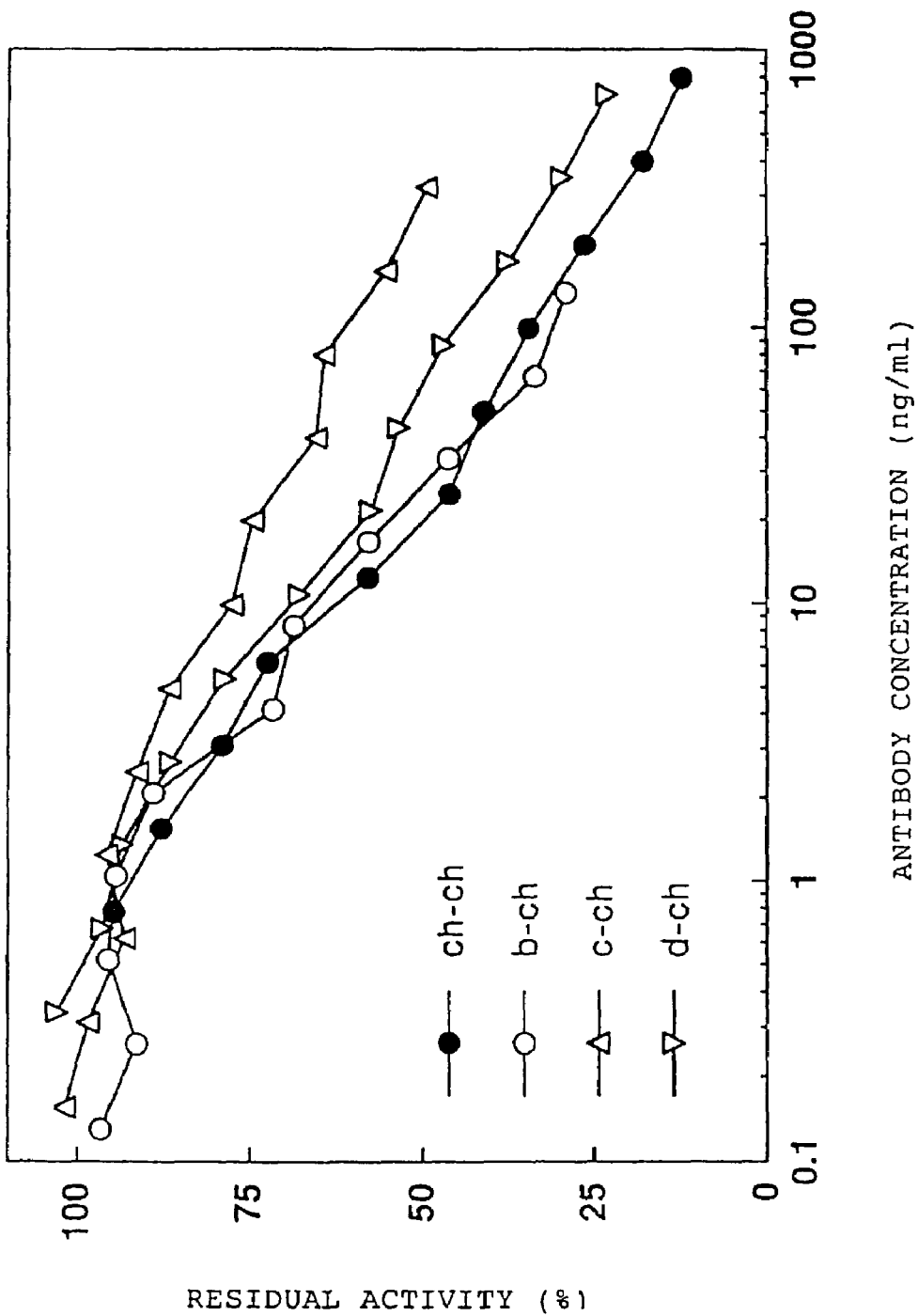
FIG. 7 is a graph that compares the activity of neutralizing human TF of a H chain chimeric/L chain chimeric antibody, a H chain humanized version b/L chimeric antibody, a H chain humanized version c/L chain chimeric antibody, and a H chain humanized version d/L chain chimeric antibody.
Figure 8:
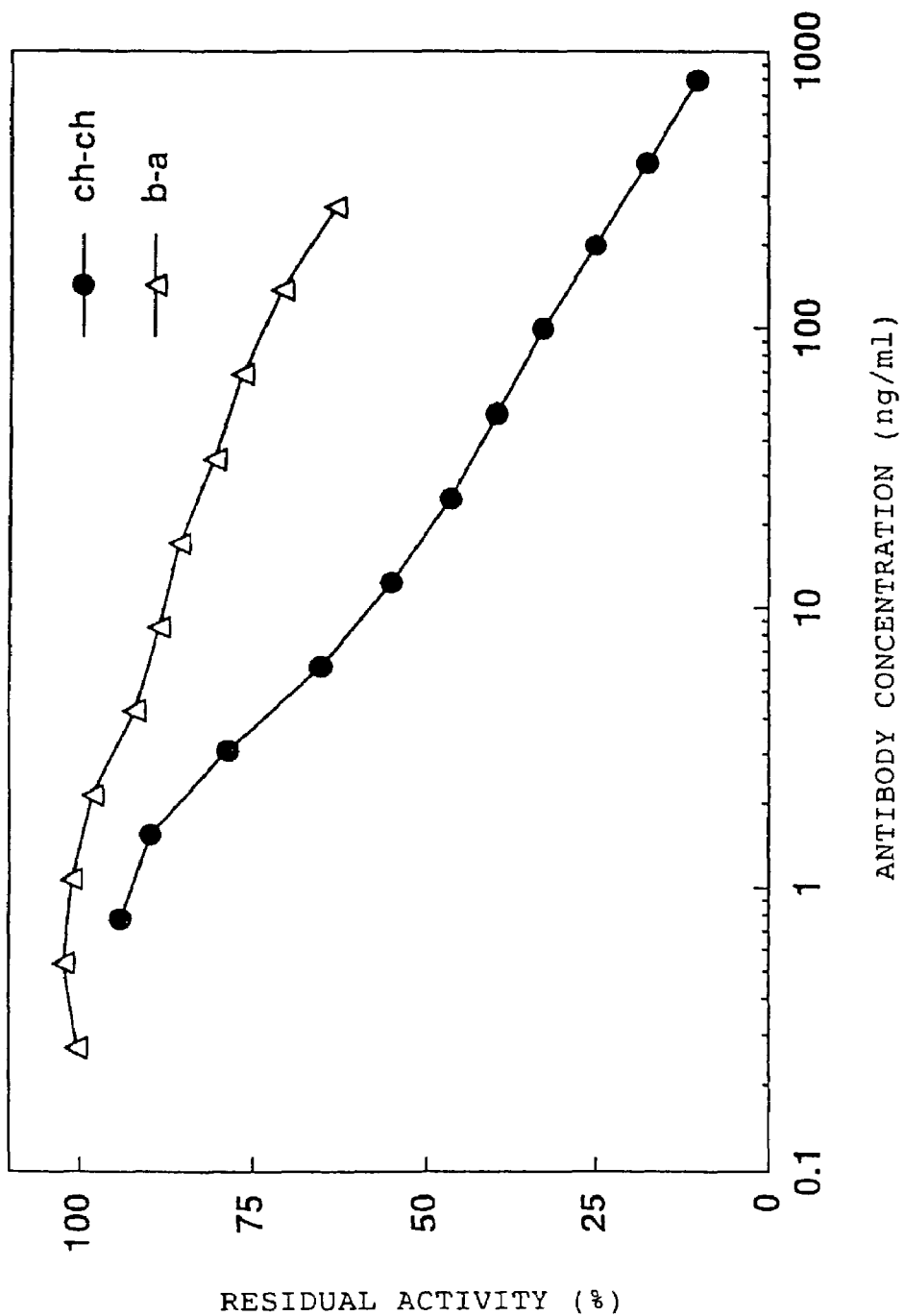
FIG. 8 is a graph that compares the activity of neutralizing human TF of a H chain chimeric/L chain chimeric antibody and a H chain humanized version b/L chain humanized version a antibody.
Figure 9:
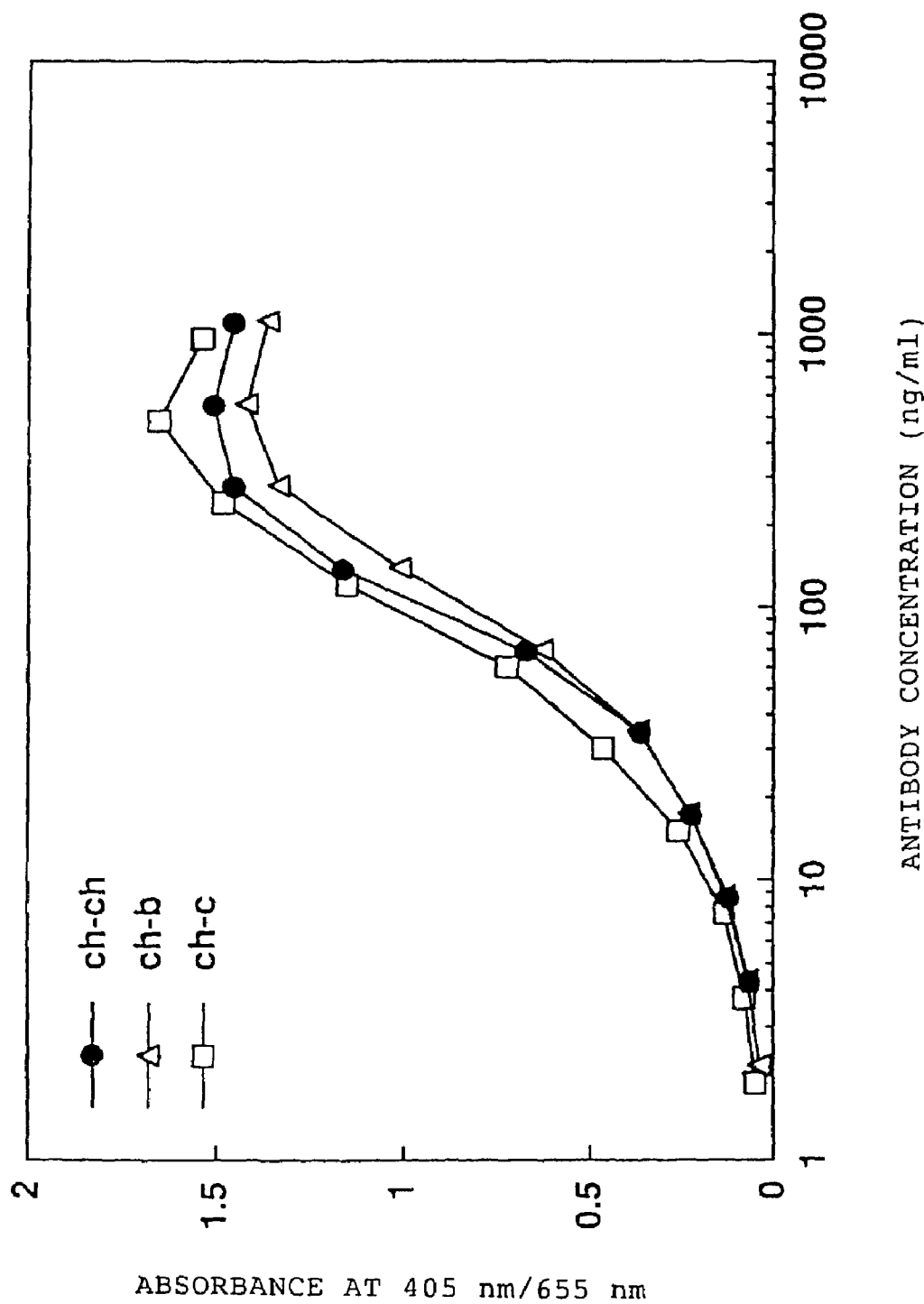
FIG. 9 is a graph that compares the activity of binding to antigen of a H chain chimeric/L chain chimeric antibody, H chain chimeric/L chain humanized version b antibody, and a H chain chimeric/L chain humanized version c antibody.
Figure 10:
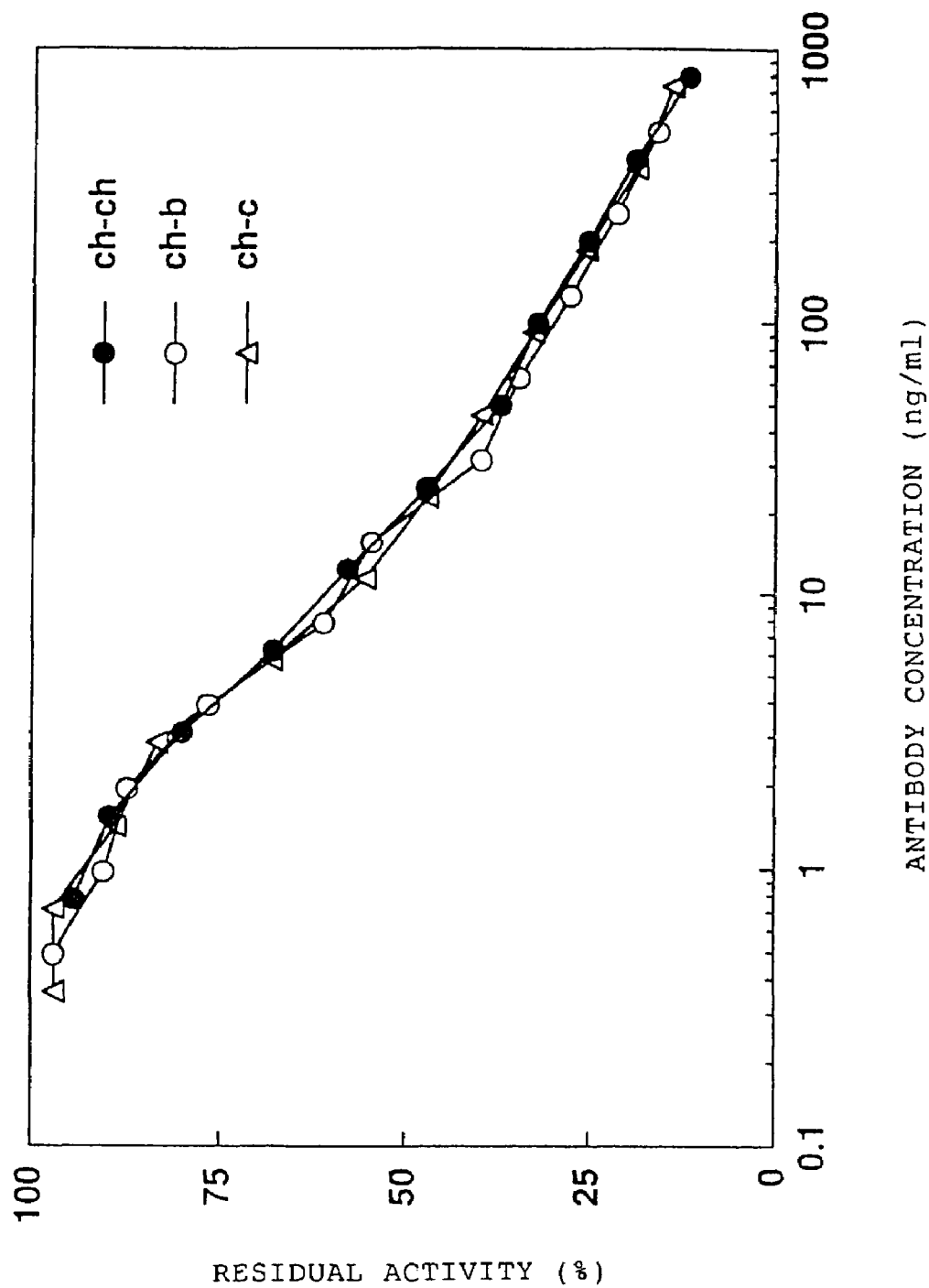
FIG. 10 is a graph that compares the activity of neutralizing human TF of a H chain chimeric/L chain chimeric antibody, a H chain chimeric/L chain humanized version b antibody, and a H chain chimeric/L chain humanized version c antibody.
Figure 11:
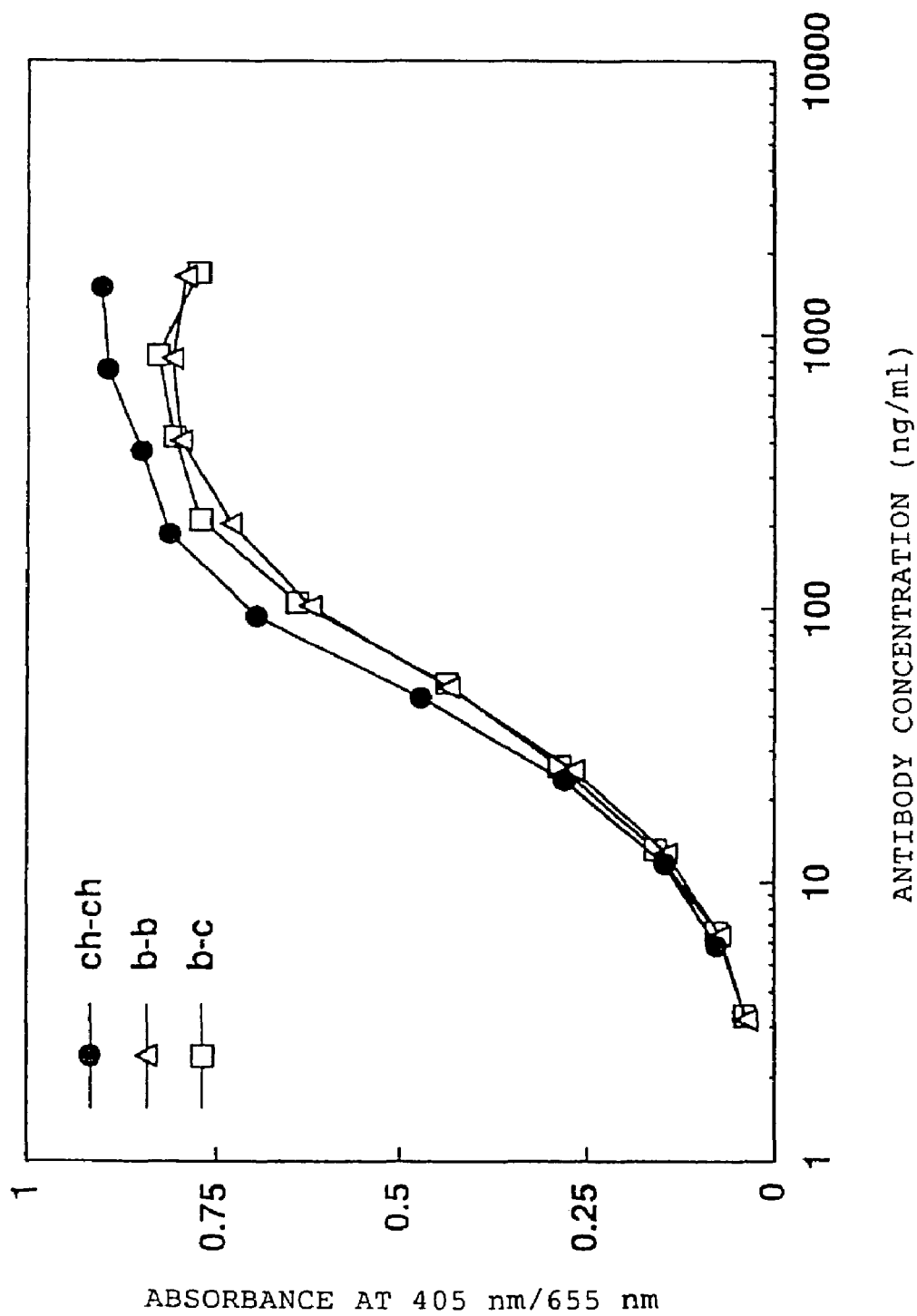
FIG. 11 is a graph that compares the activity of binding to antigen of a H chain chimeric/L chain chimeric antibody, a H chain humanized version b/L chain humanized version b antibody, and a H chain humanized version b/L chain humanized version c antibody.
Figure 12:
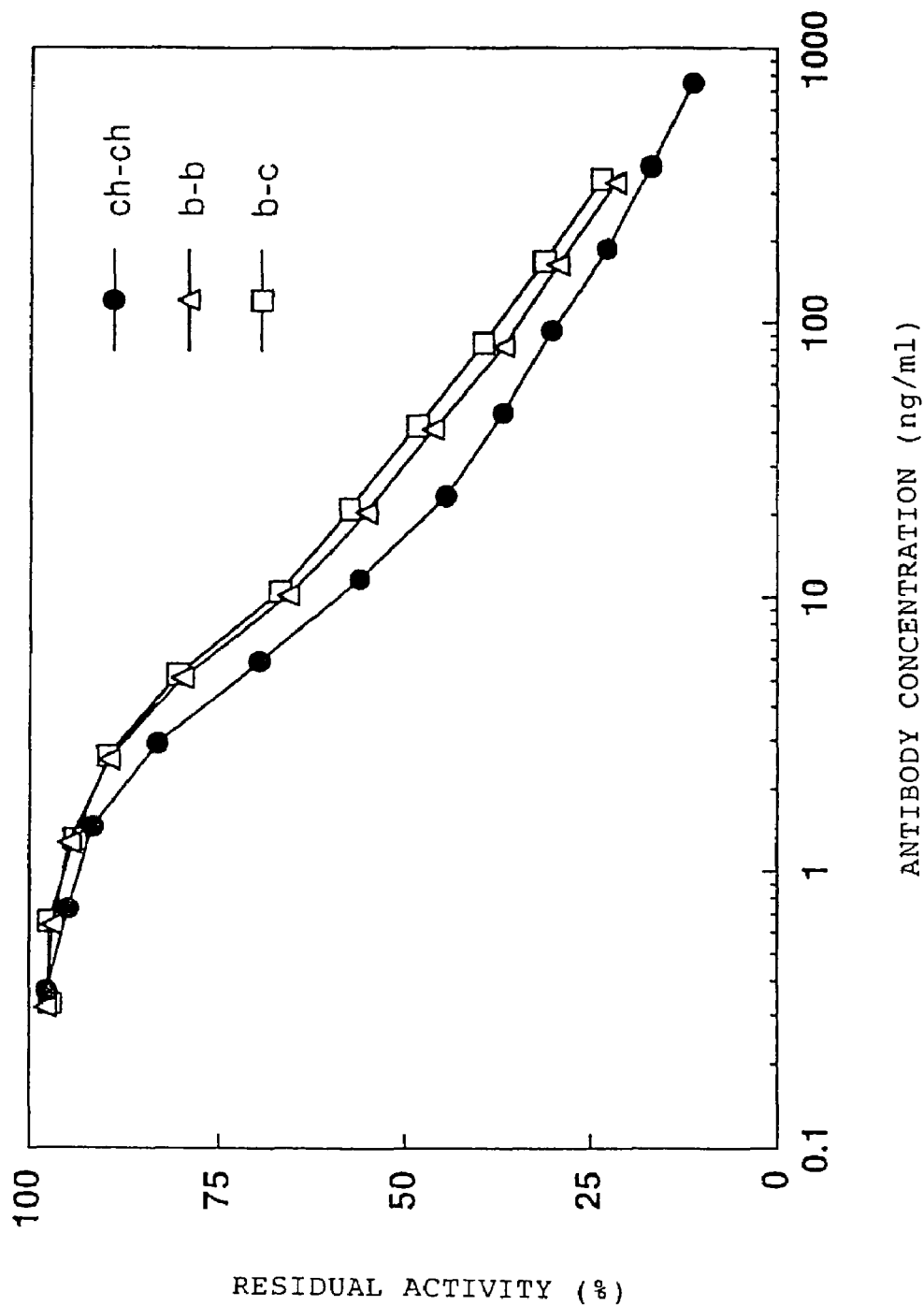
FIG. 12 is a graph that compares the activity of neutralizing human TF of a H chain chimeric/L chain chimeric antibody, a H chain humanized version b/L chain humanized version b antibody, and a H chain humanized version b/L chain humanized version c antibody.
Figure 13:
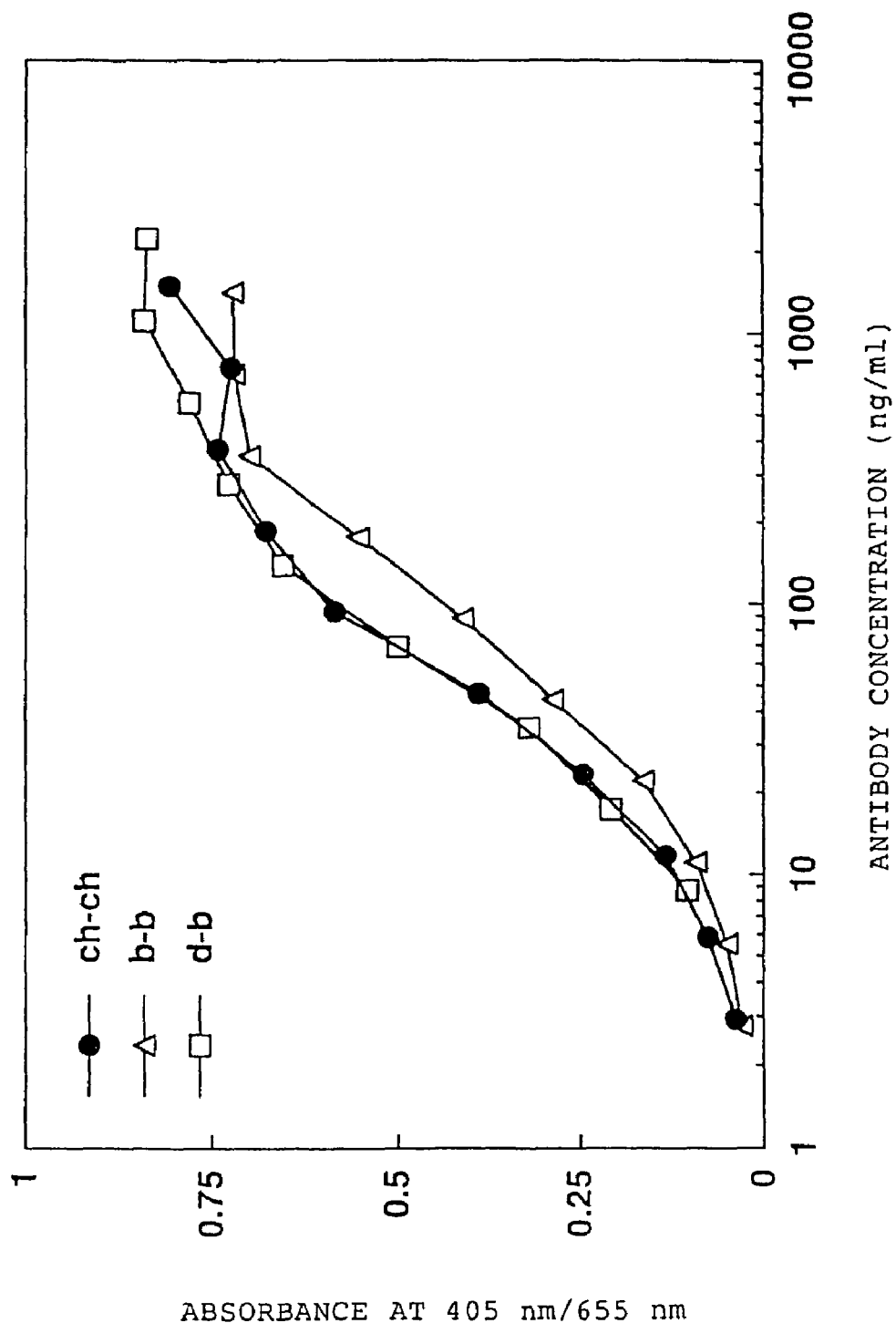
FIG. 13 is a graph that compares the activity of binding to antigen of a H chain chimeric/L chain chimeric antibody, a H chain humanized version b/L chain humanized version b antibody, and a H chain humanized version d/L chain humanized version b antibody.
Figure 14:
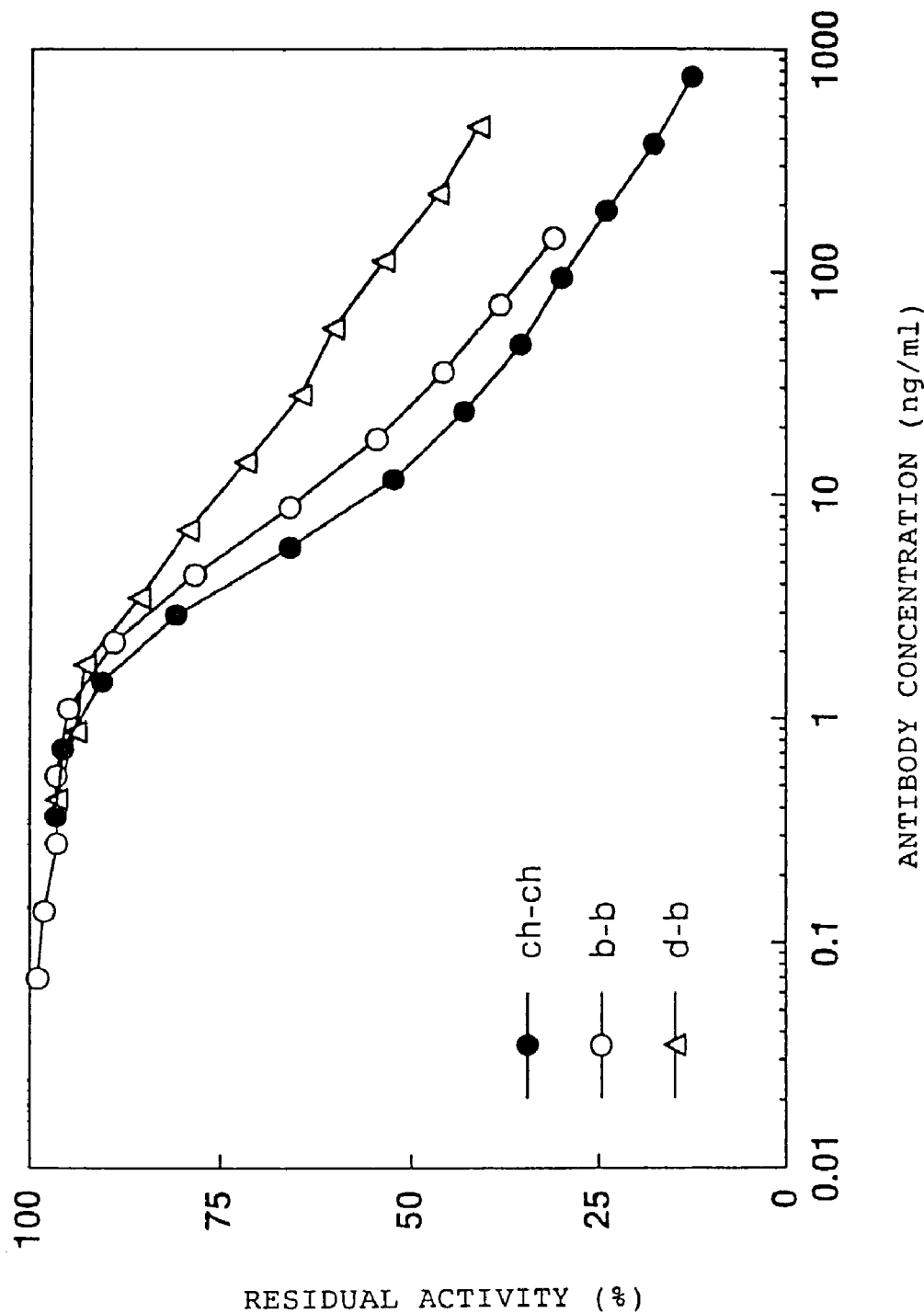
FIG. 14 is a graph that compares the activity of neutralizing human TF of a H chain chimeric/L chain chimeric antibody, a H chain humanized version b/L chain humanized version b antibody, and a H chain humanized version d/L chain humanized version b antibody.
Figure 15:
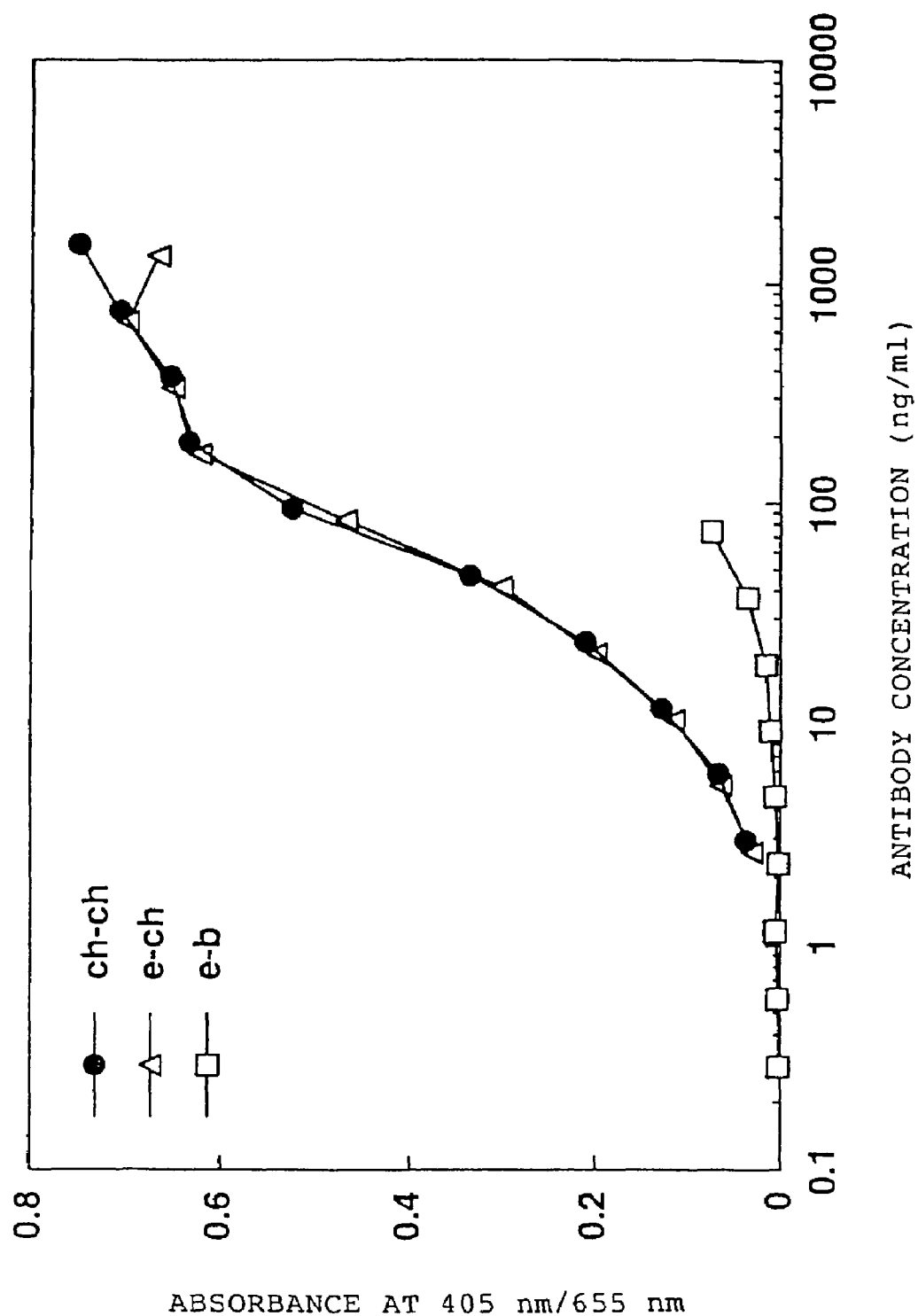
FIG. 15 is a graph that compares the activity of binding to antigen of a H chain chimeric/L chain chimeric antibody, a H chain humanized version e/L chain chimeric antibody, and a H chain humanized version e/L chain humanized version b antibody.
Figure 16:
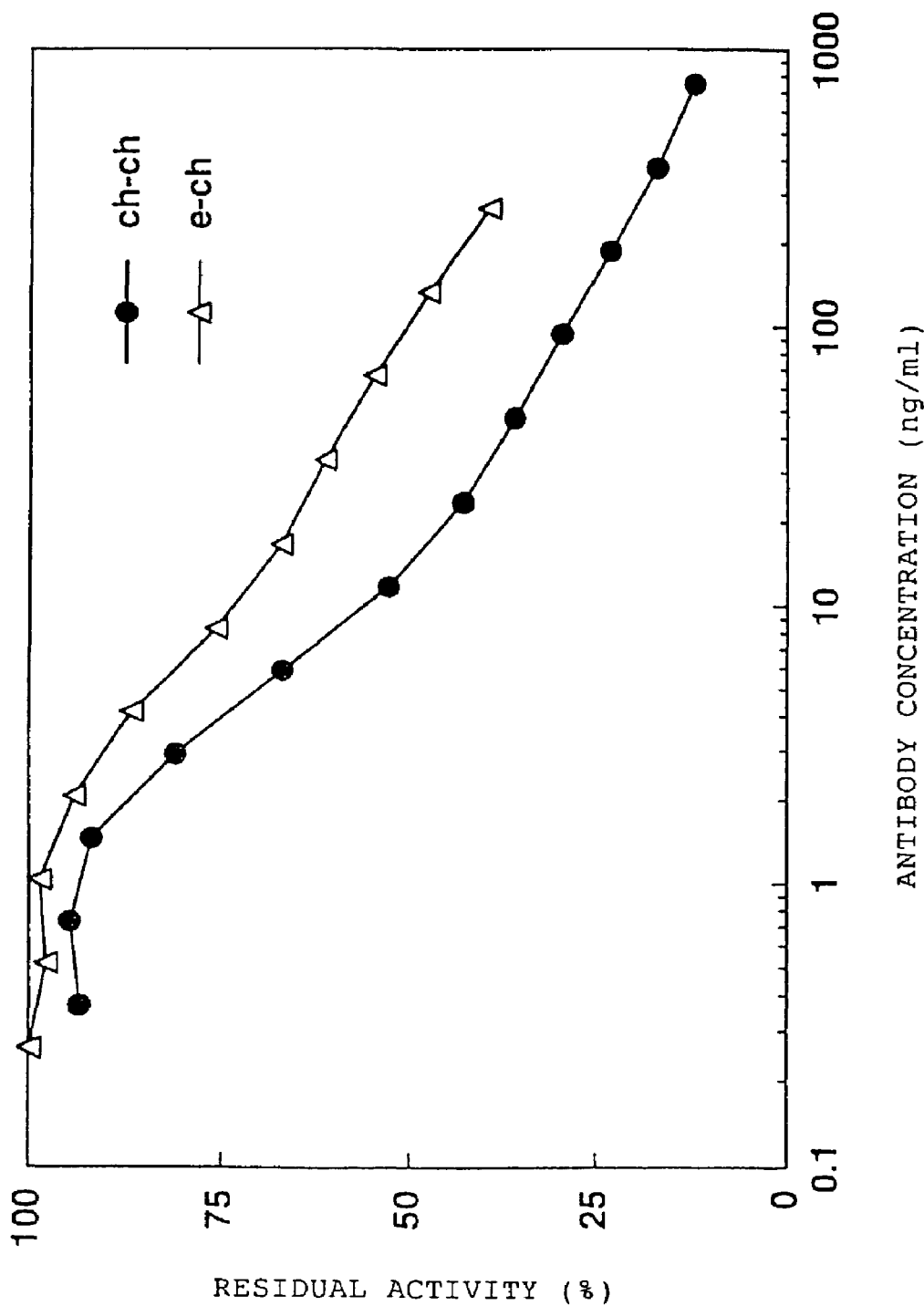
FIG. 16 is a graph that compares the activity of neutralizing human TF of a H chain chimeric/L chain chimeric antibody and H chain humanized version e/L chain chimeric antibody.
Figure 17:
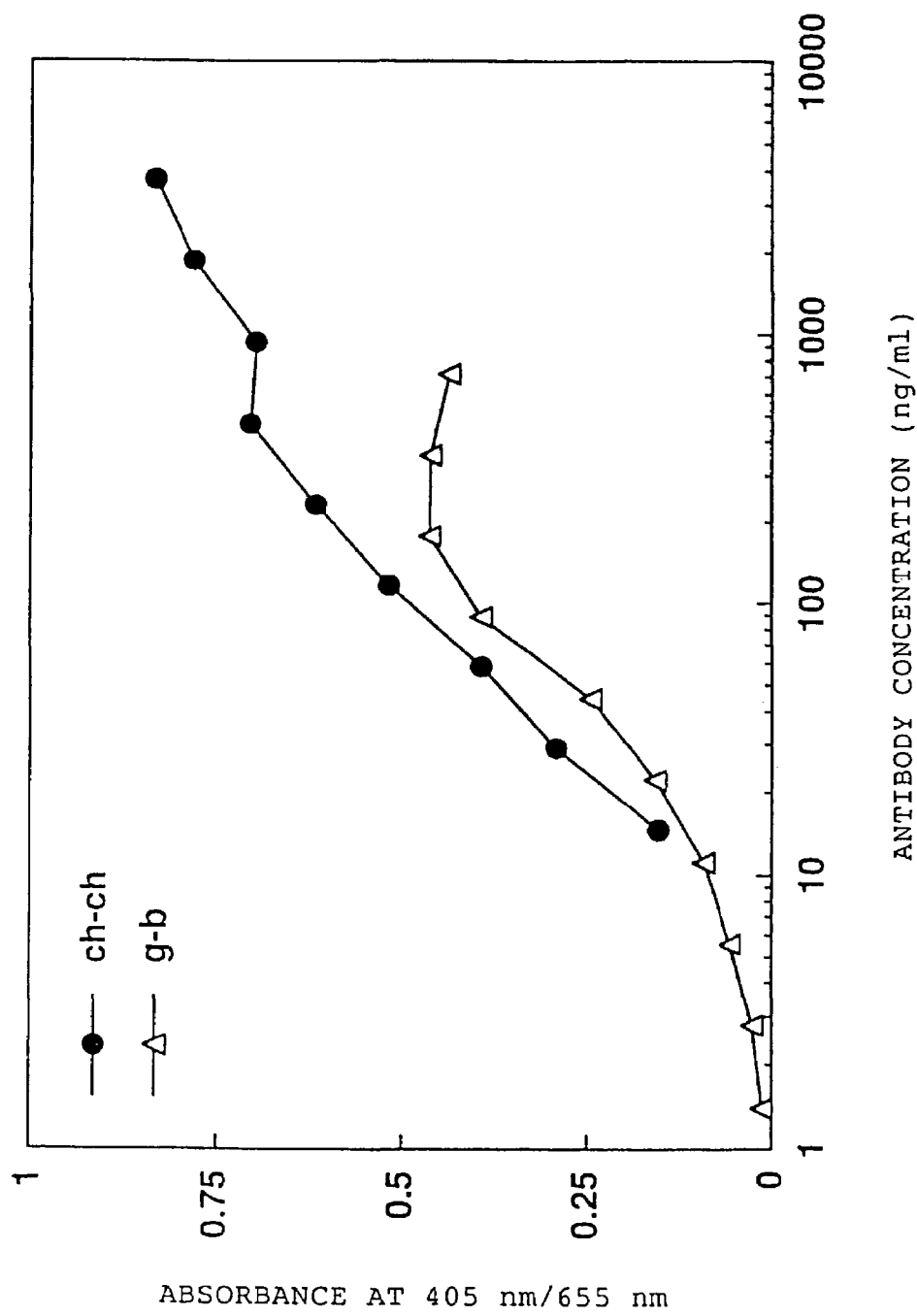
FIG. 17 is a graph that compares the activity of binding to antigen of a H chain chimeric/L chain chimeric antibody and H chain humanized version g/L chain humanized version b antibody.
Figure 18:
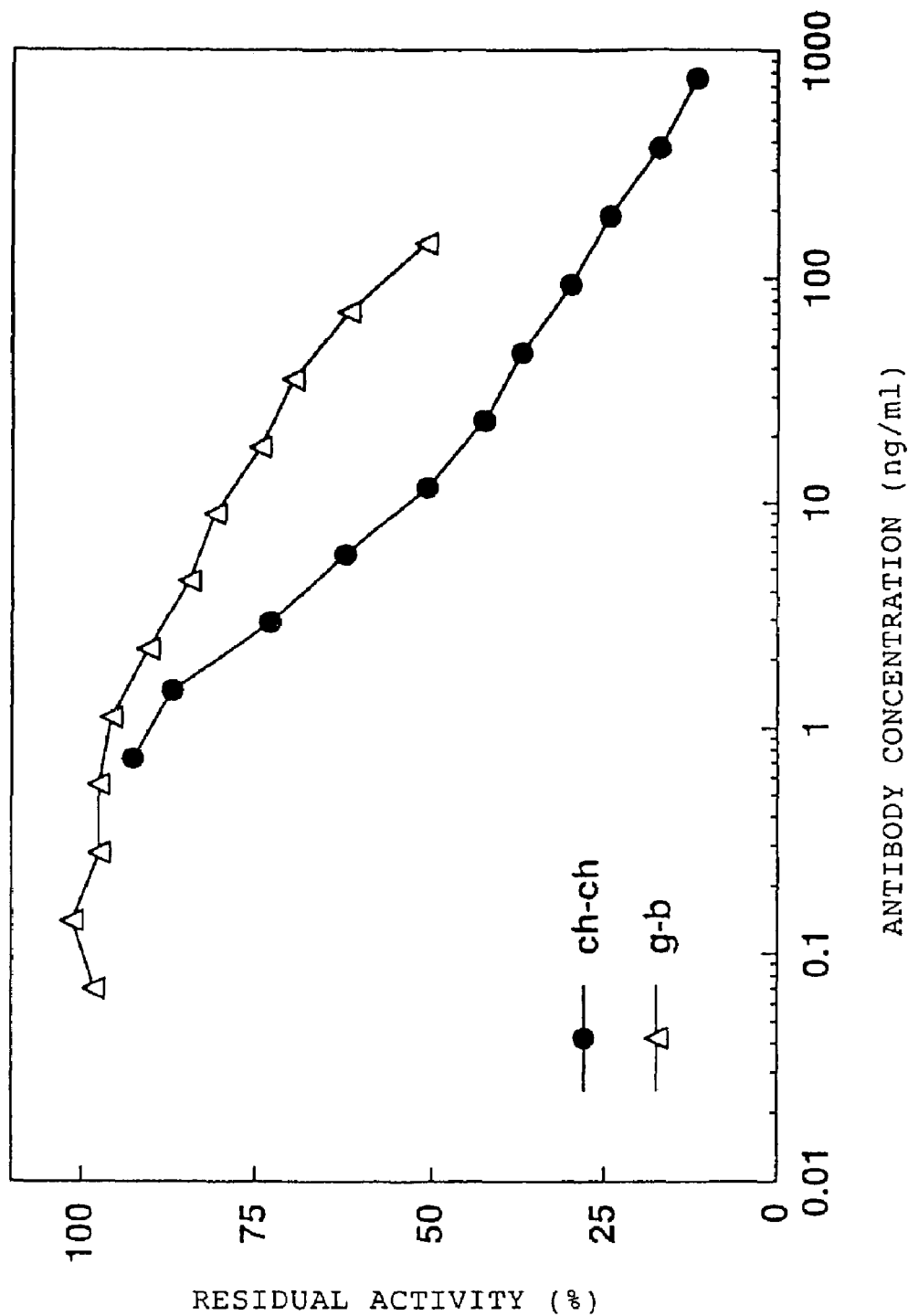
FIG. 18 is a graph that compares the activity of neutralizing human TF of a H chain chimeric/L chain chimeric antibody and H chain humanized version g/L chain humanized version b antibody.
Figure 19:
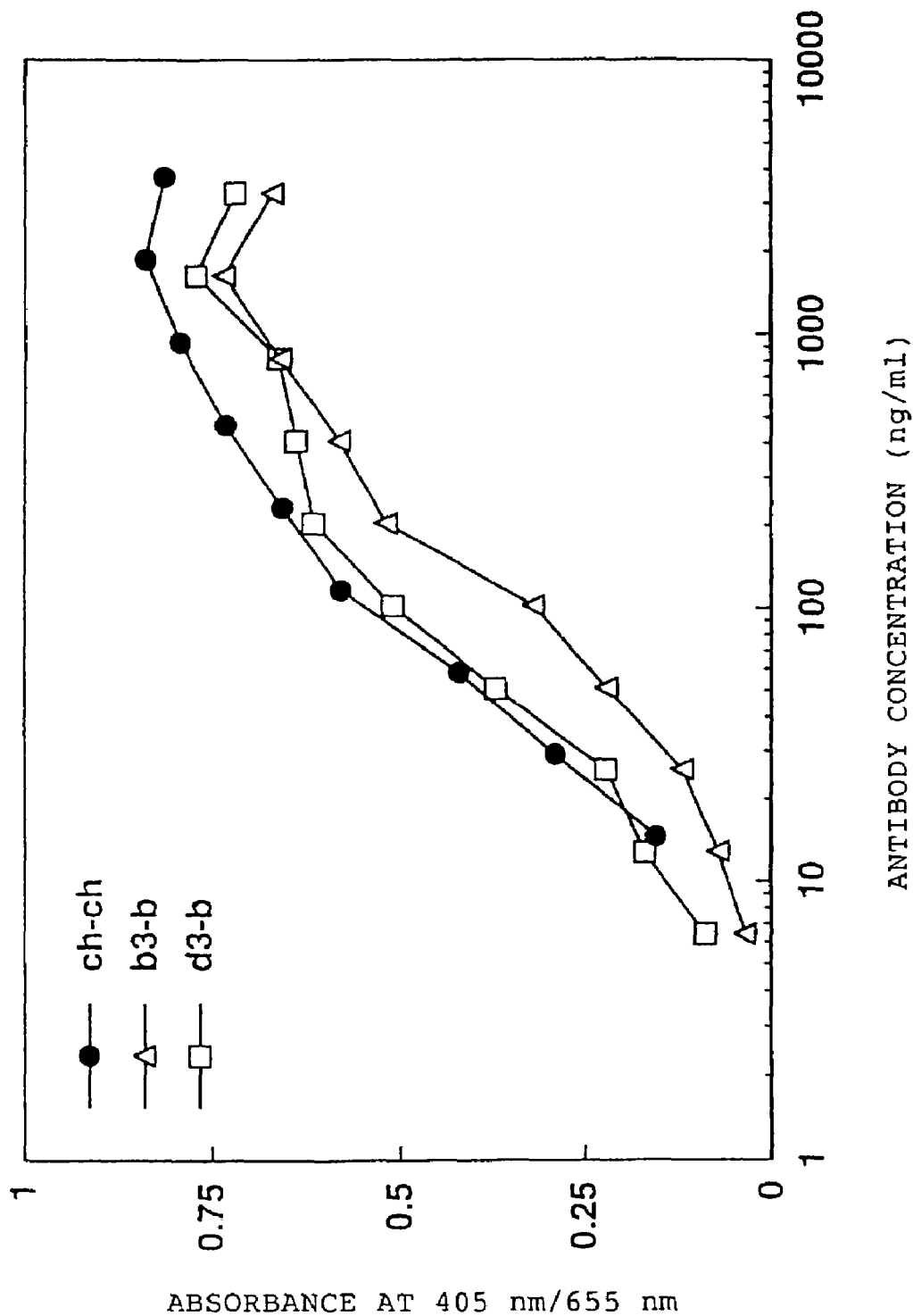
FIG. 19 is a graph that compares the activity of binding to antigen of a H chain chimeric/L chain chimeric antibody, a H chain humanized version b3/L chain humanized version b antibody, and a H chain humanized version d3/L chain humanized version b antibody.
Figure 20:
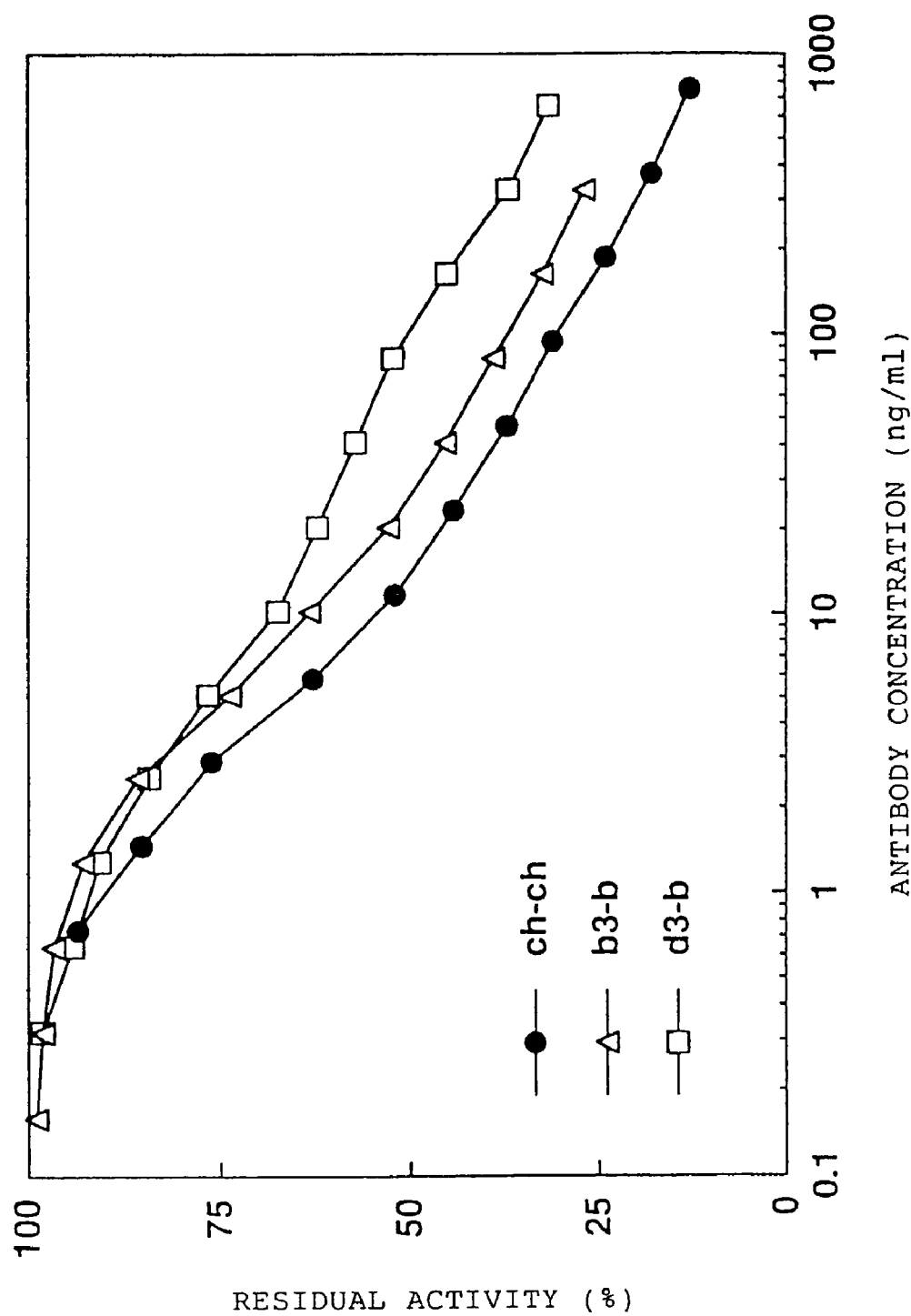
FIG. 20 is a graph that compares the activity of neutralizing human TF of a H chain chimeric/L chain chimeric antibody, a H chain humanized version b3/L chain humanized version b antibody, and a H chain humanized version d3/L chain humanized version b antibody.
Figure 21:
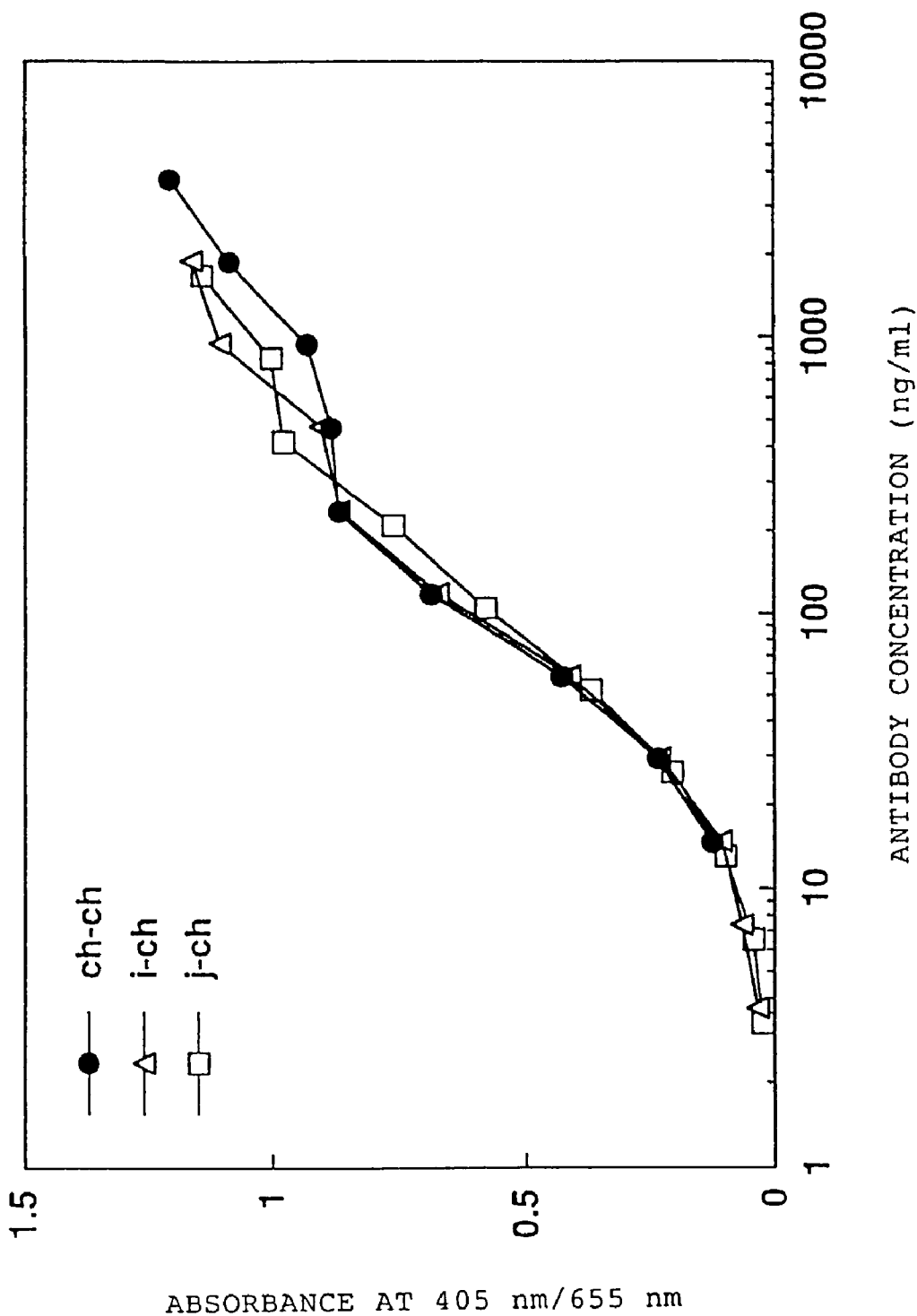
FIG. 21 is a graph that compares the activity of binding to antigen of a H chain chimeric/L chain chimeric antibody, a H chain humanized version i/L chain chimeric antibody, and a H chain humanized version j/L chain chimeric antibody.
Figure 22:
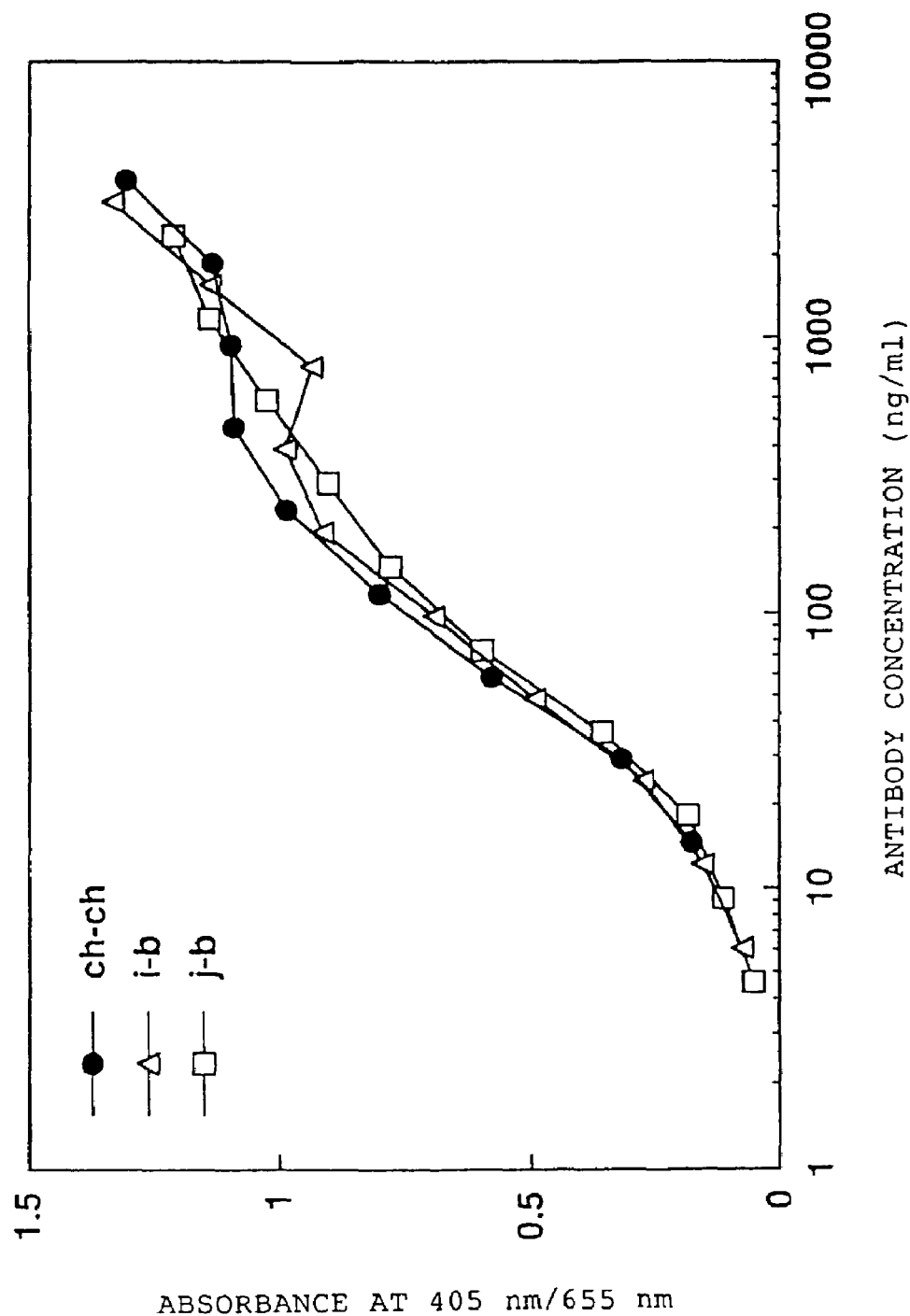
FIG. 22 is a graph that compares the activity of binding to antigen of a H chain chimeric/L chain chimeric antibody, a H chain humanized version i/L chain humanized version b antibody, and a H chain humanized version j/L chain humanized version b antibody.
Figure 23:
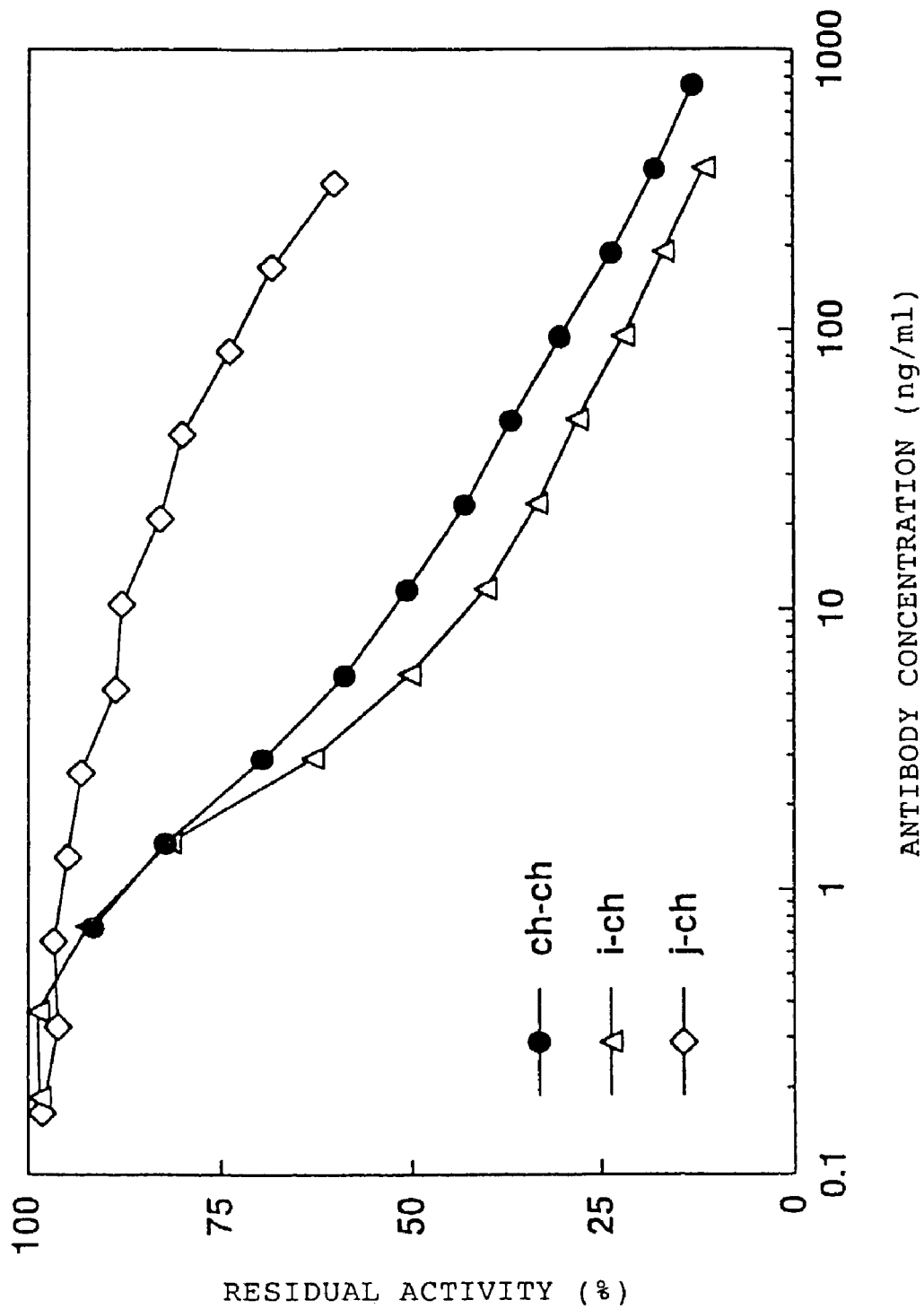
FIG. 23 is a graph that compares the activity of neutralizing human TF of a H chain chimeric/L chain chimeric antibody, a H chain humanized version i/L chain chimeric antibody, and a H chain humanized version j/L chain chimeric antibody.
Figure 24:
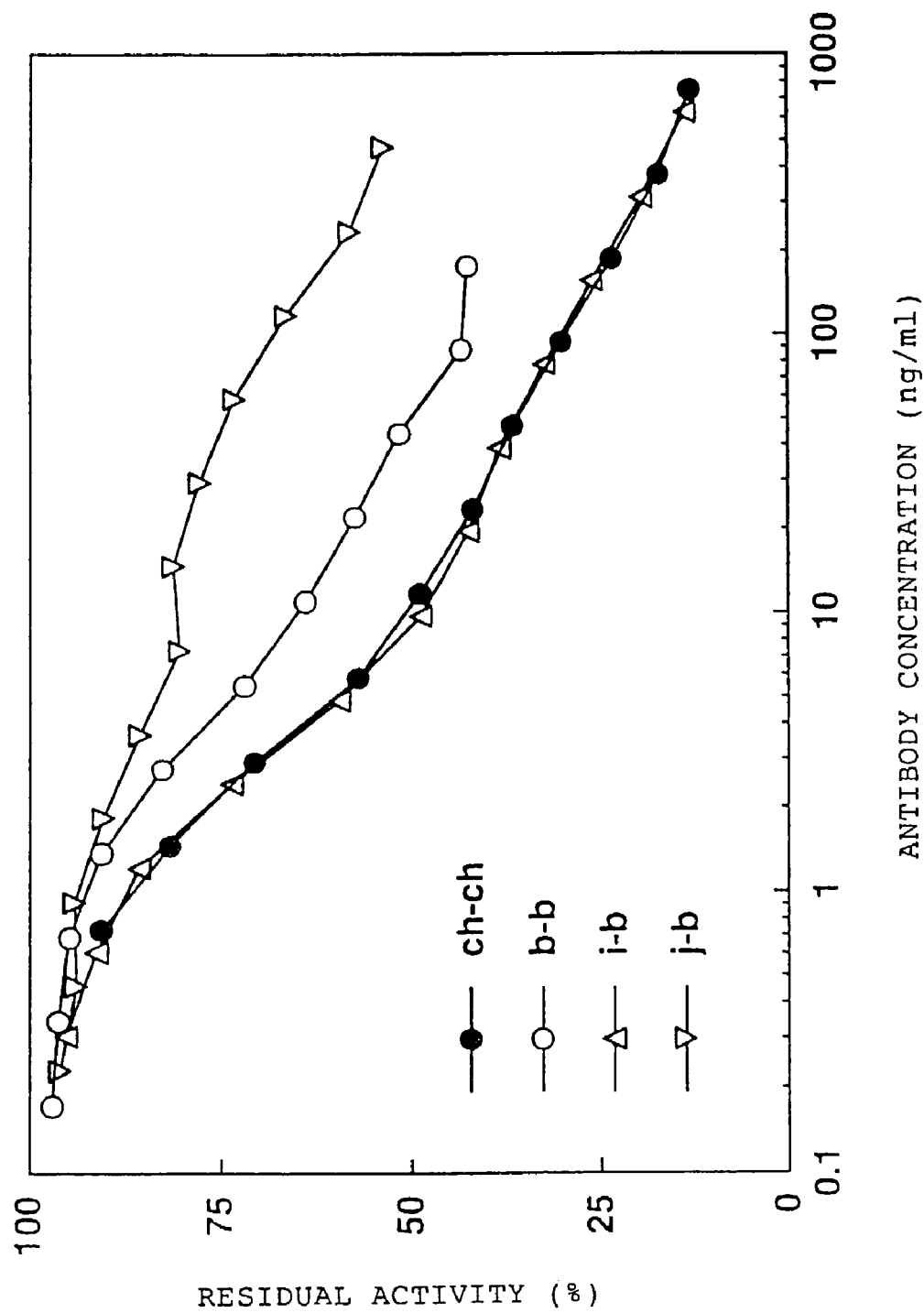
FIG. 24 is a graph that compares the activity of neutralizing human TF of a H chain chimeric/L chain chimeric antibody, a H chain humanized version b/L chain humanized version b antibody, a H chain humanized version i/L chain humanized version b antibody, and a H chain humanized version j/L chain humanized version b antibody.

An antibody (a-a) which is the humanized H chain version "a" combined with the humanized L chain version "a" was generated, and was tested for the binding activity to the antigen by the cell ELISA. The amount bound to the antigen was found to be decreased in the high concentration side (FIG. 3). The neutralizing activity against the antigen by FXa production-inhibition was weak as compared to that of the positive control chimeric antibody (FIG. 4). Therefore, it was decided to perform the version-up of the humanized H chain and L chain by FR-shuffling. The chimeric antibody used herein was the one that was expressed in COS-7 cells, purified, and evaluated.

(iv) Combination of the Humanized H Chain Versions "b", "c", and "d", and a Chimeric L Chain Antibodies ("b-ch", "c-ch", and "d-ch", respectively) which are the humanized H chain subjected to version-up by FR-shuffling combined with a chimeric L chain were generated, and were tested for the binding activity to the antigen by the cell ELISA. "d-ch" exhibited a binding activity equal to that of the chimeric antibody, and "b-ch" and "c-ch" exhibited a slightly lower binding activity (FIGS. 5 and 6). On the other hand, the neutralizing activity against the antigen as compared to the that of positive control chimeric antibody was almost equal in "b-ch", and slightly weak in "d-ch". In version "c-ch", it was significantly weaker than that of the chimeric antibody (FIG. 7). Therefore, the humanized H chain versions "b" and "d" were considered the ones of the humanized H chain to exhibit a high activity.

(v) Combination of the Humanized H Chain Version "b" and the Humanized L Chain Version "a"

An antibody (b-a) which is the humanized H chain version "b" subjected to version-up by FR-shuffling combined with the humanized L chain version "a" was generated, and was tested for the binding activity to the antigen by the cell ELISA. The amount bound to the antigen was found to be decreased at the high concentration (FIG. 5). On the other hand, the neutralizing activity against the antigen was significantly weak as compared to that of the positive control chimeric antibody (FIG. 8). Therefore, "b-a" and "a-a" were the ones that exhibit a high activity. The chimeric antibody used herein was the one that was expressed in COS-7 cells, purified, and evaluated.

(vi) Combination of the Humanized L Chain Versions "b" and "c", and a Chimeric H Chain Antibodies ("ch-b" and "ch-c", respectively) which are the humanized L chain versions "b" and "c", combined with a chimeric H chain were generated, and both of them were found to have the binding activity to the antigen and the neutralizing activity against the antigen equal to the chimeric antibody (FIGS. 9 and 10). Therefore, versions "b" and "c" were chosen as a candidate for a humanized antibody L chain. Mouse antibody-derived version "b" which is one amino acid fewer in the amino acid residue number is considered to be superior to version "c" in terms of antigenicity. The chimeric antibody used herein was the one that was expressed in CHO cells DG44, purified, and evaluated. In the evaluation hereinafter the antibody was used as the positive control.

(vii) Combination of the Humanized H Chain Version "b" and the Humanized L Chain Versions "b" and "c"

Antibodies ("b-b" and "b-c", respectively) which are the humanized H chain version "b" combined with the humanized L chain versions "b" and "c" were generated, and tested for the binding activity to the antigen and the neutralizing activity against the antigen. Both of them had a slightly lower activity than that of the chimeric antibody in both the binding activity and the neutralizing activity (FIGS. 11 and 12).

(viii) Combination of the Humanized H Chain Versions "b" and "d", and the Humanized L Chain Version "b"

Antibodies ("b-b" and "d-b", respectively) which are the humanized H chain subjected to version-up by FR-shuffling combined with the humanized L chain version "b" were generated, and were tested for the binding activity to the antigen by the cell ELISA. "d-b" exhibited a binding activity equal to that of the chimeric antibody, and "b-b" exhibited a slightly lower binding activity at the high concentration (FIG. 13). On the other hand, the neutralizing activity against the antigen as compared to that of the positive control chimeric antibody was slightly low in "b-b", and significantly weak in "d-b" (FIG. 14). Therefore, it was shown that "b-b" is a high neutralizing activity version, whereas "d-b" is a high binding activity version.

(ix) Combination of the Humanized H Chain Version "e", and a Chimeric L Chain and the Humanized L Chain Version "b"

Antibodies ("e-ch" and "e-b", respectively) which are the humanized L chain version "e" combined with a chimeric L chain and the humanized version "b" were generated. "e-ch" exhibited a binding activity to the antigen equal to that of the chimeric antibody, but in "e-b" the amount of antibody expressed was very little and most of the binding activity was lost (FIG. 15). The neutralizing activity against the antigen of "e-ch" was significantly low as compared to that of the chimeric antibody (FIG. 16). Therefore, it was concluded that the H chain version "e" combined with L chain version "b" did not work well.

(x) Combination of the Humanized H Chain Versions "f", "g", and "h", and the Humanized L Chain Version. "b"

Antibodies ("f-b", "g-b", and "h-b", respectively) which are the humanized H chain versions "f", "g", and "h" combined with the humanized L chain version "b" were generated. In "f-b" and "h-b" antibody, the amount of antibody expressed was very little. For versions "f" and "h", antibodies combined with the chimeric L chain were generated, but were not expressed. "g-b" reached saturation at a low concentration, and exhibited a binding activity weaker than that of the chimeric antibody (FIG. 17). The neutralizing activity against the antigen of "g-b" was significantly weak as compared to that of the chimeric antibody (FIG. 18).

(xi) Combination of the Humanized H Chain Versions "b1" and "d1", and the Humanized L Chain Version "b"

Antibodies ("b1-b" and "d1-b", respectively) which are the humanized H chain versions "b1" and "d1" combined with the humanized L chain version "b" were generated. Almost no antibody was expressed in any of them. For these, antibodies combined with a chimeric L chain were generated, but were not expressed.

(xii) Combination of the Humanized H Chain Versions "b3" and "d3", and the Humanized L Chain Version "b"

Antibodies ("b3-b" and "d3-b", respectively) which are the humanized H chain versions "b3", and "d3" combined with the humanized L chain version "b" were generated. The binding activity to the antigen of "d3-b" was slightly lower than that of the chimeric antibody, and that of "b3-b" was much lower (FIG. 19). The neutralizing activity against the antigen of "b3-b" was higher than that of "b-b", but was lower than that of the chimeric antibody, and "d3-b" and "b-b" remained equal in activity (FIG. 20).

(xiii) Combination of the Humanized H Chain Versions "i" and "j", and a Chimeric L Chain and the Humanized L Chain Version "b"

Antibodies ("i-ch" and "j-ch", respectively) which are the humanized H chain versions "i" and "j" combined with a chimeric L chain, and antibodies ("i-b" and "j-b", respectively) combined with the humanized L chain version "b" were generated, and were tested for the binding activity to the antigen and the neutralizing activity against the antigen. The binding activity of any of the antibodies was almost equal to that of the chimeric antibody (FIGS. 21 and 22). "i-ch" exhibited the neutralizing activity higher than that of the chimeric antibody, and "j-ch" was significantly lower than that of the chimeric antibody (FIG. 23). "i-b" exhibited the neutralizing activity equal to that of the chimeric antibody, and "j-b"

exhibited a significantly weaker neutralizing activity than that of that of the chimeric antibody (FIG. 24).

(xiv) The Humanized L Chain Versions "b1" and "b2"

Figure 25:
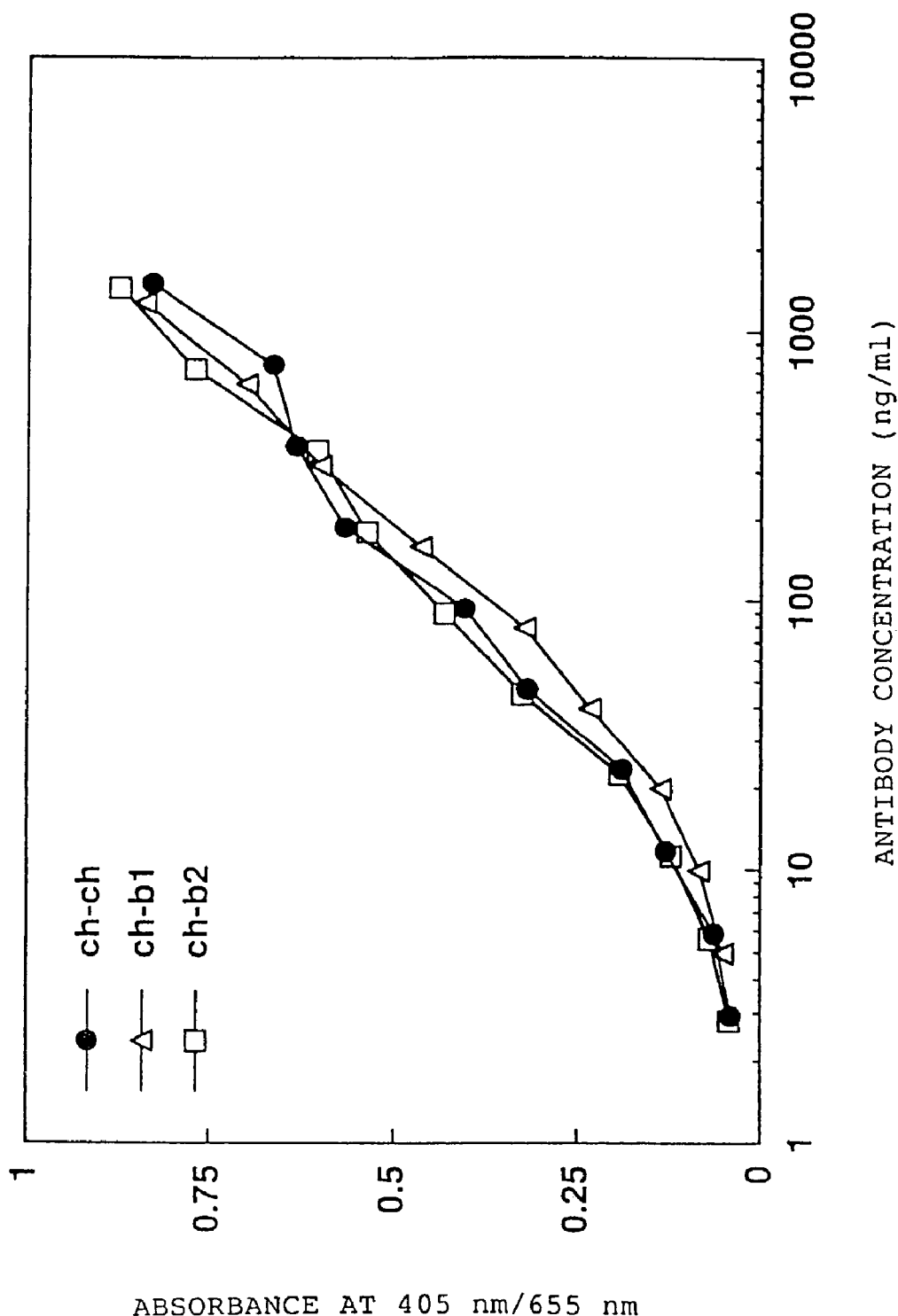
FIG. 25 is a graph that compares the activity of binding to antigen of a H chain chimeric/L chain chimeric antibody, a H chain chimeric/L chain humanized version b1 antibody, and a H chain chimeric/L chain humanized version b2 antibody.
Figure 26:
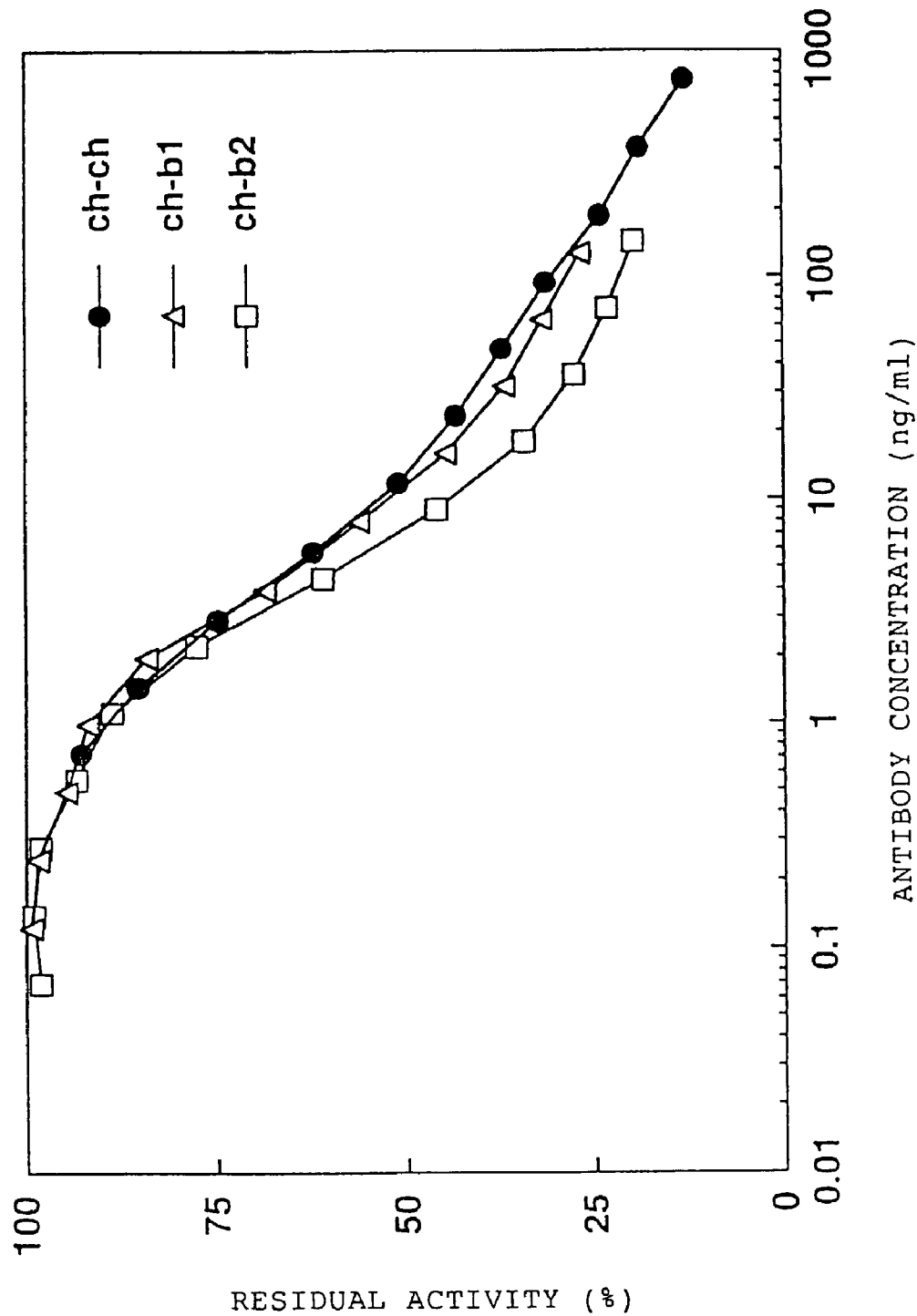
FIG. 26 is a graph that compares the activity of neutralizing human TF of a H chain chimeric/L chain chimeric antibody, a H chain chimeric/L chain humanized version b1 antibody, and a H chain chimeric/L chain humanized version b2 antibody.

When antibodies ("ch-b1" and "ch-b2", respectively) which are the humanized L chain versions "b1" and "b2" combined with a chimeric H chain were generated, both of them exhibited the binding activity to the antigen equal to that of the chimeric antibody (FIG. 25). For the neutralizing activity against the antigen, "ch-b1" exhibited the binding activity equal to that of the chimeric antibody, while "ch-b2" exhibited an activity slightly higher than that of the chimeric antibody at the high concentration (FIG. 26). Versions "b1" and "b2" can be candidates of a humanized antibody L chain, but "b2" is superior in that it has a stronger activity.

(xv) Combination of the Humanized H Chain Version "b" and the Humanized L Chain Version "b2"

Figure 27:
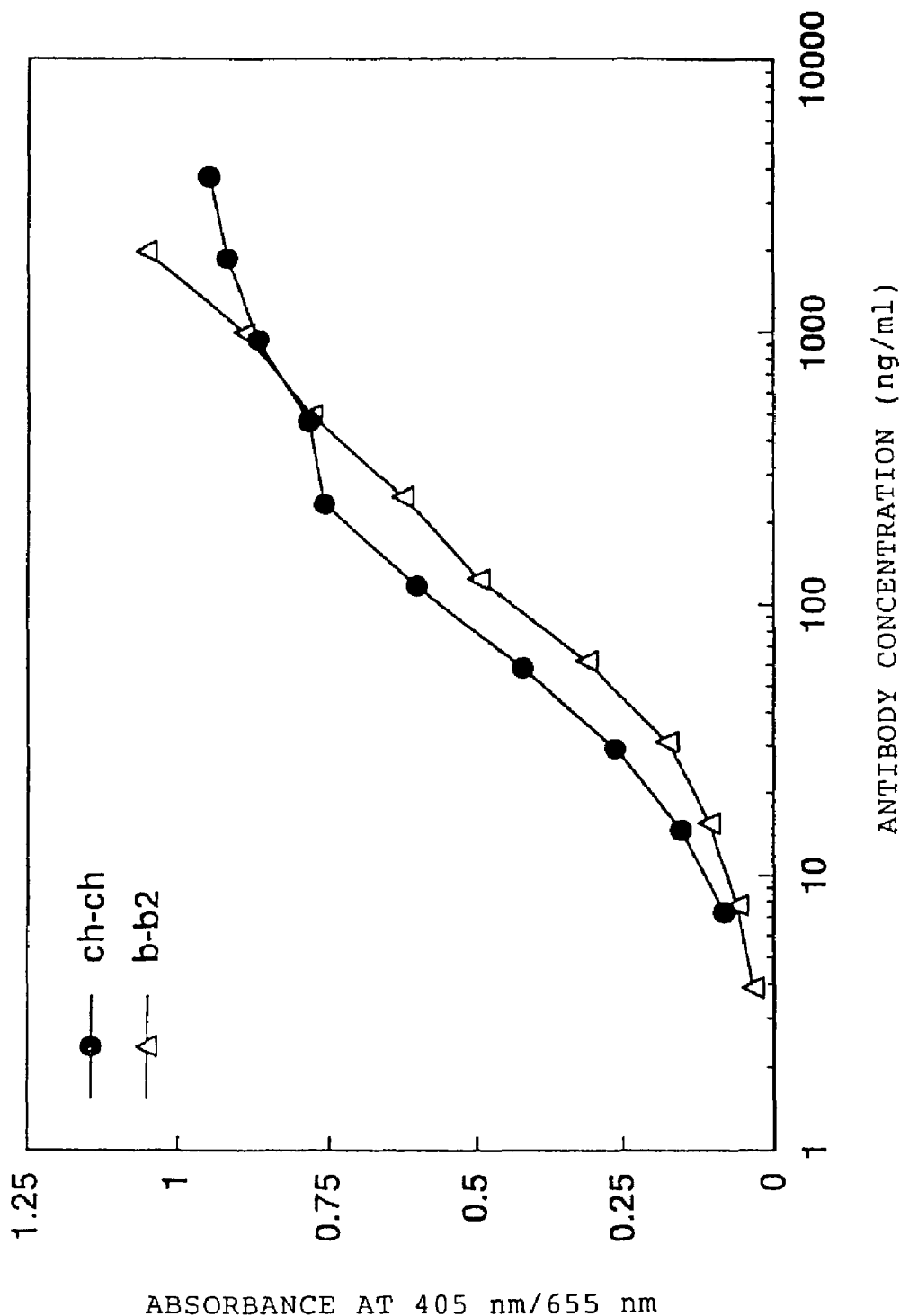
FIG. 27 is a graph that compares the activity of binding to antigen of a H chain chimeric/L chain chimeric antibody and a H chain humanized version b/L chain humanized version b2 antibody.
Figure 28:
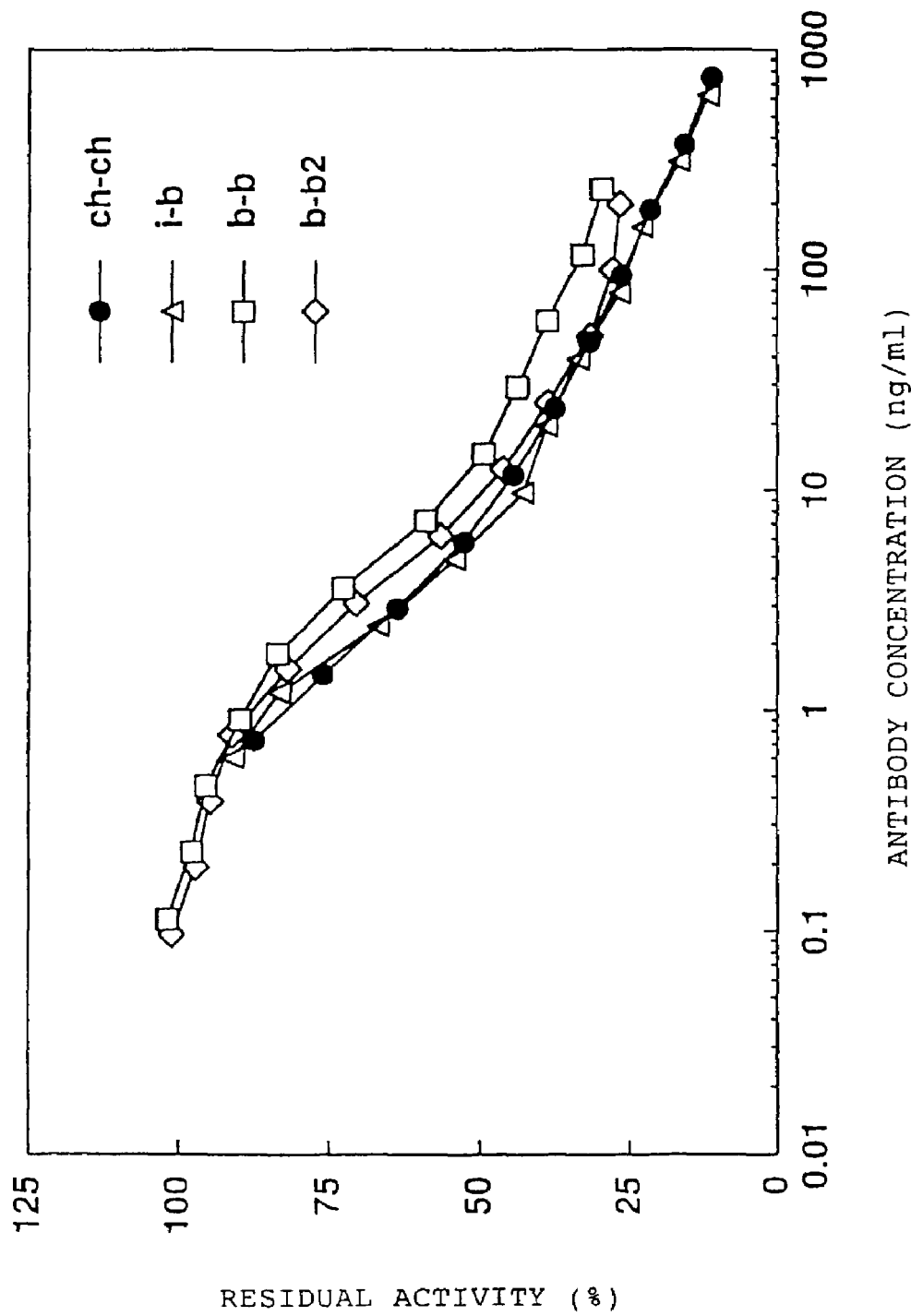
FIG. 28 is a graph that compares the activity of neutralizing human TF of a H chain chimeric/L chain chimeric antibody, a H chain humanized version i/L chain humanized version b antibody, a H chain humanized version b/L chain humanized version b antibody, and a H chain humanized version b/L chain humanized version b2 antibody.

An antibody ("b-b2") which is the humanized H chain version "b" combined with the humanized L chain version "b2" was generated, and was tested for the binding activity to the antigen and the neutralizing activity against the antigen. The binding activity was slightly lower than that of the chimeric antibody (FIG. 27). The neutralizing activity, though slightly higher than that of "b-b", was lower than that of "i-b" (FIG. 28).

(xvi) Combination of the Humanized H Chain Version "i" and, the humanized L chain version "b1" or "b2"

Figure 29:
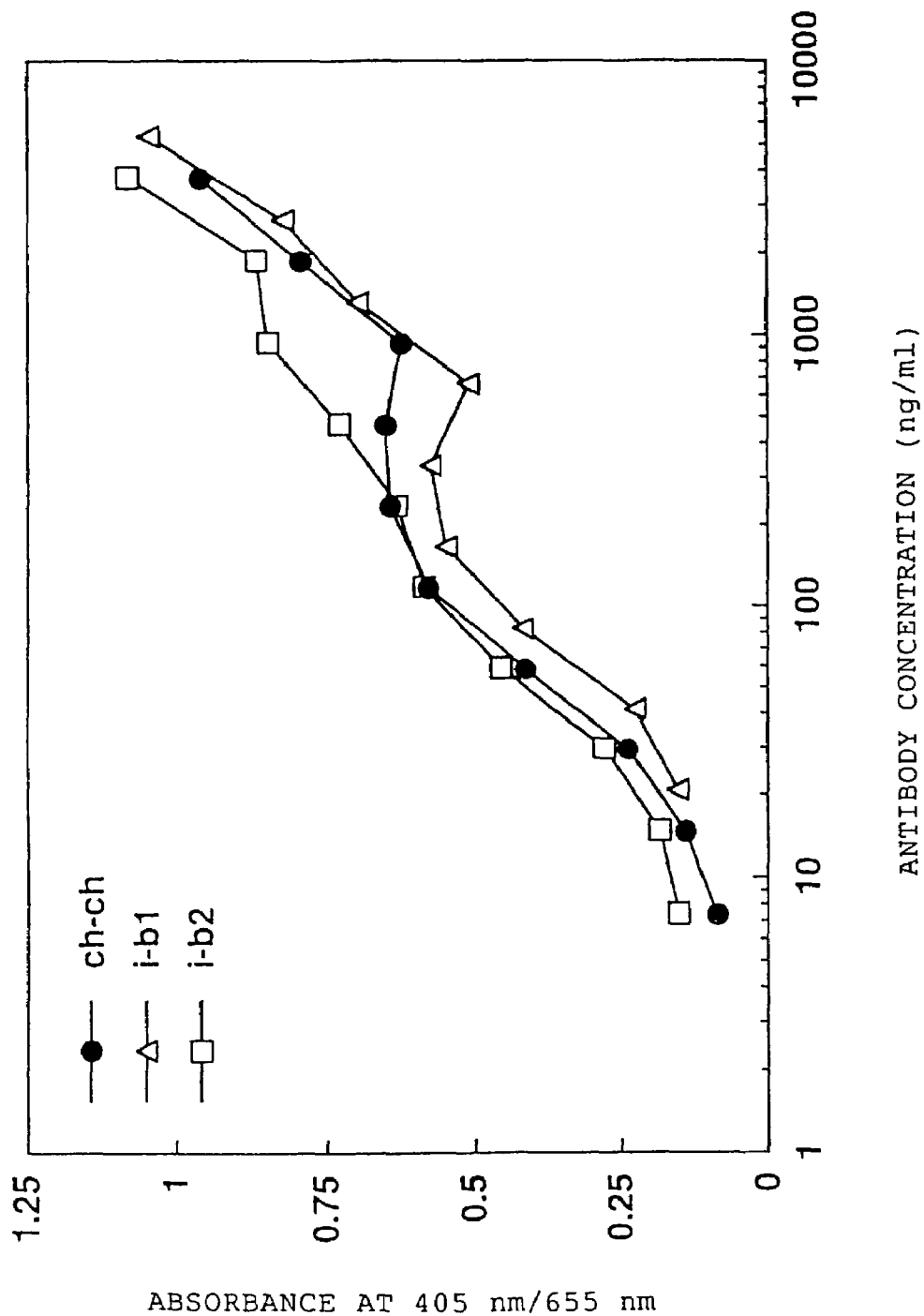
FIG. 29 is a graph that compares the activity of binding to antigen of a H chain chimeric/L chain chimeric antibody, a H chain humanized version i/L chain humanized version b1 antibody, and a H chain humanized version i/L chain humanized version b2 antibody.
Figure 30:
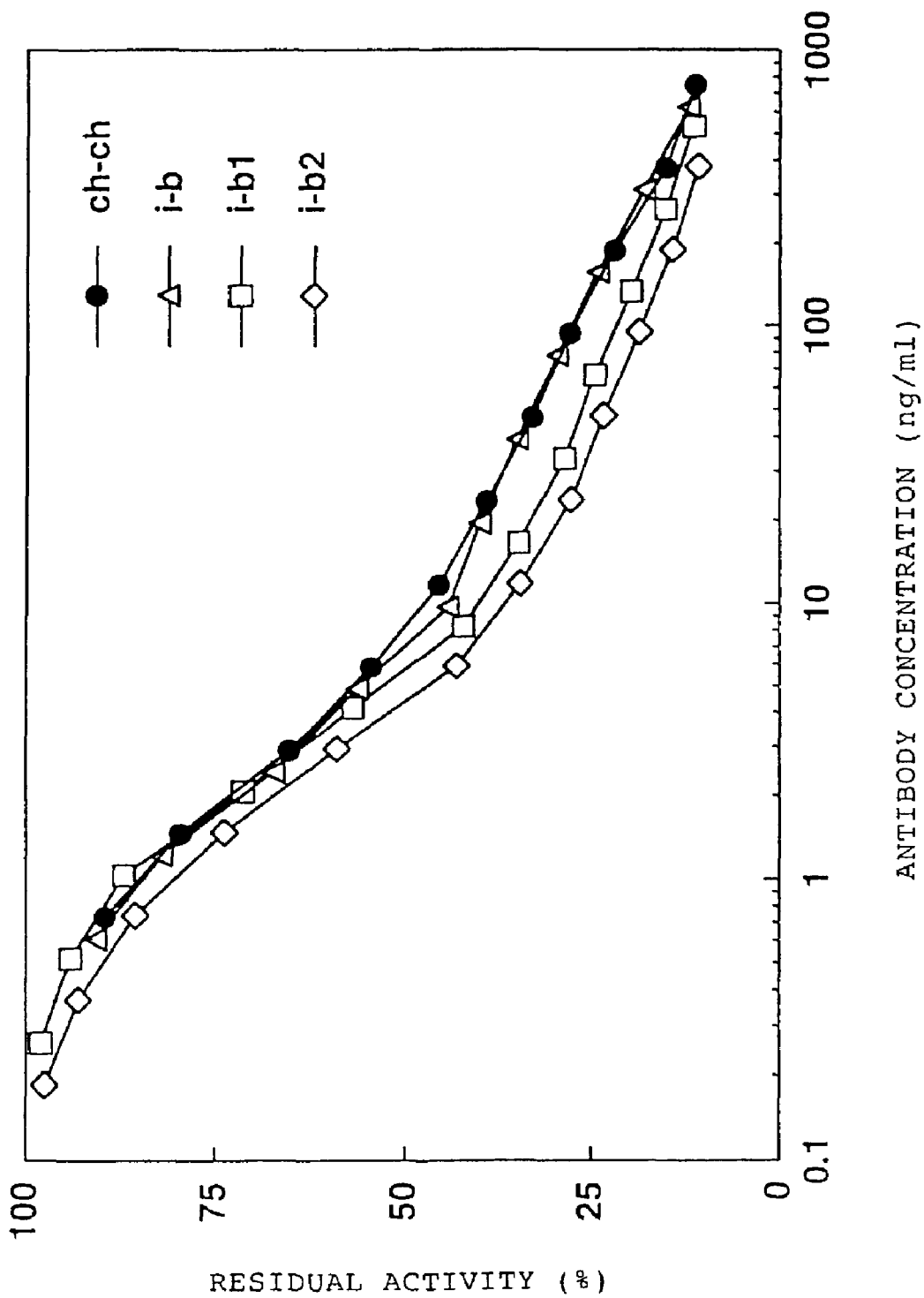
FIG. 30 is a graph that compares the activity of neutralizing human TF of a H chain chimeric/L chain chimeric antibody, a H chain humanized version i/L chain humanized version b antibody, a H chain humanized version i/L chain humanized version b1 antibody, and a H chain humanized version i/L chain humanized version b2 antibody.

Antibodies ("i-b1" and "i-b2", respectively) which are the humanized H chain version "i" combined with the humanized L chain version "b1" or "b2" were generated, and were tested for the binding activity to the antigen and the neutralizing activity against the antigen. The binding activity of "i-b2" was almost equal to that of the chimeric antibody, and that of "i-b1" was slightly lower than that of chimeric antibody (FIG. 29). The neutralizing activity of "i-b1" and "i-b2" was higher than that of the chimeric antibody and "i-b", which was in a decreasing order of "i-b2">"i-b1" (FIG. 30).

Example 5

Preparation of CHO Cell-producing Humanized Antibody and the Evaluation of its Activity (1) Establishment of a Cell Line that Stably Produces CHO In order to establish cell lines that stably produce a humanized antibody (b-b, i-b, and i-b2), an antibody expression gene vector was introduced into CHO cells (DG44) acclaimed to a serum-free medium.

Plasmid DNA, hHvb-hLvb/N5KG4P, hHvi-hLvb/N5KG4P, and hHvi-hLvb2/N5KG4P were digested with the restriction enzyme SspI (Takara Shuzo) and linearized, which was extracted with phenol and chloroform, and purified by ethanol precipitation. The linearized expression gene vector was introduced into the DG44 cells using the electroporation instrument (Gene Pulser; Bio Rad). The DG44 cells were suspended in PBS at a cell concentration of $1 \times 10^7$ cells/ml, and to about 0.8 ml of this suspension 10 or 50 μg of the DNA was added, which was subjected to pulses of 1,500 V and 25 μF capacity.

After 10 minutes of the recovery period at room temperature, the treated cells were suspended in a CHO-S-SFMII medium (GIBCO) containing hypoxanthine/thymidine (GIBCO) (hereinafter referred to as HT), which was inoculated on two 96-well plates (Falcon) at 100 μl/well, and cultured in a $CO_2$ incubator. Eight to nine hours after the start of culturing, 100 μl/well of the CHO-S-SFMII medium containing HT and 1 mg/ml GENETICIN (GIBCO) was added to change to 500 μg/ml of the GENETICIN selection medium, and the cells into which the antibody gene had been introduced were selected. The medium was changed with a fresh one once every 3-4 days with ½ the volume. At a time point about 2 weeks after changing to the selection medium, an aliquot of the culture supernatant was recovered from the well in which a favorable cell growth was observed 4-5 days later. The concentration of antibody expressed in the culture supernatant was measured by the ELISA described above for measuring antibody concentration, and cells having a high production yield of antibody were selected.

(2) Large Scale Purification of Humanized Antibody

After the DG44 cell lines selected as above that produce the humanized antibody ("b-b", "i-b", and "i-b2") were cultured for a few days in a 500 ml/bottle of the CHO-S-SFMII medium using a 2 L roller bottle (CORNING), the culture medium was harvested and a fresh CHO-S-SFMII medium was added and cultured again. The culture medium was centrifuged to remove the cell debris, and filtered with a 0.22 μm or 0.45 μm filter. By repeating this, a total of about 2 L each of the culture supernatant was obtained. From the culture supernatant obtained, antibody was purified by the ConSep LC10O system (Millipore) connected to the Protein A affinity column (Poros).

(3) Measurement of Antibody Concentration by ELISA

ELISA plates for measurement of antibody concentration were prepared as follows: Each well of a 96-well ELISA plate (Maxisorp, NUNC) was immobilized with 100 μl of goat anti-human IgGγ antibody (BioSource) prepared to a concentration of 1 μg/ml with CB. After blocking with 200 μl of DB, the culture supernatant of the CHO cells in which antibody had been expressed or the purified antibody was serially diluted with DB, and added to each well.

After incubating at room temperature for 1 hour and washing with RB, 100 μl of alkaline phosphatase-conjugated goat anti-human IgGγ antibody (BioSource) diluted 1000-fold with DB was added. After incubating at room temperature for 1 hour and washing with RB, 100 μl of the substrate solution was added, and then the absorbance at 405/655 nm was measured using the Microplate Reader (Bio Rad). As the standard for the measurement of concentration, human IgG4κ (The Binding Site) was used.

(4) Measurement of Activity of Binding to the Antigen

Cell ELISA plates for measurement of antigen binding were prepared as follows. Cells used were human bladder carcinoma cells J82 (ATCC HTB-1), which were inoculated onto a 96-well cell culture plate at a cell count of $1 \times 10^5$ cells. This was cultured (RPMI1640 medium containing 10% fetal bovine serum (GIBCO)) for one day in a $CO_2$ incubator to allow the cells to be attached thereto. After discarding the culture liquid, each well was washed twice with PBS. 100 μl of PFA/PBS was added to each well, and placed on ice for 10 minutes to immobilize the cells.

PFA/PBS was discarded, and each well was washed twice with 300 μl of PBS and then blocked with 250 μl of DB. Based on the above result of measurement, the purified antibody was serially diluted with DB starting at 10 μg/ml by a factor of 2, 100 μl of which was added to each well. After incubating at room temperature for 2 hours and washing with RB, 100 μl of alkaline phosphatase-conjugated goat anti-human IgGγ antibody (BioSource) diluted 1000-fold with DB was added. After incubating at room temperature for 1 hour and washing with RB, 100 μl of the substrate solution was added, and then absorbance at 405/655 nm was measured using the Microplate Reader (Bio-Rad).

(5) Measurement of Neutralizing Activity Against TF (Factor Inhibiting Activity Against the FXa Production)

The Factor Xa production-inhibiting activity of humanized antibody was measured with the inhibiting activity against the Factor Xa production activity by the human placenta-derived thromboplastin, Thromborel S (Boehringer AG), as an index. Thus, 60 µl of the buffer (TBS containing 5 mM $CaCl_2$ and 0.1% BSA) was added to 10 µl of 5 mg/ml Thromborel S and 10 µl of the antibody, which was then incubated in a 96-well plate at room temperature for 1 hour. The antibody was serially diluted with the buffer starting at 200 µg/ml by a factor of 5.

Ten µl each of 3.245 µg/ml human Factor X (Celsus Laboratories) and 82.5 ng/ml human Factor VIIa (Enzyme Research) were added thereto, and were further incubated at room temperature for 45 minutes. Ten µl of 0.5 M EDTA was added to stop the reaction. Fifty µl of the chromogenic substrate solution was added thereto and the absorbance at 405/655 nm was determined by the Microplate Reader (Bio Rad). After reacting at room temperature for 30 minutes, the absorbance at 405/655 nm was measured again. The residual activity (%) was determined from each change in absorbance with the absorbance change for 30 minutes at no antibody addition as a 100% activity.

The chromogenic substrate solution was prepared by dissolving the Testzyme chromogenic substrate S-2222 (Chromogenix) according to the attached instructions, and mixing with a polybrene solution (0.6 mg/ml hexadimethylene bromide, SIGMA) at 1:1.

(6) Measurement of Neutralizing Activity Against TF (Inhibiting Activity Against the FX-binding)

The inhibiting activity against the FX-binding of humanized antibody was measured using the human placenta-derived thromboplastin, Thromborel S (Boehringer AG), in which a complex of TF and Factor VIIa had previously been formed and the inhibiting activity against the FX-binding was measured with the Factor Xa production activity of the TF-FVIIa complex as an index. Thus, 60 µl of the buffer (TBS containing 5 mM $CaCl_2$ and 0.1% BSA) was added to 10 µl of 5 mg/ml Thromborel S and 10 µl of 82.5 ng/ml human Factor VIIa (Enzyme Research), which was preincubated in a 96-well plate at room temperature for 1 hour.

Ten µl of the antibody solution was added thereto, incubated at room temperature for 5 minutes, and 10 µl of 3.245 µg/ml human Factor X (Celsus Laboratories) was added and was further incubated at room temperature for 45 minutes. The antibody was serially diluted with the buffer starting at 200 µg/ml by a factor of 2. Ten µl of 0.5 M EDTA was added to stop the reaction. Fifty µl of the chromogenic substrate solution was added thereto and the absorbance at 405/655 nm was determined by the Microplate Reader (Bio Rad). After reacting at room temperature for 30 minutes, the absorbance at 405/655 nm was measured again. The residual activity (%) was determined from each change in absorbance with the absorbance change for 30 minutes at no antibody addition as a 100% activity.

The chromogenic substrate solution was prepared by dissolving the Testzyme chromogenic substrate S-2222 (Chromogenix) according to the attached instructions, and mixing with a polybrene solution (0.6 mg/ml hexadimethylene bromide, SIGMA) at 1:1.

(7) Measurement of Neutralizing Activity Against the Inhibiting Activity Against the (Plasma Coagulation)

The neutralizing activity against TF (inhibiting activity against the plasma coagulation) of humanized antibody was measured using, as an index, prothrombin time determined using the human placenta-derived thromboplastin, Thromborel S (Boehringer AG). Thus, 100 µl of human plasma (Cosmo Bio) was placed into a sample cup, to which 50 µl of antibody diluted at various concentrations was added, and heated at 37° C. for 3 minutes. Fifty µl of 1.25 mg/ml Thromborel S that had previously been preheated at 37° C. was added to start plasma coagulation. The coagulation time was measured using the Amelung KC-10A connected to the Amelung CR-A (both from M. C. Medical).

The antibody was serially diluted with TBS containing 0.1% BSA (hereinafter referred to as BSA-TBS) starting at 80 µg/ml by a factor of 2. With the coagulation time of no antibody addition as 100% TF plasma coagulation activity, the residual TF activity was calculated from each coagulation time at antibody addition based on a standard curve obtained by plotting the concentration of Thromborel S and the coagulation time.

The standard curve was created from the various concentration of Thromborel S and the coagulation time was measured. Fifty µl of BSA-TBS was added to 50 µl of appropriately diluted Thromborel S, which was heated at 37° C. for 3 minutes, 100 µl of human plasma preheated at 37° C. was added to start coagulation, and the coagulation time was determined. Thromborel S was serially diluted with the Hank's buffer (GIBCO) containing 25 mM $CaCl_2$ starting at 6.25 mg/ml by a factor of 2. The Thromborel S concentration was plotted on the abscissa, and the coagulation time on the ordinate on a log-log paper, which was rendered a standard curve.

(8) Activity Evaluation

Figure 31:
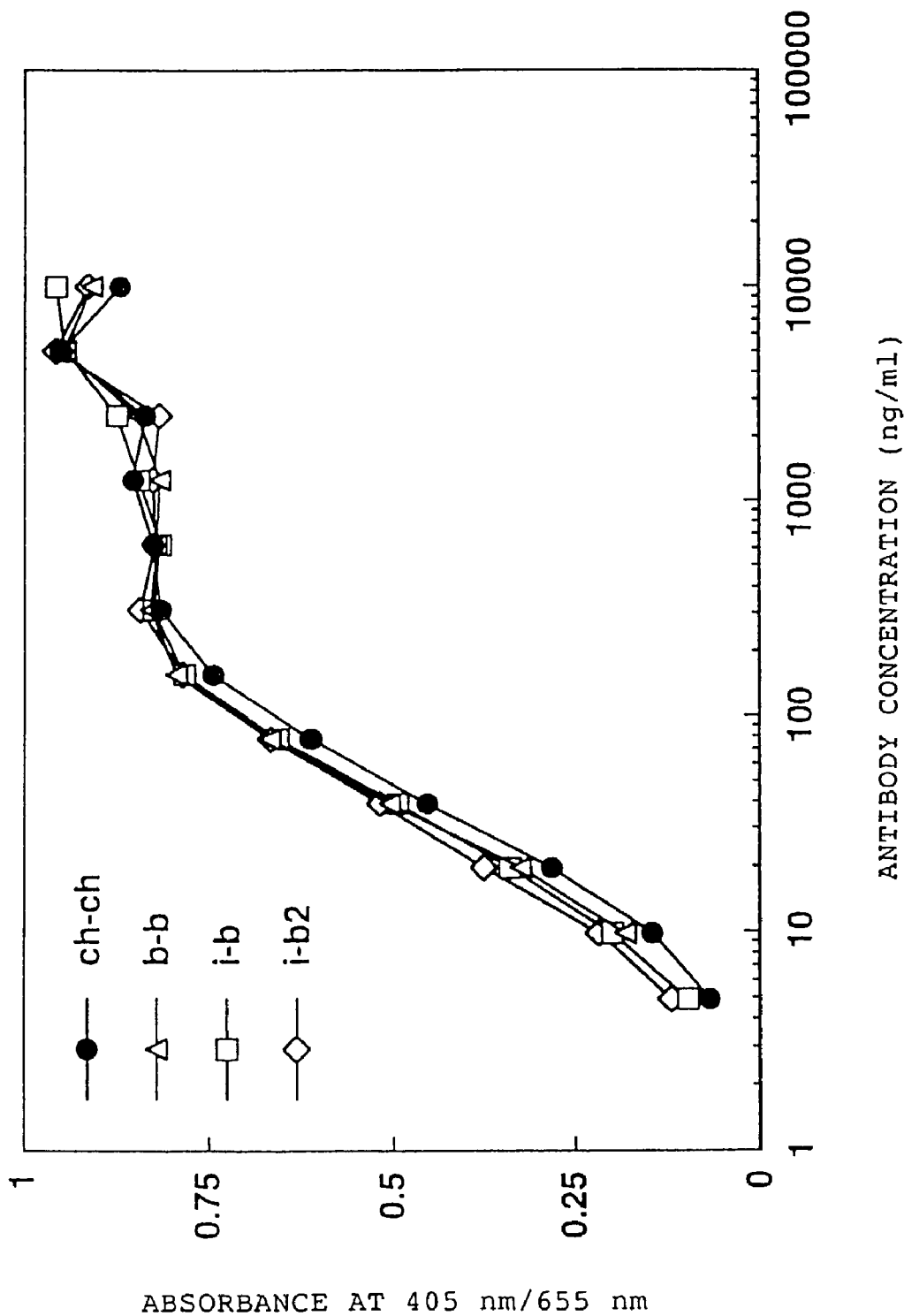
FIG. 31 is a graph that compares the activity of binding to antigen of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.
Figure 32:
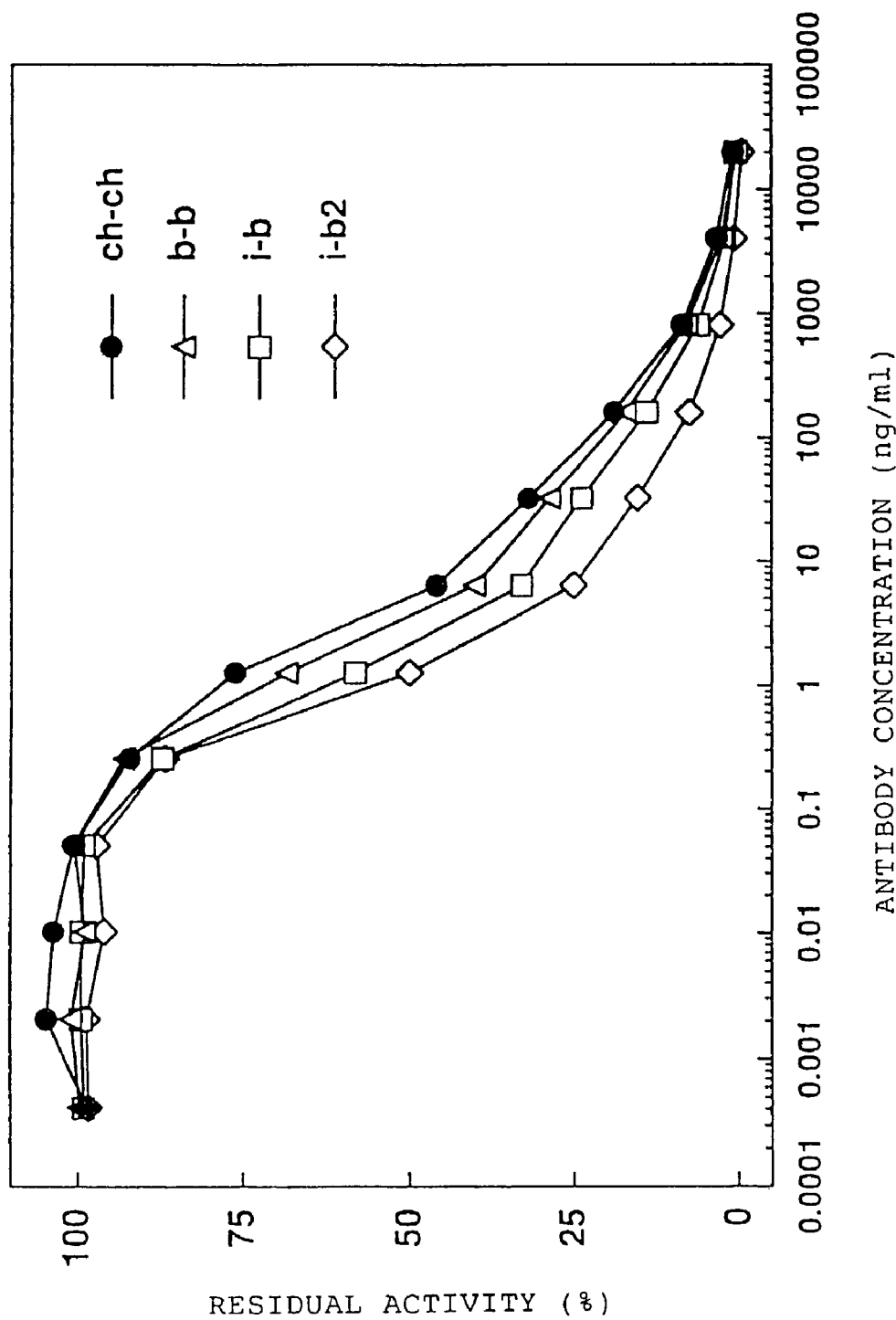
FIG. 32 is a graph that compares the activity of neutralizing human TF (the activity to inhibit the production of Factor Xa by TF) of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.
Figure 33:
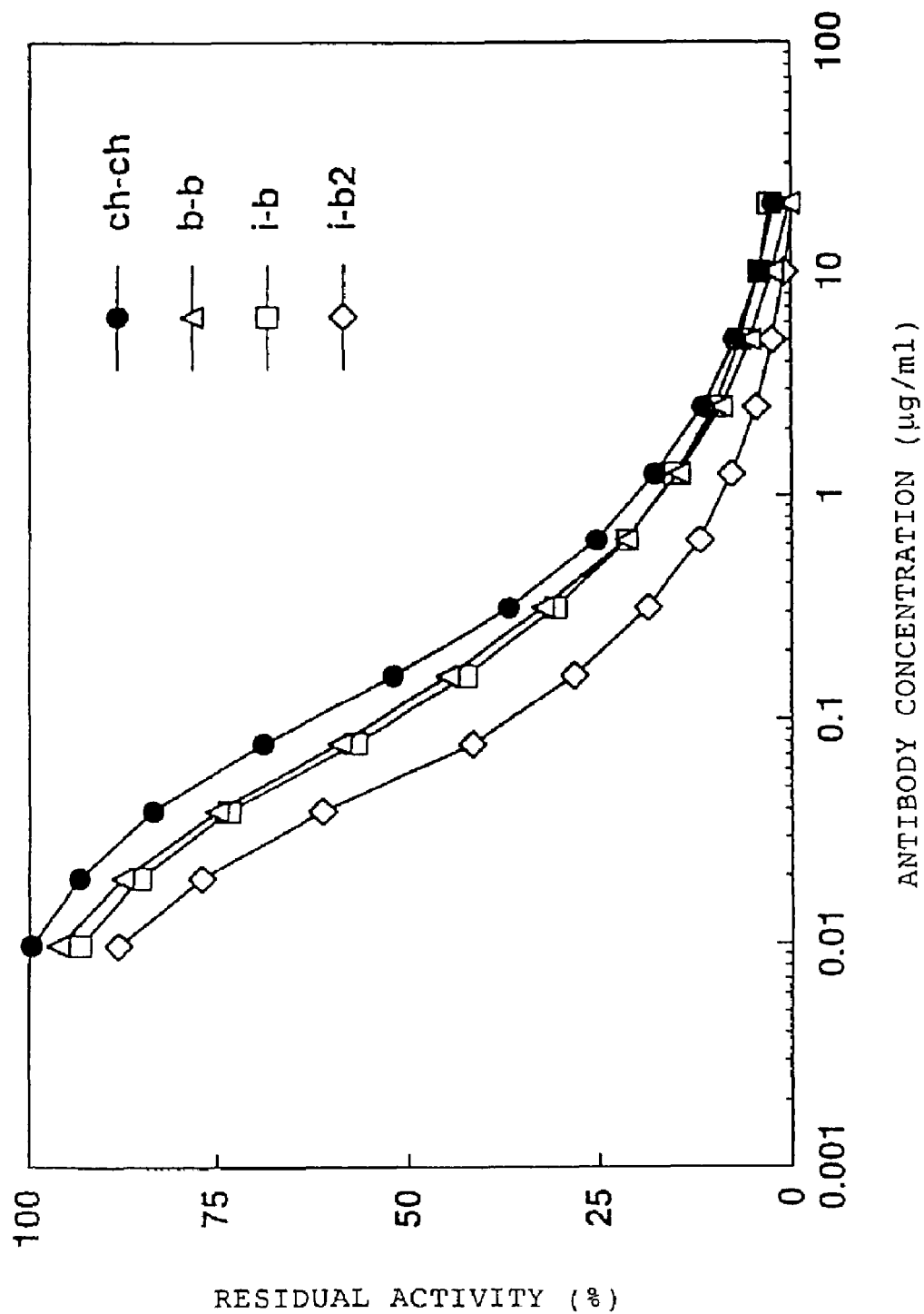
FIG. 33 is a graph that compares the activity of neutralizing human TF (the activity to inhibit the binding of Factor X) of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.
Figure 34:
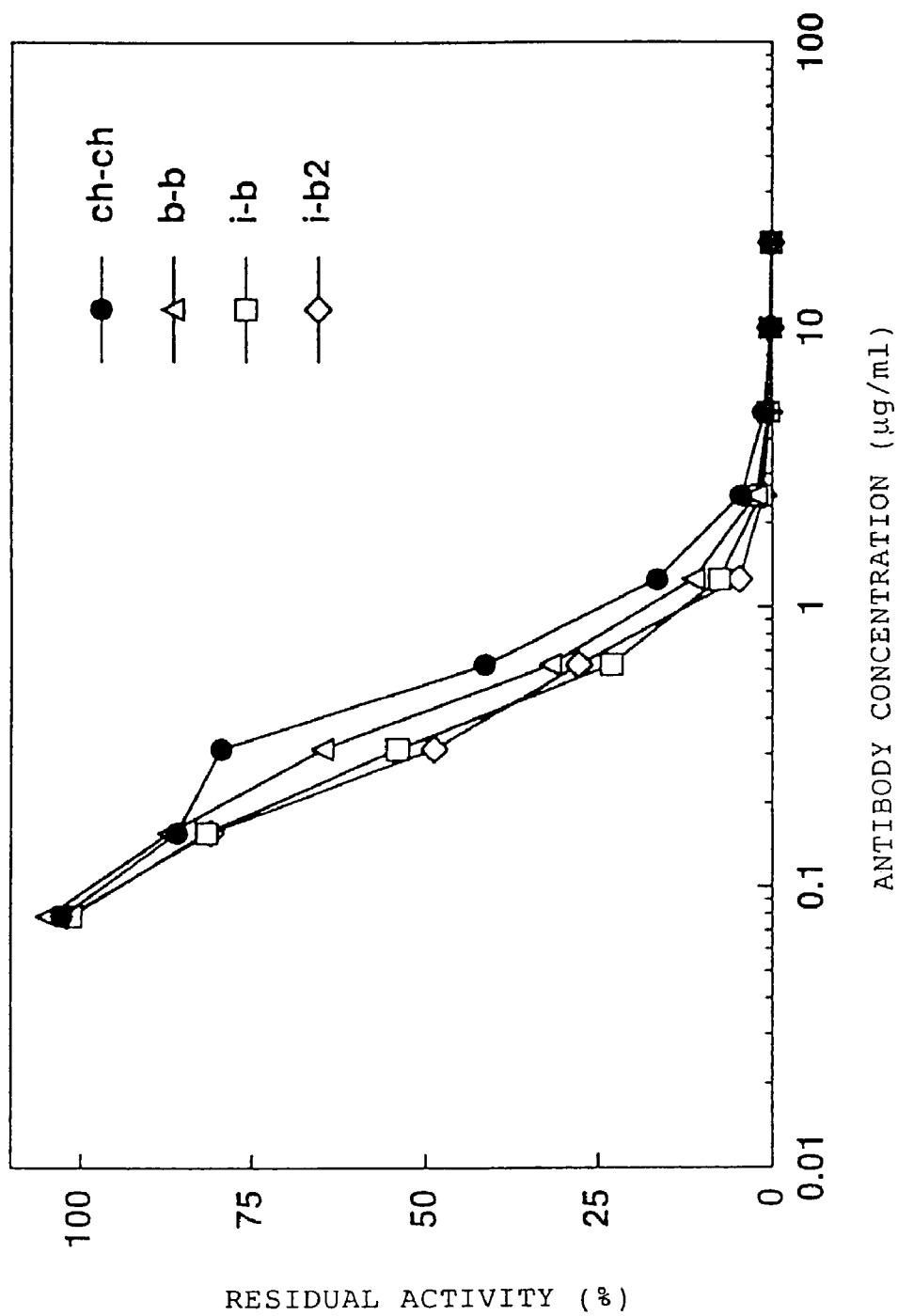
FIG. 34 is a graph that compares the activity of neutralizing human TF (the activity to inhibit the plasma coagulation by TF) of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.

All humanized antibodies, "b-b", "i-b", and "i-b2" had an activity equal to or greater than that of the chimeric antibody (FIG. 31). For inhibiting activity against FXa production, inhibiting activity FX-binding, and inhibiting activity against plasma coagulation as well, the humanized antibodies, "b-b", "i-b", and "i-b2" had an activity equal to or greater than that of the chimeric antibody, and the activity was of a decreasing order "i-b2">"i-b">"b-b" (FIGS. 32, 33, and 34).

Example 6

Kinetic Analysis in Interaction of TF and Anti-TF Antibody Using BIACORE

Kinetic analysis of the antigen-antibody reaction was carried out using BIACORE. The recombinant Protein G was immobilized on a sensor chip, to which the antibody was coupled. The purified recombinant TF (a soluble TF in which the FLAG peptide was tagged at 1-219) was used as the antigen, and the-soluble TF prepared at various concentrations were used as analytes. From the sensorgram obtained, kinetic parameters (dissociation rate constants kdiss, and binding rate constants kass) were calculated. For kinetic analysis, reference was made to "Kinetic analysis of monoclonal antibody-antigen interactions with a new biosensor based analytical system" (Karlsson, R. et al., (1991) J. Immunol. Methods 145: 229-240).

(1) Immobilization of Protein G to the Sensor Chip

Protein G (ZYMED) is immobilized to the censor chip CM5 (BIACORE).

As the running buffer the HBS-EP buffer (0.01 M HEPES, pH 7.4, 0.15 M NaCl, 3 mM EDTA, 0.005% polysorbate 20 (v/v)) (BIACORE) was used, and the flow rate was 5 µl/min. The carboxyl groups of carboxymethyl dextran on the sensor chip CM5 were activated by the injection of 0.05 M N-hydroxysuccinimide (NHS)/0.2 M N-ethyl-N'-(3-dimetylaminopropyl)-carbodiimide hydrochloride (EDC). Subsequently, 10 µl Of 50 µg/ml Protein G was injected, and this was repeated for three times for immobilization. Protein G was prepared by dissolving in 10 mM Tris-HCl buffer (pH 7.5) to a concentration of 10 mg/ml, and diluting to 50 μg/ml with 10 mM sodium acetate buffer (pH 4.0). Further 100 μl of 1.0 M ethanolamine-hydrochloride (pH 8.5) was injected to block the excess active groups. To this were injected 10 μl of 0.1 M glycine-hydrochloric acid buffer (pH 2.5) and 10 μl of 10 mM hydrochloric acid to wash off non-covalently bound substances. By conducting this for each flow cell and injecting 10 μl Of 72 nM humanized anti-TF antibody version "ib2", it was confirmed that about 1000 RU bound.

(2) Interaction of Immobilized Anti-TF Antibody and Human TF

Human TF in which the FLAG peptide had been linked to the C-terminal of the amino acid sequence 1-219 was expressed in CHO cells and was purified. This was used as the soluble TF.

As the running buffer, the HBS-EP buffer was used. Ten μl Of 72 mM antibody solution was injected at a flow rate of 20 μl/min to immobilize antibody. The antibody was diluted with the HBS-EP buffer. Forty μl Of the soluble human TF solution at various concentrations were injected at a flow rate of 30 μl/min thereto. In the analysis, 80 seconds for injection was set as the binding phase and then changed to the HBS-EP buffer to set the dissociation phase of 120 seconds. After the dissociation phase was over, 10 μl of 20 mM hydrochloric acid was injected to reconstitute the sensor chip. The binding, dissociation, and reconstitution were set as one cycle, and the sensorgram was obtained for each antibody. The soluble human TF solution was prepared at concentrations of 250 nM, 125 nM, 62.5 nM, 31.3 nM, 15.6 nM, 7.81 nM, and 3.91 nM using the HBS-EP buffer. As the blank, the sensorgram obtained by injecting the HBS-EP buffer used for dilution was used.

The above procedure was carried out for each of flow cell No. 1 to 3.

(3) Kinetic Analysis of Interaction

The data file of interest was read in, and the comparison of reaction patterns by superscription was made using as the baseline the sensorgram of the HBS-EP buffer. Furthermore, using an analytical application software "BIAevaluation 2.1" (Pharmacia) exclusively for BIACORE that calculates kinetic parameters (binding rate constants kass and dissociation rate constants kdiss) by curve-fitting, kinetic analysis of interaction was performed. In order to determine the binding rate constants kass, the analysis model type 4 was used (BIAevaluation 2.1 Software Hand book, A1-A5). Based on the values calculated from each flow cell, kinetic parameters for each antibody were obtained. The result (mean of the values calculated from each flow cell±standard deviation) is shown in Table 6.

TABLE 6

Kinetic parameters of chimeric and humanized anti-TF antibody (n = 3)

| | chimeric | b-b | i-b | i-b2 |
|---|---|---|---|---|
| kdiss [×$10^{-4}$ 1/s] | 5.06 ± 0.12 | 9.52 ± 0.22 | 6.49 ± 0.17 | 6.35 ± 0.15 |
| kass [×$10^{5}$ 1/Ms] | 4.65 ± 0.32 | 4.15 ± 0.27 | 4.67 ± 0.30 | 5.44 ± 0.36 |
| KD [×$10^{-9}$ M] | 1.09 ± 0.09 | 2.30 ± 0.15 | 1.39 ± 0.13 | 1.17 ± 0.11 |

Example 7

Measurement of Reactivity of the Humanized Anti-TF Antibody to Human TF

Using the dot-blot hybridization method ("Protein Experimental Method for Molecular Biological Research, Revised", Yodosha, edited by Takenawa Tadaomi, p. 101), the reactivity to non-denatured TF, denatured TF under non-reduced condition, and denatured TF under reduced condition was investigated. TF in which the FLAG had been tagged to the extracellular region was expressed in CHO cells and was purified (shTF) was used shTF was diluted with each of the three buffers (buffer A: 10 mM Tris-HCl, pH 8.0; buffer B: 10 mM Tris-HCl (pH 8.0), 8 M urea; buffer C: 10 mM Tris-HCl, pH 8.0, 8 M urea, 5 mM DTT). The non-reductively TF was treated with buffer A, while the non-reductively denatured TF was treated with buffer B, and the reductively denatured TF was treated with buffer C. Each sample was treated for 24 hours at room temperature. After treatment, the sample was blotted to a nitrocellulose membrane (Bio Rad). 0.5 μl, 1 μl, and 2 μl of the sample (3 μg/ml) were blotted to the membrane, and the membrane was air-dried. It was blocked with DB (50 mM Tris-HCl, pH 8.1, 0.15 M NaCl, 1 mM $MgCl_2$, 0.05%(v/v) Tween 20, 0.02%(w/v) $NaN_3$, 1%(w/v) BSA). The membrane was reacted in the DB containing the humanized anti-TF antibody or the DB (control). After washing with PBS containing 0.05%(v/v) Tween 20, it was reacted to the DB containing peroxidase-labeled anti-human IgG antibody (DAKO). After washing with PBS containing 0.05%(v/v) Tween 20, it was treated by the ECL Western Blotting reagent (Amersham), and was exposed to an X ray film for 30 seconds.

As shown in FIG. 35, the chimeric anti-TF antibody and humanized anti-TF antibodies (versions "bb", "ib", and "ib2") reacted to all of the non-denatured TF, non-reductively denatured TF, and reductively denatured TF.

Example 8

Confirmation of Antithrombotic Effects in Rat Models of Acute DIC

The antithrombotic effects of the anti-TF antibody was confirmed in a thromboplastin-induced DIC model using rats. Thus, a human thromboplastin solution was continuously injected into the vein of SD male rats at 40 mg/kg over 3 hours to create a DIC model. The anti-TF antibody (the chimeric and humanized anti-TF antibody i-b2) was intravenously administered at a dose of 0.2 mg/kg five minutes prior to the start of injection of the thromboplastin solution. Fifteen minutes after the completion of the continuous injection of the thromboplastin solution, citrate-added blood was drawn from the abdominal aorta, for which platelet count, activated partial thromboplastin time (aPTT), fibrinogen concentration (Fib), soluble fibrin monomer complex (sFMC) concentration, and thrombin/antithrombin III complex (TAT) concentration were measured.

The result shown in Table 7 indicated that the continuous injection of thromboplastin caused decreased platelet count, extended aPTT, decreased fibrinogen concentration, increased sFMC and TAT concentrations, and an evident hypercoagulated state. In contrast, both of the chimeric and humanized anti-TF antibodies inhibited these changes equally strongly.

The result revealed that the humanized anti-TF antibody is useful as an antithrombotic agent.

TABLE 7

| Measurement item | Thromboplastin non-administration normal group | Solvent administration control group | Chimeric antibody administration group | Humanized antibody administration group |
|---|---|---|---|---|
| Platelet count (×10⁴/mm³) | 115.5 ± 11.8 | 82.9 ± 14.3 | 100.7 ± 12.9 | 96.1 ± 13.3 |
| aPTT (sec) | 20.1 ± 1.1 | 36.2 ± 13.9 | 22.3 ± 0.7[a] | 21.8 ± 1.3[a] |
| Fibrinogen concentration (normal group = 100%) | 100.0 ± 4.2 | 64.8 ± 20.0 | 101.0 ± 6.6[a] | 98.9 ± 5.7[a] |
| sFMC concentration (µg/ml) | 74.2 ± 5.5 | 3517 ± 3645 | 129.9 ± 46.8[a] | 66.5 ± 23.0[a] |
| TAT concentration (ng/ml) | 3.4 ± 0.6 | 29.6 ± 31.0 | 3.8 ± 0.7[b] | 4.2 ± 0.9 |

(Mean ± standard deviation)
Significance of difference relative to the solvent administration control group:
[a] $p < 0.01$,
[b] $p < 0.05$ Reference Example 1

Preparation of Anti-TF Monoclonal Antibody

1. Purification of Human TF

The purification of TF from human placenta was carried out according to the method of Ito (Ito, T. et al., J. Biol. Chem., 114: 691-696, 1993). Thus, human placenta was homogenized in Tris buffered saline (TBS, pH 7.5) containing 1.0 mM benzamidine hydrochloride, 1 mM phenylmethylsulfonyl fluoride, 1 mM diisopropylfluoro phosphate, and 0.02% sodium azide, and then the precipitate was defatted with cold acetone. The defatted powder obtained was suspended in the above buffer containing 2% Triton X-100 to solubilize TF.

The supernatant was subjected to affinity chromatography using Concanavalin A-Sepharose 4B column (Pharmacia) and anti-TF antibody-bound Sepharose 4B column (Pharmacia), and purified TF was obtained. This was concentrated with an ultrafiltration membrane (PM-10, Amicon) and was stored as the purified sample at 4° C.

TF content in the purified sample was quantitated by Sandwich ELISA that combined a commercially available anti-TF monoclonal antibody (American Diagnostica) and polyclonal antibody (American Diagnostica) with recombinant TF as a standard.

The purity in the purified sample was confirmed by subjecting the sample to SDS-PAGE using a 4-20% density gradient polyacrylamide gel, and silver-staining the product.

2. Immunization and the Preparation of Hybridoma

After mixing the purified human TF (about 70 µg/ml) with an equal volume of Freund's complete adjuvant (Difco), it was immunized subcutaneously into the abdomen of 5-week old Balb/c male mice (Nippon Charles River) at 10 µg TF/mouse. On day 12, 18, and 25, TF mixed with Freund's incomplete adjuvant was subcutaneously boosted at 5 µg/mouse TF, and as a final immunization the TF solution diluted with PBS was intraperitoneally given at 5 µg/mouse on day 32.

Three days after the final immunization, the spleen cells were prepared from four mice, and were fused to the mouse myeloma cell line P3U1 at ⅕ cell count thereof by the polyethylene glycol method. The fused cells were suspended into the RPMI-1640 medium (hereinafter referred to as RPMI-medium) (Lifetech Oriental) containing 10% fetal bovine serum, which was inoculated in 400 wells per mouse (about 400 cells/well) of a 96-well plate. On day 1, 2, 3, and 5 after the fusion, half the volume of the medium was exchanged with the RPMI-medium (hereinafter referred to as HAT-medium) containing HAT (Dainippon Seiyaku) and condimed H1 (Boehringer Mannheim GmbH) to perform HAT selection of the hybridoma.

The hybridomas selected by the screening method described below were cloned by conducting limiting dilution twice.

For the limiting dilution, 0.8 cells was inoculated per well in two 96-well plates. For the wells in which single colony was confirmed by microscopic examination, clones were selected by the following measurement of the binding activity to TF and neutralizing activity against TF. The clones obtained were acclaimed from the HAT-medium to the RPMI-medium. After the absence of reduction in antibody production ability due to acclimation was confirmed, limiting dilution was performed again for complete cloning. By the foregoing procedure, hybridomas that produce six antibodies (ATR-2, 3, 4, 5, 7, and 8) that strongly inhibit the binding of TF/Factor VIIa complex and Factor X were established.

3. Ascites Formation and Antibody Purification

The ascites formation of the established hybridomas were carried out according to the standard method. Thus, 106 hybridomas that were subcultured in vitro were intraperitoneally grafted into BALB/c male mice that had previously received twice intravenous administration of mineral oil. Ascites was collected from the mice that showed a bloated abdomen 1-2 weeks after the grafting.

The purification of antibody from ascites was carried out using the ConSepLC100 system (Millipore) equipped with the Protein A column (Nippon Gaishi).

4. Cell-ELISA

Human bladder carcinoma cells J82 (Fair D. S. et al., J. Biol. Chem., 262: 11692-11698, 1987) that are known to express TF at a high level were obtained from ATCC, and subcultured and maintained in the RPMI-medium under the condition of 37° C., 5% $CO_2$, and 100% humidity.

Cell-ELISA plates were prepared by inoculating J82 cells to a 96-well plate at $10^5$ cells/well, culturing for one day under the above condition, removing the medium and then washing twice with phosphate buffered saline (PBS), adding a 4% paraformaldehyde solution (PFA), and allowing to stand on ice for 10 minutes for immobilization. After PFA was removed, the plate was washed with PBS, the Tris buffer (Blocking buffer) containing 1% BSA and 0.02% sodium azide was added thereto, and the plate was stored at 4° C. until use.

Cell-ELISA was carried out in the following manner. Thus, the Blocking buffer was removed from the plate prepared as above, to which an anti-TF antibody solution or a hybridoma culture supernatant was added and was reacted at room temperature for 1.5 hours. After washing with PBS containing 0.05% Tween 20, alkaline phosphatase-conjugated goat anti-mouse IgG (H+L) (Zymed) was reacted for 1 hour. After washing, 1 mg/ml p-nitrophenyl phosphate disodium (Sigma) was added, and one hour later absorbance at 405/655 nm was measured to determine the amount of anti-TF antibody that bound to the J82 cells.

5. Assay System of Neutralizing Activity Against TF with Factor Xa Activity as an Index To 50 µl of Tris buffered saline (TBS: pH 7.6) containing 5 mM $CaCl_2$ and 0.1% bovine serum albumin, 10 µl of a human placenta-derived thromboplastin solution (5 mg/ml) (Thromborel S) (Boehring) and 10 µl of a Factor VIIa solution (82.5 ng/ml) (American Diagnostics) were added, and reacted at room temperature for 1 hour to permit the formation of the TF/Factor VIIa complex. After 10 µl of a predetermined concentration of a diluted anti-TF antibody solution or the hybridoma culture supernatant and 10 µl of a Factor X solution (3.245 µg/ml) (Celsus Laboratories) were added and reacted for 45 minutes, 10 µl of 0.5 M EDTA was added to stop the reaction. Fifty µl of 2 mM S-2222 solution (Daiichi Kagaku Yakuhin) was added thereto, and changes in absorbance at 405/655 nm over 30 minutes were measured and was set as the Factor X-producing activity of TF. In this method, the activity of antibody that inhibits the binding of the TF/Factor VIIa complex and Factor X can be determined.

6. Assay System of Inhibiting Activity Against Plasma-coagulation

Fifty µl of an appropriately diluted anti-TF antibody solution was mixed with 100 µl of a commercially available normal human plasma (Kojin Bio) and reacted at 37° C. for 3 minutes. Then 50 µl of human placenta-derived thromboplastin solution (1.25 mg/ml) was added thereto, and the time to coagulation of the plasma was measured using the plasma coagulation measuring instrument (CR-A: Amelung).

7. Determination of Antibody Isotype

For the culture supernatant of the hybridoma and the purified antibody, the mouse monoclonal antibody isotyping kit (manufactured by Amersham) was used to confirm the isotype of antibody. The result is shown below.

TABLE 8

Immunoglobulin isotype of anti-TF monoclonal antibody

| | |
|---|---|
| ATR-2 | IgG1, k |
| ATR-3 | IgG1, k |
| ATR-4 | IgG1, k |
| ATR-5 | IgG1, k |
| ATR-7 | IgG2a, k |
| ATR-8 | IgG2a, k |

Reference Example 2

Method of Preparing Soluble Human TF

Soluble human TF (shTF) was prepared in the following manner.

The gene encoding the human TF penetrating region in which amino acids at position 220 and thereafter had been replaced with the FLAG peptide M2 was inserted to a mammalian cell expression vector (containing the neomycin resistant gene and the DHFR gene), and introduced into CHO cells. For the cDNA sequence of human TF, reference was made to an article by James H. Morrissey et al. (Cell (1987) 50: 129-135). The gene sequence and the amino acid sequence of this soluble human TF are shown in SEQ ID NO: 151. After drug selection with G418, the expressed cells were selected, which were then subjected to expression amplification with methotrexate, and the shTF-expressing cells were established.

The cells were cultured in the serum-free medium CHO-S-SFMII (GIBCO) to obtain a culture supernatant containing shTF. It was diluted 2-fold with an equal volume of a 40 mM Tris-HCl buffer (pH 8.5), which was added to the Q-Sepharose Fast Flow column (100 ml, Pharmacia Biotech) equilibrated with a 20 mM Tris-HCl buffer (pH 8.5). After washing with the same buffer containing 0.1 M NaCl, the concentration of NaCl was changed to 0.3 M, and shTF was eluted from the column. To the shTF fraction obtained, ammonium sulfate was added to a final concentration of 2.5 M, and was centrifuged (10,000 rpm, 20 minutes) to precipitate the contaminating proteins. The supernatant was added to Butyl TOYOPEARL (30 ml, TOSOH), and then was washed with a 50 mM Tris-HCl buffer (pH 6.8) containing 2.5 M ammonium sulfate. In the 50 mM Tris-HCl buffer (pH 6.8), the concentration of ammonium sulfate was linearly reduced from 2.5 M to 0 M to permit the elution of shTF. The peak fractions containing shTF were concentrated by the Centri-Prep 10 (Amicon). The concentrate was added to the TSKgel G3000SWG column (21.5×600 mm, TOSOH) equilibrated with a 20 mM Tris-HCl buffer (pH 7.0) containing 150 mM NaCl, and the peak fraction of shTF was collected. It was filter sterilized with a 0.22 µm membrane filter and the product was set as the soluble human TF (shTF). The concentration of the sample was calculated assuming that the molar extinction coefficient of the sample $\epsilon$=40,130 and molecular weight =43,210.

SEQUENCE LISTING FREE TEXT

The contents in the sequence listing <223> are as follows:
SEQ ID NO: 1: Primer MHC-G1
SEQ ID NO: 2: Primer MHC-G2a
SEQ ID NO: 3: Primer MKC
SEQ ID NO: 4: M13 primer M4
SEQ ID NO: 5: M13 primer RV
SEQ ID NO: 6: Amino acid sequence of the H chain V region of the anti-TF mouse monoclonal antibody ATR-2 and the nucleotide sequence encoding the same
SEQ ID NO: 7: Amino acid sequence of the H chain V region of the anti-TF mouse monoclonal antibody ATR-3 and the nucleotide sequence encoding the same
SEQ ID NO: 8: Amino acid sequence of the H chain V region of the anti-TF mouse monoclonal antibody ATR-4 and the nucleotide sequence encoding the same
SEQ ID NO: 9: Amino acid sequence of the H chain V region of the anti-TF mouse monoclonal antibody ATR-5 and the nucleotide sequence encoding the same SEQ ID NO: 10: Amino acid sequence of the H chain V region of the anti-TF mouse monoclonal antibody ATR-7 and the nucleotide sequence encoding the same SEQ ID NO: 11: Amino acid sequence of the H chain V region of the anti-TF mouse monoclonal antibody ATR-8 and the nucleotide sequence encoding the same SEQ ID NO: 12: Amino acid sequence of the L chain V region of the anti-TF mouse monoclonal antibody ATR-2 and the nucleotide sequence encoding the same SEQ ID NO: 13: Amino acid sequence of the L chain V region of the anti-TF mouse monoclonal antibody ATR-3 and the nucleotide sequence encoding the same SEQ ID NO: 14: Amino acid sequence of the L chain V region of the anti-TF mouse monoclonal antibody ATR-4 and the nucleotide sequence encoding the same SEQ ID NO: 15: Amino acid sequence of the L chain V region of the anti-TF mouse monoclonal antibody ATR-5 and the nucleotide sequence encoding the same SEQ ID NO: 16: Amino acid sequence of the L chain V region of the anti-TF mouse monoclonal antibody ATR-7 and the nucleotide sequence encoding the same SEQ ID NO: 17: Amino acid sequence of the L chain V region of the anti-TF mouse monoclonal antibody ATR-8 and the nucleotide sequence encoding the same SEQ ID NO: 18: Primer ch5HS
SEQ ID NO: 19: Primer ch5HA
SEQ ID NO: 20: Primer ch5LS
SEQ ID NO: 21: Primer ch5LA
SEQ ID NO: 22: CDR grafting primer hR5Hv1S
SEQ ID NO: 23: CDR grafting primer hR5Hv2S
SEQ ID NO: 24: CDR grafting primer hR5Hv4S
SEQ ID NO: 25: CDR grafting primer hR5Hv3A
SEQ ID NO: 26: CDR grafting primer hR5Hv5A
SEQ ID NO: 27: Primer hR5HvPrS
SEQ ID NO: 28: Primer hR5HvPrA SEQ ID NO: 29: Amino acid sequence of the humanized H chain V region version "a" and the nucleotide sequence encoding the same SEQ ID NO: 30: Amino acid sequence of the humanized H chain V region version "a"

SEQ ID NO: 31: FR shuffling primer F3RFFS
SEQ ID NO: 32: FR shuffling primer F3RFBS
SEQ ID NO: 33: FR shuffling primer F3RFFA
SEQ ID NO: 34: FR shuffling primer F3RFBA
SEQ ID NO: 35: FR shuffling primer F3NMFS
SEQ ID NO: 36: FR shuffling primer F3NMBS
SEQ ID NO: 37: FR shuffling primer F3NMFA
SEQ ID NO: 38: FR shuffling primer F3NMBA SEQ ID NO: 39: Amino acid sequence of the humanized H chain V region version "b" and the nucleotide sequence encoding the same SEQ ID NO: 40: Amino acid sequence of the humanized H chain V region version "b"

SEQ ID NO: 41: Amino acid sequence of the humanized H chain V region version "c" and the nucleotide sequence encoding the same SEQ ID NO: 42: Amino acid sequence of the humanized H chain V region version "c"

SEQ ID NO: 43: FR shuffling primer F3EPS
SEQ ID NO: 44: FR shuffling primer F3EPA
SEQ ID NO: 45: Primer F3PrS
SEQ ID NO: 46: Primer F3PrA
SEQ ID NO: 47: FR shuffling primer F3VHS
SEQ ID NO: 48: FR shuffling primer F3VHA SEQ ID NO: 49: Amino acid sequence of the humanized H chain V region version "d" and the nucleotide sequence encoding the same SEQ ID NO: 50: Amino acid sequence of the humanized H chain V region version "d"

SEQ ID NO: 51: Amino acid sequence of the humanized H chain V region version "e" and the nucleotide sequence encoding the same SEQ ID NO: 52: Amino acid sequence of the humanized H chain V region version "e"

SEQ ID NO: 53: FR shuffling primer F3SSS
SEQ ID NO: 54: FR shuffling primer F3SSA
SEQ ID NO: 55: FR shuffling primer F3CDS
SEQ ID NO: 56: FR shuffling primer F3CDA SEQ ID NO: 57: Amino acid sequence of the humanized H chain V region version "f" and the nucleotide sequence encoding the same SEQ ID NO: 58: Amino acid sequence of the humanized H chain V region version "f"

SEQ ID NO: 59: Amino acid sequence of the humanized H chain V region version "1" and the nucleotide sequence encoding the same SEQ ID NO: 60: Amino acid sequence of the humanized H chain V region version "g"

SEQ ID NO: 61: FR shuffling primer F3ADS
SEQ ID NO: 62: FR shuffling primer F3ADA SEQ ID NO: 63: Amino acid sequence of the humanized H chain V region version "h" and the nucleotide sequence encoding the same SEQ ID NO: 64: Amino acid sequence of the humanized H chain V region version "h"

SEQ ID NO: 65: FR shuffling primer F3MMS
SEQ ID NO: 66: FR shuffling primer F3MMA
SEQ ID NO: 67: FR shuffling primer F3BMS
SEQ ID NO: 68: FR shuffling primer F3BMA SEQ ID NO: 69: Amino acid sequence of the humanized H chain V region version "i" and the nucleotide sequence encoding the same SEQ ID NO: 70: Amino acid sequence of the humanized H chain V region version "i"

SEQ ID NO: 71: Amino acid sequence of the humanized H chain V region version "j" and the nucleotide sequence encoding the same SEQ ID NO: 72: Amino acid sequence of the humanized H chain V region version "j"

SEQ ID NO: 73: FR shuffling primer F2 MPS
SEQ ID NO: 74: FR shuffling primer F2 MPA SEQ ID NO: 75: Amino acid sequence of the humanized H chain V region version "b1" and the nucleotide sequence encoding the same SEQ ID NO: 76: Amino acid sequence of the humanized H chain V region version "b1"

SEQ ID NO: 77: Amino acid sequence of the humanized H chain V region version "d1" and the nucleotide sequence encoding the same SEQ ID NO: 78: Amino acid sequence of the humanized H chain V region version "d1"

SEQ ID NO: 79: FR shuffling primer F2VHS
SEQ ID NO: 80: FR shuffling primer F2VHA SEQ ID NO: 81: Amino acid sequence of the humanized H chain V region version "b3" and the nucleotide sequence encoding the same SEQ ID NO: 82: Amino acid sequence of the humanized H chain V region version "b3"

SEQ ID NO: 83: Amino acid sequence of the humanized H chain V region version "d3" and the nucleotide sequence encoding the same SEQ ID NO: 84: Amino acid sequence of the humanized H chain V region version "d3"

SEQ ID NO: 85: FR shuffling vector h5Lv1S

SEQ ID NO: 86: FR shuffling vector h5Lv4S
SEQ ID NO: 87: FR shuffling vector h5Lv2A
SEQ ID NO: 88: FR shuffling vector h5Lv3A
SEQ ID NO: 89: FR shuffling vector h5Lv5A
SEQ ID NO: 90: Primer h5LvS
SEQ ID NO: 91: Primer h5LvA
SEQ ID NO: 92: Amino acid sequence of the humanized L chain V region version "a" and the nucleotide sequence encoding the same
SEQ ID NO: 93: Amino acid sequence of the humanized L chain V region version "a"
SEQ ID NO: 94: FR shuffling primer F3SS
SEQ ID NO: 95: FR shuffling primer F3SA
SEQ ID NO: 96: FR shuffling primer F3RS
SEQ ID NO: 97: FR shuffling primer F3RA
SEQ ID NO: 98: Amino acid sequence of the humanized L chain V region version "b" and the nucleotide sequence encoding the same
SEQ ID NO: 99: Amino acid sequence of the humanized L chain V region version "b"
SEQ ID NO: 100: Amino acid sequence of the humanized L chain V region version "c" and the nucleotide sequence encoding the same
SEQ ID NO: 101: Amino acid sequence of the humanized L chain V region version "c"
SEQ ID NO: 102: FR shuffling primer F2SS
SEQ ID NO: 103: FR shuffling primer F2SA
SEQ ID NO: 104: FR shuffling primer F2XS
SEQ ID NO: 105: FR shuffling primer F2XA
SEQ ID NO: 106: Amino acid sequence of the humanized L chain V region version "b1" and the nucleotide sequence encoding the same
SEQ ID NO: 107: Amino acid sequence of the humanized L chain V region version "b1"
SEQ ID NO: 108: Amino acid sequence of the humanized L chain V region version "b2" and the nucleotide sequence encoding the same
SEQ ID NO: 109: Amino acid sequence of the humanized L chain V region version "b2"
SEQ ID NO: 110: Amino acid sequence of FR1 of the humanized H chain V region entire version
SEQ ID NO: 111: Amino acid sequence of FR2 of the humanized H chain V region versions "a" to "j"
SEQ ID NO: 112: Amino acid sequence of RF2 of the humanized H chain V region versions "b1" and "d1"
SEQ ID NO: 113: Amino acid sequence of RF2 of the humanized H chain V region versions "b3" and "d3"
SEQ ID NO: 114: Amino acid sequence of FR3 of the humanized H chain V region version "a"
SEQ ID NO: 115: Amino acid sequence of FR3 of the humanized H chain V region versions "b", "b1", and "b3"
SEQ ID NO: 116: Amino acid sequence of FR3 of the humanized H chain V region version "c"
SEQ ID NO: 117: Amino acid sequence of FR3 of the humanized H chain V region versions "d", "d1", and "d3"
SEQ ID NO: 118: Amino acid sequence of FR3 of the humanized H chain V region version "e"
SEQ ID NO: 119: Amino acid sequence of FR3 of the humanized H chain V region version "f"
SEQ ID NO: 120: Amino acid sequence of FR3 of the humanized H chain V region version "g"
SEQ ID NO: 121: Amino acid sequence of FR3 of the humanized H chain V region version "h"
SEQ ID NO: 122: Amino acid sequence of FR3 of the humanized H chain V region version "i"
SEQ ID NO: 123: Amino acid sequence of FR3 of the humanized H chain V region version "j"
SEQ ID NO: 124: Amino acid sequence of FR4 of the humanized H chain V region all versions
SEQ ID NO: 125: Amino acid sequence of FR1 of the humanized L chain V region all versions
SEQ ID NO: 126: Amino acid sequence of FR2 of the humanized L chain V region versions "a", "b" and "c"
SEQ ID NO: 127: Amino acid sequence of FR2 of the humanized L chain V region version "b1"
SEQ ID NO: 128: Amino acid sequence of FR2 of the humanized L chain V region version "b2"
SEQ ID NO: 129: Amino acid sequence of FR3 of the humanized L chain V region version "a"
SEQ ID NO: 130: Amino acid sequence of FR3 of the humanized L chain V region versions "b", "b1" and "b2"
SEQ ID NO: 131: Amino acid sequence of FR3 of the humanized L chain V region version "c"
SEQ ID NO: 132: Amino acid sequence of FR4 of the humanized L chain V region all versions
SEQ ID NO: 133: Amino acid sequence of CDR1 of the humanized H chain V region all versions
SEQ ID NO: 134: Amino acid sequence of CDR2 of the humanized H chain V region all versions
SEQ ID NO: 135: Amino acid sequence of CDR3 of the humanized H chain V region all versions
SEQ ID NO: 136: Amino acid sequence of CDR1 of the humanized L chain V region all versions
SEQ ID NO: 137: Amino acid sequence of CDR2 of the humanized L chain V region all versions
SEQ ID NO: 138: Amino acid sequence of CDR3 of the humanized L chain V region all versions
SEQ ID NO: 139: Amino acid sequence of the H chain V region of the anti-TF mouse monoclonal antibody ATR-2
SEQ ID NO: 140: Amino acid sequence of the H chain V region of the anti-TF mouse monoclonal antibody ATR-3
SEQ ID NO: 141: Amino acid sequence of the H chain V region of the anti-TF mouse monoclonal antibody ATR-4
SEQ ID NO: 142: Amino acid sequence of the H chain V region of the anti-TF mouse monoclonal antibody ATR-5
SEQ ID NO: 143: Amino acid sequence of the H chain V region of the anti-TF mouse monoclonal antibody ATR-7
SEQ ID NO: 144: Amino acid sequence of the H chain V region of the anti-TF mouse monoclonal antibody ATR-8
SEQ ID NO: 145: Amino acid sequence of the L chain V region of the anti-TF mouse monoclonal antibody ATR-2
SEQ ID NO: 146: Amino acid sequence of the L chain V region of the anti-TF mouse monoclonal antibody ATR-3
SEQ ID NO: 147: Amino acid sequence of the L chain V region of the anti-TF mouse monoclonal antibody ATR-4
SEQ ID NO: 148: Amino acid sequence of the L chain V region of the anti-TF mouse monoclonal antibody ATR-5
SEQ ID NO: 149: Amino acid sequence of the L chain V region of the anti-TF mouse monoclonal antibody ATR-7
SEQ ID NO: 150: Amino acid sequence of the L chain V region of the anti-TF mouse monoclonal antibody ATR-8
SEQ ID NO: 151: Amino acid sequence of the soluble human TF and the nucleotide sequence encoding the same
SEQ ID NO: 152: Amino acid sequence of the soluble human TF
SEQ ID NO: 153: Amino acid sequence (including negative numbering scheme) of the H chain V region of the anti-TF mouse monoclonal antibody ATR-2
SEQ ID NO: 154: Amino acid sequence (including negative numbering scheme) of the H chain V region of the anti-TF mouse monoclonal antibody ATR-3
SEQ ID NO: 155: Amino acid sequence (including negative numbering scheme) of the H chain V region of the anti-TF mouse monoclonal antibody ATR-4

SEQ ID NO: 156: Amino acid sequence (including negative numbering scheme) of the H chain V region of the anti-TF mouse monoclonal antibody ATR-5

SEQ ID NO: 157: Amino acid sequence (including negative numbering scheme) of the H chain V region of the anti-TF mouse monoclonal antibody ATR-7

SEQ ID NO: 158: Amino acid sequence (including negative numbering scheme) of the H chain V region of the anti-TF mouse monoclonal antibody ATR-8

SEQ ID NO: 159: Amino acid sequence (including negative numbering scheme) of the H chain V region of the anti-TF mouse monoclonal antibody ATR-2

SEQ ID NO: 160: Amino acid sequence (including negative numbering scheme) of the L chain V region of the anti-TF mouse monoclonal antibody ATR-3

SEQ ID NO: 161: Amino acid sequence (including negative numbering scheme) of the L chain V region of the anti-TF mouse monoclonal antibody ATR-4

SEQ ID NO: 162: Amino acid sequence (including negative numbering scheme) of the L chain V region of the anti-TF mouse monoclonal antibody ATR-5

SEQ ID NO: 163: Amino acid sequence (including negative numbering scheme) of the L chain V region of the anti-TF mouse monoclonal antibody ATR-7

SEQ ID NO: 164: Amino acid sequence (including negative numbering scheme) of the L chain V region of the anti-TF mouse monoclonal antibody ATR-8

SEQ ID NO: 165: Amino acid sequence (including negative numbering scheme) of the humanized H chain V region version "a"

SEQ ID NO: 166: Amino acid sequence (including negative numbering scheme) of the humanized H chain V region version "b"

SEQ ID NO: 167: Amino acid sequence (including negative numbering scheme) of the humanized H chain V region version "c"

SEQ ID NO: 168: Amino acid sequence (including negative numbering scheme) of the humanized H chain V region version "d"

SEQ ID NO: 169: Amino acid sequence (including negative numbering scheme) of the humanized H chain V region version "e"

SEQ ID NO: 170: Amino acid sequence (including negative numbering scheme) of the humanized H chain V region version "f"

SEQ ID NO: 171: Amino acid sequence (including negative numbering scheme) of the humanized H chain V region version g SEQ ID NO: 172: Amino acid sequence (including negative numbering scheme) of the humanized H chain V region version "h"

SEQ ID NO: 173: Amino acid sequence (including negative numbering scheme) of the humanized H chain V region version "i"

SEQ ID NO: 174: Amino acid sequence (including negative numbering scheme) of the humanized H chain V region version "j"

SEQ ID NO: 175: Amino acid sequence (including negative numbering scheme) of the humanized H chain V region version "b1"

SEQ ID NO: 176: Amino acid sequence (including negative numbering scheme) of the humanized H chain V region version "d1"

SEQ ID NO: 177: Amino acid sequence (including negative numbering scheme) of the humanized H chain V region version "b3"

SEQ ID NO: 178: Amino acid sequence (including negative numbering scheme) of the humanized H chain V region version "d3"

SEQ ID NO: 179: Amino acid sequence (including negative numbering scheme) of the humanized L chain V region version "a"

SEQ ID NO: 180: Amino acid sequence. (including negative numbering scheme) of the humanized L chain V region version "b"

SEQ ID NO: 181: Amino acid sequence (including negative numbering scheme) of the humanized L chain V region version "c"

SEQ ID NO: 182: Amino acid sequence (including negative numbering scheme) of the humanized L chain V region version "b1"

SEQ ID NO: 183: Amino acid sequence (including negative numbering scheme) of the humanized L chain V region version "b2"

The invention claimed is:

1. A process of preparing a natural humanized antibody that has complementarity determining regions (CDRs) derived from non-humans and a framework region (FR) derived from a natural human antibody and that has a reduced immunogenicity, said method comprising the steps of:
   (1) preparing a non-human monoclonal antibody responsive to an antigen of interest;
   (2) preparing a plurality of human antibodies having a high homology with the amino acid sequences of FRs of heavy chain (H chain) or light chain (L chain) in the monoclonal antibodies of the step (1);
   (3) preparing a first humanized antibody by steps comprising:
   a) replacing all FRs of H chain of the non-human antibody prepared in step (1) with corresponding FRs H chain of one human antibody prepared in step (2);
   b) replacing all FRs of L chain of the non-human antibody prepared in step (1) with corresponding FRs of L chain of one human antibody prepared in step (2); and
   c) changing constant region of the non-human antibody prepared in step (1) to constant region of a human antibody;
   (4) generating second antibodies by:
   a) in an H chain V region of the first humanized antibody prepared on said (3)a), replacing 1 to 3 FRs having at least one of FR2 and FR3, with corresponding FRs of a human antibody different from the antibody used in (3)a) selected from the human antibodies prepared in the step (2);
   b) in an L chain V region of the first humanized antibody prepared on said (3)b), replacing 1 to 3 FRs having at least one of FR2 and FR3, with corresponding FRs of a human antibody different from the antibody used in (3)b) selected from the human antibodies prepared in the step (2); and
   c) obtaining a second humanized antibody comprising an H chain obtained in a), an L chain obtained in b, and a constant region of a human antibody in (3)c);
      (5) determining ability of the first and the second humanized antibodies to bind to the antigen or ability of the first and the second humanized antibodies to neutralize a biological activity of the antigen;
      (6) comparing the ability of the first and the second antibodies determined in step (5), and selecting antibodies which have a higher antigen binding ability or higher ability to neutralize a biological activity of an antigen; and
      (7) repeating the steps of (4) to (6) while using the antibody selected in step (6) as a first humanized antibody in step (4) until a humanized antibody is selected having the same level or more of ability as the non-human monoclonal antibody in step (1), wherein said ability is to bind to the antigen or to neutralize a biological activity of the antigen.

2. The process according to claim 1, in which said antigen of interest is human tissue factor (TF).

3. The process according to claim 1, wherein said FRs to be replaced contain FR2 and FR3.

4. A process for production of a natural humanized antibody, comprising the steps of isolating nucleic acid encoding a natural humanized antibody obtainable by a process according to claim 1, and introducing the nucleic acid into a host cell, and culturing the host cell so as to obtain the natural humanized antibody.

5. A process according to 4, further comprising the steps of introducing the nucleic acid into an expression vector, and introducing the expression vector into a host cell.

* * * * *

```
                        SEQUENCE LISTING

<160> NUMBER OF SEQ ID NOS: 183

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Primer
      MHC-G1

<400> SEQUENCE: 1
ggatcccggg ccagtggata gacagatg                                          28

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer
      MHC-G2a
```

-continued

<400> SEQUENCE: 2
ggatcccggg agtggataga ccgatgg                                               27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer MKC

<400> SEQUENCE: 3
ggatcccggg tggatggtgg gaagatg                                               27

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: M13 Primer
      M4

<400> SEQUENCE: 4
gttttcccag tcacgac                                                          17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: M13 Primer
      RV

<400> SEQUENCE: 5
caggaaacag ctatgac                                                          17

<210> SEQ ID NO 6
<211> LENGTH: 411
<212> TYPE: DNA
<213> ORGANISM: Artificial Sequence
<220> FEATURE:
<223> OTHER INFORMATION: Description of Artificial Sequence: Nucleotide
      sequence coding for H chain V region of anti-TF mouse monoclonal
      antibody ATR-2
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 6

```
atg gaa tgg agc tgg atc ttt ctc ttc ctc ctg tca gga act aca ggt        48
Met Glu Trp Ser Trp Ile Phe Leu Phe Leu Leu Ser Gly Thr Thr Gly
        -15                 -10                 -5 gtc cac tct gag atc cag ctg cag cag tct gga cct gag ctg gtg aag        96
Val His Ser Glu Ile Gln Leu Gln Gln Ser Gly Pro Glu Leu Val Lys
         -1   1               5                  10 cct ggg gct tca gtg aag gta tcc tgc aag gct tct ggt tac tca ttc       144
Pro Gly Ala Ser Val Lys Val Ser Cys Lys Ala Ser Gly Tyr Ser Phe
     15                  20                  25 act gac tac aac atg tac tgg gtg aag cag agc cat gga aag agc ctt       192
Thr Asp Tyr Asn Met Tyr Trp Val Lys Gln Ser His Gly Lys Ser Leu
 30                  35                  40                  45
```

```
gag tgg att gga tat att gat cct tac aat ggt ggt act atc tac aac        240
Glu Trp Ile Gly Tyr Ile Asp Pro Tyr Asn Gly Gly Thr Ile Tyr Asn
            50                  55                  60 cag aag ttc aag ggc aag gcc aca ttg act gtt gac aag tcc tcc agc        288
Gln Lys Phe Lys Gly Lys Ala Thr Leu Thr Val Asp Lys Ser Ser Ser
        65                  70                  75 aca gcc ttc atg cat ctc aac agc ctg aca tct gag gac tct gca gtc        336
Thr Ala Phe Met His Leu Asn Ser Leu Thr Ser Glu Asp Ser Ala Val
    80                  85                  90 tat tac tgt gca aga gga ggg gaa ggg tac tac ttt gac tac tgg ggc        384
Tyr Tyr Cys Ala Arg Gly Gly Glu Gly Tyr Tyr Phe Asp Tyr Trp Gly
95                  100                 105 caa ggc acc act ctc aca gtc tcc tca                                    411
Gln Gly Thr Thr Leu Thr Val Ser Ser
110             115

<210> SEQ ID NO 7
<211> LENGTH: 411
<212> TYPE: DNA
<213> ORGANISM: Artificial Sequence
<220> FEATURE:
<223> OTHER INFORMATION: Description of Artificial Sequence: Nucleotide
      sequence coding for H chain V region of anti-TF mouse monoclonal
      antibody ATR-3
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 7 atg gaa tgg agc tgg atc ttt ctc ttc ctc ctg tca gga act aca ggt         48
Met Glu Trp Ser Trp Ile Phe Leu Phe Leu Leu Ser Gly Thr Thr Gly
                -15                 -10                 -5 gtc cac tct gag atc cag ctg cag cag tct gga cct gag ctg gtg aag         96
Val His Ser Glu Ile Gln Leu Gln Gln Ser Gly Pro Glu Leu Val Lys
        -1  1               5                   10 cct ggg gct tca gtg aag gta tcc tgc aag gct tct ggt tac tca ttc        144
Pro Gly Ala Ser Val Lys Val Ser Cys Lys Ala Ser Gly Tyr Ser Phe
    15                  20                  25 act gac tac aac atg tac tgg gtg aag cag agc cat gga aag agc ctt        192
Thr Asp Tyr Asn Met Tyr Trp Val Lys Gln Ser His Gly Lys Ser Leu
30              35                  40                  45 gag tgg att gga tat att gat cct tac aat ggt ggt act atc tac aac        240
Glu Trp Ile Gly Tyr Ile Asp Pro Tyr Asn Gly Gly Thr Ile Tyr Asn
            50                  55                  60 cag aag ttc aag ggc aag gcc aca ttg act gtt gac aag tcc tcc agc        288
Gln Lys Phe Lys Gly Lys Ala Thr Leu Thr Val Asp Lys Ser Ser Ser
        65                  70                  75 aca gcc ttc atg cat ctc aac agc ctg aca tct gag gac tct gca gtc        336
Thr Ala Phe Met His Leu Asn Ser Leu Thr Ser Glu Asp Ser Ala Val
    80                  85                  90 tat tac tgt gca aga gga ggg gaa ggg tac tac ttt gac tac tgg ggc        384
Tyr Tyr Cys Ala Arg Gly Gly Glu Gly Tyr Tyr Phe Asp Tyr Trp Gly
95                  100                 105 caa ggc acc act ctc aca gtc tcc tca                                    411
Gln Gly Thr Thr Leu Thr Val Ser Ser
110             115
```

<210> SEQ ID NO 8
<211> LENGTH: 408
<212> TYPE: DNA
<213> ORGANISM: Artificial Sequence
<220> FEATURE:
<223> OTHER INFORMATION: Description of Artificial Sequence: Nucleotide
      sequence coding for H chain V region of anti-TF mouse monoclonal
      antibody ATR-4
<220> FEATURE:
<221> NAME/KEY: CDS
<222> LOCATION: (1)..(408)
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)

<400> SEQUENCE: 8

```
atg aaa tgc agc tgg gtc atc ttc ttc ctg atg gca gtg gtt aca ggg        48
Met Lys Cys Ser Trp Val Ile Phe Phe Leu Met Ala Val Val Thr Gly
            -15                 -10                  -5 gtc aat tca gag gtt cag ctg cag cag tct ggg gct gag ctt gtg agg        96
Val Asn Ser Glu Val Gln Leu Gln Gln Ser Gly Ala Glu Leu Val Arg
         -1   1               5                  10 cca ggg gcc tta gtc aag ttg tcc tgc aaa gct tct ggc ttc aac att       144
Pro Gly Ala Leu Val Lys Leu Ser Cys Lys Ala Ser Gly Phe Asn Ile
     15                  20                  25 aaa gac tac tat atg cac tgg gtg aag cag agg cct gaa cag ggc ctg       192
Lys Asp Tyr Tyr Met His Trp Val Lys Gln Arg Pro Glu Gln Gly Leu
 30                  35                  40                  45 gag tgg att gga ttg att gat cct caa aat ggt aat act ata tat gac       240
Glu Trp Ile Gly Leu Ile Asp Pro Gln Asn Gly Asn Thr Ile Tyr Asp
                 50                  55                  60 ccg aag ttc cag ggc aag gcc agt ata aca gca gac aca tcc tcc aac       288
Pro Lys Phe Gln Gly Lys Ala Ser Ile Thr Ala Asp Thr Ser Ser Asn
             65                  70                  75 aca gcc tac ctg cag ctc agc agc ctg aca tct gag gac act gcc gtc       336
Thr Ala Tyr Leu Gln Leu Ser Ser Leu Thr Ser Glu Asp Thr Ala Val
         80                  85                  90 tat tac tgt gat aga gac tcg ggc tat gct atg gac tac tgg ggt caa       384
Tyr Tyr Cys Asp Arg Asp Ser Gly Tyr Ala Met Asp Tyr Trp Gly Gln
     95                 100                 105 gga acc tca gtc acc gtc tcc tca                                       408
Gly Thr Ser Val Thr Val Ser Ser
110                 115
```

<210> SEQ ID NO 9
<211> LENGTH: 408
<212> TYPE: DNA
<213> ORGANISM: Artificial Sequence
<220> FEATURE:
<223> OTHER INFORMATION: Description of Artificial Sequence: Nucleotide
      sequence coding for H chain V region of anti-TF mouse monoclonal
      antibody ATR-5
<220> FEATURE:
<221> NAME/KEY: CDS
<222> LOCATION: (1)..(408)
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)

<400> SEQUENCE: 9

```
atg aaa tgc agc tgg gtc atc ttc ttc ctg atg gca gtg gtt aca ggg        48
Met Lys Cys Ser Trp Val Ile Phe Phe Leu Met Ala Val Val Thr Gly
```

-continued

```
               -15                -10                 -5
gtc aat tca gag gtt cag ctg cag cag tct ggg act aac ctt gtg agg      96
Val Asn Ser Glu Val Gln Leu Gln Gln Ser Gly Thr Asn Leu Val Arg
         -1   1               5                  10 cca ggg gcc tta gtc aag ttg tcc tgc aaa ggt tct ggc ttc aac att     144
Pro Gly Ala Leu Val Lys Leu Ser Cys Lys Gly Ser Gly Phe Asn Ile
         15                 20                  25 aaa gac tac tat atg cac tgg gtg aag cag agg cct gaa cag ggc ctg     192
Lys Asp Tyr Tyr Met His Trp Val Lys Gln Arg Pro Glu Gln Gly Leu
 30                 35                  40                  45 gag tgg att gga ggg aat gat cct gcg aat ggt cat agt atg tat gac     240
Glu Trp Ile Gly Gly Asn Asp Pro Ala Asn Gly His Ser Met Tyr Asp
                 50                  55                  60 ccg aaa ttc cag ggc aag gcc agt ata aca gca gac aca tcc tcc aac     288
Pro Lys Phe Gln Gly Lys Ala Ser Ile Thr Ala Asp Thr Ser Ser Asn
             65                  70                  75 aca gcc tac ctg cag ctc agc agc ctg aca tct gag gac act gcc gtc     336
Thr Ala Tyr Leu Gln Leu Ser Ser Leu Thr Ser Glu Asp Thr Ala Val
         80                  85                  90 tat ttc tgt gct aga gac tcg ggc tat gct atg gac tac tgg ggt caa     384
Tyr Phe Cys Ala Arg Asp Ser Gly Tyr Ala Met Asp Tyr Trp Gly Gln
     95                 100                 105 gga acc tca gtc acc gtc tcc tca                                     408
Gly Thr Ser Val Thr Val Ser Ser
110                 115

<210> SEQ ID NO 10
<211> LENGTH: 411
<212> TYPE: DNA
<213> ORGANISM: Artificial Sequence
<220> FEATURE:
<223> OTHER INFORMATION: Description of Artificial Sequence: Nucleotide
      sequence coding for H chain V region of anti-TF mouse monoclonal
      antibody ATR-7
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 10 atg gaa tgg agc tgg atc ttt ctc ttc ctc ctg tca gga act aca ggt      48
Met Glu Trp Ser Trp Ile Phe Leu Phe Leu Leu Ser Gly Thr Thr Gly
             -15                 -10                  -5 gtc cac tct gac atc cag ctg cag cag tct gga cct gag ctg gtg aag      96
Val His Ser Asp Ile Gln Leu Gln Gln Ser Gly Pro Glu Leu Val Lys
         -1   1               5                  10 cct ggg tct tca gtg aag gta tcc tgc aag gct tct ggt tac tca ttc     144
Pro Gly Ser Ser Val Lys Val Ser Cys Lys Ala Ser Gly Tyr Ser Phe
         15                  20                  25 cct gac tac aac ata ttc tgg gtg aag cag agc cat gga aag agc ctt     192
Pro Asp Tyr Asn Ile Phe Trp Val Lys Gln Ser His Gly Lys Ser Leu
 30                  35                  40                  45 gag tgg att gga tat att gat cct tac act ggt ggt act ggc tac aac     240
Glu Trp Ile Gly Tyr Ile Asp Pro Tyr Thr Gly Gly Thr Gly Tyr Asn
                 50                  55                  60 cag aag ttc aac gac aag gcc aca ttg act gtt gac aag tcc tcc agc     288
Gln Lys Phe Asn Asp Lys Ala Thr Leu Thr Val Asp Lys Ser Ser Ser
             65                  70                  75
```

```
aca gcc ttc atg cat ctc aac agc cta aca tct gag gac tct gca gtc      336
Thr Ala Phe Met His Leu Asn Ser Leu Thr Ser Glu Asp Ser Ala Val
        80                  85                  90 tat tac tgt gca aga ggt ttc tac tat gat tac gac tgt tac tgg ggc      384
Tyr Tyr Cys Ala Arg Gly Phe Tyr Tyr Asp Tyr Asp Cys Tyr Trp Gly
    95                  100                 105 caa ggg act ctg gtc act gtc tct gca                                  411
Gln Gly Thr Leu Val Thr Val Ser Ala
110             115

<210> SEQ ID NO 11
<211> LENGTH: 411
<212> TYPE: DNA
<213> ORGANISM: Artificial Sequence
<220> FEATURE:
<223> OTHER INFORMATION: Description of Artificial Sequence: Nucleotide
      sequence coding for H chain V region of anti-TF mouse monoclonal
      antibody ATR-8
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 11 atg gaa tgg agc tgg atc ttt ctc ttc ctc ctg tca gga act aca ggt       48
Met Glu Trp Ser Trp Ile Phe Leu Phe Leu Leu Ser Gly Thr Thr Gly
            -15                 -10                  -5 gtc cac tct gac atc cag ctg cag cag tct gga cct gag ctg gtg aag       96
Val His Ser Asp Ile Gln Leu Gln Gln Ser Gly Pro Glu Leu Val Lys
        -1  1               5                   10 cct ggg gct tca gtg aag gta tcc tgc aag gct tct ggt tac tca ttc      144
Pro Gly Ala Ser Val Lys Val Ser Cys Lys Ala Ser Gly Tyr Ser Phe
    15                  20                  25 act gac tac aac ata ttc tgg gtg aag cag agc cat gga aag agc ctt      192
Thr Asp Tyr Asn Ile Phe Trp Val Lys Gln Ser His Gly Lys Ser Leu
30                  35                  40                  45 gag tgg att gga tat att gat cct tac act ggt ggt act ggc tac aac      240
Glu Trp Ile Gly Tyr Ile Asp Pro Tyr Thr Gly Gly Thr Gly Tyr Asn
                50                  55                  60 cag aag ttc aac gac aag gcc aca ttg act gtt gac aag tcc tcc agc      288
Gln Lys Phe Asn Asp Lys Ala Thr Leu Thr Val Asp Lys Ser Ser Ser
            65                  70                  75 aca gcc ttc atg cat ctc aac agc ctg aca tct gag gac tct gca gtc      336
Thr Ala Phe Met His Leu Asn Ser Leu Thr Ser Glu Asp Ser Ala Val
        80                  85                  90 tat tac tgt gca aga ggt ttc tac tat gat tac gac tgt tac tgg ggc      384
Tyr Tyr Cys Ala Arg Gly Phe Tyr Tyr Asp Tyr Asp Cys Tyr Trp Gly
    95                  100                 105 caa ggg act ctg gtc act gtc tct gca                                  411
Gln Gly Thr Leu Val Thr Val Ser Ala
110             115

<210> SEQ ID NO 12
<211> LENGTH: 375
<212> TYPE: DNA
<213> ORGANISM: Artificial Sequence
<220> FEATURE:
<223> OTHER INFORMATION: Description of Artificial Sequence: Nucleotide
      sequence coding for L chain V region of anti-TF mouse monoclonal
      antibody ATR-2
<220> FEATURE:
```

```
<221> NAME/KEY: CDS
<222> LOCATION: (1)..(375)
<220> FEATURE:
<221> NAME/KEY: sig_peptide
<222> LOCATION: (1)..(54)
<220> FEATURE:
<221> NAME/KEY: mat_peptide
<222> LOCATION: (55)..(375)

<400> SEQUENCE: 12 atg ctc act cag ctc ctg gga tta ctg ctg ctc tgg ttt gca ggt ggt        48
Met Leu Thr Gln Leu Leu Gly Leu Leu Leu Leu Trp Phe Ala Gly Gly
            -15                 -10                 -5 aaa tgt gac att cag atg acc cag tct cct gcc tcc cag tct gca tct        96
Lys Cys Asp Ile Gln Met Thr Gln Ser Pro Ala Ser Gln Ser Ala Ser
     -1   1               5                  10 ctg gga gaa agt gtc acc atc aca tgc ctg gca agt cag acc att ggt       144
Leu Gly Glu Ser Val Thr Ile Thr Cys Leu Ala Ser Gln Thr Ile Gly
 15              20                  25                  30 aca tgg tta gcc tgg tat cag cag aaa cca ggg aaa tct cct cag gtc       192
Thr Trp Leu Ala Trp Tyr Gln Gln Lys Pro Gly Lys Ser Pro Gln Val
             35                  40                  45 ctg att tat gct gca acc agc ttg gca gat ggg gtc cca tca agg ttc       240
Leu Ile Tyr Ala Ala Thr Ser Leu Ala Asp Gly Val Pro Ser Arg Phe
         50                  55                  60 agt ggt agt gga tct ggc aca aaa ttt tct ttc aag atc agc agc cta       288
Ser Gly Ser Gly Ser Gly Thr Lys Phe Ser Phe Lys Ile Ser Ser Leu
     65                  70                  75 cag gct gaa gat ttt gta agt tat tac tgt caa caa ctt tac agt act       336
Gln Ala Glu Asp Phe Val Ser Tyr Tyr Cys Gln Gln Leu Tyr Ser Thr
 80                  85                  90 ccg tac acg ttc gga ggg ggg acc aag ctg gaa ata aaa                   375
Pro Tyr Thr Phe Gly Gly Gly Thr Lys Leu Glu Ile Lys
 95                 100                 105

<210> SEQ ID NO 13
<211> LENGTH: 375
<212> TYPE: DNA
<213> ORGANISM: Artificial Sequence
<220> FEATURE:
<223> OTHER INFORMATION: Description of Artificial Sequence: Nucleotide
      sequence coding for L chain V region of anti-TF mouse monoclonal
      antibody ATR-3
<220> FEATURE:
<221> NAME/KEY: CDS
<222> LOCATION: (1)..(375)
<220> FEATURE:
<221> NAME/KEY: sig_peptide
<222> LOCATION: (1)..(54)
<220> FEATURE:
<221> NAME/KEY: mat_peptide
<222> LOCATION: (55)..(375)

<400> SEQUENCE: 13 atg ctc act cag ctc ctg gga tta ctg ctg ctc tgg ttt gca ggt ggt        48
Met Leu Thr Gln Leu Leu Gly Leu Leu Leu Leu Trp Phe Ala Gly Gly
            -15                 -10                 -5 aaa tgt gac att cag atg acc cag tct cct gcc tcc cag tct gca tct        96
Lys Cys Asp Ile Gln Met Thr Gln Ser Pro Ala Ser Gln Ser Ala Ser
     -1   1               5                  10 ctg gga gaa agt gtc acc atc aca tgc ctg gca agt cag acc att ggt       144
Leu Gly Glu Ser Val Thr Ile Thr Cys Leu Ala Ser Gln Thr Ile Gly
 15              20                  25                  30 aca tgg tta ggc tgg tat cag cag aaa cca ggg aaa tct cct cag gtc       192
Thr Trp Leu Gly Trp Tyr Gln Gln Lys Pro Gly Lys Ser Pro Gln Val
             35                  40                  45
```

```
ctg att tat gct gca acc agc ttg gca gat ggg gtc cca tca agg ttc    240
Leu Ile Tyr Ala Ala Thr Ser Leu Ala Asp Gly Val Pro Ser Arg Phe
        50                  55                  60 agt ggt agt gga tct ggc aca aaa ttt tct ttc aag atc agc agc cta    288
Ser Gly Ser Gly Ser Gly Thr Lys Phe Ser Phe Lys Ile Ser Ser Leu
65                  70                  75 cag gct gaa gat ttt gta agt tat tac tgt caa caa ctt tac agt act    336
Gln Ala Glu Asp Phe Val Ser Tyr Tyr Cys Gln Gln Leu Tyr Ser Thr
            80                  85                  90 ccg tac acg ttc gga ggg ggg acc aag ctg gaa ata aaa                375
Pro Tyr Thr Phe Gly Gly Gly Thr Lys Leu Glu Ile Lys
95                  100                 105

<210> SEQ ID NO 14
<211> LENGTH: 387
<212> TYPE: DNA
<213> ORGANISM: Artificial Sequence
<220> FEATURE:
<223> OTHER INFORMATION: Description of Artificial Sequence: Nucleotide
      sequence coding for L chain V region of anti-TF mouse monoclonal
      antibody ATR-4
<220> FEATURE:
<221> NAME/KEY: CDS
<222> LOCATION: (1)..(387)
<220> FEATURE:
<221> NAME/KEY: sig_peptide
<222> LOCATION: (1)..(66)
<220> FEATURE:
<221> NAME/KEY: mat_peptide
<222> LOCATION: (67)..(387)

<400> SEQUENCE: 14 atg gac atg agg gcc cct gct cag ttt ttt ggg atc ttg ttg ctc tgg     48
Met Asp Met Arg Ala Pro Ala Gln Phe Phe Gly Ile Leu Leu Leu Trp
        -20                 -15                 -10 ttt cca ggt atc aga tgt gac atc aag atg acc cag tct cca tcc tcc     96
Phe Pro Gly Ile Arg Cys Asp Ile Lys Met Thr Gln Ser Pro Ser Ser
    -5              -1   1                   5                  10 atg tat gcc tcg ctg gga gag aga gtc act atc act tgc aag gcg agt    144
Met Tyr Ala Ser Leu Gly Glu Arg Val Thr Ile Thr Cys Lys Ala Ser
                15                  20                  25 cag gac att aaa acc ttt tta agc tgg tac cag cag aaa cca tgg caa    192
Gln Asp Ile Lys Thr Phe Leu Ser Trp Tyr Gln Gln Lys Pro Trp Gln
            30                  35                  40 tct cct aag acc ctg atc tat tat gca aca agc ttg gca gat ggg gtc    240
Ser Pro Lys Thr Leu Ile Tyr Tyr Ala Thr Ser Leu Ala Asp Gly Val
        45                  50                  55 cca tca aga ttc agt ggc agt gga tct ggg caa gat tat tct cta acc    288
Pro Ser Arg Phe Ser Gly Ser Gly Ser Gly Gln Asp Tyr Ser Leu Thr
60                  65                  70 atc agc agc ctg gag tct gac gat tca gca act tat tac tgt cta cag    336
Ile Ser Ser Leu Glu Ser Asp Asp Ser Ala Thr Tyr Tyr Cys Leu Gln
75                  80                  85                  90 cat ggt gag agc ccg tac acg ttc gga ggg ggg acc aaa ctg gaa ata    384
His Gly Glu Ser Pro Tyr Thr Phe Gly Gly Gly Thr Lys Leu Glu Ile
                95                  100                 105 aaa                                                                387
Lys

<210> SEQ ID NO 15
<211> LENGTH: 381
<212> TYPE: DNA
<213> ORGANISM: Artificial Sequence
<220> FEATURE:
```

-continued

<223> OTHER INFORMATION: Description of Artificial Sequence: Nucleotide
      sequence coding for L chain V region of anti-TF mouse monoclonal
      antibody ATR-5
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)

<400> SEQUENCE: 15

```
atg agg gcc cct gct cag ttt ttt ggg atc ttg ttg ctc tgg ttt cca      48
Met Arg Ala Pro Ala Gln Phe Phe Gly Ile Leu Leu Leu Trp Phe Pro
-20             -15                 -10                 -5 ggt atc aga tgt gac atc aag atg acc cag tct cca tcc tct atg tat      96
Gly Ile Arg Cys Asp Ile Lys Met Thr Gln Ser Pro Ser Ser Met Tyr
            -1  1               5                   10 gca tcg ctg gga gag aga gtc act atc act tgc aag gcg agt cag gac     144
Ala Ser Leu Gly Glu Arg Val Thr Ile Thr Cys Lys Ala Ser Gln Asp
        15                  20                  25 att aaa agc ttt tta agt tgg tac cag caa aaa cca tgg aaa tct cct     192
Ile Lys Ser Phe Leu Ser Trp Tyr Gln Gln Lys Pro Trp Lys Ser Pro
    30                  35                  40 aag acc ctg atc tat tat gca aca agc ttg gca gat ggg gtc cca tca     240
Lys Thr Leu Ile Tyr Tyr Ala Thr Ser Leu Ala Asp Gly Val Pro Ser
45                  50                  55                  60 aga ttc agt ggc agt gga tct ggg caa gat tat tct cta acc atc aac     288
Arg Phe Ser Gly Ser Gly Ser Gly Gln Asp Tyr Ser Leu Thr Ile Asn
                65                  70                  75 aac ctg gag tct gac gat aca gca act tat tat tgt cta cag cat ggt     336
Asn Leu Glu Ser Asp Asp Thr Ala Thr Tyr Tyr Cys Leu Gln His Gly
        80                  85                  90 gag agc ccg tac acg ttc gga ggg ggg acc aag ctg gaa ata aaa         381
Glu Ser Pro Tyr Thr Phe Gly Gly Gly Thr Lys Leu Glu Ile Lys
    95                  100                 105
```

<210> SEQ ID NO 16
<211> LENGTH: 393
<212> TYPE: DNA
<213> ORGANISM: Artificial Sequence
<220> FEATURE:
<223> OTHER INFORMATION: Description of Artificial Sequence: Nucleotide
      sequence coding for L chain V region of anti-TF mouse monoclonal
      antibody ATR-7
<220> FEATURE:
<221> NAME/KEY: CDS
<222> LOCATION: (1)..(393)
<220> FEATURE:
<221> NAME/KEY: sig_peptide
<222> LOCATION: (1)..(57)
<220> FEATURE:
<221> NAME/KEY: mat_peptide
<222> LOCATION: (58)..(393)

<400> SEQUENCE: 16

```
atg agt cct gcc cag ttc ctg ttt ctg tta gtg ctc tgg att cgg gaa      48
Met Ser Pro Ala Gln Phe Leu Phe Leu Leu Val Leu Trp Ile Arg Glu
                -15                 -10                 -5 atc aac ggt gat gtt gtg ctg acc cag act cca ctc act ttg tcg gtt      96
Ile Asn Gly Asp Val Val Leu Thr Gln Thr Pro Leu Thr Leu Ser Val
            -1  1               5                   10 acc att gga caa cca gcc tcc gtc tct tgc aag tca agt cag agc ctc     144
Thr Ile Gly Gln Pro Ala Ser Val Ser Cys Lys Ser Ser Gln Ser Leu
        15                  20                  25
```

| | | | | | | | | | | | | | | | | |
|---|---|---|---|---|---|---|---|---|---|---|---|---|---|---|---|---|
| tta | gat | agt | gat | gga | aag | aca | tat | ttg | aat | tgg | ttg | tta | cag | agg | cca | 192 |
| Leu | Asp | Ser | Asp | Gly | Lys | Thr | Tyr | Leu | Asn | Trp | Leu | Leu | Gln | Arg | Pro | |
| | 30 | | | | 35 | | | | 40 | | | | | 45 | | |

| | | | | | | | | | | | | | | | | |
|---|---|---|---|---|---|---|---|---|---|---|---|---|---|---|---|---|
| ggc | cag | tct | cca | aag | cgc | ctg | atc | tat | ctt | gtg | tct | aaa | ctg | gac | tct | 240 |
| Gly | Gln | Ser | Pro | Lys | Arg | Leu | Ile | Tyr | Leu | Val | Ser | Lys | Leu | Asp | Ser | |
| | | | 50 | | | | | 55 | | | | | 60 | | | |

| | | | | | | | | | | | | | | | | |
|---|---|---|---|---|---|---|---|---|---|---|---|---|---|---|---|---|
| gga | gtc | cct | gac | agg | ttc | act | ggc | agt | gga | tca | ggg | aca | gat | ttc | aca | 288 |
| Gly | Val | Pro | Asp | Arg | Phe | Thr | Gly | Ser | Gly | Ser | Gly | Thr | Asp | Phe | Thr | |
| | | | | 65 | | | | | 70 | | | | | 75 | | |

| | | | | | | | | | | | | | | | | |
|---|---|---|---|---|---|---|---|---|---|---|---|---|---|---|---|---|
| ctg | aaa | atc | agc | aga | gtg | gag | gct | gag | gat | ttg | gga | gtt | tat | tat | tgt | 336 |
| Leu | Lys | Ile | Ser | Arg | Val | Glu | Ala | Glu | Asp | Leu | Gly | Val | Tyr | Tyr | Cys | |
| | | | | 80 | | | | | 85 | | | | | 90 | | |

| | | | | | | | | | | | | | | | | |
|---|---|---|---|---|---|---|---|---|---|---|---|---|---|---|---|---|
| tgg | caa | gat | aca | cat | ttt | ccg | gac | acg | ttc | gga | ggg | ggg | acc | aag | ctg | 384 |
| Trp | Gln | Asp | Thr | His | Phe | Pro | Asp | Thr | Phe | Gly | Gly | Gly | Thr | Lys | Leu | |
| | 95 | | | | 100 | | | | | | 105 | | | | | |

| | | | |
|---|---|---|---|
| gaa | ata | aaa | 393 |
| Glu | Ile | Lys | |
| 110 | | | |

<210> SEQ ID NO 17
<211> LENGTH: 393
<212> TYPE: DNA
<213> ORGANISM: Artificial Sequence
<220> FEATURE:
<223> OTHER INFORMATION: Description of Artificial Sequence: Nucleotide
sequence coding for L chain V region of anti-TF mouse monoclonal
antibody ATR-8
<220> FEATURE:
<221> NAME/KEY: CDS
<222> LOCATION: (1)..(393)
<220> FEATURE:
<221> NAME/KEY: sig_peptide
<222> LOCATION: (1)..(57)
<220> FEATURE:
<221> NAME/KEY: mat_peptide
<222> LOCATION: (58)..(393)

<400> SEQUENCE: 17

| | | | | | | | | | | | | | | | | |
|---|---|---|---|---|---|---|---|---|---|---|---|---|---|---|---|---|
| atg | agt | cct | gcc | cag | ttc | ctg | ttt | ctg | tta | gtg | ctc | tgg | att | cgg | gat | 48 |
| Met | Ser | Pro | Ala | Gln | Phe | Leu | Phe | Leu | Leu | Val | Leu | Trp | Ile | Arg | Asp | |
| | | | | -15 | | | | | -10 | | | | | -5 | | |

| | | | | | | | | | | | | | | | | |
|---|---|---|---|---|---|---|---|---|---|---|---|---|---|---|---|---|
| atc | aac | ggt | gat | gtt | gta | ctg | acc | cag | act | cca | ctc | act | ttg | tcg | gtt | 96 |
| Ile | Asn | Gly | Asp | Val | Val | Leu | Thr | Gln | Thr | Pro | Leu | Thr | Leu | Ser | Val | |
| | -1 | 1 | | | | 5 | | | | | 10 | | | | | |

| | | | | | | | | | | | | | | | | |
|---|---|---|---|---|---|---|---|---|---|---|---|---|---|---|---|---|
| acc | att | gga | caa | cca | gcc | tcc | gtc | tct | tgc | aag | tca | agt | cag | agc | ctc | 144 |
| Thr | Ile | Gly | Gln | Pro | Ala | Ser | Val | Ser | Cys | Lys | Ser | Ser | Gln | Ser | Leu | |
| | 15 | | | | 20 | | | | | 25 | | | | | | |

| | | | | | | | | | | | | | | | | |
|---|---|---|---|---|---|---|---|---|---|---|---|---|---|---|---|---|
| tta | gat | agt | gat | gga | aag | aca | tat | ttg | aat | tgg | ttg | tta | cag | agg | cca | 192 |
| Leu | Asp | Ser | Asp | Gly | Lys | Thr | Tyr | Leu | Asn | Trp | Leu | Leu | Gln | Arg | Pro | |
| | 30 | | | | 35 | | | | 40 | | | | | 45 | | |

| | | | | | | | | | | | | | | | | |
|---|---|---|---|---|---|---|---|---|---|---|---|---|---|---|---|---|
| ggc | cag | tct | cca | aag | cgc | cta | atc | tat | ctg | gtg | tct | aaa | ctg | gac | tct | 240 |
| Gly | Gln | Ser | Pro | Lys | Arg | Leu | Ile | Tyr | Leu | Val | Ser | Lys | Leu | Asp | Ser | |
| | | | 50 | | | | | 55 | | | | | 60 | | | |

| | | | | | | | | | | | | | | | | |
|---|---|---|---|---|---|---|---|---|---|---|---|---|---|---|---|---|
| gga | gtc | cct | gac | agg | ttc | act | ggc | agt | gga | tca | ggg | aca | gat | ttc | aca | 288 |
| Gly | Val | Pro | Asp | Arg | Phe | Thr | Gly | Ser | Gly | Ser | Gly | Thr | Asp | Phe | Thr | |
| | | | | 65 | | | | | 70 | | | | | 75 | | |

| | | | | | | | | | | | | | | | | |
|---|---|---|---|---|---|---|---|---|---|---|---|---|---|---|---|---|
| ctg | aaa | atc | agc | aga | gtg | gag | gct | gag | gat | ttg | gga | gtt | tat | tat | tgt | 336 |
| Leu | Lys | Ile | Ser | Arg | Val | Glu | Ala | Glu | Asp | Leu | Gly | Val | Tyr | Tyr | Cys | |
| | | | | 80 | | | | | 85 | | | | | 90 | | |

| | | | | | | | | | | | | | | | | |
|---|---|---|---|---|---|---|---|---|---|---|---|---|---|---|---|---|
| tgg | caa | gat | aca | cat | ttt | ccg | gac | acg | ttc | gga | ggg | ggg | acc | aag | ctg | 384 |
| Trp | Gln | Asp | Thr | His | Phe | Pro | Asp | Thr | Phe | Gly | Gly | Gly | Thr | Lys | Leu | |
| | 95 | | | | 100 | | | | | | 105 | | | | | |

| | | | |
|---|---|---|---|
| gaa | ata | aaa | 393 |

Glu Ile Lys
110

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Primer
      ch5HS

<400> SEQUENCE: 18
gtctgtcgac ccaccatgaa atgcagctgg gtcat                         35

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Primer
      ch5HA

<400> SEQUENCE: 19
tgttgctagc tgaggagacg gtgactga                                 28

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Primer
      ch5LS

<400> SEQUENCE: 20
gtctagatct ccaccatgag ggcccctgct cagtt                         35

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Primer
      ch5LA

<400> SEQUENCE: 21
tgttcgtacg ttttatttcc agcttggt                                 28

<210> SEQ ID NO 22
<211> LENGTH: 104
<212> TYPE: DNA
<213> ORGANISM: Artificial Sequence
<220> FEATURE:
<223> OTHER INFORMATION: Description of Artificial Sequence: CDR
      grafting primer hR5Hv1S

<400> SEQUENCE: 22
ttctgtcgac ccaccatgaa atgcagctgg gtcatcttct tcctgatggc agtggttaca    60
ggggttaact cacaggtgca gctgttggag tctggagctg tgct                   104

<210> SEQ ID NO 23
<211> LENGTH: 108
<212> TYPE: DNA
<213> ORGANISM: Artificial Sequence
<220> FEATURE:
<223> OTHER INFORMATION: Description of Artificial Sequence: CDR
      grafting primer hR5Hv2S -continued

```
<400> SEQUENCE: 23
acaggtgcag ctgttggagt ctggagctgt gctggcaagg cctgggactt ccgtgaagat      60
ctcctgcaag gcttccggat tcaacattaa agactactat atgcattg                  108

<210> SEQ ID NO 24
<211> LENGTH: 108
<212> TYPE: DNA
<213> ORGANISM: Artificial Sequence
<220> FEATURE:
<223> OTHER INFORMATION: Description of Artificial Sequence: CDR
      grafting primer hR5Hv4S

<400> SEQUENCE: 24
gaatggccat agtatgtatg acccgaaatt ccagggcagg gccaaactga ctgcagccac      60
atccgccagt attgcctact tggagttctc gagcctgaca aatgagga                  108

<210> SEQ ID NO 25
<211> LENGTH: 110
<212> TYPE: DNA
<213> ORGANISM: Artificial Sequence
<220> FEATURE:
<223> OTHER INFORMATION: Description of Artificial Sequence: CDR
      grafting primer hR5Hv3A

<400> SEQUENCE: 25
tcatacatac tatggccatt cgcaggatca ttcccaccaa tccattctag accctgtcca      60
ggcctctgtt ttacccaatg catatagtag tctttaatgt tgaatccgga                110

<210> SEQ ID NO 26
<211> LENGTH: 110
<212> TYPE: DNA
<213> ORGANISM: Artificial Sequence
<220> FEATURE:
<223> OTHER INFORMATION: Description of Artificial Sequence: CDR
      grafting primer hR5Hv5A

<400> SEQUENCE: 26
agaagctagc tgaggagacg gtgaccaggg tgccttggcc ccagtagtcc atggcatagc      60
ccgagtctct tgcacagtaa tagaccgcag aatcctcatt tgtcaggctc                110

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Primer
      hR5HvPrS

<400> SEQUENCE: 27
ttctgtcgac ccaccatga                                                   19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Primer
      hR5HvPrA

<400> SEQUENCE: 28
agaagctagc tgaggagac                                                   19

<210> SEQ ID NO 29
```

-continued

```
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "a" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 29 atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
       -1   1                 5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
     15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc agg gcc aaa ctg act gca gcc aca tcc gcc agt     288
Pro Lys Phe Gln Gly Arg Ala Lys Leu Thr Ala Ala Thr Ser Ala Ser
             65                  70                  75 att gcc tac ttg gag ttc tcg agc ctg aca aat gag gat tct gcg gtc     336
Ile Ala Tyr Leu Glu Phe Ser Ser Leu Thr Asn Glu Asp Ser Ala Val
         80                  85                  90 tat tac tgt gca aga gac tcg ggc tat gcc atg gac tac tgg ggc caa     384
Tyr Tyr Cys Ala Arg Asp Ser Gly Tyr Ala Met Asp Tyr Trp Gly Gln
     95                 100                 105 ggc acc ctg gtc acc gtc tcc tca gct agc                             414
Gly Thr Leu Val Thr Val Ser Ser Ala Ser
110                 115

<210> SEQ ID NO 30
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "a" of humanized H chain V region

<400> SEQUENCE: 30

Gln Val Gln Leu Leu Glu Ser Gly Ala Val Leu Ala Arg Pro Gly Thr
 1               5                  10                  15

Ser Val Lys Ile Ser Cys Lys Ala Ser Gly Phe Asn Ile Lys Asp Tyr
             20                  25                  30

Tyr Met His Trp Val Arg Gln Ala Pro Gly Gln Gly Leu Glu Trp Ile
         35                  40                  45

Gly Gly Asn Asp Pro Ala Asn Gly His Ser Met Tyr Asp Pro Lys Phe
     50                  55                  60

Gln Gly Arg Val Thr Ile Thr Ala Asp Thr Ser Thr Asn Thr Ala Tyr
 65                  70                  75                  80
```

```
Met Glu Leu Ser Ser Leu Arg Ser Glu Asp Thr Ala Ile Tyr Tyr Cys
                85                  90                  95

Ala Arg Asp Ser Gly Tyr Ala Met Asp Tyr Trp Gly Gln Gly Thr Leu
            100                 105                 110

Val Thr Val Ser Ser Ala Ser
        115

<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3RFFS

<400> SEQUENCE: 31
ttcttggcca tagtatgtat gacccgaaat tccagggccg agtcacaatc actgcagaca      60
catccacgaa cacagcctac atggagctct cgagtctgag                          100

<210> SEQ ID NO 32
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3RFBS

<400> SEQUENCE: 32
ggagctctcg agtctgagat ctgaggacac agccatttat tactgtgcaa gagactcggg      60
ctatgccatg gttct                                                      75

<210> SEQ ID NO 33
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3RFFA

<400> SEQUENCE: 33
ctcagactcg agagctccat gtaggctgtg ttcgtggatg tgtctgcagt gattgtgact      60
cggccctgga atttcgggtc atacatacta tggccaagaa                          100

<210> SEQ ID NO 34
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3RFBA

<400> SEQUENCE: 34
agaaccatgg catagcccga gtctcttgca cagtaataaa tggctgtgtc ctcagatctc      60
agactcgaga gctcc                                                      75

<210> SEQ ID NO 35
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3NMFS
```

```
<400> SEQUENCE: 35
ttcttggcca tagtatgtat gacccgaaat tccagggccg agtcacaatg ctggtagaca      60
catccaagaa ccagttctcc ctgaggctct cgagtgtgac                           100

<210> SEQ ID NO 36
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3NMBS

<400> SEQUENCE: 36
gaggctctcg agtgtgacag ccgcggacac agccgtatat tactgtgcaa gagactcggg      60
ctatgccatg gttct                                                      75

<210> SEQ ID NO 37
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3NMFA

<400> SEQUENCE: 37
gtcacactcg agagcctcag ggagaactgg ttcttggatg tgtctaccag cattgtgact      60
cggccctgga atttcgggtc atacatacta tggccaagaa                          100

<210> SEQ ID NO 38
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3NMBA

<400> SEQUENCE: 38
agaaccatgg catagcccga gtctcttgca cagtaatata cggctgtgtc cgcggctgtc      60
acactcgaga gcctc                                                      75

<210> SEQ ID NO 39
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "b" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 39 atg aaa tgc agc tgg gtc atc ttc ttc ctg atg gca gtg gtt aca ggg       48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg       96
Val Asn Ser Gln Val Gln Leu Leu Glu Ser Gly Ala Val Leu Ala Arg
     -1   1               5                  10
```

```
cct ggg act tcc gtg aag atc tcc tgc aag gct tcc gga ttc aac att      144
Pro Gly Thr Ser Val Lys Ile Ser Cys Lys Ala Ser Gly Phe Asn Ile
        15                  20                  25 aaa gac tac tat atg cat tgg gta aaa cag agg cct gga cag ggt cta      192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac      240
Glu Trp Ile Gly Gly Asn Asp Pro Ala Asn Gly His Ser Met Tyr Asp
                 50                  55                  60 ccg aaa ttc cag ggc cga gtc aca atc act gca gac aca tcc acg aac      288
Pro Lys Phe Gln Gly Arg Val Thr Ile Thr Ala Asp Thr Ser Thr Asn
             65                  70                  75 aca gcc tac atg gag ctc tcg agt ctg aga tct gag gac aca gcc att      336
Thr Ala Tyr Met Glu Leu Ser Ser Leu Arg Ser Glu Asp Thr Ala Ile
         80                  85                  90 tat tac tgt gca aga gac tcg ggc tat gcc atg gac tac tgg ggc caa      384
Tyr Tyr Cys Ala Arg Asp Ser Gly Tyr Ala Met Asp Tyr Trp Gly Gln
     95                 100                 105 ggc acc ctg gtc acc gtc tcc tca gct agc                              414
Gly Thr Leu Val Thr Val Ser Ser Ala Ser
110                 115
```

<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "b" of humanized H chain V region

<400> SEQUENCE: 40

Gln Val Gln Leu Leu Glu Ser Gly Ala Val Leu Ala Arg Pro Gly Thr
 1               5                   10                  15

Ser Val Lys Ile Ser Cys Lys Ala Ser Gly Phe Asn Ile Lys Asp Tyr
             20                  25                  30

Tyr Met His Trp Val Arg Gln Ala Pro Gly Gln Gly Leu Glu Trp Ile
         35                  40                  45

Gly Gly Asn Asp Pro Ala Asn Gly His Ser Met Tyr Asp Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Ser Ala Val Tyr Phe Cys
                 85                  90                  95

Ala Arg Asp Ser Gly Tyr Ala Met Asp Tyr Trp Gly Gln Gly Thr Leu
            100                 105                 110

Val Thr Val Ser Ser Ala Ser
        115

<210> SEQ ID NO 41
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "c" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide

<222> LOCATION: (58)..(414)

<400> SEQUENCE: 41

```
atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
     -1   1                   5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
     15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc cga gtc aca atg ctg gta gac aca tcc aag aac     288
Pro Lys Phe Gln Gly Arg Val Thr Met Leu Val Asp Thr Ser Lys Asn
             65                  70                  75 cag ttc tcc ctg agg ctc tcg agt gtg aca gcc gcg gac aca gcc gta     336
Gln Phe Ser Leu Arg Leu Ser Ser Val Thr Ala Ala Asp Thr Ala Val
         80                  85                  90 tat tac tgt gca aga gac tcg ggc tat gcc atg gac tac tgg ggc caa     384
Tyr Tyr Cys Ala Arg Asp Ser Gly Tyr Ala Met Asp Tyr Trp Gly Gln
     95                 100                 105 ggc acc ctg gtc acc gtc tcc tca gct agc                              414
Gly Thr Leu Val Thr Val Ser Ser Ala Ser
110                 115
```

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Amino acid sequence for version "c" of humanized H chain V region

<400> SEQUENCE: 42

```
Gln Val Gln Leu Leu Glu Ser Gly Ala Val Leu Ala Arg Pro Gly Thr
 1               5                  10                  15

Ser Val Lys Ile Ser Cys Lys Ala Ser Gly Phe Asn Ile Lys Asp Tyr
             20                  25                  30

Tyr Met His Trp Val Lys Gln Arg Pro Gly Gln Gly Leu Glu Trp Ile
         35                  40                  45

Gly Gly Asn Asp Pro Ala Asn Gly His Ser Met Tyr Asp Pro Lys Phe
     50                  55                  60

Gln Gly Arg Val Thr Met Leu Val Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Asp Ser Gly Tyr Ala Met Asp Tyr Trp Gly Gln Gly Thr Leu
            100                 105                 110

Val Thr Val Ser Ser Ala Ser
        115
```

<210> SEQ ID NO 43
<211> LENGTH: 100
<212> TYPE: DNA

```
<213> ORGANISM: Artificial Sequence
<220> FEATURE:
<223> OTHER INFORMATION: Description of Artificial Sequence: FR
      shuffling primer F3EPS

<400> SEQUENCE: 43
ttcttggcca tagtatgtat gacccgaaat tccagggcag agtcacgatt actgcggacg      60
aatccacgag cacagcctac atggagctct cgagtctgag                           100

<210> SEQ ID NO 44
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3EPA

<400> SEQUENCE: 44
agaaccatgg catagcccga gtctctcgca cagaaatata cggccgagtc ctcagatctc      60
agactcgaga gctcc                                                      75

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Primer
      F3PrS

<400> SEQUENCE: 45
ttcttggcca tagtatgtat                                                 20

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Primer
      F3PrA

<400> SEQUENCE: 46
agaaccatgg catagccc                                                   18

<210> SEQ ID NO 47
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3vHS

<400> SEQUENCE: 47
ttcttggcca tagtatgtat gacccgaaat tccagggcag agtctcgatt accgcggacg      60
agtcaacgaa gatagcctac atggagctca acagtctgag                           100

<210> SEQ ID NO 48
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3vHA

<400> SEQUENCE: 48
agaaccatgg catagcccga gtctctcgca cagaaataaa cggccgtgtc ctcagatctc      60
```

```
agactgttga gctcc                                                        75
```

<210> SEQ ID NO 49
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "d" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 49

```
atg aaa tgc agc tgg gtc atc ttc ttc ctg atg gca gtg gtt aca ggg      48
Met Lys Cys Ser Trp Val Ile Phe Phe Leu Met Ala Val Val Thr Gly
         -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
      -1   1               5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
 15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc aga gtc acg att act gcg gac gaa tcc acg agc     288
Pro Lys Phe Gln Gly Arg Val Thr Ile Thr Ala Asp Glu Ser Thr Ser
             65                  70                  75 aca gcc tac atg gag ctc tcg agt ctg aga tct gag gac tcg gcc gta     336
Thr Ala Tyr Met Glu Leu Ser Ser Leu Arg Ser Glu Asp Ser Ala Val
         80                  85                  90 tat ttc tgt gcg aga gac tcg ggc tat gcc atg gac tac tgg ggc caa     384
Tyr Phe Cys Ala Arg Asp Ser Gly Tyr Ala Met Asp Tyr Trp Gly Gln
     95                 100                 105 ggc acc ctg gtc acc gtc tcc tca gct agc                             414
Gly Thr Leu Val Thr Val Ser Ser Ala Ser
110                 115
```

<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "d" of humanized H chain V region

<400> SEQUENCE: 50

Gln Val Gln Leu Leu Glu Ser Gly Ala Val Leu Ala Arg Pro Gly Thr
 1               5                  10                  15

Ser Val Lys Ile Ser Cys Lys Ala Ser Gly Phe Asn Ile Lys Asp Tyr
             20                  25                  30

Tyr Met His Trp Val Lys Gln Arg Pro Gly Gln Gly Leu Glu Trp Ile
         35                  40                  45

```
Gly Gly Asn Asp Pro Ala Asn Gly His Ser Met Tyr Asp Pro Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Ser Ala Val Tyr Phe Cys
                85                  90                  95
Ala Arg Asp Ser Gly Tyr Ala Met Asp Tyr Trp Gly Gln Gly Thr Leu
            100                 105                 110
Val Thr Val Ser Ser Ala Ser
        115
```

<210> SEQ ID NO 51
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "e" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 51

```
atg aaa tgc agc tgg gtc atc ttc ttc ctg atg gca gtg gtt aca ggg     48
Met Lys Cys Ser Trp Val Ile Phe Phe Leu Met Ala Val Val Thr Gly
            -15                 -10                 -5 gtt aac tca cag gtg cag ctg ttg gag tct gga gct gtg ctg gca agg     96
Val Asn Ser Gln Val Gln Leu Leu Glu Ser Gly Ala Val Leu Ala Arg
        -1   1                   5                  10 cct ggg act tcc gtg aag atc tcc tgc aag gct tcc gga ttc aac att    144
Pro Gly Thr Ser Val Lys Ile Ser Cys Lys Ala Ser Gly Phe Asn Ile
        15                  20                  25 aaa gac tac tat atg cat tgg gta aaa cag agg cct gga cag ggt cta    192
Lys Asp Tyr Tyr Met His Trp Val Lys Gln Arg Pro Gly Gln Gly Leu
30                  35                  40                  45 gaa tgg att ggt ggg aat gat cct gcg aat ggc cat agt atg tat gac    240
Glu Trp Ile Gly Gly Asn Asp Pro Ala Asn Gly His Ser Met Tyr Asp
                50                  55                  60 ccg aaa ttc cag ggc aga gtc tcg att acc gcg gac gag tca acg aag    288
Pro Lys Phe Gln Gly Arg Val Ser Ile Thr Ala Asp Glu Ser Thr Lys
            65                  70                  75 ata gcc tac atg gag ctc aac agt ctg aga tct gag gac acg gcc gtt    336
Ile Ala Tyr Met Glu Leu Asn Ser Leu Arg Ser Glu Asp Thr Ala Val
        80                  85                  90 tat ttc tgt gcg aga gac tcg ggc tat gcc atg gac tac tgg ggc caa    384
Tyr Phe Cys Ala Arg Asp Ser Gly Tyr Ala Met Asp Tyr Trp Gly Gln
    95                 100                 105 ggc acc ctg gtc acc gtc tcc tca gct agc                            414
Gly Thr Leu Val Thr Val Ser Ser Ala Ser
110                 115
```

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "e" of humanized H chain V region

<400> SEQUENCE: 52

Gln Val Gln Leu Leu Glu Ser Gly Ala Val Leu Ala Arg Pro Gly Thr
1               5                   10                  15

Ser Val Lys Ile Ser Cys Lys Ala Ser Gly Phe Asn Ile Lys Asp Tyr
                20                  25                  30

Tyr Met His Trp Val Lys Gln Arg Pro Gly Gln Gly Leu Glu Trp Ile
            35                  40                  45

Gly Gly Asn Asp Pro Ala Asn Gly His Ser Met Tyr Asp Pro Lys Phe
        50                  55                  60

Gln Gly Arg Val Ser Ile Thr Ala Asp Glu Ser Thr Lys Ile Ala Tyr
65                  70                  75                  80

Met Glu Leu Asn Ser Leu Arg Ser Glu Asp Thr Ala Val Tyr Phe Cys
                85                  90                  95

Ala Arg Asp Ser Gly Tyr Ala Met Asp Tyr Trp Gly Gln Gly Thr Leu
            100                 105                 110

Val Thr Val Ser Ser Ala Ser
        115

<210> SEQ ID NO 53
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3SSS

<400> SEQUENCE: 53
ttcttggcca tagtatgtat gacccgaaat tccagggcag agtcacgatt accgcggaca     60
catccacgag cacagcctac atggagctca ggagcctgag                         100

<210> SEQ ID NO 54
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3SSA

<400> SEQUENCE: 54
agaaccatgg catagcccga gtctctcgca cagtaataca cggccgtgtc gtcagatctc     60
aggctcctga gctcc                                                     75

<210> SEQ ID NO 55
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3CDS

<400> SEQUENCE: 55
ttcttggcca tagtatgtat gacccgaaat tccagggcaa agccactctg actgcagacg     60
aatcctccag cacagcctac atgcaactct cgagcctacg                         100

<210> SEQ ID NO 56
<211> LENGTH: 75
<212> TYPE: DNA
<213> ORGANISM: Artificial Sequence
<220> FEATURE:
<223> OTHER INFORMATION: Description of Artificial Sequence: FR shuffling primer F3CDA

<400> SEQUENCE: 56
agaaccatgg catagcccga gtctcttgca caagaataga ccgcagagtc ctcagatcgt    60
aggctcgaga gttgc    75

<210> SEQ ID NO 57
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "f" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 57 atg aaa tgc agc tgg gtc atc ttc ttc ctg atg gca gtg gtt aca ggg    48
Met Lys Cys Ser Trp Val Ile Phe Phe Leu Met Ala Val Val Thr Gly
            -15                 -10                 -5 gtt aac tca cag gtg cag ctg ttg gag tct gga gct gtg ctg gca agg    96
Val Asn Ser Gln Val Gln Leu Leu Glu Ser Gly Ala Val Leu Ala Arg
        -1   1               5                   10 cct ggg act tcc gtg aag atc tcc tgc aag gct tcc gga ttc aac att    144
Pro Gly Thr Ser Val Lys Ile Ser Cys Lys Ala Ser Gly Phe Asn Ile
 15                  20                  25 aaa gac tac tat atg cat tgg gta aaa cag agg cct gga cag ggt cta    192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac    240
Glu Trp Ile Gly Gly Asn Asp Pro Ala Asn Gly His Ser Met Tyr Asp
                 50                  55                  60 ccg aaa ttc cag ggc aga gtc acg att acc gcg gac aca tcc acg agc    288
Pro Lys Phe Gln Gly Arg Val Thr Ile Thr Ala Asp Thr Ser Thr Ser
             65                  70                  75 aca gcc tac atg gag ctc agg agc ctg aga tct gac gac acg gcc gtg    336
Thr Ala Tyr Met Glu Leu Arg Ser Leu Arg Ser Asp Asp Thr Ala Val
         80                  85                  90 tat tac tgt gcg aga gac tcg ggc tat gcc atg gac tac tgg ggc caa    384
Tyr Tyr Cys Ala Arg Asp Ser Gly Tyr Ala Met Asp Tyr Trp Gly Gln
     95                 100                 105 ggc acc ctg gtc acc gtc tcc tca gct agc    414
Gly Thr Leu Val Thr Val Ser Ser Ala Ser
110                 115

<210> SEQ ID NO 58
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "f" of humanized H chain V region

<400> SEQUENCE: 58

Gln Val Gln Leu Leu Glu Ser Gly Ala Val Leu Ala Arg Pro Gly Thr
 1               5                   10                  15

Ser Val Lys Ile Ser Cys Lys Ala Ser Gly Phe Asn Ile Lys Asp Tyr

```
                20                  25                  30
Tyr Met His Trp Val Lys Gln Arg Pro Gly Gln Gly Leu Glu Trp Ile
         35                  40                  45

Gly Gly Asn Asp Pro Ala Asn Gly His Ser Met Tyr Asp Pro Lys Phe
 50                  55                  60

Gln Gly Arg Val Thr Ile Thr Ala Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Ser Gly Tyr Ala Met Asp Tyr Trp Gly Gln Gly Thr Leu
             100                 105                 110

Val Thr Val Ser Ser Ala Ser
         115

<210> SEQ ID NO 59
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "g" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 59 atg aaa tgc agc tgg gtc atc ttc ttc ctg atg gca gtg gtt aca ggg        48
Met Lys Cys Ser Trp Val Ile Phe Phe Leu Met Ala Val Val Thr Gly
             -15                 -10                  -5 gtt aac tca cag gtg cag ctg ttg gag tct gga gct gtg ctg gca agg        96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att       144
Pro Gly Thr Ser Val Lys Ile Ser Cys Lys Ala Ser Gly Phe Asn Ile
     15                  20                  25 aaa gac tac tat atg cat tgg gta aaa cag agg cct gga cag ggt cta       192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac       240
Glu Trp Ile Gly Gly Asn Asp Pro Ala Asn Gly His Ser Met Tyr Asp
                 50                  55                  60 ccg aaa ttc cag ggc aaa gcc act ctg act gca gac gaa tcc tcc agc       288
Pro Lys Phe Gln Gly Lys Ala Thr Leu Thr Ala Asp Glu Ser Ser Ser
             65                  70                  75 aca gcc tac atg caa ctc tcg agc cta cga tct gag gac tct gcg gtc       336
Thr Ala Tyr Met Gln Leu Ser Ser Leu Arg Ser Glu Asp Ser Ala Val
         80                  85                  90 tat tct tgt gca aga gac tcg ggc tat gcc atg gac tac tgg ggc caa       384
Tyr Ser Cys Ala Arg Asp Ser Gly Tyr Ala Met Asp Tyr Trp Gly Gln
     95                 100                 105 ggc acc ctg gtc acc gtc tcc tca gct agc                               414
Gly Thr Leu Val Thr Val Ser Ser Ala Ser
110                 115

<210> SEQ ID NO 60
<211> LENGTH: 119
```

<212> TYPE: PRT
<213> ORGANISM: Artificial Sequence
<220> FEATURE:
<223> OTHER INFORMATION: Description of Artificial Sequence: Amino acid
      sequence for version "g" of humanized H chain V region

<400> SEQUENCE: 60

Gln Val Gln Leu Leu Glu Ser Gly Ala Val Leu Ala Arg Pro Gly Thr
 1               5                  10                  15

Ser Val Lys Ile Ser Cys Lys Ala Ser Gly Phe Asn Ile Lys Asp Tyr
                20                  25                  30

Tyr Met His Trp Val Lys Gln Arg Pro Gly Gln Gly Leu Glu Trp Ile
            35                  40                  45

Gly Gly Asn Asp Pro Ala Asn Gly His Ser Met Tyr Asp Pro Lys Phe
        50                  55                  60

Gln Gly Lys Ala Thr Leu Thr Ala Asp Glu Ser Ser Ser Thr Ala Tyr
65                  70                  75                  80

Met Gln Leu Ser Ser Leu Arg Ser Glu Asp Ser Ala Val Tyr Ser Cys
                85                  90                  95

Ala Arg Asp Ser Gly Tyr Ala Met Asp Tyr Trp Gly Gln Gly Thr Leu
            100                 105                 110

Val Thr Val Ser Ser Ala Ser
        115

<210> SEQ ID NO 61
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3ADS

<400> SEQUENCE: 61
ttcttggcca tagtatgtat gacccgaaat tccagggccg cgtcaccatg tcagccgaca    60
agtcctccag cgccgcctat ttacagtgga ccagccttaa                        100

<210> SEQ ID NO 62
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3ADA

<400> SEQUENCE: 62
agaaccatgg catagcccga gtctctcgcg cagaaatata tggcggtgtc cgaggcctta    60
aggctggtcc actgt                                                    75

<210> SEQ ID NO 63
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "h" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 63

```
atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
     -1   1              5                  10 cct ggg act tcc gtg aag atc tcc tgc aag gct tcc gga ttc aac aat     144
Pro Gly Thr Ser Val Lys Ile Ser Cys Lys Ala Ser Gly Phe Asn Asn
 15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc cgc gtc acc atg tca gcc gac aag tcc tcc agc     288
Pro Lys Phe Gln Gly Arg Val Thr Met Ser Ala Asp Lys Ser Ser Ser
             65                  70                  75 gcc gcc tat tta cag tgg acc agc ctt aag gcc tcg gac acc gcc ata     336
Ala Ala Tyr Leu Gln Trp Thr Ser Leu Lys Ala Ser Asp Thr Ala Ile
         80                  85                  90 tat ttc tgc gcg aga gac tcg ggc tat gcc atg gac tac tgg ggc caa     384
Tyr Phe Cys Ala Arg Asp Ser Gly Tyr Ala Met Asp Tyr Trp Gly Gln
     95                 100                 105 ggc acc ctg gtc acc gtc tcc tca gct agc                              414
Gly Thr Leu Val Thr Val Ser Ser Ala Ser
110                 115
```

<210> SEQ ID NO 64
<211> LENGTH: 119
<212> TYPE: PRT
<213> ORGANISM: Artificial Sequence
<220> FEATURE:
<223> OTHER INFORMATION: Description of Artificial Sequence: Amino acid sequence for version "h" of humanized H chain V region

<400> SEQUENCE: 64

```
Gln Val Gln Leu Leu Glu Ser Gly Ala Val Leu Ala Arg Pro Gly Thr
  1               5                  10                  15

Ser Val Lys Ile Ser Cys Lys Ala Ser Gly Phe Asn Asn Lys Asp Tyr
             20                  25                  30

Tyr Met His Trp Val Lys Gln Arg Pro Gly Gln Gly Leu Glu Trp Ile
         35                  40                  45

Gly Gly Asn Asp Pro Ala Asn Gly His Ser Met Tyr Asp Pro Lys Phe
     50                  55                  60

Gln Gly Arg Val Thr Met Ser Ala Asp Lys Ser Ser Ser Ala Ala Tyr
 65                  70                  75                  80

Leu Gln Trp Thr Ser Leu Lys Ala Ser Asp Thr Ala Ile Tyr Phe Cys
                 85                  90                  95

Ala Arg Asp Ser Gly Tyr Ala Met Asp Tyr Trp Gly Gln Gly Thr Leu
            100                 105                 110

Val Thr Val Ser Ser Ala Ser
        115
```

<210> SEQ ID NO 65
<211> LENGTH: 100
<212> TYPE: DNA
<213> ORGANISM: Artificial Sequence -continued

```
<220> FEATURE:
<223> OTHER INFORMATION: Description of Artificial Sequence: FR
      shuffling primer F3MMS

<400> SEQUENCE: 65
ttcttggcca tagtatgtat gacccgaaat tccagggcag agtcacgatt accgcggaca      60
catcgacgag cacagtcttc atggaactga gcagcctgag                           100

<210> SEQ ID NO 66
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3MMA

<400> SEQUENCE: 66
agaaccatgg catagcccga gtctctcgca cagtaataca cggccgtgtc ttcagatctc      60
aggctgctca gttcc                                                      75

<210> SEQ ID NO 67
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3RBMS

<400> SEQUENCE: 67
ttcttggcca tagtatgtat gacccgaaat tccagggcag agtcaccttt accgcggaca      60
catccgcgaa cacagcctac atggagttga ggagcctcag                           100

<210> SEQ ID NO 68
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3BMA

<400> SEQUENCE: 68
agaaccatgg catagcccga gtctctcgca caataataaa cagccgtgtc tgcagatctg      60
aggctcctca actcc                                                      75

<210> SEQ ID NO 69
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "i" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 69 atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5
```

```
gtt aac tca cag gtg cag ctg ttg gag tct gga gct gtg ctg gca agg      96
Val Asn Ser Gln Val Gln Leu Leu Glu Ser Gly Ala Val Leu Ala Arg
     -1   1              5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
         15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc aga gtc acg att acc gcg gac aca tcg acg agc     288
Pro Lys Phe Gln Gly Arg Val Thr Ile Thr Ala Asp Thr Ser Thr Ser
             65                  70                  75 aca gtc ttc atg gaa ctg agc agc ctg aga tct gaa gac acg gcc gtg     336
Thr Val Phe Met Glu Leu Ser Ser Leu Arg Ser Glu Asp Thr Ala Val
         80                  85                  90 tat tac tgt gcg aga gac tcg ggc tat gcc atg gac tac tgg ggc caa     384
Tyr Tyr Cys Ala Arg Asp Ser Gly Tyr Ala Met Asp Tyr Trp Gly Gln
 95                 100                 105 ggc acc ctg gtc acc gtc tcc tca gct agc                              414
Gly Thr Leu Val Thr Val Ser Ser Ala Ser
110                 115

<210> SEQ ID NO 70
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "i" of humanized H chain V region

<400> SEQUENCE: 70

Gln Val Gln Leu Leu Glu Ser Gly Ala Val Leu Ala Arg Pro Gly Thr
 1               5                  10                  15

Ser Val Lys Ile Ser Cys Lys Ala Ser Gly Phe Asn Ile Lys Asp Tyr
             20                  25                  30

Tyr Met His Trp Val Lys Gln Arg Pro Gly Gln Gly Leu Glu Trp Ile
         35                  40                  45

Gly Gly Asn Asp Pro Ala Asn Gly His Ser Met Tyr Asp Pro Lys Phe
     50                  55                  60

Gln Gly Arg Val Thr Ile Thr Ala Asp Thr Ser Thr Ser Thr Ala Tyr
 65                  70                  75                  80

Met Glu Leu Arg Ser Leu Arg Ser Asp Thr Ala Val Tyr Cys
                 85                  90                  95

Ala Arg Asp Ser Gly Tyr Ala Met Asp Tyr Trp Gly Gln Gly Thr Leu
            100                 105                 110

Val Thr Val Ser Ser Ala Ser
        115

<210> SEQ ID NO 71
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "j" of humanized H chain V region
<220> FEATURE:
<221> NAME/KEY: CDS
<222> LOCATION: (1)..(414)
<220> FEATURE:
```

<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 71

```
atg aaa tgc agc tgg gtc atc ttc ttc ctg atg gca gtg gtt aca ggg       48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg       96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att      144
Pro Gly Thr Ser Val Lys Ile Ser Cys Lys Ala Ser Gly Phe Asn Ile
 15                  20                  25 aaa gac tac tat atg cat tgg gta aaa cag agg cct gga cag ggt cta      192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac      240
Glu Trp Ile Gly Gly Asn Asp Pro Ala Asn Gly His Ser Met Tyr Asp
                 50                  55                  60 ccg aaa ttc cag ggc aga gtc acc ttt acc gcg gac aca tcc gcg aac      288
Pro Lys Phe Gln Gly Arg Val Thr Phe Thr Ala Asp Thr Ser Ala Asn
             65                  70                  75 aca gcc tac atg gag ttg agg agc ctc aga tct gca gac acg gct gtt      336
Thr Ala Tyr Met Glu Leu Arg Ser Leu Arg Ser Ala Asp Thr Ala Val
         80                  85                  90 tat tat tgt gcg aga gac tcg ggc tat gcc atg gac tac tgg ggc caa      384
Tyr Tyr Cys Ala Arg Asp Ser Gly Tyr Ala Met Asp Tyr Trp Gly Gln
     95                 100                 105 ggc acc ctg gtc acc gtc tcc tca gct agc                              414
Gly Thr Leu Val Thr Val Ser Ser Ala Ser
110                 115
```

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Amino acid sequence for version "j" of humanized H chain V region

<400> SEQUENCE: 72

```
Gln Val Gln Leu Leu Glu Ser Gly Ala Val Leu Ala Arg Pro Gly Thr
  1               5                  10                  15

Ser Val Lys Ile Ser Cys Lys Ala Ser Gly Phe Asn Ile Lys Asp Tyr
             20                  25                  30

Tyr Met His Trp Val Lys Gln Arg Pro Gly Gln Gly Leu Glu Trp Ile
         35                  40                  45

Gly Gly Asn Asp Pro Ala Asn Gly His Ser Met Tyr Asp Pro Lys Phe
     50                  55                  60

Gln Gly Arg Val Thr Phe Thr Ala Asp Thr Ser Ala Asn Thr Ala Tyr
 65                  70                  75                  80

Met Glu Leu Arg Ser Leu Arg Ser Ala Asp Thr Ala Val Tyr Tyr Cys
                 85                  90                  95

Ala Arg Asp Ser Gly Tyr Ala Met Asp Tyr Trp Gly Gln Gly Thr Leu
            100                 105                 110

Val Thr Val Ser Ser Ala Ser
        115
```

<210> SEQ ID NO 73
<211> LENGTH: 79
<212> TYPE: DNA
<213> ORGANISM: Artificial Sequence
<220> FEATURE:
<223> OTHER INFORMATION: Description of Artificial Sequence: FR
      shuffling primer F2MPS

<400> SEQUENCE: 73
ttctatgcat tgggtgcgcc aggctccagg acagggcctg gagtggatgg gagggaatga    60
tcctgcgaat ggccattct                                                 79

<210> SEQ ID NO 74
<211> LENGTH: 79
<212> TYPE: DNA
<213> ORGANISM: Artificial Sequence
<220> FEATURE:
<223> OTHER INFORMATION: Description of Artificial Sequence: FR
      shuffling primer F2MPA

<400> SEQUENCE: 74
agaatggcca ttcgcaggat cattccctcc catccactcc aggccctgtc ctggagcctg    60
gcgcacccaa tgcatagaa                                                 79

<210> SEQ ID NO 75
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "b1" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 75 atg aaa tgc agc tgg gtc atc ttc ttc ctg atg gca gtg gtt aca ggg     48
Met Lys Cys Ser Trp Val Ile Phe Phe Leu Met Ala Val Val Thr Gly
        -15                 -10                  -5 gtt aac tca cag gtg cag ctg ttg gag tct gga gct gtg ctg gca agg     96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att    144
Pro Gly Thr Ser Val Lys Ile Ser Cys Lys Ala Ser Gly Phe Asn Ile
     15                  20                  25 aaa gac tac tat atg cat tgg gtg cgc cag gct cca gga cag ggc ctg    192
Lys Asp Tyr Tyr Met His Trp Val Arg Gln Ala Pro Gly Gln Gly Leu
 30                  35                  40                  45 gag tgg atg gga ggg aat gat cct gcg aat ggc cat agt atg tat gac    240
Glu Trp Met Gly Gly Asn Asp Pro Ala Asn Gly His Ser Met Tyr Asp
                 50                  55                  60 ccg aaa ttc cag ggc cga gtc aca atc act gca gac aca tcc acg aac    288
Pro Lys Phe Gln Gly Arg Val Thr Ile Thr Ala Asp Thr Ser Thr Asn
             65                  70                  75 aca gcc tac atg gag ctc tcg agt ctg aga tct gag gac aca gcc att    336
Thr Ala Tyr Met Glu Leu Ser Ser Leu Arg Ser Glu Asp Thr Ala Ile
         80                  85                  90 tat tac tgt gca aga gac tcg ggc tat gcc atg gac tac tgg ggc caa    384
Tyr Tyr Cys Ala Arg Asp Ser Gly Tyr Ala Met Asp Tyr Trp Gly Gln

```
Tyr Tyr Cys Ala Arg Asp Ser Gly Tyr Ala Met Asp Tyr Trp Gly Gln
         95                  100                 105 ggc acc ctg gtc acc gtc tcc tca gct agc                              414
Gly Thr Leu Val Thr Val Ser Ser Ala Ser
110                 115

<210> SEQ ID NO 76
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "b1" of humanized H chain V region

<400> SEQUENCE: 76

Gln Val Gln Leu Leu Glu Ser Gly Ala Val Leu Ala Arg Pro Gly Thr
  1               5                  10                  15

Ser Val Lys Ile Ser Cys Lys Ala Ser Gly Phe Asn Ile Lys Asp Tyr
             20                  25                  30

Tyr Met His Trp Val Arg Gln Ala Pro Gly Gln Gly Leu Glu Trp Met
         35                  40                  45

Gly Gly Asn Asp Pro Ala Asn Gly His Ser Met Tyr Asp Pro Lys Phe
     50                  55                  60

Gln Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Ile Tyr Tyr Cys
             85                   90                  95

Ala Arg Asp Ser Gly Tyr Ala Met Asp Tyr Trp Gly Gln Gly Thr Leu
            100                 105                 110

Val Thr Val Ser Ser Ala Ser
        115

<210> SEQ ID NO 77
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "d1" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 77 atg aaa tgc agc tgg gtc atc ttc ttc ctg atg gca gtg gtt aca ggg    48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg    96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att   144
Pro Gly Thr Ser Val Lys Ile Ser Cys Lys Ala Ser Gly Phe Asn Ile
             15                  20                  25 aaa gac tac tat atg cat tgg gtg cgc cag gct cca gga cag ggc ctg   192
Lys Asp Tyr Tyr Met His Trp Val Arg Gln Ala Pro Gly Gln Gly Leu
 30                  35                  40                  45 gag tgg atg gga ggg aat gat cct gcg aat ggc cat agt atg tat gac   240
```

```
Glu Trp Met Gly Gly Asn Asp Pro Ala Asn Gly His Ser Met Tyr Asp
             50                  55                  60 ccg aaa ttc cag ggc aga gtc acg att act gcg gac gaa tcc acg agc       288
Pro Lys Phe Gln Gly Arg Val Thr Ile Thr Ala Asp Glu Ser Thr Ser
         65                  70                  75 aca gcc tac atg gag ctc tcg agt ctg aga tct gag gac tcg gcc gta       336
Thr Ala Tyr Met Glu Leu Ser Ser Leu Arg Ser Glu Asp Ser Ala Val
     80                  85                  90 tat ttc tgt gcg aga gac tcg ggc tat gcc atg gac tac tgg ggc caa       384
Tyr Phe Cys Ala Arg Asp Ser Gly Tyr Ala Met Asp Tyr Trp Gly Gln
 95                 100                 105 ggc acc ctg gtc acc gtc tcc tca gct agc                               414
Gly Thr Leu Val Thr Val Ser Ser Ala Ser
110             115
```

<210> SEQ ID NO 78
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "d1" of humanized H chain V region

<400> SEQUENCE: 78

```
Gln Val Gln Leu Leu Glu Ser Gly Ala Val Leu Ala Arg Pro Gly Thr
 1               5                  10                  15

Ser Val Lys Ile Ser Cys Lys Ala Ser Gly Phe Asn Ile Lys Asp Tyr
             20                  25                  30

Tyr Met His Trp Val Arg Gln Ala Pro Gly Gln Gly Leu Glu Trp Met
         35                  40                  45

Gly Gly Asn Asp Pro Ala Asn Gly His Ser Met Tyr Asp Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Ser Ala Val Tyr Phe Cys
                 85                  90                  95

Ala Arg Asp Ser Gly Tyr Ala Met Asp Tyr Trp Gly Gln Gly Thr Leu
            100                 105                 110

Val Thr Val Ser Ser Ala Ser
        115
```

<210> SEQ ID NO 79
<211> LENGTH: 79
<212> TYPE: DNA
<213> ORGANISM: Artificial Sequence
<220> FEATURE:
<223> OTHER INFORMATION: Description of Artificial Sequence: FR
      shuffling primer F2VHS

<400> SEQUENCE: 79
ttctatgcat tgggtgcgac aggcccctgg acaagggctt gagtggattg gagggaatga      60
tcctgcgaat ggccatctt                                                   79

<210> SEQ ID NO 80
<211> LENGTH: 79
<212> TYPE: DNA
<213> ORGANISM: Artificial Sequence
<220> FEATURE:
<223> OTHER INFORMATION: Description of Artificial Sequence: FR
      shuffling primer F2VHA

<400> SEQUENCE: 80

```
aagatggcca ttcgcaggat cattccctcc aatccactca agcccttgtc cagggggcctg    60 tcgcacccaa tgcatagaa                                                  79
```

<210> SEQ ID NO 81
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "b3" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 81

```
atg aaa tgc agc tgg gtc atc ttc ttc ctg atg gca gtg gtt aca ggg     48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg     96
Val Asn Ser Gln Val Gln Leu Leu Glu Ser Gly Ala Val Leu Ala Arg
     -1  1               5                  10 cct ggg act tcc gtg aag atc tcc tgc aag gct tcc gga ttc aac att    144
Pro Gly Thr Ser Val Lys Ile Ser Cys Lys Ala Ser Gly Phe Asn Ile
         15                  20                  25 aaa gac tac tat atg cat tgg gtg cga cag gcc cct gga caa ggg ctt    192
Lys Asp Tyr Tyr Met His Trp Val Arg Gln Ala Pro Gly Gln Gly Leu
 30                  35                  40                  45 gag tgg att gga ggg aat gat cct gcg aat ggc cat agt atg tat gac    240
Glu Trp Ile Gly Gly Asn Asp Pro Ala Asn Gly His Ser Met Tyr Asp
                 50                  55                  60 ccg aaa ttc cag ggc cga gtc aca atc act gca gac aca tcc acg aac    288
Pro Lys Phe Gln Gly Arg Val Thr Ile Thr Ala Asp Thr Ser Thr Asn
             65                  70                  75 aca gcc tac atg gag ctc tcg agt ctg aga tct gag gac aca gcc att    336
Thr Ala Tyr Met Glu Leu Ser Ser Leu Arg Ser Glu Asp Thr Ala Ile
         80                  85                  90 tat tac tgt gca aga gac tcg ggc tat gcc atg gac tac tgg ggc caa    384
Tyr Tyr Cys Ala Arg Asp Ser Gly Tyr Ala Met Asp Tyr Trp Gly Gln
     95                 100                 105 ggc acc ctg gtc acc gtc tcc tca gct agc                            414
Gly Thr Leu Val Thr Val Ser Ser Ala Ser
110                 115
```

<210> SEQ ID NO 82
<211> LENGTH: 119
<212> TYPE: PRT
<213> ORGANISM: Artificial Sequence
<220> FEATURE:
<223> OTHER INFORMATION: Description of Artificial Sequence: Amino acid
      sequence for version "b3" of humanized H chain V region

<400> SEQUENCE: 82

```
Gln Val Gln Leu Leu Glu Ser Gly Ala Val Leu Ala Arg Pro Gly Thr
  1               5                  10                  15

Ser Val Lys Ile Ser Cys Lys Ala Ser Gly Phe Asn Ile Lys Asp Tyr
             20                  25                  30

Tyr Met His Trp Val Arg Gln Ala Pro Gly Gln Gly Leu Glu Trp Ile
```

```
                 35                  40                  45
Gly Gly Asn Asp Pro Ala Asn Gly His Ser Met Tyr Asp Pro Lys Phe
     50                  55                  60

Gln Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Ile Tyr Tyr Cys
                 85                  90                  95

Ala Arg Asp Ser Gly Tyr Ala Met Asp Tyr Trp Gly Gln Gly Thr Leu
                100                 105                 110

Val Thr Val Ser Ser Ala Ser
            115

<210> SEQ ID NO 83
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "d3" of humanized H chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 83 atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
     -1   1                   5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
 15                  20                  25 aaa gac tac tat atg cat tgg gtg cga cag gcc cct gga caa ggg ctt     192
Lys Asp Tyr Tyr Met His Trp Val Arg Gln Ala Pro Gly Gln Gly Leu
 30                  35                  40                  45 gag tgg att gga ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc aga gtc acg att act gcg gac gaa tcc acg agc     288
Pro Lys Phe Gln Gly Arg Val Thr Ile Thr Ala Asp Glu Ser Thr Ser
 65                  70                  75 aca gcc tac atg gag ctc tcg agt ctg aga tct gag gac tcg gcc gta     336
Thr Ala Tyr Met Glu Leu Ser Ser Leu Arg Ser Glu Asp Ser Ala Val
         80                  85                  90 tat ttc tgt gcg aga gac tcg ggc tat gcc atg gac tac tgg ggc caa     384
Tyr Phe Cys Ala Arg Asp Ser Gly Tyr Ala Met Asp Tyr Trp Gly Gln
 95                 100                 105 ggc acc ctg gtc acc gtc tcc tca gct agc                             414
Gly Thr Leu Val Thr Val Ser Ser Ala Ser
110                 115

<210> SEQ ID NO 84
<211> LENGTH: 119
<212> TYPE: PRT
<213> ORGANISM: Artificial Sequence
<220> FEATURE:
```

OTHER INFORMATION: Description of Artificial Sequence: Amino acid
sequence for version "d3" of humanized H chain V region

<400> SEQUENCE: 84

Gln Val Gln Leu Leu Glu Ser Gly Ala Val Leu Ala Arg Pro Gly Thr
1               5                   10                  15

Ser Val Lys Ile Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Gly Asn Asp Pro Ala Asn Gly His Ser Met Tyr Asp Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Ser Ala Val Tyr Phe Cys
                85                  90                  95

Ala Arg Asp Ser Gly Tyr Ala Met Asp Tyr Trp Gly Gln Gly Thr Leu
            100                 105                 110

Val Thr Val Ser Ser Ala Ser
        115

<210> SEQ ID NO 85
<211> LENGTH: 98
<212> TYPE: DNA
<213> ORGANISM: Artificial Sequence
<220> FEATURE:
<223> OTHER INFORMATION: Description of Artificial Sequence: FR
      shuffling vector Lv1S

<400> SEQUENCE: 85
gtctagatct ccaccatgag ggcccctgct cagttttttg ggatcttgtt gctctggttt      60
ccagggatcc gatgtgacat ccagatgacc cagtctcc                              98

<210> SEQ ID NO 86
<211> LENGTH: 98
<212> TYPE: DNA
<213> ORGANISM: Artificial Sequence
<220> FEATURE:
<223> OTHER INFORMATION: Description of Artificial Sequence: FR
      shuffling vector h5Lv4S

<400> SEQUENCE: 86
ttggcagatg gggtcccatc aaggttcagt ggctccggat ctggtaccga tttcactctc      60
accatctcga gtctgcaacc tgaagatttt gcaactta                              98

<210> SEQ ID NO 87
<211> LENGTH: 98
<212> TYPE: DNA
<213> ORGANISM: Artificial Sequence
<220> FEATURE:
<223> OTHER INFORMATION: Description of Artificial Sequence: FR
      shuffling vector h5Lv2A

<400> SEQUENCE: 87
cttaagaagc ttttaatgtc ctgtgaggcc ttgcacgtga tggtgactct gtctcctaca      60
gatgcagaca gggaggatgg agactgggtc atctggat                              98

<210> SEQ ID NO 88
<211> LENGTH: 98
<212> TYPE: DNA
<213> ORGANISM: Artificial Sequence

```
<220> FEATURE:
<223> OTHER INFORMATION: Description of Artificial Sequence: FR
      shuffling vector h5Lv3A

<400> SEQUENCE: 88
gatgggaccc catctgccaa actagttgca taatagatca ggagcttagg ggctttccct      60
ggtttctgct gataccaact taagaagctt ttaatgtc                              98

<210> SEQ ID NO 89
<211> LENGTH: 94
<212> TYPE: DNA
<213> ORGANISM: Artificial Sequence
<220> FEATURE:
<223> OTHER INFORMATION: Description of Artificial Sequence: FR
      shuffling vector h5Lv5A

<400> SEQUENCE: 89
tgttcgtacg tttgatctcc accttggtcc ctccgccgaa cgtgtacggg ctctcaccat      60
gctgcagaca gtagtaagtt gcaaaatctt cagg                                  94

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Primer
      h5LvS

<400> SEQUENCE: 90
gtctagatct ccaccatgag                                                  20

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Primer
      h5LvA

<400> SEQUENCE: 91
tgttcgtacg tttgatctc                                                   19

<210> SEQ ID NO 92
<211> LENGTH: 381
<212> TYPE: DNA
<213> ORGANISM: Artificial Sequence
<220> FEATURE:
<223> OTHER INFORMATION: Description of Artificial Sequence: Nucleotide
      sequence coding for version "a" of humanized L chain V region
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)

<400> SEQUENCE: 92 atg agg gcc cct gct cag ttt ttt ggg atc ttg ttg ctc tgg ttt cca       48
Met Arg Ala Pro Ala Gln Phe Phe Gly Ile Leu Leu Leu Trp Phe Pro
-20              -15                 -10                 -5 ggg atc cga tgt gac atc cag atg acc cag tct cca tcc tcc ctg tct       96
Gly Ile Arg Cys Asp Ile Gln Met Thr Gln Ser Pro Ser Ser Leu Ser
         -1   1               5                  10
```

```
gca tct gta gga gac aga gtc acc atc acg tgc aag gcc tca cag gac    144
Ala Ser Val Gly Asp Arg Val Thr Ile Thr Cys Lys Ala Ser Gln Asp
         15                  20                  25 att aaa agc ttc tta agt tgg tat cag cag aaa cca ggg aaa gcc cct    192
Ile Lys Ser Phe Leu Ser Trp Tyr Gln Gln Lys Pro Gly Lys Ala Pro
 30                  35                  40 aag ctc ctg atc tat tat gca act agt ttg gca gat ggg gtc cca tca    240
Lys Leu Leu Ile Tyr Tyr Ala Thr Ser Leu Ala Asp Gly Val Pro Ser
 45                  50                  55                  60 agg ttc agt ggc tcc gga tct ggt acc gat ttc act ctc acc atc tcg    288
Arg Phe Ser Gly Ser Gly Ser Gly Thr Asp Phe Thr Leu Thr Ile Ser
             65                  70                  75 agt ctg caa cct gaa gat ttt gca act tac tac tgt ctg cag cat ggt    336
Ser Leu Gln Pro Glu Asp Phe Ala Thr Tyr Tyr Cys Leu Gln His Gly
         80                  85                  90 gag agc ccg tac acg ttc ggc gga ggg acc aag gtg gag atc aaa        381
Glu Ser Pro Tyr Thr Phe Gly Gly Gly Thr Lys Val Glu Ile Lys
 95                  100                 105
```

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence for version "a" of humanized L chain V region

<400> SEQUENCE: 93

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Lys Ser Phe
             20                  25                  30

Leu Ser Trp Tyr Gln Gln Lys Pro Gly Lys Ala Pro Lys Leu Leu Ile
         35                  40                  45

Tyr Tyr Ala Thr Ser Leu Ala Asp Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Gly Glu Ser Pro Tyr
                 85                  90                  95

Thr Phe Gly Gly Gly Thr Lys Val Glu Ile Lys
             100                 105

<210> SEQ ID NO 94
<211> LENGTH: 77
<212> TYPE: DNA
<213> ORGANISM: Artificial Sequence
<220> FEATURE:
<223> OTHER INFORMATION: Description of Artificial Sequence: FR
      shuffling primer F3SS

<400> SEQUENCE: 94
gtctggtacc gattacactc tcaccatctc gagcctccag cctgaagatt ttgcaactta    60
ctattgtctg cagaaca                                                   77

<210> SEQ ID NO 95
<211> LENGTH: 77
<212> TYPE: DNA
<213> ORGANISM: Artificial Sequence
<220> FEATURE:
<223> OTHER INFORMATION: Description of Artificial Sequence: FR
      shuffling primer F3SA

<400> SEQUENCE: 95

```
tgttctgcag acaatagtaa gttgcaaaat cttcaggctg gaggctcgag atggtgagag      60
tgtaatcggt accagac                                                    77
```

<210> SEQ ID NO 96
<211> LENGTH: 77
<212> TYPE: DNA
<213> ORGANISM: Artificial Sequence
<220> FEATURE:
<223> OTHER INFORMATION: Description of Artificial Sequence: FR
      shuffling primer F3RS

<400> SEQUENCE: 96

```
gtctggtacc gattacactc tcaccatctc gagcctccag cctgaagata ttgcaactta      60
ctattgtctg cagaaca                                                    77
```

<210> SEQ ID NO 97
<211> LENGTH: 77
<212> TYPE: DNA
<213> ORGANISM: Artificial Sequence
<220> FEATURE:
<223> OTHER INFORMATION: Description of Artificial Sequence: FR
      shuffling primer F3RA

<400> SEQUENCE: 97

```
tgttctgcag acaatagtaa gttgcaatat cttcaggctg gaggctcgag atggtgagag      60
tgtaatcggt accagac                                                    77
```

<210> SEQ ID NO 98
<211> LENGTH: 381
<212> TYPE: DNA
<213> ORGANISM: Artificial Sequence
<220> FEATURE:
<223> OTHER INFORMATION: Description of Artificial Sequence: Nucleotide
      sequence coding for version "b" of humanized L chain V region
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)

<400> SEQUENCE: 98

```
atg agg gcc cct gct cag ttt ttt ggg atc ttg ttg ctc tgg ttt cca       48
Met Arg Ala Pro Ala Gln Phe Phe Gly Ile Leu Leu Leu Trp Phe Pro
-20             -15                 -10                 -5 ggg atc cga tgt gac atc cag atg acc cag tct cca tcc tcc ctg tct       96
Gly Ile Arg Cys Asp Ile Gln Met Thr Gln Ser Pro Ser Ser Leu Ser
            -1   1               5                  10 gca tct gta gga gac aga gtc acc atc acg tgc aag gcc tca cag gac      144
Ala Ser Val Gly Asp Arg Val Thr Ile Thr Cys Lys Ala Ser Gln Asp
         15                 20                  25 att aaa agc ttc tta agt tgg tat cag cag aaa cca ggg aaa gcc cct      192
Ile Lys Ser Phe Leu Ser Trp Tyr Gln Gln Lys Pro Gly Lys Ala Pro
    30                  35                  40 aag ctc ctg atc tat tat gca act agt ttg gca gat ggg gtc cca tca      240
Lys Leu Leu Ile Tyr Tyr Ala Thr Ser Leu Ala Asp Gly Val Pro Ser
45                  50                  55                  60 agg ttc agt ggc tcc gga tct ggt acc gat tac act ctc acc atc tcg      288
Arg Phe Ser Gly Ser Gly Ser Gly Thr Asp Tyr Thr Leu Thr Ile Ser
```

-continued

```
                         65                  70                  75
agc ctc cag cct gaa gat ttt gca act tac tat tgt ctg cag cat ggt        336
Ser Leu Gln Pro Glu Asp Phe Ala Thr Tyr Tyr Cys Leu Gln His Gly
                 80                  85                  90 gag agc ccg tac acg ttc ggc gga ggg acc aag gtg gag atc aaa            381
Glu Ser Pro Tyr Thr Phe Gly Gly Gly Thr Lys Val Glu Ile Lys
         95                 100                 105
```

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence for version "b" of humanized L chain V region

<400> SEQUENCE: 99

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Lys Ser Phe
             20                  25                  30

Leu Ser Trp Tyr Gln Gln Lys Pro Gly Lys Ala Pro Lys Leu Leu Ile
         35                  40                  45

Tyr Tyr Ala Thr Ser Leu Ala Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln His Gly Glu Ser Pro Tyr
                 85                  90                  95

Thr Phe Gly Gly Gly Thr Lys Val Glu Ile Lys
            100                 105
```

<210> SEQ ID NO 100
<211> LENGTH: 381
<212> TYPE: DNA
<213> ORGANISM: Artificial Sequence
<220> FEATURE:
<223> OTHER INFORMATION: Description of Artificial Sequence: Nucleotide
      sequence coding for version "c" of humanized L chain V region
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)

<400> SEQUENCE: 100

```
atg agg gcc cct gct cag ttt ttt ggg atc ttg ttg ctc tgg ttt cca        48
Met Arg Ala Pro Ala Gln Phe Phe Gly Ile Leu Leu Leu Trp Phe Pro
-20                 -15                 -10                  -5 ggg atc cga tgt gac atc cag atg acc cag tct cca tcc tcc ctg tct        96
Gly Ile Arg Cys Asp Ile Gln Met Thr Gln Ser Pro Ser Ser Leu Ser
             -1   1               5                  10 gca tct gta gga gac aga gtc acc atc acg tgc aag gcc tca cag gac        144
Ala Ser Val Gly Asp Arg Val Thr Ile Thr Cys Lys Ala Ser Gln Asp
         15                  20                  25 att aaa agc ttc tta agt tgg tat cag cag aaa cca ggg aaa gcc cct        192
Ile Lys Ser Phe Leu Ser Trp Tyr Gln Gln Lys Pro Gly Lys Ala Pro
             30                  35                  40 aag ctc ctg atc tat tat gca act agt ttg gca gat ggg gtc cca tca        240
```

```
Lys Leu Leu Ile Tyr Tyr Ala Thr Ser Leu Ala Asp Gly Val Pro Ser
 45                  50                  55                  60 agg ttc agt ggc tcc gga tct ggt acc gat tac act ctc acc atc tcg    288
Arg Phe Ser Gly Ser Gly Ser Gly Thr Asp Tyr Thr Leu Thr Ile Ser
             65                  70                  75 agc ctc cag cct gaa gat att gca act tac tat tgt ctg cag cat ggt    336
Ser Leu Gln Pro Glu Asp Ile Ala Thr Tyr Tyr Cys Leu Gln His Gly
         80                  85                  90 gag agc ccg tac acg ttc ggc gga ggg acc aag gtg gag atc aaa        381
Glu Ser Pro Tyr Thr Phe Gly Gly Gly Thr Lys Val Glu Ile Lys
     95                 100                 105
```

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence for version "c" of humanized L chain V region

<400> SEQUENCE: 101

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Ile Lys Ser Phe
             20                  25                  30

Leu Ser Trp Tyr Gln Gln Lys Pro Gly Lys Ala Pro Lys Leu Leu Ile
         35                  40                  45

Tyr Tyr Ala Thr Ser Leu Ala Asp Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Tyr Cys Leu Gln His Gly Glu Ser Pro Tyr
                 85                  90                  95

Thr Phe Gly Gly Gly Thr Lys Val Glu Ile Lys
            100                 105
```

<210> SEQ ID NO 102
<211> LENGTH: 72
<212> TYPE: DNA
<213> ORGANISM: Artificial Sequence
<220> FEATURE:
<223> OTHER INFORMATION: Description of Artificial Sequence: FR
      shuffling primer F2SS

<400> SEQUENCE: 102
gtctcttaag ttggttccag cagaaaccag ggaaatctcc taagaccctg atctactatg    60
caactagtaa ca                                                        72

<210> SEQ ID NO 103
<211> LENGTH: 72
<212> TYPE: DNA
<213> ORGANISM: Artificial Sequence
<220> FEATURE:
<223> OTHER INFORMATION: Description of Artificial Sequence: FR
      shuffling primer F2SA

<400> SEQUENCE: 103
tgttactagt tgcatagtag atcagggtct taggagattt ccctggtttc tgctggaacc    60
aacttaagag ac                                                        72

<210> SEQ ID NO 104

```
<211> LENGTH: 72
<212> TYPE: DNA
<213> ORGANISM: Artificial Sequence
<220> FEATURE:
<223> OTHER INFORMATION: Description of Artificial Sequence: FR
      shuffling primer F2XS

<400> SEQUENCE: 104
gtctcttaag ttggtatcag cagaaaccag agaaagcccc taagtccctg atctattatg      60
caactagtaa ca                                                          72

<210> SEQ ID NO 105
<211> LENGTH: 72
<212> TYPE: DNA
<213> ORGANISM: Artificial Sequence
<220> FEATURE:
<223> OTHER INFORMATION: Description of Artificial Sequence: FR
      shuffling primer F2XA

<400> SEQUENCE: 105
tgttactagt tgcataatag atcagggact tagggggcttt ctctggtttc tgctgatacc     60
aacttaagag ac                                                          72

<210> SEQ ID NO 106
<211> LENGTH: 381
<212> TYPE: DNA
<213> ORGANISM: Artificial Sequence
<220> FEATURE:
<223> OTHER INFORMATION: Description of Artificial Sequence: Nucleotide
      sequence coding for version "b1" of humanized L chain V region
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)

<400> SEQUENCE: 106 atg agg gcc cct gct cag ttt ttt ggg atc ttg ttg ctc tgg ttt cca        48
Met Arg Ala Pro Ala Gln Phe Phe Gly Ile Leu Leu Leu Trp Phe Pro
-20             -15                 -10                 -5 ggg atc cga tgt gac atc cag atg acc cag tct cca tcc tcc ctg tct        96
Gly Ile Arg Cys Asp Ile Gln Met Thr Gln Ser Pro Ser Ser Leu Ser
            -1   1               5                  10 gca tct gta gga gac aga gtc acc atc acg tgc aag gcc tca cag gac       144
Ala Ser Val Gly Asp Arg Val Thr Ile Thr Cys Lys Ala Ser Gln Asp
        15                  20                  25 att aaa agc ttc tta agt tgg ttc cag cag aaa cca ggg aaa tct cct       192
Ile Lys Ser Phe Leu Ser Trp Phe Gln Gln Lys Pro Gly Lys Ser Pro
    30                  35                  40 aag acc ctg atc tac tat gca act agt ttg gca gat ggg gtc cca tca       240
Lys Thr Leu Ile Tyr Tyr Ala Thr Ser Leu Ala Asp Gly Val Pro Ser
45                  50                  55                  60 agg ttc agt ggc tcc gga tct ggt acc gat tac act ctc acc atc tcg       288
Arg Phe Ser Gly Ser Gly Ser Gly Thr Asp Tyr Thr Leu Thr Ile Ser
                65                  70                  75 agc ctc cag cct gaa gat ttt gca act tac tat tgt ctg cag cat ggt       336
Ser Leu Gln Pro Glu Asp Phe Ala Thr Tyr Tyr Cys Leu Gln His Gly
            80                  85                  90 gag agc ccg tac acg ttc ggc gga ggg acc aag gtg gag atc aaa           381
Glu Ser Pro Tyr Thr Phe Gly Gly Gly Thr Lys Val Glu Ile Lys
        95                  100                 105
```

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence for version "b1" of humanized L chain V region

<400> SEQUENCE: 107

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Lys Ser Phe
             20                  25                  30

Leu Ser Trp Phe Gln Gln Lys Pro Gly Lys Ser Pro Lys Thr Leu Ile
         35                  40                  45

Tyr Tyr Ala Thr Ser Leu Ala Asp Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln His Gly Glu Ser Pro Tyr
                 85                  90                  95

Thr Phe Gly Gly Gly Thr Lys Val Glu Ile Lys
            100                 105
```

<210> SEQ ID NO 108
<211> LENGTH: 381
<212> TYPE: DNA
<213> ORGANISM: Artificial Sequence
<220> FEATURE:
<223> OTHER INFORMATION: Description of Artificial Sequence: Nucleotide
      sequence coding for version "b2" of humanized L chain V region
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)

<400> SEQUENCE: 108

```
atg agg gcc cct gct cag ttt ttt ggg atc ttg ttg ctc tgg ttt cca      48
Met Arg Ala Pro Ala Gln Phe Phe Gly Ile Leu Leu Leu Trp Phe Pro
-20                 -15                 -10                  -5 ggg atc cga tgt gac atc cag atg acc cag tct cca tcc tcc ctg tct      96
Gly Ile Arg Cys Asp Ile Gln Met Thr Gln Ser Pro Ser Ser Leu Ser
             -1   1               5                  10 gca tct gta gga gac aga gtc acc atc acg tgc aag gcc tca cag gac     144
Ala Ser Val Gly Asp Arg Val Thr Ile Thr Cys Lys Ala Ser Gln Asp
         15                  20                  25 att aaa agc ttc tta agt tgg tat cag cag aaa cca gag aaa gcc cct     192
Ile Lys Ser Phe Leu Ser Trp Tyr Gln Gln Lys Pro Glu Lys Ala Pro
     30                  35                  40 aag tcc ctg atc tat tat gca act agt ttg gca gat ggg gtc cca tca     240
Lys Ser Leu Ile Tyr Tyr Ala Thr Ser Leu Ala Asp Gly Val Pro Ser
 45                  50                  55                  60 agg ttc agt ggc tcc gga tct ggt acc gat tac act ctc acc atc tcg     288
Arg Phe Ser Gly Ser Gly Ser Gly Thr Asp Tyr Thr Leu Thr Ile Ser
                 65                  70                  75 agc ctc cag cct gaa gat ttt gca act tac tat tgt ctg cag cat ggt     336
Ser Leu Gln Pro Glu Asp Phe Ala Thr Tyr Tyr Cys Leu Gln His Gly
```

```
                      80                  85                  90
gag agc ccg tac acg ttc ggc gga ggg acc aag gtg gag atc aaa          381
Glu Ser Pro Tyr Thr Phe Gly Gly Gly Thr Lys Val Glu Ile Lys
         95                 100                 105
```

<210> SEQ ID NO 109
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence for version "b2" of humanized L chain V region

<400> SEQUENCE: 109

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Lys Ser Phe
             20                  25                  30

Leu Ser Trp Tyr Gln Gln Lys Pro Glu Lys Ala Pro Lys Ser Leu Ile
         35                  40                  45

Tyr Tyr Ala Thr Ser Leu Ala Asp Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln His Gly Glu Ser Pro Tyr
                 85                  90                  95

Thr Phe Gly Gly Gly Thr Lys Val Glu Ile Lys
            100                 105

<210> SEQ ID NO 110
<211> LENGTH: 30
<212> TYPE: PRT
<213> ORGANISM: Artificial Sequence
<220> FEATURE:
<223> OTHER INFORMATION: Description of Artificial Sequence: Amino acid
      sequence of FR1 of all versions of humanized H chain V region

<400> SEQUENCE: 110

Gln Val Gln Leu Leu Glu Ser Gly Ala Val Leu Ala Arg Pro Gly Thr
 1               5                  10                  15

Ser Val Lys Ile Ser Cys Lys Ala Ser Gly Phe Asn Ile Lys
             20                  25                  30

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Amino acid
      sequence of FR2 versions "a" to "j" of humanized H chain V region

<400> SEQUENCE: 111

Trp Val Lys Gln Arg Pro Gly Gln Gly Leu Glu Trp Ile Gly
 1               5                  10

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Amino acid
      sequence of FR2 versions "b1" and "d1" of humanized H chain V
      region

```
<400> SEQUENCE: 112

Trp Val Arg Gln Ala Pro Gly Gln Gly Leu Glu Trp Met Gly
 1               5                  10

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Amino acid
      sequence of FR2 versions "b3" and "d3" of humanized H chain V
      region

<400> SEQUENCE: 113

Trp Val Arg Gln Ala Pro Gly Gln Gly Leu Glu Trp Ile Gly
 1               5                  10

<210> SEQ ID NO 114
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "a" of humanized H chain V region

<400> SEQUENCE: 114

Arg Ala Lys Leu Thr Ala Ala Thr Ser Ala Ser Ile Ala Tyr Leu Glu
 1               5                  10                  15

Phe Ser Ser Leu Thr Asn Glu Asp Ser Ala Val Tyr Tyr Cys Ala Arg
                 20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of versions "b", "b1" and "b3" of humanized H
      chain V region

<400> SEQUENCE: 115

Arg Val Thr Ile Thr Ala Asp Thr Ser Thr Asn Thr Ala Tyr Met Glu
 1               5                  10                  15

Leu Ser Ser Leu Arg Ser Glu Asp Thr Ala Ile Tyr Tyr Cys Ala Arg
                 20                  25                  30

<210> SEQ ID NO 116
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "c" of humanized H chain V region

<400> SEQUENCE: 116

Arg Val Thr Met Leu Val Asp Thr Ser Lys Asn Gln Phe Ser Leu Arg
 1               5                  10                  15

Leu Ser Ser Val Thr Ala Ala Asp Thr Ala Val Tyr Tyr Cys Ala Arg
                 20                  25                  30

<210> SEQ ID NO 117
<211> LENGTH: 32
<212> TYPE: PRT
<213> ORGANISM: Artificial Sequence
<220> FEATURE:
<223> OTHER INFORMATION: Description of Artificial Sequence: Amino acid
``` sequence of FR3 of versions "d", "d1" and "d3" of humanized H chain V region

<400> SEQUENCE: 117

Arg Val Thr Ile Thr Ala Asp Glu Ser Thr Ser Thr Ala Tyr Met Glu
1               5                   10                  15

Leu Ser Ser Leu Arg Ser Glu Asp Ser Ala Val Tyr Phe Cys Ala Arg
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "e" of humanized H chain V region

<400> SEQUENCE: 118

Arg Val Ser Ile Thr Ala Asp Glu Ser Thr Lys Ile Ala Tyr Met Glu
1               5                   10                  15

Leu Asn Ser Leu Arg Ser Glu Asp Thr Ala Val Tyr Phe Cys Ala Arg
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "f" of humanized H chain V region

<400> SEQUENCE: 119

Arg Val Thr Ile Thr Ala Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 120
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "g" of humanized H chain V region

<400> SEQUENCE: 120

Lys Ala Thr Leu Thr Ala Asp Glu Ser Ser Ser Thr Ala Tyr Met Gln
1               5                   10                  15

Leu Ser Ser Leu Arg Ser Glu Asp Ser Ala Val Tyr Ser Cys Ala Arg
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "h" of humanized H chain V region

<400> SEQUENCE: 121

Arg Val Thr Met Ser Ala Asp Lys Ser Ser Ser Ala Ala Tyr Leu Gln
1               5                   10                  15

Trp Thr Ser Leu Lys Ala Ser Asp Thr Ala Ile Tyr Phe Cys Ala Arg
            20                  25                  30

```
<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "i" of humanized H chain V region

<400> SEQUENCE: 122

Arg Val Thr Ile Thr Ala Asp Thr Ser Thr Ser Thr Val Phe Met Glu
 1               5                  10                  15

Leu Ser Ser Leu Arg Ser Glu Asp Thr Ala Val Tyr Tyr Cys Ala Arg
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "j" of humanized H chain V region

<400> SEQUENCE: 123

Arg Val Thr Phe Thr Ala Asp Thr Ser Ala Asn Thr Ala Tyr Met Glu
 1               5                  10                  15

Leu Arg Ser Leu Arg Ser Ala Asp Thr Ala Val Tyr Tyr Cys Ala Arg
            20                  25                  30

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence: Amino acid
      sequence of FR4 of all versions of humanized H chain V region

<400> SEQUENCE: 124

Trp Gly Gln Gly Thr Leu Val Thr Val Ser Ser Ala Ser
 1               5                  10

<210> SEQ ID NO 125
<211> LENGTH: 23
<212> TYPE: PRT
<213> ORGANISM: Artificial Sequence
<220> FEATURE:
<223> OTHER INFORMATION: Description of Artificial Sequence: Amino acid
      sequence of FR1 of all versions of humanized L chain V region

<400> SEQUENCE: 125

Asp Ile Gln Met Thr Gln Ser Pro Ser Ser Leu Ser Ala Ser Val Gly
 1               5                  10                  15

Asp Arg Val Thr Ile Thr Cys
            20

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Amino acid
      sequence of FR2 of versions "a", "b" and "c" of humanized L chain
      V region

<400> SEQUENCE: 126

Trp Tyr Gln Gln Lys Pro Gly Lys Ala Pro Lys Leu Leu Ile Tyr
 1               5                  10                  15
```

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Amino acid
      sequence of FR2 of version "b1" of humanized L chain V region

<400> SEQUENCE: 127

Trp Phe Gln Gln Lys Pro Gly Lys Ser Pro Lys Thr Leu Ile Tyr
 1               5                  10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Amino acid
      sequence of FR2 of version "b2" of humanized L chain V region

<400> SEQUENCE: 128

Trp Tyr Gln Gln Lys Pro Glu Lys Ala Pro Lys Ser Leu Ile Tyr
 1               5                  10                  15

<210> SEQ ID NO 129
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of version "a" of humanized L chain V region

<400> SEQUENCE: 129

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
             20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of FR3 of versions "b", "b1" and "b2" of humanized L
      chain V region

<400> SEQUENCE: 130

Gly Val Pro Ser Arg Phe Ser Gly Ser Gly Ser Gly Thr Asp Tyr Thr
 1               5                  10                  15

Leu Thr Ile Ser Ser Leu Gln Pro Glu Asp Phe Ala Thr Tyr Tyr Cys
             20                  25                  30

<210> SEQ ID NO 131
<211> LENGTH: 31
<212> TYPE: PRT
<213> ORGANISM: Artificial Sequence
<220> FEATURE:
<223> OTHER INFORMATION: Description of Artificial Sequence: Amino acid
      sequence of FR3 of version "c" of humanized L chain V region

<400> SEQUENCE: 131

Gly Val Pro Ser Arg Phe Ser Gly Ser Gly Ser Gly Thr Asp Tyr Thr
 1               5                  10                  15

Leu Thr Ile Ser Ser Leu Gln Pro Glu Asp Ile Ala Tyr Tyr Cys

-continued

```
                   20                  25                  30
```

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Amino acid
      sequence of FR4 of all versions of humanized L chain V region

<400> SEQUENCE: 132

Phe Gly Gly Gly Thr Lys Val Glu Ile Lys
  1               5                  10

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Amino acid
      sequence of CDR1 of all versions of humanized H chain V region

<400> SEQUENCE: 133

Asp Tyr Tyr Met His
  1               5

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Amino acid
      sequence of CDR2 of all versions of humanized H chain V region

<400> SEQUENCE: 134

Gly Asn Asp Pro Ala Asn Gly His Ser Met Tyr Asp Pro Lys Phe Gln
  1               5                  10                  15

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Amino acid
      sequence of CDR3 of all versions of humanized H chain V region

<400> SEQUENCE: 135

Asp Ser Gly Tyr Ala Met Asp Tyr
  1               5

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Amino acid
      sequence of CDR1 of all versions of humanized L chain V region

<400> SEQUENCE: 136

Lys Ala Ser Gln Asp Ile Lys Ser Phe Leu Ser
  1               5                  10

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Amino acid sequence of CDR2 of all versions of humanized L chain V region

<400> SEQUENCE: 137

Tyr Ala Thr Ser Leu Ala Asp
  1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Amino acid
      sequence of CDR3 of all versions of humanized L chain V region

<400> SEQUENCE: 138

Leu Gln His Gly Glu Ser Pro Tyr Thr
  1               5

<210> SEQ ID NO 139
<211> LENGTH: 118
<212> TYPE: PRT
<213> ORGANISM: Artificial Sequence
<220> FEATURE:
<223> OTHER INFORMATION: Description of Artificial Sequence: Amino acid
      sequence of H chain V region of anti TF mouse monoclonal antibody
      ATR-2

<400> SEQUENCE: 139

Glu Ile Gln Leu Gln Gln Ser Gly Pro Glu Leu Val Lys Pro Gly Ala
  1               5                  10                  15

Ser Val Lys Val Ser Cys Lys Ala Ser Gly Tyr Ser Phe Thr Asp Tyr
             20                  25                  30

Asn Met Tyr Trp Val Lys Gln Ser His Gly Lys Ser Leu Glu Trp Ile
         35                  40                  45

Gly Tyr Ile Asp Pro Tyr Asn Gly Gly Thr Ile Tyr Asn Gln Lys Phe
     50                  55                  60

Lys Gly Lys Ala Thr Leu Thr Val Asp Lys Ser Ser Ser Thr Ala Phe
 65                  70                  75                  80

Met His Leu Asn Ser Leu Thr Ser Glu Asp Ser Ala Val Tyr Tyr Cys
                 85                  90                  95

Ala Arg Gly Gly Glu Gly Tyr Tyr Phe Asp Tyr Trp Gly Gln Gly Thr
            100                 105                 110

Thr Leu Thr Val Ser Ser
        115

<210> SEQ ID NO 140
<211> LENGTH: 118
<212> TYPE: PRT
<213> ORGANISM: Artificial Sequence
<220> FEATURE:
<223> OTHER INFORMATION: Description of Artificial Sequence: Amino acid
      sequence of H chain V region of anti TF mouse monoclonal antibody
      ATR-3

<400> SEQUENCE: 140

Glu Ile Gln Leu Gln Gln Ser Gly Pro Glu Leu Val Lys Pro Gly Ala
  1               5                  10                  15

Ser Val Lys Val Ser Cys Lys Ala Ser Gly Tyr Ser Phe Thr Asp Tyr
             20                  25                  30

Asn Met Tyr Trp Val Lys Gln Ser His Gly Lys Ser Leu Glu Trp Ile
         35                  40                  45

Gly Tyr Ile Asp Pro Tyr Asn Gly Gly Thr Ile Tyr Asn Gln Lys Phe

```
              50                  55                  60
Lys Gly Lys Ala Thr Leu Thr Val Asp Lys Ser Ser Thr Ala Phe
 65                  70                  75                  80

Met His Leu Asn Ser Leu Thr Ser Glu Asp Ser Ala Val Tyr Tyr Cys
                 85                  90                  95

Ala Arg Gly Gly Glu Gly Tyr Tyr Phe Asp Tyr Trp Gly Gln Gly Thr
            100                 105                 110

Thr Leu Thr Val Ser Ser
        115

<210> SEQ ID NO 141
<211> LENGTH: 117
<212> TYPE: PRT
<213> ORGANISM: Artificial Sequence
<220> FEATURE:
<223> OTHER INFORMATION: Description of Artificial Sequence: Amino acid
      sequence of H chain V region of anti TF mouse monoclonal antibody
      ATR-4

<400> SEQUENCE: 141

Glu Val Gln Leu Gln Gln Ser Gly Ala Glu Leu Val Arg Pro Gly Ala
  1               5                  10                  15

Leu Val Lys Leu Ser Cys Lys Ala Ser Gly Phe Asn Ile Lys Asp Tyr
                 20                  25                  30

Tyr Met His Trp Val Lys Gln Arg Pro Glu Gln Gly Leu Glu Trp Ile
             35                  40                  45

Gly Leu Ile Asp Pro Gln Asn Gly Asn Thr Ile Tyr Asp Pro Lys Phe
         50                  55                  60

Gln Gly Lys Ala Ser Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asp Arg Asp Ser Gly Tyr Ala Met Asp Tyr Trp Gly Gln Gly Thr Ser
            100                 105                 110

Val Thr Val Ser Ser
        115

<210> SEQ ID NO 142
<211> LENGTH: 117
<212> TYPE: PRT
<213> ORGANISM: Artificial Sequence
<220> FEATURE:
<223> OTHER INFORMATION: Description of Artificial Sequence: Amino acid
      sequence of H chain V region of anti TF mouse monoclonal antibody
      ATR-5

<400> SEQUENCE: 142

Glu Val Gln Leu Gln Gln Ser Gly Thr Asn Leu Val Arg Pro Gly Ala
  1               5                  10                  15

Leu Val Lys Leu Ser Cys Lys Gly Ser Gly Phe Asn Ile Lys Asp Tyr
                 20                  25                  30

Tyr Met His Trp Val Lys Gln Arg Pro Glu Gln Gly Leu Glu Trp Ile
             35                  40                  45

Gly Gly Asn Asp Pro Ala Asn Gly His Ser Met Tyr Asp Pro Lys Phe
         50                  55                  60

Gln Gly Lys Ala Ser Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Phe Cys
                 85                  90                  95
```

```
Ala Arg Asp Ser Gly Tyr Ala Met Asp Tyr Trp Gly Gln Gly Thr Ser
            100                 105                 110

Val Thr Val Ser Ser
        115

<210> SEQ ID NO 143
<211> LENGTH: 118
<212> TYPE: PRT
<213> ORGANISM: Artificial Sequence
<220> FEATURE:
<223> OTHER INFORMATION: Description of Artificial Sequence: Amino acid
      sequence of H chain V region of anti TF mouse monoclonal antibody
      ATR-7

<400> SEQUENCE: 143

Asp Ile Gln Leu Gln Gln Ser Gly Pro Glu Leu Val Lys Pro Gly Ser
  1               5                  10                  15

Ser Val Lys Val Ser Cys Lys Ala Ser Gly Tyr Ser Phe Pro Asp Tyr
             20                  25                  30

Asn Ile Phe Trp Val Lys Gln Ser His Gly Lys Ser Leu Glu Trp Ile
         35                  40                  45

Gly Tyr Ile Asp Pro Tyr Thr Gly Gly Thr Gly Tyr Asn Gln Lys Phe
     50                  55                  60

Asn Asp Lys Ala Thr Leu Thr Val Asp Lys Ser Ser Ser Thr Ala Phe
 65                  70                  75                  80

Met His Leu Asn Ser Leu Thr Ser Glu Asp Ser Ala Val Tyr Tyr Cys
                 85                  90                  95

Ala Arg Gly Phe Tyr Tyr Asp Tyr Asp Cys Tyr Trp Gly Gln Gly Thr
            100                 105                 110

Leu Val Thr Val Ser Ala
        115

<210> SEQ ID NO 144
<211> LENGTH: 118
<212> TYPE: PRT
<213> ORGANISM: Artificial Sequence
<220> FEATURE:
<223> OTHER INFORMATION: Description of Artificial Sequence: Amino acid
      sequence of H chain V region of anti TF mouse monoclonal antibody
      ATR-8

<400> SEQUENCE: 144

Asp Ile Gln Leu Gln Gln Ser Gly Pro Glu Leu Val Lys Pro Gly Ala
  1               5                  10                  15

Ser Val Lys Val Ser Cys Lys Ala Ser Gly Tyr Ser Phe Thr Asp Tyr
             20                  25                  30

Asn Ile Phe Trp Val Lys Gln Ser His Gly Lys Ser Leu Glu Trp Ile
         35                  40                  45

Gly Tyr Ile Asp Pro Tyr Thr Gly Gly Thr Gly Tyr Asn Gln Lys Phe
     50                  55                  60

Asn Asp Lys Ala Thr Leu Thr Val Asp Lys Ser Ser Ser Thr Ala Phe
 65                  70                  75                  80

Met His Leu Asn Ser Leu Thr Ser Glu Asp Ser Ala Val Tyr Tyr Cys
                 85                  90                  95

Ala Arg Gly Phe Tyr Tyr Asp Tyr Asp Cys Tyr Trp Gly Gln Gly Thr
            100                 105                 110

Leu Val Thr Val Ser Ala
        115
```

```
<210> SEQ ID NO 145
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence of L chain V region of anti TF mouse monoclonal antibody
      ATR-2

<400> SEQUENCE: 145

Asp Ile Gln Met Thr Gln Ser Pro Ala Ser Gln Ser Ala Ser Leu Gly
  1               5                  10                  15

Glu Ser Val Thr Ile Thr Cys Leu Ala Ser Gln Thr Ile Gly Thr Trp
             20                  25                  30

Leu Ala Trp Tyr Gln Gln Lys Pro Gly Lys Ser Pro Gln Val Leu Ile
         35                  40                  45

Tyr Ala Ala Thr Ser Leu Ala Asp Gly Val Pro Ser Arg Phe Ser Gly
 50                  55                  60

Ser Gly Ser Gly Thr Lys Phe Ser Phe Lys Ile Ser Ser Leu Gln Ala
 65                  70                  75                  80

Glu Asp Phe Val Ser Tyr Tyr Cys Gln Gln Leu Tyr Ser Thr Pro Tyr
                 85                  90                  95

Thr Phe Gly Gly Gly Thr Lys Leu Glu Ile Lys
            100                 105

<210> SEQ ID NO 146
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence of L chain V region of anti TF mouse monoclonal antibody
      ATR-3

<400> SEQUENCE: 146

Asp Ile Gln Met Thr Gln Ser Pro Ala Ser Gln Ser Ala Ser Leu Gly
  1               5                  10                  15

Glu Ser Val Thr Ile Thr Cys Leu Ala Ser Gln Thr Ile Gly Thr Trp
             20                  25                  30

Leu Gly Trp Tyr Gln Gln Lys Pro Gly Lys Ser Pro Gln Val Leu Ile
         35                  40                  45

Tyr Ala Ala Thr Ser Leu Ala Asp Gly Val Pro Ser Arg Phe Ser Gly
 50                  55                  60

Ser Gly Ser Gly Thr Lys Phe Ser Phe Lys Ile Ser Ser Leu Gln Ala
 65                  70                  75                  80

Glu Asp Phe Val Ser Tyr Tyr Cys Gln Gln Leu Tyr Ser Thr Pro Tyr
                 85                  90                  95

Thr Phe Gly Gly Gly Thr Lys Leu Glu Ile Lys
            100                 105

<210> SEQ ID NO 147
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence of L chain V region of anti TF mouse monoclonal antibody
      ATR-4

<400> SEQUENCE: 147

Asp Ile Lys Met Thr Gln Ser Pro Ser Ser Met Tyr Ala Ser Leu Gly
  1               5                  10                  15
```

```
                 1               5              10              15

Glu Arg Val Thr Ile Thr Cys Lys Ala Ser Gln Asp Ile Lys Thr Phe
                20              25              30

Leu Ser Trp Tyr Gln Gln Lys Pro Trp Gln Ser Pro Lys Thr Leu Ile
                35              40              45

Tyr Tyr Ala Thr Ser Leu Ala Asp Gly Val Pro Ser Arg Phe Ser Gly
                50              55              60

Ser Gly Ser Gly Gln Asp Tyr Ser Leu Thr Ile Ser Ser Leu Glu Ser
 65              70              75              80

Asp Asp Ser Ala Thr Tyr Tyr Cys Leu Gln His Gly Glu Ser Pro Tyr
                85              90              95

Thr Phe Gly Gly Gly Thr Lys Leu Glu Ile Lys
                100             105
```

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence of L chain V region of anti TF mouse monoclonal antibody
      ATR-5

<400> SEQUENCE: 148

```
Asp Ile Lys Met Thr Gln Ser Pro Ser Ser Met Tyr Ala Ser Leu Gly
 1               5              10              15

Glu Arg Val Thr Ile Thr Cys Lys Ala Ser Gln Asp Ile Lys Ser Phe
                20              25              30

Leu Ser Trp Tyr Gln Gln Lys Pro Trp Lys Ser Pro Lys Thr Leu Ile
                35              40              45

Tyr Tyr Ala Thr Ser Leu Ala Asp Gly Val Pro Ser Arg Phe Ser Gly
                50              55              60

Ser Gly Ser Gly Gln Asp Tyr Ser Leu Thr Ile Asn Asn Leu Glu Ser
 65              70              75              80

Asp Asp Thr Ala Thr Tyr Tyr Cys Leu Gln His Gly Glu Ser Pro Tyr
                85              90              95

Thr Phe Gly Gly Gly Thr Lys Leu Glu Ile Lys
                100             105
```

<210> SEQ ID NO 149
<211> LENGTH: 112
<212> TYPE: PRT
<213> ORGANISM: Artificial Sequence
<220> FEATURE:
<223> OTHER INFORMATION: Description of Artificial Sequence: Amino acid
      sequence of L chain V region of anti TF mouse monoclonal antibody
      ATR-7

<400> SEQUENCE: 149

```
Asp Val Val Leu Thr Gln Thr Pro Leu Thr Leu Ser Val Thr Ile Gly
 1               5              10              15

Gln Pro Ala Ser Val Ser Cys Lys Ser Ser Gln Ser Leu Leu Asp Ser
                20              25              30

Asp Gly Lys Thr Tyr Leu Asn Trp Leu Leu Gln Arg Pro Gly Gln Ser
                35              40              45

Pro Lys Arg Leu Ile Tyr Leu Val Ser Lys Leu Asp Ser Gly Val Pro
                50              55              60

Asp Arg Phe Thr Gly Ser Gly Ser Gly Thr Asp Phe Thr Leu Lys Ile
 65              70              75              80
```

```
Ser Arg Val Glu Ala Glu Asp Leu Gly Val Tyr Tyr Cys Trp Gln Asp
             85                  90                  95

Thr His Phe Pro Asp Thr Phe Gly Gly Gly Thr Lys Leu Glu Ile Lys
            100                 105                 110

<210> SEQ ID NO 150
<211> LENGTH: 112
<212> TYPE: PRT
<213> ORGANISM: Artificial Sequence
<220> FEATURE:
<223> OTHER INFORMATION: Description of Artificial Sequence: Amino acid
      sequence of L chain V region of anti TF mouse monoclonal antibody
      ATR-8

<400> SEQUENCE: 150

Asp Val Val Leu Thr Gln Thr Pro Leu Thr Leu Ser Val Thr Ile Gly
 1               5                  10                  15

Gln Pro Ala Ser Val Ser Cys Lys Ser Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Asp
             85                  90                  95

Thr His Phe Pro Asp Thr Phe Gly Gly Gly Thr Lys Leu Glu Ile Lys
            100                 105                 110

<210> SEQ ID NO 151
<211> LENGTH: 780
<212> TYPE: DNA
<213> ORGANISM: Homo sapiens
<220> FEATURE:
<221> NAME/KEY: CDS
<222> LOCATION: (1)..(777)
<220> FEATURE:
<221> NAME/KEY: sig_peptide
<222> LOCATION: (1)..(96)
<220> FEATURE:
<221> NAME/KEY: mat_peptide
<222> LOCATION: (97)..(777)

<400> SEQUENCE: 151 atg gag acc cct gcc tgg ccc cgg gtc ccg cgc ccc gag acc gcc gtc     48
Met Glu Thr Pro Ala Trp Pro Arg Val Pro Arg Pro Glu Thr Ala Val
        -30                 -25                 -20 gct cgg acg ctc ctg ctc ggc tgg gtc ttc gcc cag gtg gcc ggc gct     96
Ala Arg Thr Leu Leu Leu Gly Trp Val Phe Ala Gln Val Ala Gly Ala
    -15                 -10                  -5                  -1 tca ggc act aca aat act gtg gca gca tat aat tta act tgg aaa tca    144
Ser Gly Thr Thr Asn Thr Val Ala Ala Tyr Asn Leu Thr Trp Lys Ser
  1               5                  10                  15 act aat ttc aag aca att ttg gag tgg gaa ccc aaa ccc gtc aat caa    192
Thr Asn Phe Lys Thr Ile Leu Glu Trp Glu Pro Lys Pro Val Asn Gln
             20                  25                  30 gtc tac act gtt caa ata agc act aag tca gga gat tgg aaa agc aaa    240
Val Tyr Thr Val Gln Ile Ser Thr Lys Ser Gly Asp Trp Lys Ser Lys
         35                  40                  45 tgc ttt tac aca aca gac aca gag tgt gac ctc acc gac gag att gtg    288
Cys Phe Tyr Thr Thr Asp Thr Glu Cys Asp Leu Thr Asp Glu Ile Val
```

```
                    50                  55                  60
aag gat gtg aag cag acg tac ttg gca cgg gtc ttc tcc tac ccg gca        336
Lys Asp Val Lys Gln Thr Tyr Leu Ala Arg Val Phe Ser Tyr Pro Ala
 65                  70                  75                  80 ggg aat gtg gag agc acc ggt tct gct ggg gag cct ctg tat gag aac        384
Gly Asn Val Glu Ser Thr Gly Ser Ala Gly Glu Pro Leu Tyr Glu Asn
                 85                  90                  95 tcc cca gag ttc aca cct tac ctg gag aca aac ctc gga cag cca aca        432
Ser Pro Glu Phe Thr Pro Tyr Leu Glu Thr Asn Leu Gly Gln Pro Thr
            100                 105                 110 att cag agt ttt gaa cag gtg gga aca aaa gtg aat gtg acc gta gaa        480
Ile Gln Ser Phe Glu Gln Val Gly Thr Lys Val Asn Val Thr Val Glu
        115                 120                 125 gat gaa cgg act tta gtc aga agg aac aac act ttc cta agc ctc cgg        528
Asp Glu Arg Thr Leu Val Arg Arg Asn Asn Thr Phe Leu Ser Leu Arg
    130                 135                 140 gat gtt ttt ggc aag gac tta att tat aca ctt tat tat tgg aaa tct        576
Asp Val Phe Gly Lys Asp Leu Ile Tyr Thr Leu Tyr Tyr Trp Lys Ser
145                 150                 155                 160 tca agt tca gga aag aaa aca gcc aaa aca aac act aat gag ttt ttg        624
Ser Ser Ser Gly Lys Lys Thr Ala Lys Thr Asn Thr Asn Glu Phe Leu
                165                 170                 175 att gat gtg gat aaa gga gaa aac tac tgt ttc agt gtt caa gca gtg        672
Ile Asp Val Asp Lys Gly Glu Asn Tyr Cys Phe Ser Val Gln Ala Val
            180                 185                 190 att ccc tcc cga aca gtt aac cgg aag agt aca gac agc ccg gta gag        720
Ile Pro Ser Arg Thr Val Asn Arg Lys Ser Thr Asp Ser Pro Val Glu
        195                 200                 205 tgt atg ggc cag gag aaa ggg gaa ttc aga gaa gac tac aaa gac gat        768
Cys Met Gly Gln Glu Lys Gly Glu Phe Arg Glu Asp Tyr Lys Asp Asp
    210                 215                 220 gac gat aaa taa                                                         780
Asp Asp Lys
225

<210> SEQ ID NO 152
<211> LENGTH: 259
<212> TYPE: PRT
<213> ORGANISM: Homo sapiens

<400> SEQUENCE: 152

Met Glu Thr Pro Ala Trp Pro Arg Val Pro Arg Pro Glu Thr Ala Val
        -30                 -25                 -20

Ala Arg Thr Leu Leu Leu Gly Trp Val Phe Ala Gln Val Ala Gly Ala
    -15                 -10                  -5                  -1

Ser Gly Thr Thr Asn Thr Val Ala Ala Tyr Asn Leu Thr Trp Lys Ser
  1                   5                  10                  15

Thr Asn Phe Lys Thr Ile Leu Glu Trp Glu Pro Lys Pro Val Asn Gln
             20                  25                  30

Val Tyr Thr Val Gln Ile Ser Thr Lys Ser Gly Asp Trp Lys Ser Lys
         35                  40                  45

Cys Phe Tyr Thr Thr Asp Thr Glu Cys Asp Leu Thr Asp Glu Ile Val
     50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
```

```
                      100                 105                 110
Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu Asp Tyr Lys Asp Asp
210                 215                 220

Asp Asp Lys
225

<210> SEQ ID NO 153
<211> LENGTH: 137
<212> TYPE: PRT
<213> ORGANISM: Artificial Sequence
<220> FEATURE:
<223> OTHER INFORMATION: Description of Artificial Sequence: Full-length
      amino acid sequence for H chain V region of anti-TF mouse
      monoclonal antibody ATR-2

<400> SEQUENCE: 153

Met Glu Trp Ser Trp Ile Phe Leu Phe Leu Leu Ser Gly Thr Thr Gly
                -15                 -10                  -5

Val His Ser Glu Ile Gln Leu Gln Gln Ser Gly Pro Glu Leu Val Lys
         -1   1                   5                  10

Pro Gly Ala Ser Val Lys Val Ser Cys Lys Ala Ser Gly Tyr Ser Phe
         15                  20                  25

Thr Asp Tyr Asn Met Tyr Trp Val Lys Gln Ser His Gly Lys Ser Leu
 30                  35                  40                  45

Glu Trp Ile Gly Tyr Ile Asp Pro Tyr Asn Gly Gly Thr Ile Tyr Asn
             50                  55                  60

Gln Lys Phe Lys Gly Lys Ala Thr Leu Thr Val Asp Lys Ser Ser Ser
         65                  70                  75

Thr Ala Phe Met His Leu Asn Ser Leu Thr Ser Glu Asp Ser Ala Val
             80                  85                  90

Tyr Tyr Cys Ala Arg Gly Gly Glu Gly Tyr Tyr Phe Asp Tyr Trp Gly
         95                 100                 105

Gln Gly Thr Thr Leu Thr Val Ser Ser
110                 115

<210> SEQ ID NO 154
<211> LENGTH: 137
<212> TYPE: PRT
<213> ORGANISM: Artificial Sequence
<220> FEATURE:
<223> OTHER INFORMATION: Description of Artificial Sequence: Full-length
      amino acid sequence for H chain V region of anti-TF mouse
      monoclonal antibody ATR-3

<400> SEQUENCE: 154

Met Glu Trp Ser Trp Ile Phe Leu Phe Leu Leu Ser Gly Thr Thr Gly
                -15                 -10                  -5
```

Val His Ser Glu Ile Gln Leu Gln Gln Ser Gly Pro Glu Leu Val Lys
        -1   1               5                      10

Pro Gly Ala Ser Val Lys Val Ser Cys Lys Ala Ser Gly Tyr Ser Phe
         15              20                  25

Thr Asp Tyr Asn Met Tyr Trp Val Lys Gln Ser His Gly Lys Ser Leu
 30              35                  40                      45

Glu Trp Ile Gly Tyr Ile Asp Pro Tyr Asn Gly Gly Thr Ile Tyr Asn
             50                  55                  60

Gln Lys Phe Lys Gly Lys Ala Thr Leu Thr Val Asp Lys Ser Ser Ser
         65                  70                  75

Thr Ala Phe Met His Leu Asn Ser Leu Thr Ser Glu Asp Ser Ala Val
             80                  85                  90

Tyr Tyr Cys Ala Arg Gly Gly Glu Gly Tyr Tyr Phe Asp Tyr Trp Gly
 95                     100                 105

Gln Gly Thr Thr Leu Thr Val Ser Ser
110                 115

<210> SEQ ID NO 155
<211> LENGTH: 136
<212> TYPE: PRT
<213> ORGANISM: Artificial Sequence
<220> FEATURE:
<223> OTHER INFORMATION: Description of Artificial Sequence: Full-length
      amino acid sequence for H chain V region of anti-TF mouse
      monoclonal antibody ATR-4

<400> SEQUENCE: 155

Met Lys Cys Ser Trp Val Ile Phe Phe Leu Met Ala Val Val Thr Gly
                -15             -10                 -5

Val Asn Ser Glu Val Gln Leu Gln Gln Ser Gly Ala Glu Leu Val Arg
        -1   1               5                      10

Pro Gly Ala Leu Val Lys Leu Ser Cys Lys Ala Ser Gly Phe Asn Ile
         15              20                  25

Lys Asp Tyr Tyr Met His Trp Val Lys Gln Arg Pro Glu Gln Gly Leu
 30              35                  40                      45

Glu Trp Ile Gly Leu Ile Asp Pro Gln Asn Gly Asn Thr Ile Tyr Asp
             50                  55                  60

Pro Lys Phe Gln Gly Lys Ala Ser Ile Thr Ala Asp Thr Ser Ser Asn
         65                  70                  75

Thr Ala Tyr Leu Gln Leu Ser Ser Leu Thr Ser Glu Asp Thr Ala Val
             80                  85                  90

Tyr Tyr Cys Asp Arg Asp Ser Gly Tyr Ala Met Asp Tyr Trp Gly Gln
 95                     100                 105

Gly Thr Ser Val Thr Val Ser Ser
110                 115

<210> SEQ ID NO 156
<211> LENGTH: 136
<212> TYPE: PRT
<213> ORGANISM: Artificial Sequence
<220> FEATURE:
<223> OTHER INFORMATION: Description of Artificial Sequence: Full-length
      amino acid sequence for H chain V region of anti-TF mouse
      monoclonal antibody ATR-5

<400> SEQUENCE: 156

Met Lys Cys Ser Trp Val Ile Phe Phe Leu Met Ala Val Val Thr Gly
                -15             -10                 -5

Val Asn Ser Glu Val Gln Leu Gln Gln Ser Gly Thr Asn Leu Val Arg
    -1   1               5                   10

Pro Gly Ala Leu Val Lys Leu Ser Cys Lys Gly Ser Gly Phe Asn Ile
        15              20                  25

Lys Asp Tyr Tyr Met His Trp Val Lys Gln Arg Pro Glu Gln Gly Leu
30              35                  40                  45

Glu Trp Ile Gly Gly Asn Asp Pro Ala Asn Gly His Ser Met Tyr Asp
            50                  55                  60

Pro Lys Phe Gln Gly Lys Ala Ser Ile Thr Ala Asp Thr Ser Ser Asn
            65                  70                  75

Thr Ala Tyr Leu Gln Leu Ser Ser Leu Thr Ser Glu Asp Thr Ala Val
        80                  85                  90

Tyr Phe Cys Ala Arg Asp Ser Gly Tyr Ala Met Asp Tyr Trp Gly Gln
    95                  100                 105

Gly Thr Ser Val Thr Val Ser Ser
110             115

<210> SEQ ID NO 157
<211> LENGTH: 137
<212> TYPE: PRT
<213> ORGANISM: Artificial Sequence
<220> FEATURE:
<223> OTHER INFORMATION: Description of Artificial Sequence: Full-length
      amino acid sequence for H chain V region of anti-TF mouse
      monoclonal antibody ATR-7

<400> SEQUENCE: 157

Met Glu Trp Ser Trp Ile Phe Leu Phe Leu Leu Ser Gly Thr Thr Gly
                -15                 -10                 -5

Val His Ser Asp Ile Gln Leu Gln Gln Ser Gly Pro Glu Leu Val Lys
    -1   1               5                   10

Pro Gly Ser Ser Val Lys Val Ser Cys Lys Ala Ser Gly Tyr Ser Phe
        15              20                  25

Pro Asp Tyr Asn Ile Phe Trp Val Lys Gln Ser His Gly Lys Ser Leu
30              35                  40                  45

Glu Trp Ile Gly Tyr Ile Asp Pro Tyr Thr Gly Thr Gly Tyr Asn
            50                  55                  60

Gln Lys Phe Asn Asp Lys Ala Thr Leu Thr Val Asp Lys Ser Ser Ser
            65                  70                  75

Thr Ala Phe Met His Leu Asn Ser Leu Thr Ser Glu Asp Ser Ala Val
        80                  85                  90

Tyr Tyr Cys Ala Arg Gly Phe Tyr Tyr Asp Tyr Asp Cys Tyr Trp Gly
    95                  100                 105

Gln Gly Thr Leu Val Thr Val Ser Ala
110             115

<210> SEQ ID NO 158
<211> LENGTH: 137
<212> TYPE: PRT
<213> ORGANISM: Artificial Sequence
<220> FEATURE:
<223> OTHER INFORMATION: Description of Artificial Sequence: Full-length
      amino acid sequence for H chain V region of anti-TF mouse
      monoclonal antibody ATR-8

<400> SEQUENCE: 158

Met Glu Trp Ser Trp Ile Phe Leu Phe Leu Leu Ser Gly Thr Thr Gly
                -15                 -10                 -5

Val His Ser Asp Ile Gln Leu Gln Gln Ser Gly Pro Glu Leu Val Lys

```
            -1    1              5                    10
Pro Gly Ala Ser Val Lys Val Ser Cys Lys Ala Gly Tyr Ser Phe
         15              20                  25

Thr Asp Tyr Asn Ile Phe Trp Val Lys Gln Ser His Gly Lys Ser Leu
 30                  35              40                      45

Glu Trp Ile Gly Tyr Ile Asp Pro Tyr Thr Gly Thr Gly Tyr Asn
                 50              55              60

Gln Lys Phe Asn Asp Lys Ala Thr Leu Thr Val Asp Lys Ser Ser Ser
             65              70              75

Thr Ala Phe Met His Leu Asn Ser Leu Thr Ser Glu Asp Ser Ala Val
         80              85              90

Tyr Tyr Cys Ala Arg Gly Phe Tyr Tyr Asp Tyr Asp Cys Tyr Trp Gly
         95              100             105

Gln Gly Thr Leu Val Thr Val Ser Ala
110             115
```

<210> SEQ ID NO 159
<211> LENGTH: 125
<212> TYPE: PRT
<213> ORGANISM: Artificial Sequence
<220> FEATURE:
<223> OTHER INFORMATION: Description of Artificial Sequence: Full-length
      amino acid sequence for L chain V region of anti-TF mouse
      monoclonal antibody ATR-2

<400> SEQUENCE: 159

```
Met Leu Thr Gln Leu Leu Gly Leu Leu Leu Trp Phe Ala Gly Gly
            -15                 -10                 -5

Lys Cys Asp Ile Gln Met Thr Gln Ser Pro Ala Ser Gln Ser Ala Ser
     -1   1              5                  10

Leu Gly Glu Ser Val Thr Ile Thr Cys Leu Ala Ser Gln Thr Ile Gly
 15              20              25                  30

Thr Trp Leu Ala Trp Tyr Gln Gln Lys Pro Gly Lys Ser Pro Gln Val
             35              40                  45

Leu Ile Tyr Ala Ala Thr Ser Leu Ala Asp Gly Val Pro Ser Arg Phe
         50              55                  60

Ser Gly Ser Gly Ser Gly Thr Lys Phe Ser Phe Lys Ile Ser Ser Leu
         65              70              75

Gln Ala Glu Asp Phe Val Ser Tyr Tyr Cys Gln Gln Leu Tyr Ser Thr
         80              85              90

Pro Tyr Thr Phe Gly Gly Gly Thr Lys Leu Glu Ile Lys
 95              100             105
```

<210> SEQ ID NO 160
<211> LENGTH: 125
<212> TYPE: PRT
<213> ORGANISM: Artificial Sequence
<220> FEATURE:
<223> OTHER INFORMATION: Description of Artificial Sequence: Full-length
      amino acid sequence for L chain V region of anti-TF mouse
      monoclonal antibody ATR-3

<400> SEQUENCE: 160

```
Met Leu Thr Gln Leu Leu Gly Leu Leu Leu Trp Phe Ala Gly Gly
            -15                 -10                 -5

Lys Cys Asp Ile Gln Met Thr Gln Ser Pro Ala Ser Gln Ser Ala Ser
     -1   1              5                  10

Leu Gly Glu Ser Val Thr Ile Thr Cys Leu Ala Ser Gln Thr Ile Gly
 15              20              25                  30
```

Thr Trp Leu Gly Trp Tyr Gln Gln Lys Pro Gly Lys Ser Pro Gln Val
                35                  40                  45

Leu Ile Tyr Ala Ala Thr Ser Leu Ala Asp Gly Val Pro Ser Arg Phe
            50                  55                  60

Ser Gly Ser Gly Ser Gly Thr Lys Phe Ser Phe Lys Ile Ser Ser Leu
        65                  70                  75

Gln Ala Glu Asp Phe Val Ser Tyr Tyr Cys Gln Gln Leu Tyr Ser Thr
    80                  85                  90

Pro Tyr Thr Phe Gly Gly Gly Thr Lys Leu Glu Ile Lys
95                  100                 105

<210> SEQ ID NO 161
<211> LENGTH: 129
<212> TYPE: PRT
<213> ORGANISM: Artificial Sequence
<220> FEATURE:
<223> OTHER INFORMATION: Description of Artificial Sequence: Full-length
    amino acid sequence for L chain V region of anti-TF mouse
    monoclonal antibody ATR-4

<400> SEQUENCE: 161

Met Asp Met Arg Ala Pro Ala Gln Phe Phe Gly Ile Leu Leu Leu Trp
        -20                 -15                 -10

Phe Pro Gly Ile Arg Cys Asp Ile Lys Met Thr Gln Ser Pro Ser Ser
    -5                  -1   1               5                   10

Met Tyr Ala Ser Leu Gly Glu Arg Val Thr Ile Thr Cys Lys Ala Ser
                15                  20                  25

Gln Asp Ile Lys Thr Phe Leu Ser Trp Tyr Gln Gln Lys Pro Trp Gln
            30                  35                  40

Ser Pro Lys Thr Leu Ile Tyr Tyr Ala Thr Ser Leu Ala Asp Gly Val
        45                  50                  55

Pro Ser Arg Phe Ser Gly Ser Gly Ser Gly Gln Asp Tyr Ser Leu Thr
    60                  65                  70

Ile Ser Ser Leu Glu Ser Asp Asp Ser Ala Thr Tyr Tyr Cys Leu Gln
75                  80                  85                  90

His Gly Glu Ser Pro Tyr Thr Phe Gly Gly Gly Thr Lys Leu Glu Ile
                95                  100                 105

Lys

<210> SEQ ID NO 162
<211> LENGTH: 127
<212> TYPE: PRT
<213> ORGANISM: Artificial Sequence
<220> FEATURE:
<223> OTHER INFORMATION: Description of Artificial Sequence: Full-length
    amino acid sequence for L chain V region of anti-TF mouse
    monoclonal antibody ATR-5

<400> SEQUENCE: 162

Met Arg Ala Pro Ala Gln Phe Phe Gly Ile Leu Leu Leu Trp Phe Pro
-20                 -15                 -10                 -5

Gly Ile Arg Cys Asp Ile Lys Met Thr Gln Ser Pro Ser Ser Met Tyr
            -1   1               5                   10

Ala Ser Leu Gly Glu Arg Val Thr Ile Thr Cys Lys Ala Ser Gln Asp
        15                  20                  25

Ile Lys Ser Phe Leu Ser Trp Tyr Gln Gln Lys Pro Trp Lys Ser Pro
    30                  35                  40

Lys Thr Leu Ile Tyr Tyr Ala Thr Ser Leu Ala Asp Gly Val Pro Ser

```
                45                  50                  55                  60
Arg Phe Ser Gly Ser Gly Ser Gly Gln Asp Tyr Ser Leu Thr Ile Asn
                    65                  70                  75

Asn Leu Glu Ser Asp Asp Thr Ala Thr Tyr Tyr Cys Leu Gln His Gly
                80                  85                  90

Glu Ser Pro Tyr Thr Phe Gly Gly Gly Thr Lys Leu Glu Ile Lys
            95                  100                 105

<210> SEQ ID NO 163
<211> LENGTH: 131
<212> TYPE: PRT
<213> ORGANISM: Artificial Sequence
<220> FEATURE:
<223> OTHER INFORMATION: Description of Artificial Sequence: Full-length
      amino acid sequence for L chain V region of anti-TF mouse
      monoclonal antibody ATR-7

<400> SEQUENCE: 163

Met Ser Pro Ala Gln Phe Leu Phe Leu Leu Val Leu Trp Ile Arg Glu
                    -15                 -10                 -5

Ile Asn Gly Asp Val Val Leu Thr Gln Thr Pro Leu Thr Leu Ser Val
        -1  1                   5                   10

Thr Ile Gly Gln Pro Ala Ser Val Ser Cys Lys Ser Gln Ser Leu
        15                  20                  25

Leu Asp Ser Asp Gly Lys Thr Tyr Leu Asn Trp Leu Leu Gln Arg Pro
    30                  35                  40                  45

Gly Gln Ser Pro Lys Arg Leu Ile Tyr Leu Val Ser Lys Leu Asp Ser
                50                  55                  60

Gly Val Pro Asp Arg Phe Thr Gly Ser Gly Ser Gly Thr Asp Phe Thr
                    65                  70                  75

Leu Lys Ile Ser Arg Val Glu Ala Glu Asp Leu Gly Val Tyr Tyr Cys
            80                  85                  90

Trp Gln Asp Thr His Phe Pro Asp Thr Phe Gly Gly Gly Thr Lys Leu
            95                  100                 105

Glu Ile Lys
110

<210> SEQ ID NO 164
<211> LENGTH: 131
<212> TYPE: PRT
<213> ORGANISM: Artificial Sequence
<220> FEATURE:
<223> OTHER INFORMATION: Description of Artificial Sequence: Full-length
      amino acid sequence for L chain V region of anti-TF mouse
      monoclonal antibody ATR-8

<400> SEQUENCE: 164

Met Ser Pro Ala Gln Phe Leu Phe Leu Leu Val Leu Trp Ile Arg Asp
                    -15                 -10                 -5

Ile Asn Gly Asp Val Val Leu Thr Gln Thr Pro Leu Thr Leu Ser Val
        -1  1                   5                   10

Thr Ile Gly Gln Pro Ala Ser Val Ser Cys Lys Ser Ser Gln Ser Leu
        15                  20                  25

Leu Asp Ser Asp Gly Lys Thr Tyr Leu Asn Trp Leu Leu Gln Arg Pro
    30                  35                  40                  45

Gly Gln Ser Pro Lys Arg Leu Ile Tyr Leu Val Ser Lys Leu Asp Ser
                50                  55                  60

Gly Val Pro Asp Arg Phe Thr Gly Ser Gly Ser Gly Thr Asp Phe Thr
                    65                  70                  75
```

```
Leu Lys Ile Ser Arg Val Glu Ala Glu Asp Leu Gly Val Tyr Tyr Cys
        80                  85                  90

Trp Gln Asp Thr His Phe Pro Asp Thr Phe Gly Gly Gly Thr Lys Leu
    95                  100                 105

Glu Ile Lys
110

<210> SEQ ID NO 165
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "a" of humanized H chain V
      region> SEQUENCE: 165

Met Lys Cys Ser Trp Val Ile Phe Phe Leu Met Ala Val Val Thr Gly
                -15                 -10                 -5

Val Asn Ser Gln Val Gln Leu Leu Glu Ser Gly Ala Val Leu Ala Arg
        -1  1               5                   10

Pro Gly Thr Ser Val Lys Ile Ser Cys Lys Ala Ser Gly Phe Asn Ile
    15                  20                  25

Lys Asp Tyr Tyr Met His Trp Val Lys Gln Arg Pro Gly Gln Gly Leu
30                  35                  40                  45

Glu Trp Ile Gly Gly Asn Asp Pro Ala Asn Gly His Ser Met Tyr Asp
                50                  55                  60

Pro Lys Phe Gln Gly Arg Ala Lys Leu Thr Ala Ala Thr Ser Ala Ser
            65                  70                  75

Ile Ala Tyr Leu Glu Phe Ser Ser Leu Thr Asn Glu Asp Ser Ala Val
        80                  85                  90

Tyr Tyr Cys Ala Arg Asp Ser Gly Tyr Ala Met Asp Tyr Trp Gly Gln
    95                  100                 105

Gly Thr Leu Val Thr Val Ser Ser Ala Ser
110                 115

<210> SEQ ID NO 166
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "b" of humanized H chain V
      region> SEQUENCE: 166

Met Lys Cys Ser Trp Val Ile Phe Phe Leu Met Ala Val Val Thr Gly
                -15                 -10                 -5

Val Asn Ser Gln Val Gln Leu Leu Glu Ser Gly Ala Val Leu Ala Arg
        -1  1               5                   10

Pro Gly Thr Ser Val Lys Ile Ser Cys Lys Ala Ser Gly Phe Asn Ile
    15                  20                  25

Lys Asp Tyr Tyr Met His Trp Val Lys Gln Arg Pro Gly Gln Gly Leu
30                  35                  40                  45

Glu Trp Ile Gly Gly Asn Asp Pro Ala Asn Gly His Ser Met Tyr Asp
                50                  55                  60

Pro Lys Phe Gln Gly Arg Val Thr Ile Thr Ala Asp Thr Ser Thr Asn
            65                  70                  75

Thr Ala Tyr Met Glu Leu Ser Ser Leu Arg Ser Glu Asp Thr Ala Ile
        80                  85                  90

Tyr Tyr Cys Ala Arg Asp Ser Gly Tyr Ala Met Asp Tyr Trp Gly Gln
```

```
                95                  100                 105
Gly Thr Leu Val Thr Val Ser Ser Ala Ser
110                 115

<210> SEQ ID NO 167
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "c" of humanized H chain V
      region> SEQUENCE: 167

Met Lys Cys Ser Trp Val Ile Phe Phe Leu Met Ala Val Val Thr Gly
                -15                 -10                 -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
             15                 20                  25

Lys Asp Tyr Tyr Met His Trp Val Lys Gln Arg Pro Gly Gln Gly Leu
 30                  35                  40                  45

Glu Trp Ile Gly Gly Asn Asp Pro Ala Asn Gly His Ser Met Tyr Asp
                 50                  55                  60

Pro Lys Phe Gln Gly Arg Val Thr Met Leu Val Asp Thr Ser Lys Asn
             65                  70                  75

Gln Phe Ser Leu Arg Leu Ser Ser Val Thr Ala Ala Asp Thr Ala Val
         80                  85                  90

Tyr Tyr Cys Ala Arg Asp Ser Gly Tyr Ala Met Asp Tyr Trp Gly Gln
     95                 100                 105

Gly Thr Leu Val Thr Val Ser Ser Ala Ser
110                 115

<210> SEQ ID NO 168
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "d" of humanized H chain V
      region> SEQUENCE: 168

Met Lys Cys Ser Trp Val Ile Phe Phe Leu Met Ala Val Val Thr Gly
                -15                 -10                 -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
             15                 20                  25

Lys Asp Tyr Tyr Met His Trp Val Lys Gln Arg Pro Gly Gln Gly Leu
 30                  35                  40                  45

Glu Trp Ile Gly Gly Asn Asp Pro Ala Asn Gly His Ser Met Tyr Asp
                 50                  55                  60

Pro Lys Phe Gln Gly Arg Val Thr Ile Thr Ala Asp Glu Ser Thr Ser
             65                  70                  75

Thr Ala Tyr Met Glu Leu Ser Ser Leu Arg Ser Glu Asp Ser Ala Val
         80                  85                  90

Tyr Phe Cys Ala Arg Asp Ser Gly Tyr Ala Met Asp Tyr Trp Gly Gln
     95                 100                 105

Gly Thr Leu Val Thr Val Ser Ser Ala Ser
110                 115
```

```
<210> SEQ ID NO 169
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "e" of humanized H chain V
      region> SEQUENCE: 169

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
             15                  20                  25

Lys Asp Tyr Tyr Met His Trp Val Lys Gln Arg Pro Gly Gln Gly Leu
 30              35                  40                  45

Glu Trp Ile Gly Gly Asn Asp Pro Ala Asn Gly His Ser Met Tyr Asp
                 50                  55                  60

Pro Lys Phe Gln Gly Arg Val Ser Ile Thr Ala Asp Glu Ser Thr Lys
             65                  70                  75

Ile Ala Tyr Met Glu Leu Asn Ser Leu Arg Ser Glu Asp Thr Ala Val
             80                  85                  90

Tyr Phe Cys Ala Arg Asp Ser Gly Tyr Ala Met Asp Tyr Trp Gly Gln
             95                 100                 105

Gly Thr Leu Val Thr Val Ser Ser Ala Ser
110                 115

<210> SEQ ID NO 170
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "f" of humanized H chain V
      region> SEQUENCE: 170

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
             15                  20                  25

Lys Asp Tyr Tyr Met His Trp Val Lys Gln Arg Pro Gly Gln Gly Leu
 30              35                  40                  45

Glu Trp Ile Gly Gly Asn Asp Pro Ala Asn Gly His Ser Met Tyr Asp
                 50                  55                  60

Pro Lys Phe Gln Gly Arg Val Thr Ile Thr Ala Asp Thr Ser Thr Ser
             65                  70                  75

Thr Ala Tyr Met Glu Leu Arg Ser Leu Arg Ser Asp Asp Thr Ala Val
             80                  85                  90

Tyr Tyr Cys Ala Arg Asp Ser Gly Tyr Ala Met Asp Tyr Trp Gly Gln
             95                 100                 105

Gly Thr Leu Val Thr Val Ser Ser Ala Ser
110                 115

<210> SEQ ID NO 171
<211> LENGTH: 138
<212> TYPE: PRT
<213> ORGANISM: Artificial Sequence
```

```
<220> FEATURE:
<223> OTHER INFORMATION: Description of Artificial Sequence: Full-length
      amino acid sequence of version "g" of humanized H chain V
      region> SEQUENCE: 171

Met Lys Cys Ser Trp Val Ile Phe Phe Leu Met Ala Val Val Thr Gly
            -15                 -10                 -5

Val Asn Ser Gln Val Gln Leu Leu Glu Ser Gly Ala Val Leu Ala Arg
        -1   1               5                  10

Pro Gly Thr Ser Val Lys Ile Ser Cys Lys Ala Ser Gly Phe Asn Ile
            15              20              25

Lys Asp Tyr Tyr Met His Trp Val Lys Gln Arg Pro Gly Gln Gly Leu
 30              35              40              45

Glu Trp Ile Gly Gly Asn Asp Pro Ala Asn Gly His Ser Met Tyr Asp
                50              55              60

Pro Lys Phe Gln Gly Lys Ala Thr Leu Thr Ala Asp Glu Ser Ser Ser
            65              70              75

Thr Ala Tyr Met Gln Leu Ser Ser Leu Arg Ser Glu Asp Ser Ala Val
         80              85              90

Tyr Ser Cys Ala Arg Asp Ser Gly Tyr Ala Met Asp Tyr Trp Gly Gln
     95             100             105

Gly Thr Leu Val Thr Val Ser Ser Ala Ser
110              115

<210> SEQ ID NO 172
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "h" of humanized H chain V
      region> SEQUENCE: 172

Met Lys Cys Ser Trp Val Ile Phe Phe Leu Met Ala Val Val Thr Gly
            -15                 -10                 -5

Val Asn Ser Gln Val Gln Leu Leu Glu Ser Gly Ala Val Leu Ala Arg
        -1   1               5                  10

Pro Gly Thr Ser Val Lys Ile Ser Cys Lys Ala Ser Gly Phe Asn Asn
            15              20              25

Lys Asp Tyr Tyr Met His Trp Val Lys Gln Arg Pro Gly Gln Gly Leu
 30              35              40              45

Glu Trp Ile Gly Gly Asn Asp Pro Ala Asn Gly His Ser Met Tyr Asp
                50              55              60

Pro Lys Phe Gln Gly Arg Val Thr Met Ser Ala Asp Lys Ser Ser Ser
            65              70              75

Ala Ala Tyr Leu Gln Trp Thr Ser Leu Lys Ala Ser Asp Thr Ala Ile
         80              85              90

Tyr Phe Cys Ala Arg Asp Ser Gly Tyr Ala Met Asp Tyr Trp Gly Gln
     95             100             105

Gly Thr Leu Val Thr Val Ser Ser Ala Ser
110              115

<210> SEQ ID NO 173
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "i" of humanized H chain V
      region> SEQUENCE: 173
```

```
Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1              5                  10

Pro Gly Thr Ser Val Lys Ile Ser Cys Lys Ala Ser Gly Phe Asn Ile
         15              20              25

Lys Asp Tyr Tyr Met His Trp Val Lys Gln Arg Pro Gly Gln Gly Leu
 30              35              40              45

Glu Trp Ile Gly Gly Asn Asp Pro Ala Asn Gly His Ser Met Tyr Asp
                 50              55              60

Pro Lys Phe Gln Gly Arg Val Thr Ile Thr Ala Asp Thr Ser Thr Ser
             65              70              75

Thr Val Phe Met Glu Leu Ser Ser Leu Arg Ser Glu Asp Thr Ala Val
             80              85              90

Tyr Tyr Cys Ala Arg Asp Ser Gly Tyr Ala Met Asp Tyr Trp Gly Gln
 95              100             105

Gly Thr Leu Val Thr Val Ser Ser Ala Ser
110             115

<210> SEQ ID NO 174
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "j" of humanized H chain V
      region> SEQUENCE: 174

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1              5                  10

Pro Gly Thr Ser Val Lys Ile Ser Cys Lys Ala Ser Gly Phe Asn Ile
         15              20              25

Lys Asp Tyr Tyr Met His Trp Val Lys Gln Arg Pro Gly Gln Gly Leu
 30              35              40              45

Glu Trp Ile Gly Gly Asn Asp Pro Ala Asn Gly His Ser Met Tyr Asp
                 50              55              60

Pro Lys Phe Gln Gly Arg Val Thr Phe Thr Ala Asp Thr Ser Ala Asn
             65              70              75

Thr Ala Tyr Met Glu Leu Arg Ser Leu Arg Ser Ala Asp Thr Ala Val
             80              85              90

Tyr Tyr Cys Ala Arg Asp Ser Gly Tyr Ala Met Asp Tyr Trp Gly Gln
 95              100             105

Gly Thr Leu Val Thr Val Ser Ser Ala Ser
110             115

<210> SEQ ID NO 175
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "b1" of humanized H chain
      V region> SEQUENCE: 175

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1              5                  10
```

Pro Gly Thr Ser Val Lys Ile Ser Cys Lys Ala Ser Gly Phe Asn Ile
        15                  20                  25

Lys Asp Tyr Tyr Met His Trp Val Arg Gln Ala Pro Gly Gln Gly Leu
 30                  35                  40                  45

Glu Trp Met Gly Gly Asn Asp Pro Ala Asn Gly His Ser Met Tyr Asp
                 50                  55                  60

Pro Lys Phe Gln Gly Arg Val Thr Ile Thr Ala Asp Thr Ser Thr Asn
             65                  70                  75

Thr Ala Tyr Met Glu Leu Ser Ser Leu Arg Ser Glu Asp Thr Ala Ile
         80                  85                  90

Tyr Tyr Cys Ala Arg Asp Ser Gly Tyr Ala Met Asp Tyr Trp Gly Gln
     95                 100                 105

Gly Thr Leu Val Thr Val Ser Ser Ala Ser
110                 115

<210> SEQ ID NO 176
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "d1" of humanized H chain
      V region> SEQUENCE: 176

Met Lys Cys Ser Trp Val Ile Phe Phe Leu Met Ala Val Val Thr Gly
             -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
        15                  20                  25

Lys Asp Tyr Tyr Met His Trp Val Arg Gln Ala Pro Gly Gln Gly Leu
 30                  35                  40                  45

Glu Trp Met Gly Gly Asn Asp Pro Ala Asn Gly His Ser Met Tyr Asp
                 50                  55                  60

Pro Lys Phe Gln Gly Arg Val Thr Ile Thr Ala Asp Glu Ser Thr Ser
             65                  70                  75

Thr Ala Tyr Met Glu Leu Ser Ser Leu Arg Ser Glu Asp Ser Ala Val
         80                  85                  90

Tyr Phe Cys Ala Arg Asp Ser Gly Tyr Ala Met Asp Tyr Trp Gly Gln
     95                 100                 105

Gly Thr Leu Val Thr Val Ser Ser Ala Ser
110                 115

<210> SEQ ID NO 177
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "b3" of humanized H chain
      V region> SEQUENCE: 177

Met Lys Cys Ser Trp Val Ile Phe Phe Leu Met Ala Val Val Thr Gly
             -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
        15                  20                  25

Lys Asp Tyr Tyr Met His Trp Val Arg Gln Ala Pro Gly Gln Gly Leu

```
                30                  35                  40                  45

Glu Trp Ile Gly Gly Asn Asp Pro Ala Asn Gly His Ser Met Tyr Asp
                50                  55                  60

Pro Lys Phe Gln Gly Arg Val Thr Ile Thr Ala Asp Thr Ser Thr Asn
            65                  70                  75

Thr Ala Tyr Met Glu Leu Ser Ser Leu Arg Ser Glu Asp Thr Ala Ile
        80                  85                  90

Tyr Tyr Cys Ala Arg Asp Ser Gly Tyr Ala Met Asp Tyr Trp Gly Gln
    95                  100                 105

Gly Thr Leu Val Thr Val Ser Ser Ala Ser
110                 115

<210> SEQ ID NO 178
<211> LENGTH: 138
<212> TYPE: PRT
<213> ORGANISM: Artificial Sequence
<220> FEATURE:
<223> OTHER INFORMATION: Description of Artificial Sequence: Full-length
      amino acid sequence of version "d3" of humanized H chain
      V region> SEQUENCE: 178

Met Lys Cys Ser Trp Val Ile Phe Phe Leu Met Ala Val Val Thr Gly
                -15                 -10                 -5

Val Asn Ser Gln Val Gln Leu Leu Glu Ser Gly Ala Val Leu Ala Arg
        -1  1                   5                   10

Pro Gly Thr Ser Val Lys Ile Ser Cys Lys Ala Ser Gly Phe Asn Ile
            15                  20                  25

Lys Asp Tyr Tyr Met His Trp Val Arg Gln Ala Pro Gly Gln Gly Leu
30                  35                  40                  45

Glu Trp Ile Gly Gly Asn Asp Pro Ala Asn Gly His Ser Met Tyr Asp
                50                  55                  60

Pro Lys Phe Gln Gly Arg Val Thr Ile Thr Ala Asp Glu Ser Thr Ser
            65                  70                  75

Thr Ala Tyr Met Glu Leu Ser Ser Leu Arg Ser Glu Asp Ser Ala Val
        80                  85                  90

Tyr Phe Cys Ala Arg Asp Ser Gly Tyr Ala Met Asp Tyr Trp Gly Gln
    95                  100                 105

Gly Thr Leu Val Thr Val Ser Ser Ala Ser
110                 115

<210> SEQ ID NO 179
<211> LENGTH: 127
<212> TYPE: PRT
<213> ORGANISM: Artificial Sequence
<220> FEATURE:
<223> OTHER INFORMATION: Description of Artificial Sequence: Full-length
      amino acid sequence of version "a" of humanized L chain V
      region> SEQUENCE: 179

Met Arg Ala Pro Ala Gln Phe Phe Gly Ile Leu Leu Leu Trp Phe Pro
-20                 -15                 -10                 -5

Gly Ile Arg Cys Asp Ile Gln Met Thr Gln Ser Pro Ser Ser Leu Ser
            -1  1                   5                   10

Ala Ser Val Gly Asp Arg Val Thr Ile Thr Cys Lys Ala Ser Gln Asp
            15                  20                  25

Ile Lys Ser Phe Leu Ser Trp Tyr Gln Gln Lys Pro Gly Lys Ala Pro
        30                  35                  40

Lys Leu Leu Ile Tyr Tyr Ala Thr Ser Leu Ala Asp Gly Val Pro Ser
45                  50                  55                  60
```

Arg Phe Ser Gly Ser Gly Ser Gly Thr Asp Phe Thr Leu Thr Ile Ser
            65                  70                  75

Ser Leu Gln Pro Glu Asp Phe Ala Thr Tyr Tyr Cys Leu Gln His Gly
            80                  85                  90

Glu Ser Pro Tyr Thr Phe Gly Gly Gly Thr Lys Val Glu Ile Lys
            95                  100                 105

<210> SEQ ID NO 180
<211> LENGTH: 127
<212> TYPE: PRT
<213> ORGANISM: Artificial Sequence
<220> FEATURE:
<223> OTHER INFORMATION: Description of Artificial Sequence: Full-length
      amino acid sequence of version "b" of humanized L chain V
      region> SEQUENCE: 180

Met Arg Ala Pro Ala Gln Phe Phe Gly Ile Leu Leu Leu Trp Phe Pro
-20                 -15                 -10                 -5

Gly Ile Arg Cys Asp Ile Gln Met Thr Gln Ser Pro Ser Ser Leu Ser
            -1   1               5                   10

Ala Ser Val Gly Asp Arg Val Thr Ile Thr Cys Lys Ala Ser Gln Asp
            15                  20                  25

Ile Lys Ser Phe Leu Ser Trp Tyr Gln Gln Lys Pro Gly Lys Ala Pro
            30                  35                  40

Lys Leu Leu Ile Tyr Tyr Ala Thr Ser Leu Ala Asp Gly Val Pro Ser
45                  50                  55                  60

Arg Phe Ser Gly Ser Gly Ser Gly Thr Asp Tyr Thr Leu Thr Ile Ser
            65                  70                  75

Ser Leu Gln Pro Glu Asp Phe Ala Thr Tyr Tyr Cys Leu Gln His Gly
            80                  85                  90

Glu Ser Pro Tyr Thr Phe Gly Gly Gly Thr Lys Val Glu Ile Lys
            95                  100                 105

<210> SEQ ID NO 181
<211> LENGTH: 127
<212> TYPE: PRT
<213> ORGANISM: Artificial Sequence
<220> FEATURE:
<223> OTHER INFORMATION: Description of Artificial Sequence: Full-length
      amino acid sequence of version "c" of humanized L chain V
      region> SEQUENCE: 181

Met Arg Ala Pro Ala Gln Phe Phe Gly Ile Leu Leu Leu Trp Phe Pro
-20                 -15                 -10                 -5

Gly Ile Arg Cys Asp Ile Gln Met Thr Gln Ser Pro Ser Ser Leu Ser
            -1   1               5                   10

Ala Ser Val Gly Asp Arg Val Thr Ile Thr Cys Lys Ala Ser Gln Asp
            15                  20                  25

Ile Lys Ser Phe Leu Ser Trp Tyr Gln Gln Lys Pro Gly Lys Ala Pro
            30                  35                  40

Lys Leu Leu Ile Tyr Tyr Ala Thr Ser Leu Ala Asp Gly Val Pro Ser
45                  50                  55                  60

Arg Phe Ser Gly Ser Gly Ser Gly Thr Asp Tyr Thr Leu Thr Ile Ser
            65                  70                  75

Ser Leu Gln Pro Glu Asp Ile Ala Thr Tyr Tyr Cys Leu Gln His Gly
            80                  85                  90

Glu Ser Pro Tyr Thr Phe Gly Gly Gly Thr Lys Val Glu Ile Lys
            95                  100                 105

<210> SEQ ID NO 182

```
<211> LENGTH: 127
<212> TYPE: PRT
<213> ORGANISM: Artificial Sequence
<220> FEATURE:
<223> OTHER INFORMATION: Description of Artificial Sequence: Full-length
      amino acid sequence of version "b1" of humanized L chain
      V region> SEQUENCE: 182

Met Arg Ala Pro Ala Gln Phe Phe Gly Ile Leu Leu Leu Trp Phe Pro
-20                 -15                 -10                 -5

Gly Ile Arg Cys Asp Ile Gln Met Thr Gln Ser Pro Ser Ser Leu Ser
            -1   1               5                  10

Ala Ser Val Gly Asp Arg Val Thr Ile Thr Cys Lys Ala Ser Gln Asp
        15                  20                  25

Ile Lys Ser Phe Leu Ser Trp Phe Gln Gln Lys Pro Gly Lys Ser Pro
    30                  35                  40

Lys Thr Leu Ile Tyr Tyr Ala Thr Ser Leu Ala Asp Gly Val Pro Ser
45                  50                  55                  60

Arg Phe Ser Gly Ser Gly Ser Gly Thr Asp Tyr Thr Leu Thr Ile Ser
                65                  70                  75

Ser Leu Gln Pro Glu Asp Phe Ala Thr Tyr Tyr Cys Leu Gln His Gly
            80                  85                  90

Glu Ser Pro Tyr Thr Phe Gly Gly Gly Thr Lys Val Glu Ile Lys
            95                  100                 105

<210> SEQ ID NO 183
<211> LENGTH: 127
<212> TYPE: PRT
<213> ORGANISM: Artificial Sequence
<220> FEATURE:
<223> OTHER INFORMATION: Description of Artificial Sequence: Full-length
      amino acid sequence of version "b2" of humanized L chain
      V region> SEQUENCE: 183

Met Arg Ala Pro Ala Gln Phe Phe Gly Ile Leu Leu Leu Trp Phe Pro
-20                 -15                 -10                 -5

Gly Ile Arg Cys Asp Ile Gln Met Thr Gln Ser Pro Ser Ser Leu Ser
            -1   1               5                  10

Ala Ser Val Gly Asp Arg Val Thr Ile Thr Cys Lys Ala Ser Gln Asp
        15                  20                  25

Ile Lys Ser Phe Leu Ser Trp Tyr Gln Gln Lys Pro Glu Lys Ala Pro
    30                  35                  40

Lys Ser Leu Ile Tyr Tyr Ala Thr Ser Leu Ala Asp Gly Val Pro Ser
45                  50                  55                  60

Arg Phe Ser Gly Ser Gly Ser Gly Thr Asp Tyr Thr Leu Thr Ile Ser
                65                  70                  75

Ser Leu Gln Pro Glu Asp Phe Ala Thr Tyr Tyr Cys Leu Gln His Gly
            80                  85                  90

Glu Ser Pro Tyr Thr Phe Gly Gly Gly Thr Lys Val Glu Ile Lys
            95                  100                 105
```